United States Patent
Saligrama et al.

(10) Patent No.: US 12,377,396 B2
(45) Date of Patent: Aug. 5, 2025

(54) SYSTEMS AND METHODS FOR MULTIPLEXED MEASUREMENTS IN SINGLE AND ENSEMBLE CELLS

(71) Applicant: The Board of Trustees of the Leland Stanford Junior University, Stanford, CA (US)

(72) Inventors: Naresha Saligrama, Stanford, CA (US); Ansuman Satpathy, Stanford, CA (US); Howard Y. Chang, Stanford, CA (US); Mark M. Davis, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1344 days.

(21) Appl. No.: 16/967,402

(22) PCT Filed: Dec. 19, 2018

(86) PCT No.: PCT/US2018/066592
§ 371 (c)(1),
(2) Date: Aug. 4, 2020

(87) PCT Pub. No.: WO2019/152108
PCT Pub. Date: Aug. 8, 2019

(65) Prior Publication Data
US 2021/0213413 A1 Jul. 15, 2021

Related U.S. Application Data

(60) Provisional application No. 62/626,603, filed on Feb. 5, 2018.

(51) Int. Cl.
*B01J 19/00* (2006.01)
*C12N 15/10* (2006.01)
*C12Q 1/6874* (2018.01)

(52) U.S. Cl.
CPC ...... *B01J 19/0046* (2013.01); *C12N 15/1096* (2013.01); *C12Q 1/6874* (2013.01); *B01J 2219/00596* (2013.01); *B01J 2219/00722* (2013.01); *C12Q 2537/165* (2013.01)

(58) Field of Classification Search
None
See application file for complete search history.

(56) References Cited

U.S. PATENT DOCUMENTS

| | | |
|---|---|---|
| 5,137,829 A | 8/1992 | Nag et al. |
| 5,965,443 A | 10/1999 | Reznikoff et al. |
| 6,159,717 A | 12/2000 | Savakis et al. |
| 6,207,384 B1 | 3/2001 | Mekalanos et al. |
| 6,258,571 B1 | 7/2001 | Chumakov et al. |
| 6,291,243 B1 | 9/2001 | Fogarty et al. |
| 6,294,385 B1 | 9/2001 | Goryshin et al. |
| 6,593,113 B1 | 7/2003 | Tenkanen et al. |
| 6,613,752 B2 | 9/2003 | Kay et al. |
| 7,135,296 B2 | 11/2006 | Baranov et al. |
| 7,138,267 B1 | 11/2006 | Jendrisak et al. |
| 7,316,903 B2 | 1/2008 | Yanagihara et al. |
| 7,479,630 B2 | 1/2009 | Bandura et al. |
| 7,608,434 B2 | 10/2009 | Reznikoff et al. |
| 7,608,451 B2 | 10/2009 | Cooper et al. |
| 7,745,218 B2 | 6/2010 | Kim et al. |
| 8,124,404 B2 | 2/2012 | Alphey |
| 8,420,386 B2 | 4/2013 | Ivics et al. |
| 8,598,328 B2 | 12/2013 | Koga et al. |
| 8,829,171 B2 | 9/2014 | Steemers et al. |
| 8,927,218 B2 | 1/2015 | Forsyth |
| 9,005,935 B2 | 4/2015 | Belyaev |
| 9,074,251 B2 | 7/2015 | Steemers et al. |
| 9,080,211 B2 | 7/2015 | Grunenwald et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,328,382 B2 | 5/2016 | Drmanac et al. |
| 9,574,226 B2 | 2/2017 | Gormley et al. |
| 10,059,989 B2 | 8/2018 | Giresi et al. |
| 10,150,995 B1 | 12/2018 | Giresi et al. |
| 10,337,062 B2 | 7/2019 | Giresi et al. |
| 10,619,207 B2 | 4/2020 | Giresi et al. |
| 10,689,643 B2 | 6/2020 | Jelinek et al. |

(Continued)

FOREIGN PATENT DOCUMENTS

| | | |
|---|---|---|
| CN | 1230226 A | 9/1999 |
| CN | 1612931 A | 5/2005 |

(Continued)

OTHER PUBLICATIONS

Grbesa et al., "Mapping Genome-wide Accessible Chromatin in Primary Human T Lymphocytes by ATAC-Seq" 129 Journal of Visualized Experiments e56313 1-11 (Year: 2017).*
Scharer et al., "ATAC-seq on biobanked specimens defines a unique chromatin accessibility structure in naive SLE B cells" 6 Scientific Reports 27030 1-9 (Year: 2016).*
Buenrostro et al., "Transposition of native chromatin for multimodal regulatory analysis and personal epigenomics", Nature Methods, 2013, 10(12): 1213-1218.
Qu et al., "Chromatin Accessibility Landscape of Cutaneous T Cell Lymphoma and Dynamic Response to HDAC Inhibitors", Cancer Cell, 2017, 32(1): 27-41.
Roybal et al., "Engineering T Cells with Customized Therapeutic Response Programs Using Synthetic Notch Receptors", Cell, 2016; 167 (2): 419-432.

(Continued)

*Primary Examiner* — Nancy J Leith
(74) *Attorney, Agent, or Firm* — Casimir Jones, S.C.; Tanya A. Arenson

(57) ABSTRACT

Provided are systems and methods that can combine T cell receptor sequencing (TCRseq) and Assay for Transposase Accessible Chromatin using sequencing (ATAC-seq), and/or respective aspects thereof. Further provided are systems and methods that can combine ATAC-seq and perturbation sequencing (Perturb-seq), and/or respective aspects thereof.

28 Claims, 149 Drawing Sheets
Specification includes a Sequence Listing.

(56) References Cited

U.S. PATENT DOCUMENTS

| | | | |
|---|---|---|---|
| 10,738,357 | B2 | 8/2020 | Giresi et al. |
| 10,889,859 | B2 | 1/2021 | Giresi et al. |
| 11,306,307 | B2 | 4/2022 | Jelinek et al. |
| 2003/0032141 | A1 | 2/2003 | Nguyen et al. |
| 2004/0101680 | A1 | 5/2004 | Barber |
| 2004/0101880 | A1 | 5/2004 | Rozwadowski et al. |
| 2006/0040382 | A1 | 2/2006 | Heffron et al. |
| 2008/0046194 | A1 | 2/2008 | Antonov et al. |
| 2010/0120098 | A1 | 5/2010 | Grunenwald et al. |
| 2011/0206042 | A1 | 8/2011 | Tarrab et al. |
| 2011/0306042 | A1 | 12/2011 | Jouvenot |
| 2012/0297493 | A1 | 11/2012 | Cooper et al. |
| 2013/0079251 | A1 | 3/2013 | Boles |
| 2013/0203605 | A1 | 8/2013 | Shendure et al. |
| 2014/0274740 | A1 | 9/2014 | Srinivasan et al. |
| 2015/0111788 | A1 | 4/2015 | Fernandez et al. |
| 2015/0267191 | A1 | 9/2015 | Steelman et al. |
| 2015/0291942 | A1 | 10/2015 | Gloeckner et al. |
| 2015/0337298 | A1 | 11/2015 | Xi et al. |
| 2015/0337369 | A1 | 11/2015 | Davis et al. |
| 2015/0368638 | A1 | 12/2015 | Steemers et al. |
| 2015/0376608 | A1 | 12/2015 | Kaper et al. |
| 2016/0001248 | A1* | 1/2016 | Fan ............ B01J 19/0046 506/4 |
| 2016/0040234 | A1 | 2/2016 | Hutchins et al. |
| 2016/0053253 | A1 | 2/2016 | Salathia et al. |
| 2016/0060691 | A1 | 3/2016 | Giresi et al. |
| 2016/0115474 | A1 | 4/2016 | Jelinek et al. |
| 2016/0122753 | A1 | 5/2016 | Mikkelsen et al. |
| 2016/0160235 | A1 | 6/2016 | Solodushko et al. |
| 2016/0177359 | A1 | 6/2016 | Ukanis et al. |
| 2016/0208323 | A1 | 7/2016 | Bernstein et al. |
| 2016/0209319 | A1 | 7/2016 | Adalsteinsson et al. |
| 2016/0376663 | A1 | 12/2016 | Brown |

FOREIGN PATENT DOCUMENTS

| | | |
|---|---|---|
| CN | 102292455 A | 12/2011 |
| CN | 105189748 A | 12/2015 |
| CN | 105339503 A | 2/2016 |
| EP | 3470530 B1 | 11/2020 |
| EP | 3828285 A1 | 6/2021 |
| WO | WO-2007093819 A2 | 8/2007 |
| WO | WO-2009147386 A1 | 12/2009 |
| WO | WO-2010048605 A1 | 4/2010 |
| WO | WO-2012061832 A1 | 5/2012 |
| WO | WO-2012106546 A2 | 8/2012 |
| WO | WO-2013181265 A1 | 12/2013 |
| WO | WO-2014108810 A2 | 7/2014 |
| WO | WO-2014189957 A2 | 11/2014 |
| WO | WO-2014190214 A1 | 11/2014 |
| WO | WO-2015179706 A1 | 11/2015 |
| WO | WO-2016123692 A1 | 8/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017040306 A1 | 3/2017 |
| WO | WO-2017075294 A1 | 5/2017 |
| WO | WO 2017/123559 A2 | 7/2017 |

OTHER PUBLICATIONS

Roybal et al., "Synthetic immunology: Hacking immune cells to expand their therapeutic capabilities", Annual Review of Immunology, Jan. 2017; 35: 229-253.

Hayward et al., "Harnessing Notch signaling to decode mechanisms of proteolytic regulation in diverse cell-surface receptors", bioRxiv, 2018; XP055849739, URL: https://www.biorxiv.org/content/10.1101/436592v1.full.pdf.

Office Action for CN 201880092114.X, mailed Jul. 30, 2023, 9 pages.

Extended European Search Report for EP 23193525.5, mailed Mar. 12, 2024, 9 pages.

Cusanovich D.A. et al. Multiplex single-cell profiling of chromatin accessibility by combinatorial cellular indexing. Science, vol. 348, No. 6237, May 22, 2015, pp. 910-914.

Han, A. et al. Linking T-cell receptor sequence to functional phenotype at the single-cell level. Nature Biotechnology, vol. 32, No. 7, Jun. 22, 2014, pp. 684-692.

Corces, R.M. et al. Lineage-specific and single-cell chromatin accessibility charts human hematopoiesis and leukemia evolution. Nature Genetics, vol. 48, No. 10, Oct. 1, 2016 (Oct. 1, 2016), pp. 1193-1203.

Satpathy, A. et al. Transcript-indexed ATAC-seq for precision immune profiling. Nature Medicine, Nature Pub. Co, New York, vol. 24, No. 5, Apr. 23, 2018, pp. 580-590.

Buenrostro J.D. et al. Integrated Single-Cell Analysis Maps the Continuous Regulatory Landscape of Human Hematopoietic Differentiation. Cell vol. 173, No. 6 May 1, 2018, pp. 1535-1548.e16.

Adey A., et al., "Ultra-low-input, Tagmentation-based whole-genome Bisulfite Sequencing," Genome Research, Jun. 2012, vol. 22, No. 6, pp. 1139-1143, Published Online Mar. 30, 2012, DOI: 10.1101/gr.136242.111, PMID: 22466172, PMCID: PMC3371708.

Adey et al., Rapid, low-input, low-bias construction of shotgun fragment libraries by high-density in vitro transposition. Genome Biol. 2010;11 (12):R119. 1-17.

Ahern, "Tools & Technology, Biochemical, Reagent Kits Offer Scientists Good Return On Investment", The Scientist, 1995, vol. 20, pp. 20 and 22.

Aleem E., et al., "Cdc2-Cyclin E Complexes Regulate the G1/S Phase Transition," Nature Cell Biology, Aug. 2005, vol. 7, No. 8, pp. 831-836 (10 Pages).

Amendola M., et al., "Nuclear Lamins Are Not Required for Lamina—Associated Domain Organization in Mouse Embryonic Stem Cells," EMBO Reports, May 2015, vol. 16, No. 5, pp. 610-617 (2 Pages).

Amini S., et al., "Haplotype-Resolved Whole-Genome Sequencing by Contiguity-Preserving Transposition and Combinatorial Indexing," Nature Genetics, Dec. 2014, vol. 46, vol. 12, pp. 1343-1349 (9 Pages).

Ason B., et al., "DNA Sequence Bias During Tn5 Transposition," Journal of Molecular Biology, 2004, vol. 335, pp. 1213-1255.

Audit B., et al., "Open Chromatin Encoded in DNA Sequence is the Signature of 'Master' Replication Origins in Human Cells," Nucleic Acids Research, 2009, vol. 37, No. 18, pp. 6064-6075.

Aziz R.K., et al., "Transposases are the most Abundant, most Ubiquitous Genes in Nature," Nucleic Acids Research, Jul. 1, 2010, vol. 38, Issue 13, pp. 4207-4217, doi.org/10.1093/nar/gkq 140.

Bandura D.R., et al., "Mass Cytometry: Technique for Real Time Single Cell Multitarget Immunoassay based on Inductively Coupled Plasma Time-of-Flight Mass Spectrometry," Analytical Chemistry, Aug. 15, 2009, vol. 81, No. 16, pp. 6813-6822.

Bickmore W. A., et al., "Genome Architecture: Domain Organization of Interphase Chromosomes," Cell, Mar. 14, 2013, vol. 152, No. 6, pp. 1270-1284.

Biery M.C., et al., "A Simple in Vitro Tn7-Based Transposition System With Low Target Site Selectivity for Genome and Gene Analysis," Nucleic Acids Research, Mar. 1, 2000, vol. 28, No. 5, pp. 1067-1077.

Bjornsson H.T., et al., "Intra-individiual Change Over Time in DNA Methylation with Familial Clustering," JAMA, Jun. 25, 2008, vol. 299, No. 24, pp. 2877-2883 (11 Pages).

Boyle A. P., et al., "High-Resolution Genome-Wide in Vivo Footprinting of Diverse Transcription Factors in Human Cells," Genome Research, Mar. 2011, vol. 21, No. 3, pp. 456-464 (10 Pages).

Boyle A.P., et al., "High-resolution Mapping and Characterization of Open Chromatin across the Genome," Cell, Jan. 25, 2008, vol. 132, No. 2, pp. 311-322, DOI: 10.1016/j.cell.2007.12.014, PMID: 18243105, PMCID: PMC2669738.

Brinkmann V., et al., "Neutrophil Extracellular Traps Kill Bacteria," Science, Mar. 5, 2004, vol. 303, pp. 1532-1535.

(56) References Cited

OTHER PUBLICATIONS

Brouilette S., et al., "A Simple and Novel Method for RNA-Seq Library Preparation of Single Cell cDNA Analysis by Hyperactive Tn5 Transposase," Developmental Dynamics, 2012, vol. 241, pp. 1584-1590.

Buenrostro J., et al., "ATAC-seq: A Method for Assaying Chromatin Accessibility Genome-Wide," Current Protocols in Molecular Biology, New York, NY, Wiley, Jan. 5, 2015, vol. 109, pp. 21.29.1-21.29.9, doi:10.1002/0471142727.mb2129s109, ISBN 978-0-471-14272-0, XP055504007.

Buenrostro J., et al., "ATAC-seq: A Method of Assaying Chromatin Accessibility Genome-Wide," Current Protocols in Molecular Biology, Jan. 5, 2016, vol. 109, pp. 1-10.

Buenrostro J.D., et al., "Single-cell Chromatin Accessibility Reveals Principles of Regulatory Variation," Nature, Jul. 23, 2015, vol. 523, No. 7561, pp. 486-490.

Caruccio N., et al., "Chapter 17: Preparation of Next-Generation Sequencing Libraries using Nextera™ Technology: Simultaneous DNA Fragmentation and Adaptor Tagging by in Vitro Transposition," Methods in Molecular Biology, 2011, vol. 733, pp. 241-255.

Chen X., et al., "ATAC-see Reveals the Accessible Genome by Transposase-mediated Imaging and Sequencing," Nature Methods, New York, Oct. 17, 2016, vol. 13, No. 12, pp. 1013-1020(12 Pages), doi:10.1038/nmeth.4031, ISSN 1548-7091, XP055511584.

Christophorou M.A., et al., "Citrullination Regulates Pluripotency and Histone H1 Binding to Chromatin," Nature, Mar. 6, 2014, vol. 507, No. 7490, pp. 104-108 (27 Pages).

Epicentre: "EZ-Tn5(TM) Custom Transposome Construction Kits," www.epicentre.com, Dec. 2012, vol. 327, pp. 1-17.

Extended European Search Report for European Application No. 18903080.2, mailed Oct. 14, 2021, 7 Pages.

Fey P.D., et al., "A Genetic Resource for Rapid and Comprehensive Phenotype Screening of Nonessential *Staphylococcus aureus* Genes," MBio, Jan./Feb. 2013, vol. 4, Issue 1:e00537-12, pp. 1-8, DOI: 10.1128/mbio.00537-12.

Gangadharan S., et al., "DNA Transposon Hermes Insert Into Dna in Nucleosome-free Regions in Vivo," Proceedings of the National Academy of Sciences, Dec. 21, 2010, vol. 107, No. 51, pp. 21966-21972 (13 Pages).

Gaspar-Maia A., et al., "Open Chromatin in Pluripotency and Reprogramming," Nature Reviews, Molecular Cell Biology, Jan. 2011, vol. 12, pp. 36-47, doi.org/10.1038/nrm3036.

Genbank: "Hermes Transposase [*Musca domestica*]," NCBI GenBank Accession No. AAB60236.1 Oct. 19, 1995, 2 Pages.

Gertz J., et al., "Transposase Mediated Construction of RNA-seq Libraries," Genome Research, 2012, vol. 22, No. 1, pp. 134-141.

Gibcus J.H., et al., "Connecting the Genome: Dynamics and Stochasticity in a New Hierarchy for Chromosome Conformation," Molecular Cell, Mar. 7, 2013, vol. 49, No. 5, pp. 773-782 (18 Pages).

Gloecker C., et al., "Score Report for Instant SEQ No. 1," for US20150291942, Published on Oct. 2015, 1 Page.

Gloecker C., et al., "Score Report for Instant SEQ No. 2," for US20150291942, Published on Oct. 2015.

Gloecker C., et al., "Score Report for Instant SEQ No. 3," for US20150291942, Published on Oct. 2015.

Goryshin I.Y., et al., "Tn5 In Vitro Transposition," The Journal of Biological Chemistry, Mar. 27, 1998, vol. 273, No. 13, pp. 7367-7374, DOI: 10.1074/jbc.273.13.7367, PMID: 9516433.

Green B., et al., "Insertion Site Preference of Mu, Tn5, and Tn7 Transposons," Mobile DNA, 2012, vol. 3 (3), 6 Pages.

Guimond N., et al., "Patterns of Hermes Transposition in *Drosophila melanogaster*," Molecular Genetics and Genomics, Apr. 2003, vol. 268, pp. 779-790, (13 Pages).

Haapa S., et al., "An Efficient DNA Sequencing Strategy Based on the Bacteriophage Mu in Vitro DNA Transposition Reaction," Genome Research, 1999, vol. 9, No. 3, pp. 308-315.

Haring M., et al., "Chromatin Immunoprecipitation: Optimization, Quantitative Analysis and Data Normalization," Plant Methods, Sep. 24, 2007, vol. 3, No. 11, 25 Pages.

Hickman A.B., et al., "Molecular Architecture of a Eukaryotic DNA Transposase," Nature Structural & Molecular Biology, Aug. 2005, vol. 12, No. 8, pp. 715-721.

Hinde E., et al., "Changes in Chromatin Compaction During the Cell Cycle Revealed by Micrometer-Scale Measurement of Molecular Flow in the Nucleus," Biophysical Journal, Feb. 8, 2012, vol. 102, No. 3, pp. 691-697.

International Search Report and Written Opinion for International Application No. PCT/US2018/066592, mailed Apr. 15, 2019, 11 Pages.

Jacques P-E., et al., "The Majority of Primate-specific Regulatory Sequences Are Derived from Transposable Elements," PLOS Genetics, May 2013, vol. 9, Issue. 5, e1003504, pp. 1-12.

Jursch T., et al., "Regulation of DNA Transposition by CpG Methylation and Chromatin Structure in Human Cells," Mobile DNA, May 15, 2013, vol. 4, No. 15, 11 Pages, doi.org/10.1186/1759-8753-4-15.

Kolaczkowska E., et al., "Neutrophil Recruitment and Function in Health and Inflammation," Nature Reviews Immunology, Mar. 2013, vol. 13, No. 3, pp. 159-175.

Lanctot C., et al., "Dynamic Genome Architecture in the Nuclear Space: Regulation of Gene Expression in Three Dimensions," Nature Reviews Genetics, Feb. 2007, vol. 8, No. 2, pp. 104-115.

Lewis H.D., et al., Inhibition of PAD4 Activity is Sufficient to Disrupt Mouse and Human NET Formation, Nature Chemical Biology, Mar. 2015, vol. 11 , No. 3, pp. 189-191 (16 Pages).

Li P., et al., "PAD4 is Essential for Antibacterial Innate Immunity Mediated by Neutrophil Extracellular Traps," Journal of Experimental Medicine, Aug. 30, 2010, vol. 207, No. 9, pp. 1853-1862.

Lieberman-Aiden E., et al., "Comprehensive Mapping of Long-range Interactions Reveals Folding Principles of the Human Genome," Science, Oct. 9, 2009, vol. 326, No. 5950, pp. 289-293, (11 Pages).

Liu S., et al., "Mu Transposon Insertion Sites and Meiotic Recombination Events Co-localize with Epigenetic Marks for Open Chromatin Across the Maize Genome," PLoS Genetics, Nov. 2009, vol. 5, Issue 11: e1000733, pp. 1-13, Published Online Nov. 20, 2009, DOI: 10.1371/journal.pgen.1000733, PMID: 19936291, PMCID: PMC2774946.

Munoz-Lopez M., et al., "DNA Transposons: Nature and Applications in Genomics," Current Genomics, 2010, vol. 11, No. 8, pp. 115-128.

NCBI GenBank: "*Musca domestica* Hermes Transposon Transposase Gene, Complete Cds," GenBank Accession No. L34807.1, May 24, 2005, 3 Pages.

O'brochta D.A., et al., "Hemes, A Functional Non-drosophilid Insect Gene Vector From *Musca domestica*," Genetics, Mar. 1996, vol. 142, pp. 907-914.

Park C.W., et al., "Sleeping Beauty Transposition in the Mouse Genome is Associated with Changes in DNA Methylation at the Site of Insertion," Genomics, Aug. 2006, vol. 88, No. 2, pp. 204-213, Published online May 22, 2006, DOI: 10.1016/j.ygeno.2006.04.007, PMID: 16714096.

Parks P.J., "ChIP-Seq: Advantages and Challenges of a Maturing Technology," Nature Reviews, Oct. 2009, vol. 10, pp. 669-680.

Perez Z.N., et al., "Purification, Crystallization and Preliminary Crystallographic Analysis of the Hermes Transposase," Acta Crystallographica, 2005, vol. F61, pp. 587-590.

Picelli S., et al., "Tn5 Transposase and Tagmentation Procedures for Massively Scaled Sequencing Projects," Genome Research, Dec. 2014, vol. 24, No. 12, pp. 2033-2040.

Simon J.M., et al., "Using FAIRE (Formaldehyde-assisted Isolation of Regulatory Elements) to Isolate Active Regulatory DNA," Nature Protocols, 2012, vol. 7, No. 2, pp. 256-267(23 Pages).

Solovei I., et al., "Nuclear Architecture of Rod Photoreceptor Cells Adapts to Vision in Mammalian Evolution," Cell, Apr. 17, 2009, vol. 137, No. 2, pp. 356-368.

Song L., et al., "DNase-seq: A High-resolution Technique for Mapping Active Gene Regulatory Elements across the Jenome from Mammalian Cells," Cold Spring Harbor Laboratory Press, Feb. 2, 2010, vol. 2010, Issue. 2, 12 Pages, DOI:10 1101/pdbprot5384.

Sos B.C., et al., "Characterization of Chromatin Accessibility With a Transposome Hypersensitive Sites Sequencing (THS-seq) Assay",

(56) References Cited

OTHER PUBLICATIONS

Genome Biology, Feb. 4, 2016, vol. 17, No. 20, DOI: 10.1186/s13059-016-0882-7, pp. 1-15, XP055463306.

Tanner S.D., et al., "Flow Cytometer with Mass Spectrometer Detection for Massively Multiplexed Single-Cell Biomarker Assay," Pure and Applied Chemistry, 2008, vol. 80, pp. 2627-2641.

Vaezeslami S., et al., "Site-directed Mutagenesis Studies of Tn5 Transposase Residues Involved in Synaptic Complex Formation," Journal of Bacteriology, Oct. 2007, vol. 189, No. 20, pp. 7436-7441.

Van Steensel B., "Chromatin: Constructing the Big Picture," EMBO Journal, EMBO Members's Review, May 18, 2011, vol. 30, No. 10, pp. 1885-1895, Published Online Apr. 28, 2011, DOI: 10.1038/emboj.2011.135, PMID: 21527910, PMCID: PMC3098493.

Zentner G.E., et al., "Surveying the Epigenomic Landscape, One Base at a Time," Genome Biology, 2012, vol. 13, No. 250, 8 Pages.

Zhou L., et al., "Transposition of hAT Elements Links Transposable Elements and V(D)J Recombination," Nature, Dec. 23/30, 2004, vol. 432, pp. 995-1001.

* cited by examiner

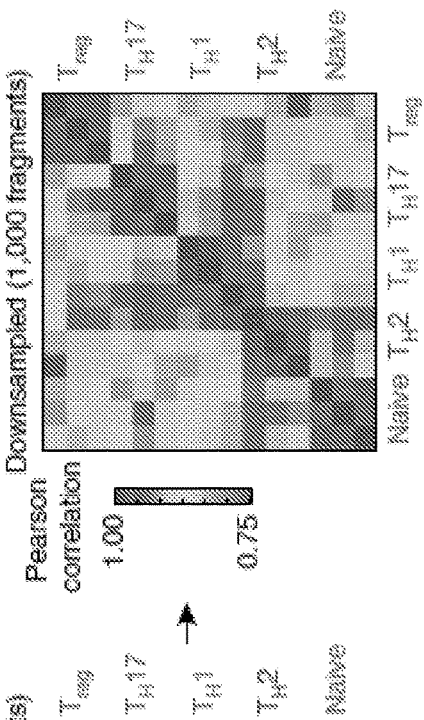
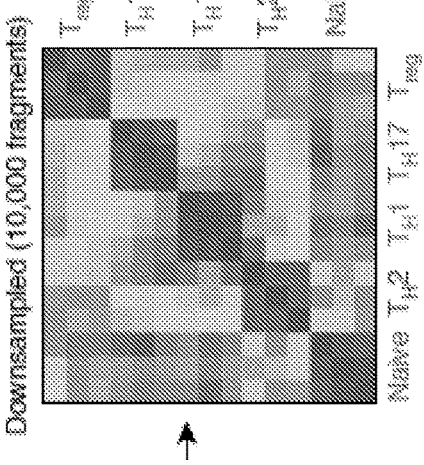
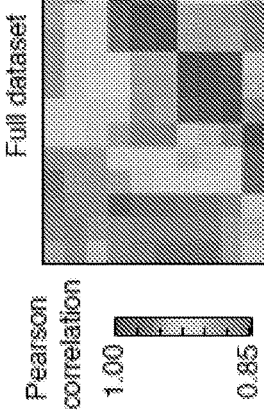
*FIG. 14*

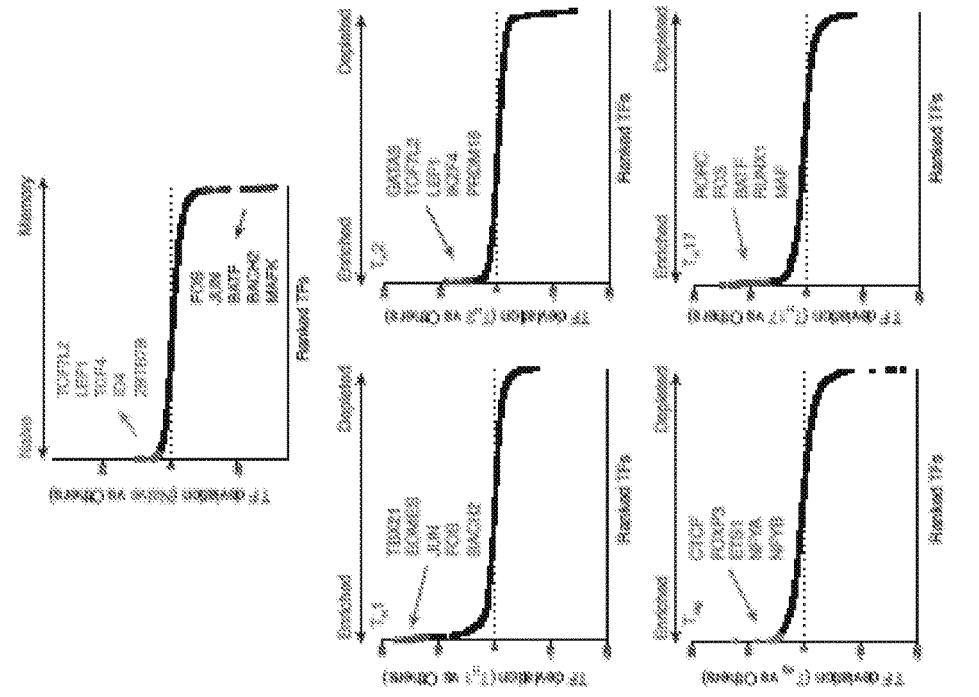
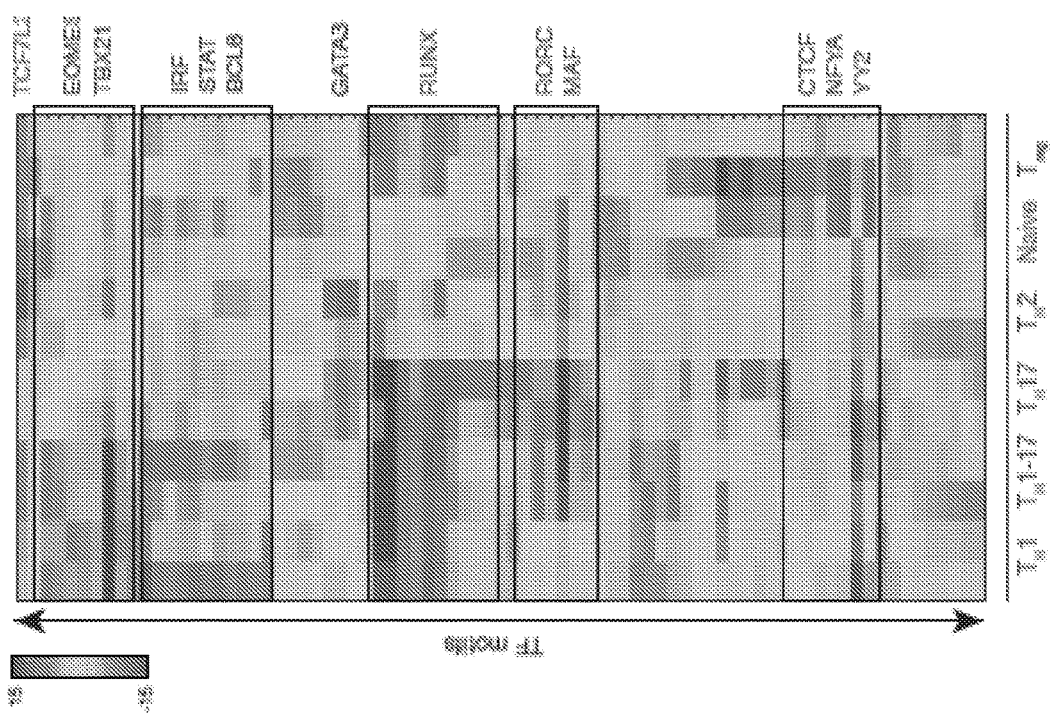
FIG. 41

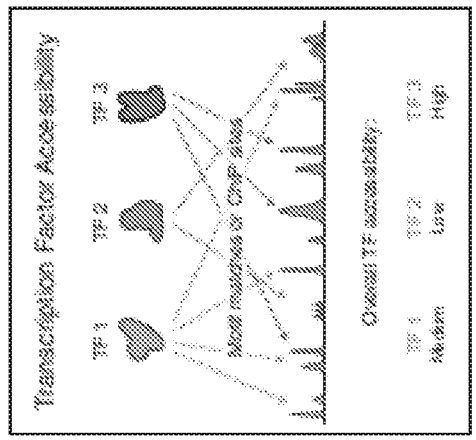
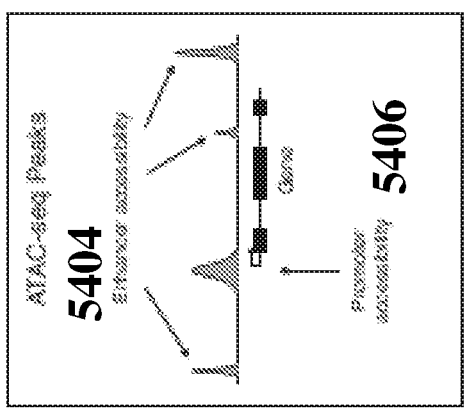
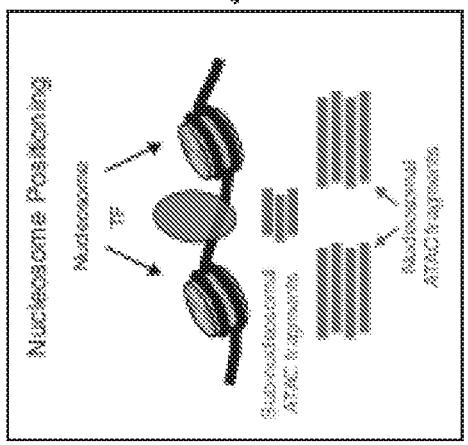
FIG. 54

Motif/ChIP Annotations in Clusters

CTCF, H3K4me3, POLR2A, SMAD5, SMC3, STAT1, TRIM22

BCLAF1, ELF5, ETV6, FOXB1, FOXK2, GABPA, NFYA, NFYB, NRF1, POU2F2, POU5F1B

CREM, EP300, IKZF1, IKZF2, RELB

BCL11A, EBF1, FOSL1, JUNB, JUND, NFKB1, RELA

BMI1, CBFB, H3K27ac, IRF5, PKNOX1, SP1, TBX21, YBX1

EMX1, GSX1, HOXA2, HOXB3, LHX2, LHX9, MEOX2, RAX,

CEBPE, CUX1, CUX2, NEUROG2, REST, SOX10, SREBF1, TP53

EGR2, GLI2, KLF13, MNT, NR3C1, OLIG2, TBX21, SOX9, SOX21, XBP1, ZBTB7C

*FIG. 131*

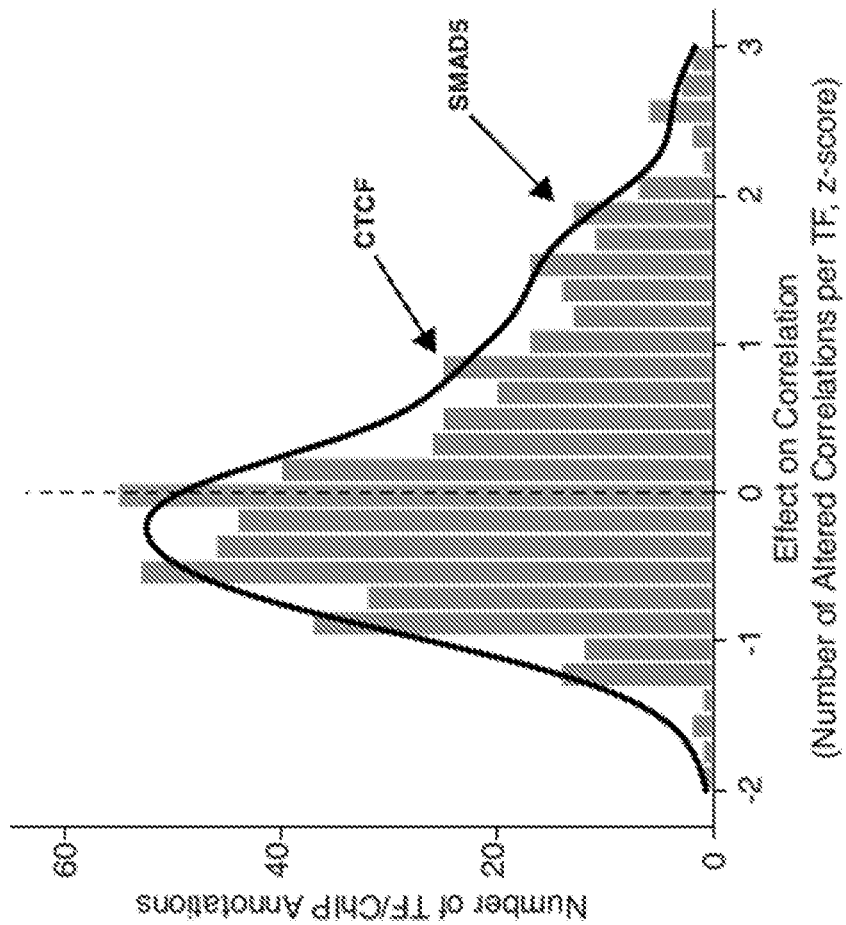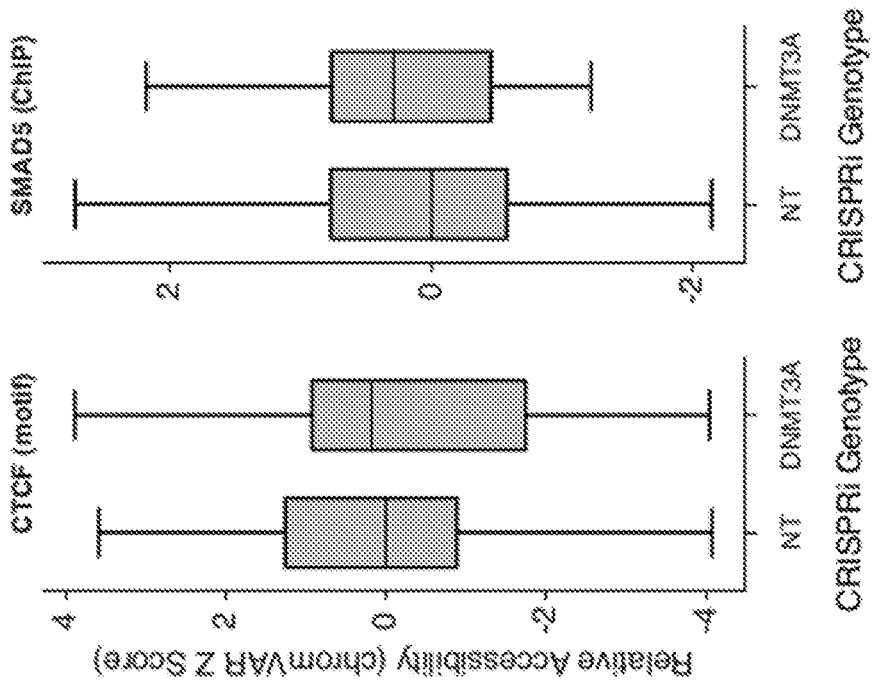
FIG. 133

| Gene | Number Past 5% FDR | Most Frequently Affected TF Annotations |
|---|---|---|
| 7SK | 1253 | RELA, NFKB2, TFAP2A (var. 3), VSX2, NFKB1 |
| BRG1 | 1214 | PAX5, E2F2, NR2C1, FOXA1, SOX10 |
| DNMT3A | 1277 | LARP7, FOXC2, NFIC, EMX1, LBX1 |
| EBER1 | 1006 | MZF1 (var. 2), NKX1, ZNF384, MEF2A, ZBTB40 |
| EBER2 | 1265 | ELF4, RAD51, ELF5, ZIC3, SPIB |
| EBF1 | 1283 | CHD2, PLAG1, RCOR1, RELB, TFAP2A |
| EZH2 | 791 | PROM1, EWSR1-FLI1, NOTO, POU3F3, E2F6 |
| IRF8 | 2117 | MEF2, EP300, SP8, FOS::JUN, JUN (var. 2) |
| NFKB1 | 1149 | FOXD1, FOXO3, FOXI1, SMAD2::SMAD3::SMAD4, ZIC4 |
| RELA | 1234 | ZEB1, ETV5, ELK1, IRF1, E2F4 |
| SPI1 | 1025 | TCF7, LHX6, LHX2, POU1F1, EMX2 |
| TET2 | 1281 | BMI1, IKZF2, DPF2, MLLT1, EED |

FIG. 137

SEQUENCE LISTING

```
<160> NUMBER OF SEQ ID NOS: 19

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ala Val Pro Asn Gln Ala Gly Thr Ala Leu Ile Phe
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Ala Val Asn Lys Asn Ala Arg Leu Met Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ala Thr Asp Asp Ser Ser Ala Ser Lys Ile Ile Phe
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Cys Ser Ala Pro Gly Leu Ala Arg Thr Asp Thr Gln Tyr Phe
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ala Ser Ser Phe Gly Gly Gly Pro Gly Asp Glu Ala Phe Phe
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ala Ser Ser Pro Leu Ala Gly Val Val Thr Asp Thr Gln Tyr Phe
1               5                   10                  15

<210> SEQ ID NO 7
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagatccagc gcacagagca gggggactcg gccatgtatc tctgtgccag cagcttgggt    60
agcaatcagc cccagcattt tggtgat                                        87

<210> SEQ ID NO 8
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accaaccagc tggatgccaa ttgtatccct ttccaagagt cgacatcaa cggcgagcac     60 ctctgcagca tgagtttgca ggagttcacc cgggcggca                           99

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
accaaccagc tggatgccaa ttgtatccct ttccaagagt cgacatcca ccgccaaccc     60 cttctgcaga atgagtttga gggagttcac ccggcgggca                         100
```

```
<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gcgaccgtgg ccacagacct ggagagcggc ggagccggtg cggcttgcgg cggtagcaac    60
ctggcgcccc tacctcggag agagaccgag gagttcaacg                         100

<210> SEQ ID NO 11
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (73)..(74)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (79)..(79)
<223> OTHER INFORMATION: a, c, t, g, unknown or other
<220> FEATURE:
<221> NAME/KEY: modified_base
<222> LOCATION: (85)..(86)
<223> OTHER INFORMATION: a, c, t, g, unknown or other

<400> SEQUENCE: 11
gcgaccgtgg ccacagacct ggagagcggc ggagcctttg cggctgagct cctgcggcca    60
caattgcacc aannganant tccgnntaag agt                                93

<210> SEQ ID NO 12
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tgcatttgtt ccagtcggcg agcacagact caaggggcca gacaacgccg aggcgcccga    60
gacactggct ttacacaacc ccactgccaa ggccgtgtct                         100

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (45)..(46)
<223> OTHER INFORMATION: a, c, t, g, unknown or other
<220> FEATURE:
<221> NAME/KEY: modified_base
<222> LOCATION: (71)..(71)
<223> OTHER INFORMATION: a, c, t, g, unknown or other
<220> FEATURE:
<221> NAME/KEY: modified_base
<222> LOCATION: (73)..(73)
```

```
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other

<400> SEQUENCE: 13
tgcatttgtt ccagtcggcg agcacagact caaggggcca gacannggga tttctccacc    60
cccctgtgtc ntncctgtct ttccacattg ctttcgnctt                         100

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gccgccgccc tcgcacccgc acccgcaccc gccgccgcg cacctggccg ccccgcacct    60
gcagttccag atcgcgcact gcggccagac caccatgcac                         100

<210> SEQ ID NO 15
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gccgccgccc tcgcacccgc acccgcaccc gccgccgcg cacctggccg ccccgaccgt    60
ggacttcccg aagacgcccc tgcccccgac ccccctgcac                         100

<210> SEQ ID NO 16
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cccttctacc acgacgactc atacacagct acgggatacg gccgggcccc tggtggcctc    60
tctctacacg actacaaact cctgaaaccg agcctggcgg tca                     103

<210> SEQ ID NO 17
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (65)..(65)
<223> OTHER INFORMATION: a, c, t, g, unknown or other

<400> SEQUENCE: 17
cccttctacc acgacgactc atacacagct acgggatacg gccgggcccc tgtgtcttct    60
cactnattat tagaaaccca gcaagccggt ccgggggggcc a                      101

<210> SEQ ID NO 18
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Ala Val Ser Asp Leu Glu Pro Asn Ser Ser Ala Ser Lys Ile Ile
1               5                   10                  15

Phe

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Ala Ser Ser Phe Ser Thr Cys Ser Ala Asn Tyr Gly Tyr Thr Phe
1               5                   10                  15
```

SYSTEMS AND METHODS FOR MULTIPLEXED MEASUREMENTS IN SINGLE AND ENSEMBLE CELLS

CROSS-REFERENCE

This application is a § 371 national phase of International Application No. PCT/US2018/066592, filed on Dec. 19, 2018, which claims the benefit of U.S. Provisional Patent Application No. 62/626,603, filed Feb. 5, 2018, which applications are entirely incorporated herein by reference.

STATEMENT REGARDING FEDERALLY SPONSORED RESEARCH

This invention was made with Government support under contract HG007735 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 1, 2024, is named STDU2-41396 SL.txt and is 6,774 bytes in size.

BACKGROUND

A sample may be processed for a variety of purposes, such as identification of a species within a sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets or other compartments within a microfluidic device. Partitions may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

Eukaryotic genomes are hierarchically packaged into chromatin, and the nature of this packaging plays a central role in gene regulation. Major insights into the epigenetic information encoded within the nucleoprotein structure of chromatin have come from high-throughput, genome-wide methods for separately assaying the chromatin accessibility ("open chromatin"), nucleosome positioning, and transcription factor (TF) occupancy. While published protocols exist, those methods require millions of cells as starting material, involve complex and time-consuming sample preparations, and cannot simultaneously probe the interplay of nucleosome positioning, chromatin accessibility, and TF binding. Therefore, recognized herein is a need to address at least the abovementioned issues.

In an aspect, provided is a method of processing immune cells, comprising: (a) capturing an immune cell, wherein the immune cell comprises genomic deoxyribonucleic acid (gDNA) and messenger ribonucleic acid (mRNA) molecules; (b) contacting gDNA from the immune cell with a transposase to generate tagged gDNA fragments in a tagmentation reaction; and (c) generating complementary DNA (cDNA) molecules from the mRNA molecules, wherein the cDNA molecules comprise sequences that correspond to a V(D)J region of a genome of the immune cell.

In some embodiments, the immune cell is a T cell.

In some embodiments, the immune cell is a B cell.

In some embodiments, the capturing comprises partitioning in a partition. In some embodiments, the partition is a chamber. In some embodiments, the partition is a well. In some embodiments, the partition is a droplet.

In some embodiments, the method further comprises prior to (b), lysing the immune cell.

In some embodiments, the capturing comprises isolating the immune cell from a plurality of immune cells. In some embodiments, the isolating comprises flow cytometry sorting or magnetic cell sorting.

In some embodiments, each of the tagged gDNA fragments comprises one or more adapters. In some embodiments, the one or more adapters comprise an adapter sequence.

In some embodiments, (c) comprises contacting the mRNA molecules from the immune cell with primers and a reverse transcriptase. In some embodiments, the primers comprise a sequence specific to or targeted for a sequence of the mRNA molecules.

In some embodiments, the mRNA molecules comprise T cell receptor alpha (TRA) or T cell receptor beta (TRB) RNA molecules. In some embodiments, the mRNA molecules comprise T cell receptor alpha (TRA) and T cell receptor beta (TRB) RNA molecules. In some embodiments, (c) comprises contacting mRNA molecules with primers, wherein the primers comprise a sequence specific to or targeted for a sequence encoding a constant region of the TRA and TRB RNA molecules.

In some embodiments, the method further comprises contacting the tagged gDNA fragments and the cDNA molecules with a plurality of primers and a polymerase to generate tagged gDNA fragment amplicons or cDNA molecule amplicons. In some embodiments, the method further comprises contacting the tagged gDNA fragments and the cDNA molecules with a plurality of primers and a polymerase to generate tagged gDNA fragment amplicons and cDNA molecule amplicons. In some embodiments, each of at least a subset of the plurality of primers comprises a sequence specific to or targeted for a sequence encoding a constant region or variable region of a T cell receptor (TCR). In some embodiments, each of at least a subset of the plurality of primers comprises a sequence specific to or targeted for a sequence encoding a constant region and variable region of a T cell receptor (TCR).

In some embodiments, the method further comprises generating amplicons from the tagged genomic DNA fragments and the cDNA molecules, wherein the amplicons each comprises a barcode sequence that identifies the immune cell. In some embodiments, the amplicons each comprising the barcode sequence that identifies the immune cell are generated from other amplicons of the tagged gDNA fragments or cDNA molecules. In some embodiments, the method further comprises sequencing the amplicons. In some embodiments, the method further comprises determining in the immune cell a correlation between accessible genomic DNA of the genomic DNA and the sequences that correspond to the V(D)J region from the genome of the immune cell.

In some embodiments, the method further comprises sequencing the tagged gDNA fragments and the cDNA molecules, or derivatives thereof.

The method of claim 1, the method further comprises, subsequent to (b), terminating the tagmentation reaction. In some embodiments, the terminating comprises using a chelating agent. In some embodiments, the tagmentation reaction comprises chelating a divalent metal ion required by a transposase complex from the transposase and releasing the transposase complex from the tagged gDNA fragments. In some embodiments, the chelating agent is selected from the group consisting of ethylenediamine tetraacetatic acid (EDTA), nitriloacetic acid (NTA), and diethylenetriamine pentaacetic acid (DTPA).

In some embodiments, the tagmentation reaction comprises using a detergent. In some embodiments, the detergent is a non-ionic surfactant. In some embodiments, the detergent is an ethoxylated nonylphenol.

In another aspect, provided is a method of processing immune cells, comprising: (a) capturing an immune cell, wherein the immune cell comprises genomic deoxyribonucleic acid (gDNA) and messenger ribonucleic acid (mRNA) molecules; (b) generating tagged gDNA fragments from accessible gDNA and complementary DNA (cDNA) from the mRNA molecules of the immune cell, wherein the cDNA molecules comprise sequences that correspond to a V(D)J region of a genome of the immune cell; and (c) mapping a correlation between the accessible genomic DNA and the sequences that correspond to the V(D)J region from one or more sequencing reads of the tagged gDNA fragments, or derivatives thereof, and of the cDNA molecules, or derivatives thereof.

In another aspect, provided is a method of processing cells, comprising: (a) capturing a cell, wherein the cell comprises genomic deoxyribonucleic acid (gDNA) and guide ribonucleic acid (gRNA) molecules, or gRNA-identifying barcodes thereof; (b) contacting accessible gDNA from the cell with a transposase to generate tagged gDNA fragments in a tagmentation reaction; and (c) generating complementary DNA (cDNA) molecules from the gRNA molecules, or the gRNA-identifying barcodes thereof.

In some embodiments, the cell is an immune cell. In some embodiments, the immune cell is a T cell. In some embodiments, the immune cell is a B cell.

In some embodiments, the capturing comprises partitioning in a partition. In some embodiments, the partition is a chamber. In some embodiments, the partition is a well. In some embodiments, the partition is a droplet.

In some embodiments, the method further comprises, prior to (b), lysing the cell.

In some embodiments, the capturing comprises isolating the cell from a plurality of cells. In some embodiments, each of the tagged gDNA fragments comprises one or more adapters.

In some embodiments, the one or more adapters comprise an adapter sequence.

In some embodiments, a barcode of the barcodes thereof identifies an identity of a gRNA molecule of the gRNA molecules. In some embodiments, the barcode is attached to the gRNA molecule.

In some embodiments, the gRNA molecules comprise a target sequence configured to target a sequence associated with a transcription factor, a chromatin modifier, or noncoding RNA. In some embodiments, the gRNA molecules comprise a plurality of different target sequences. In some embodiments, a first gRNA molecule of the gRNA molecules comprises a first target sequence of the plurality of different target sequences, and wherein a second gRNA molecule of the gRNA molecules comprises a second target sequence of the plurality of different target sequences, wherein the first target sequence and the second target sequence are different.

In some embodiments, the method further comprises, prior to (a), introducing the gRNA molecules to the cell.

In some embodiments, (c) comprises contacting the gRNA molecules, or barcodes thereof, from the cell with primers and a reverse transcriptase. In some embodiments, the primers comprise a reverse primer comprising a sequence specific to or targeted for a 3' end of the gRNA molecule. In some embodiments, the method further comprises contacting the gRNA molecule with another set of primers comprising a forward primer comprising a sequence specific to or targeted for a 5' variable end of the gRNA molecule.

In some embodiments, the method further comprises contacting the tagged gDNA fragments and the cDNA molecules with a plurality of primers and a polymerase to generate tagged gDNA fragment amplicons or cDNA molecule amplicons. In some embodiments, the method further comprises contacting the tagged gDNA fragments and the cDNA molecules with a plurality of primers and a polymerase to generate tagged gDNA fragment amplicons and cDNA molecule amplicons.

In some embodiments, the method further comprises generating amplicons from the tagged genomic DNA fragments and the cDNA molecules, wherein the amplicons each comprises a barcode sequence that identifies the cell. In some embodiments, the amplicons each comprising the barcode sequence that identifies the cell are generated from other amplicons of the tagged gDNA fragments or cDNA molecules. In some embodiments, the method further comprises sequencing the amplicons.

In some embodiments, the method further comprises determining in the cell a correlation between an accessibility of the genomic DNA in response to a perturbation by a gRNA molecule of the gRNA molecules.

In some embodiments, the method further comprises sequencing the tagged gDNA fragments and the cDNA molecules, or derivatives thereof.

In some embodiments, the method further comprises, subsequent to (b), terminating the tagmentation reaction. In some embodiments, the terminating comprises using a chelating agent. In some embodiments, the tagmentation reaction comprises chelating a divalent metal ion required by a transposase complex from the transposase and releasing the transposase complex from the tagged gDNA fragments. In some embodiments, the chelating agent is selected from the group consisting of ethylenediamine tetraacetatic acid (EDTA), nitriloacetic acid (NTA), and diethylenetriamine pentaacetic acid (DTPA).

In some embodiments, the tagmentation reaction comprises using a detergent. In some embodiments, the detergent is a non-ionic surfactant. In some embodiments, the detergent is an ethoxylated nonylphenol.

Another aspect of the present disclosure provides systems, methods, and compositions for barcoding, processing, and analysis of nucleic acid molecules from cells.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 14 shows plots of Pearson correlation of PC scores of ensemble ATAC-seq profiles.

FIG. 41 shows a heat map of TF deviation z-scores for ensemble T cell ATAC-seq profiles.

FIG. 54 shows an overview of classes of biological questions that can be interrogated from Perturb-ATAC data.

FIG. 122 shows bar plots indicating categories of sgRNA mismatch loci based on ATAC peak proximity and observed accessibility compared to non-targeting cells.

FIG. 123 shows tSNE plots of all cells assayed in GM12878 experiment based on chromVAR feature deviation z scores.

FIG. 124 shows violin plots of single cell accessibility relative to mean accessibility in non-targeting cells for significantly altered features in either EBER1, EBF1, EZH2, or SPI1 targeted cells.

FIG. 125 shows scatter plots of accessibility in knockdown conditions, NFKB1 versus RELA (left) or EBER1 versus EBER1 (right).

FIG. 126 shows volcano plots for each single perturbation condition comparing perturbed cells to non-targeting control cells.

FIG. 127 shows a schematic depicting generation of short (<100 bp) ATAC fragments from sub-nucleosome regions and large fragments (180-247 bp) spanning nucleosome-protected regions.

FIG. 128 shows metaplots of sub-nucleosome and nucleosome fragment signal at CTCF motif regions overlapping with CTCF ChIP seq peaks in GM12878.

FIG. 129 shows metaplots of sub-nucleosome and nucleosome signal at differentially accessible regions.

FIG. 130 shows a heatmap of correlation matrices for genomic features.

FIG. 131 shows a listing of key features in each module.

FIG. 132 shows a heatmap of correlation matrix for genomic features in IRF8 knockdown cells.

FIG. 133 shows box plots of single cell accessibility for CTCF and SMAD5 features in non-targeting and DNMT3A knockdown cells.

Figure 134:
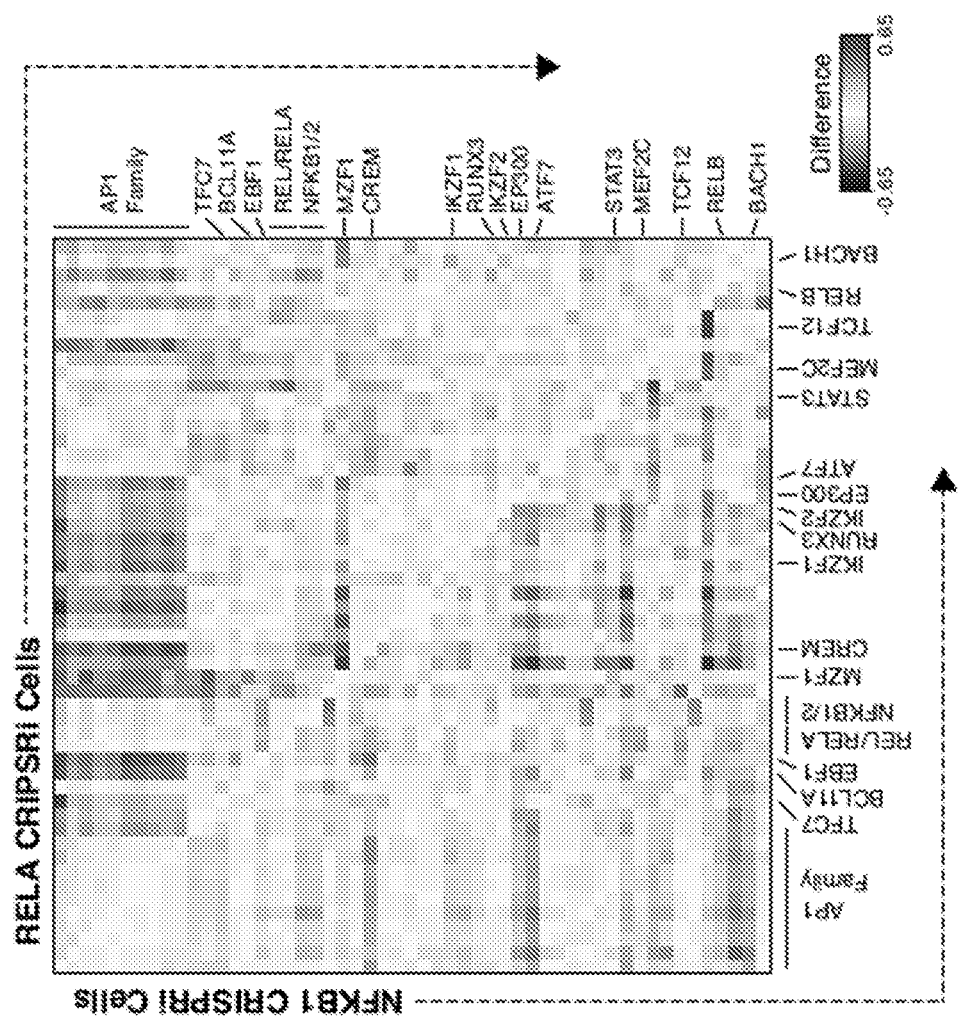

FIG. 134 shows a heatmap of difference in feature correlations between NFKB1 knockdown cells (bottom) and RELA knockdown cells (top).

Figure 135:
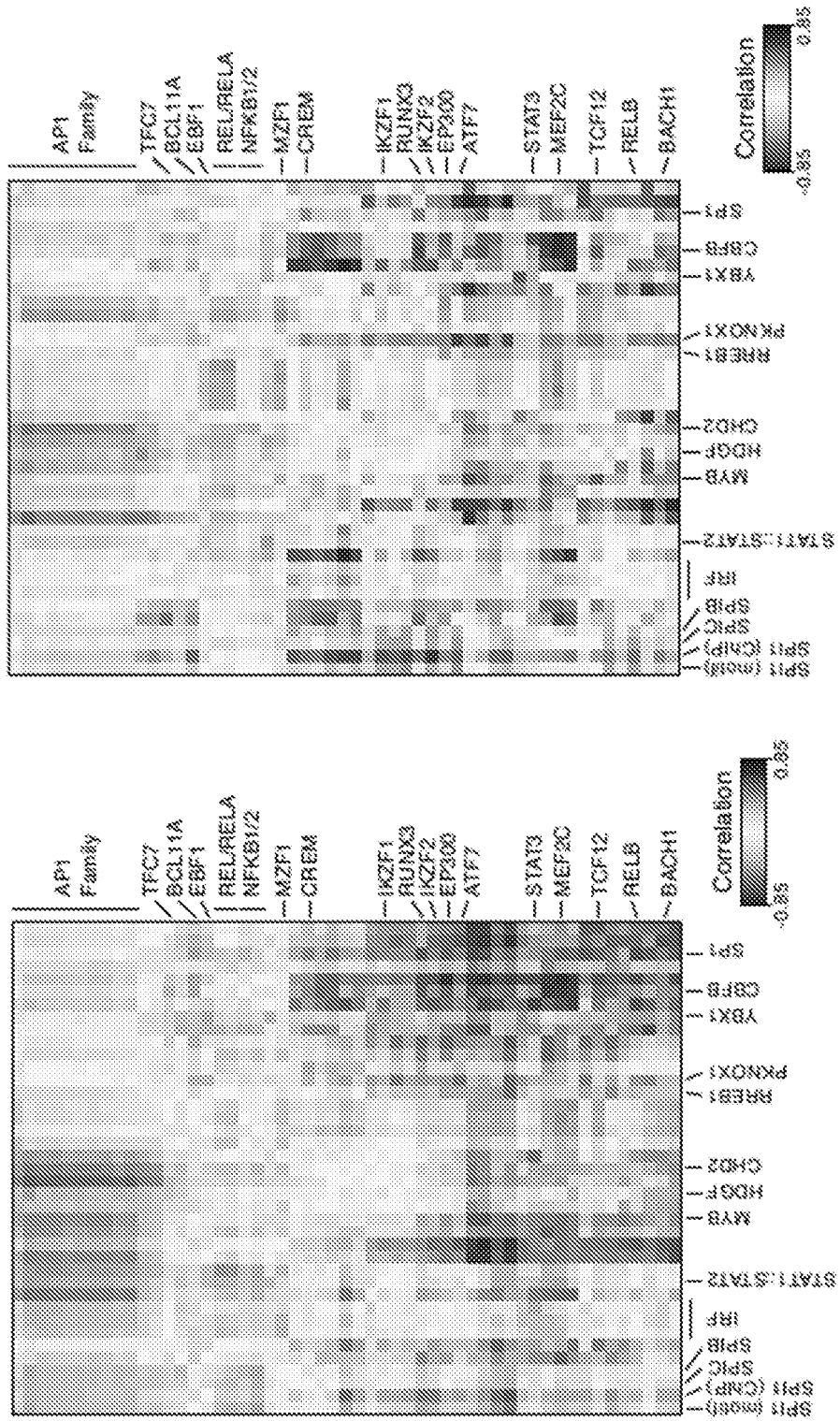

FIG. 135 shows heatmaps of feature correlations for Module 1 vs. Module 5 in non-targeting cells or EBER2 knockdown cells.

Figure 136:
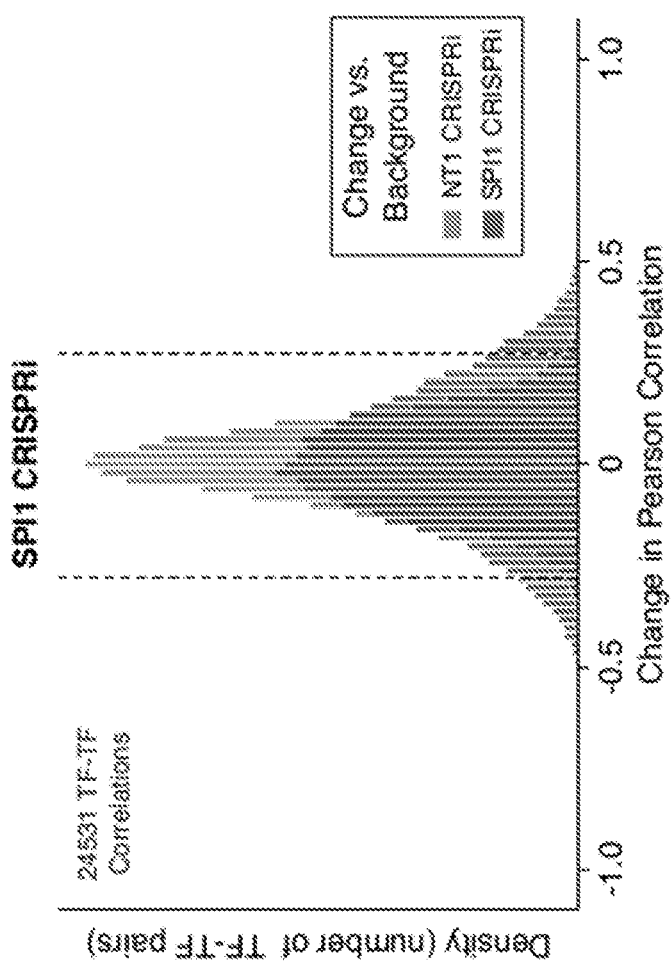

FIG. 136 shows a histogram of change in feature correlations for SPI1 knockdown versus non-targeting 1 cells, used to inform thresholds for designation of altered correlation.

Figure 138:
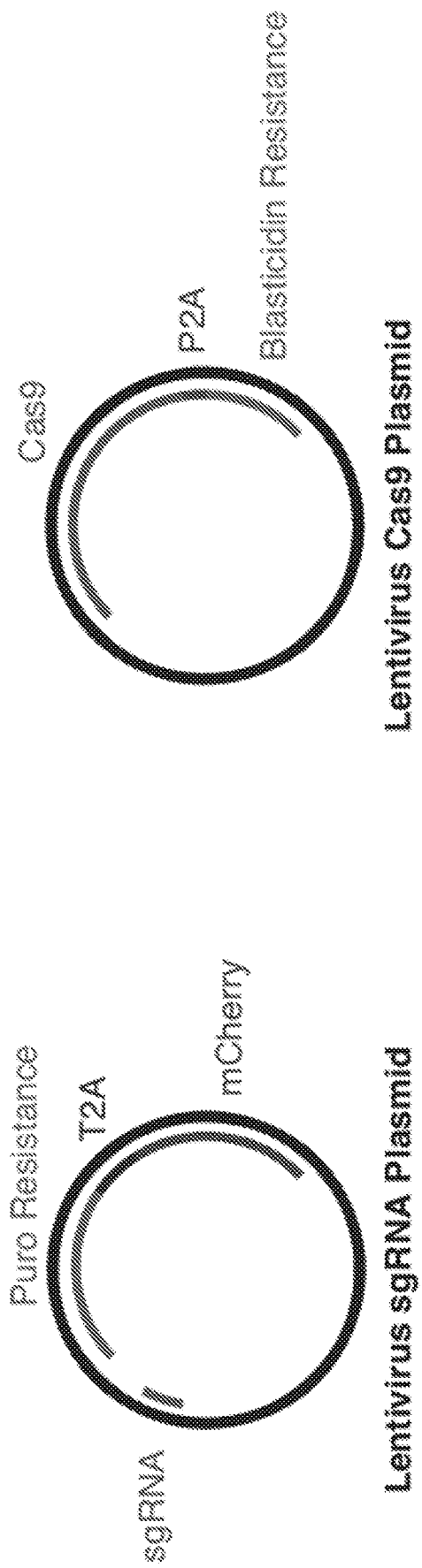

FIG. 137 shows a table of counts and highlighted top altered-correlation features based on 5% FDR threshold FIG. 138 shows a schematic of lentiviral plasmids for sgRNA and Cas9 expression.

Figure 139:
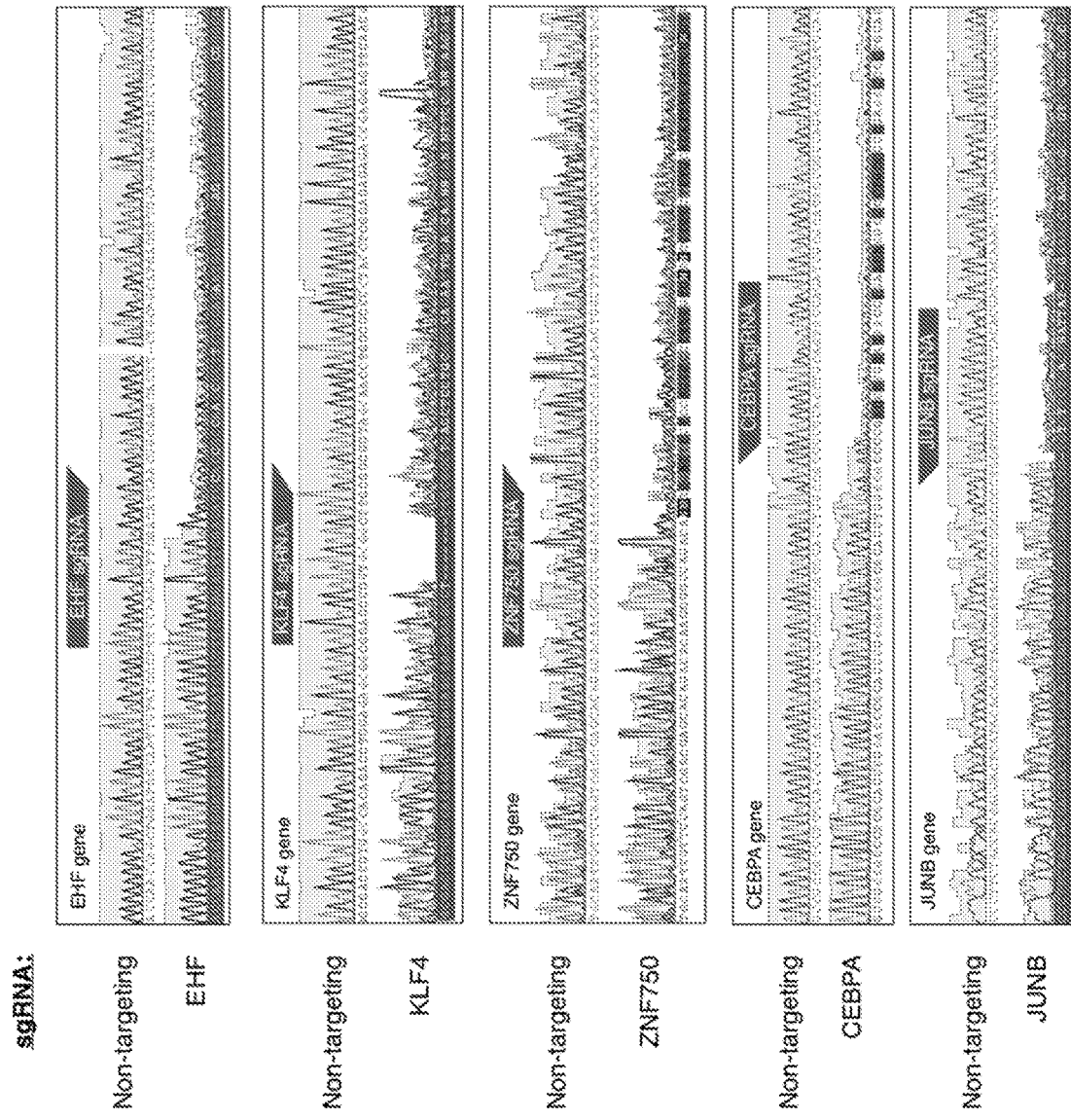

FIG. 139 shows Sanger sequencing traces of the 100 bp surrounding sgRNA 3' end for each target gene. Figure discloses SEQ ID NOS 8-17, respectively, in order of appearance.

Figure 140:
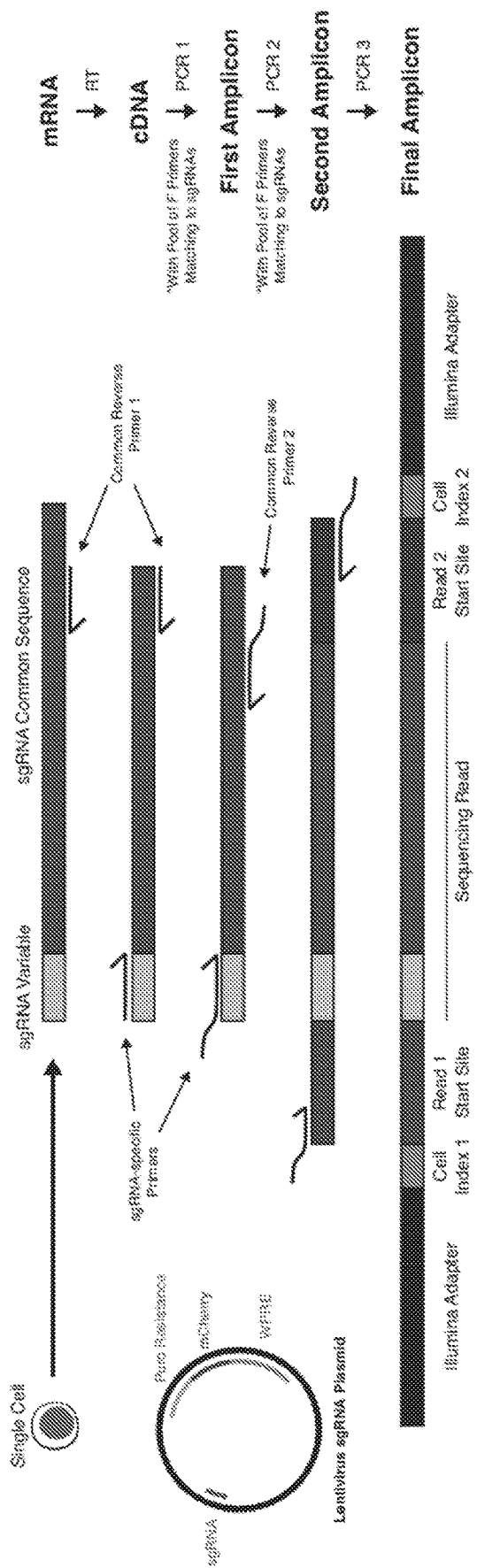

FIG. 140 shows a schematic of lentiviral plasmid encoding sgRNA for CRISPR knockout.

Figure 141:
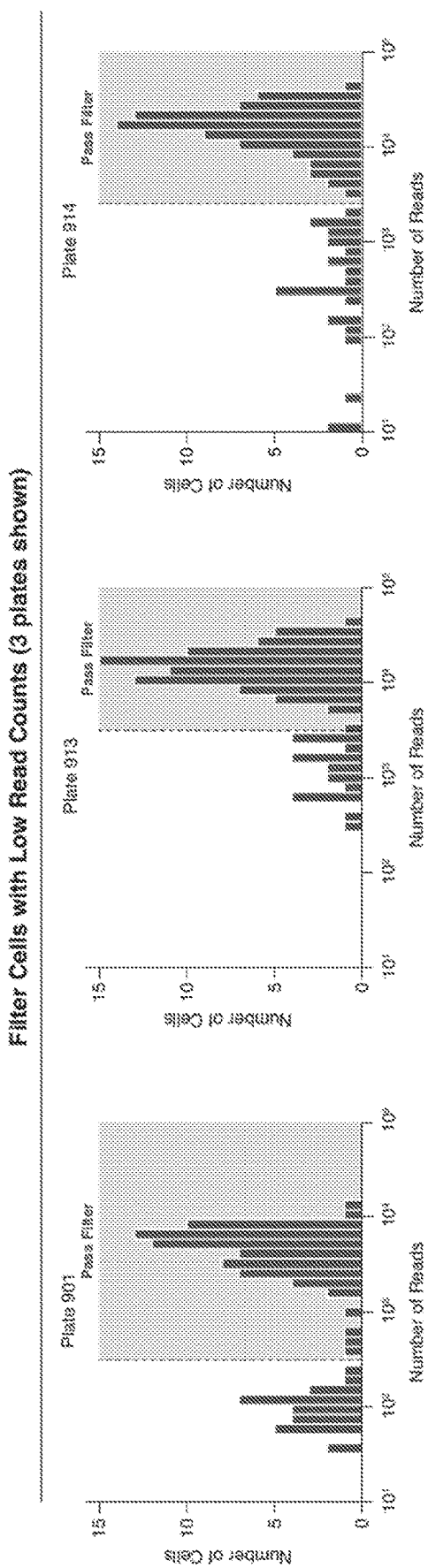

FIG. 141 shows the distributions of reads per cell mapping to a sgRNA variable sequence. For each plate, a clear high mode of reads was identified and used to determine a depth cutoff.

Figure 142:
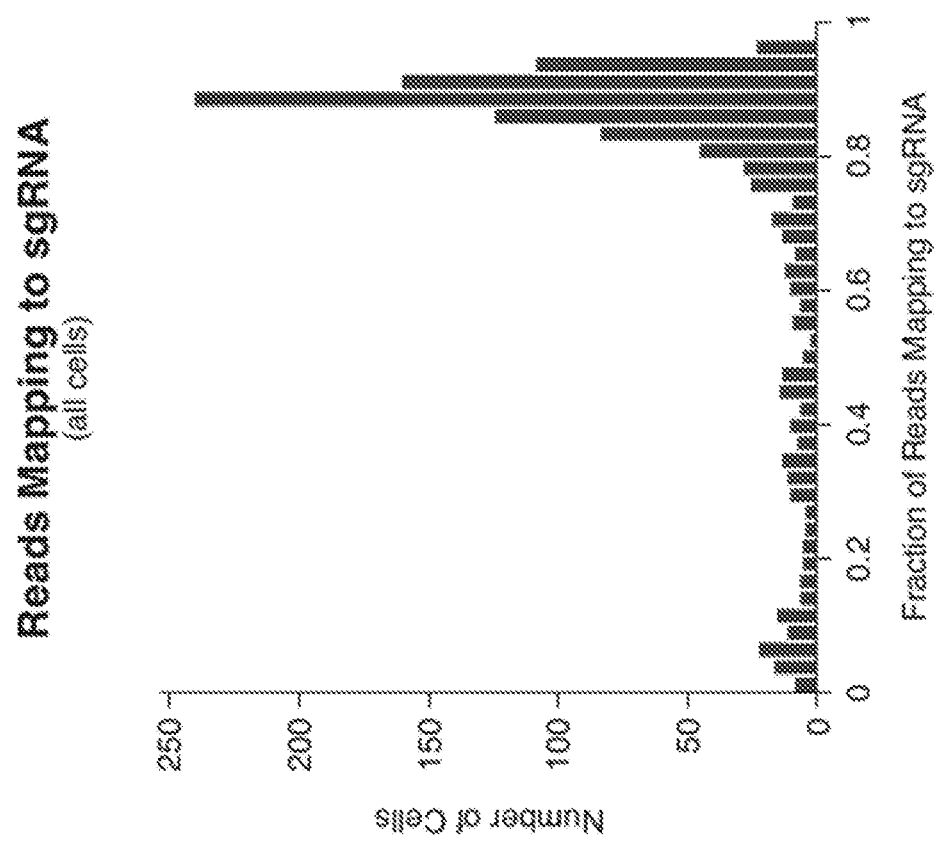
Figure 143:
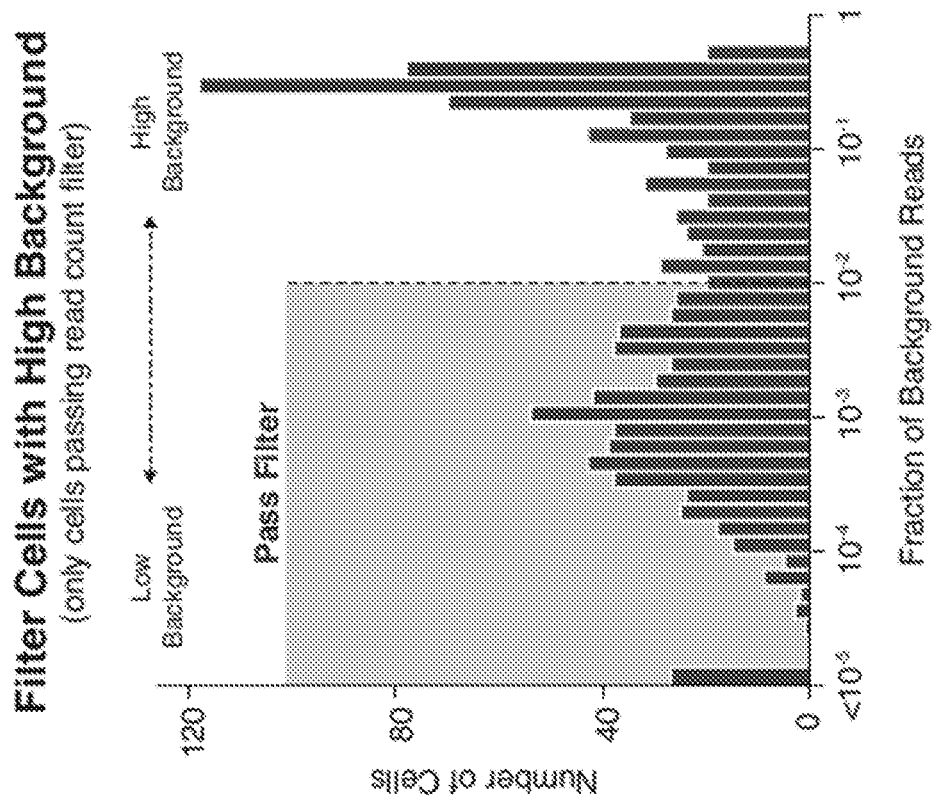

FIG. 142 shows the distribution of proportion of all reads per cell mapping to known sgRNA sequence FIG. 143 shows the distribution of proportion of reads per cell associated with background (third most common) guide sequence.

Figure 144:
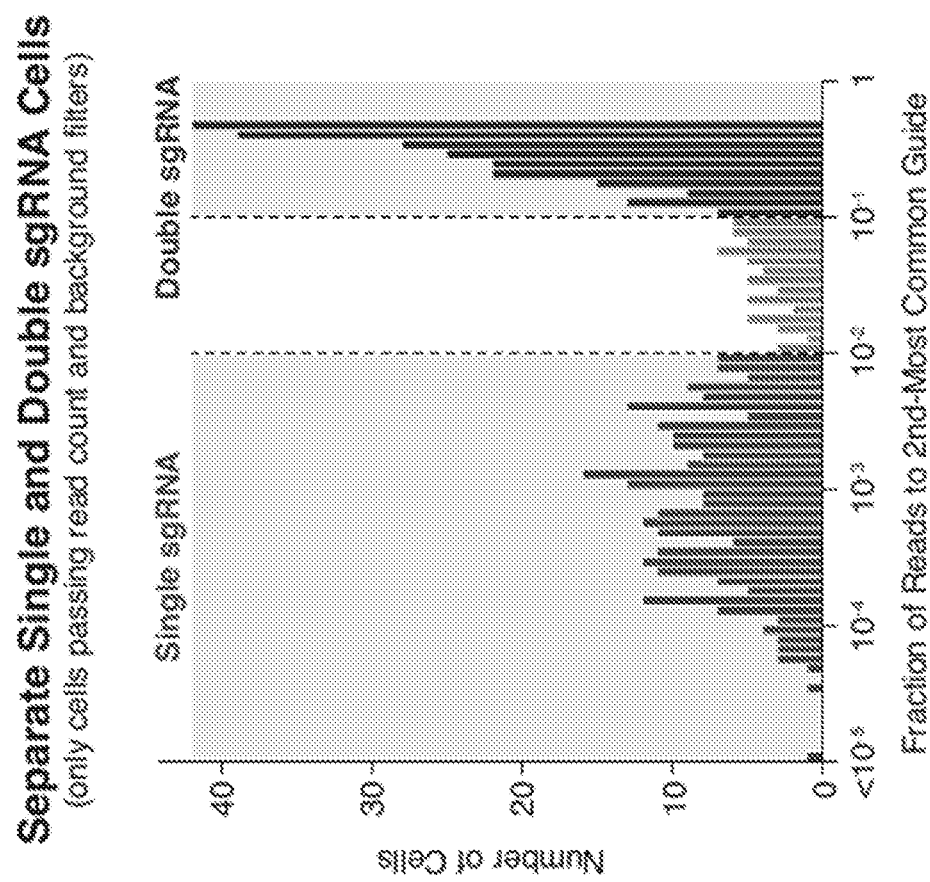

FIG. 144 shows the distribution of proportion of reads associated with second most common guide.

Figure 145:
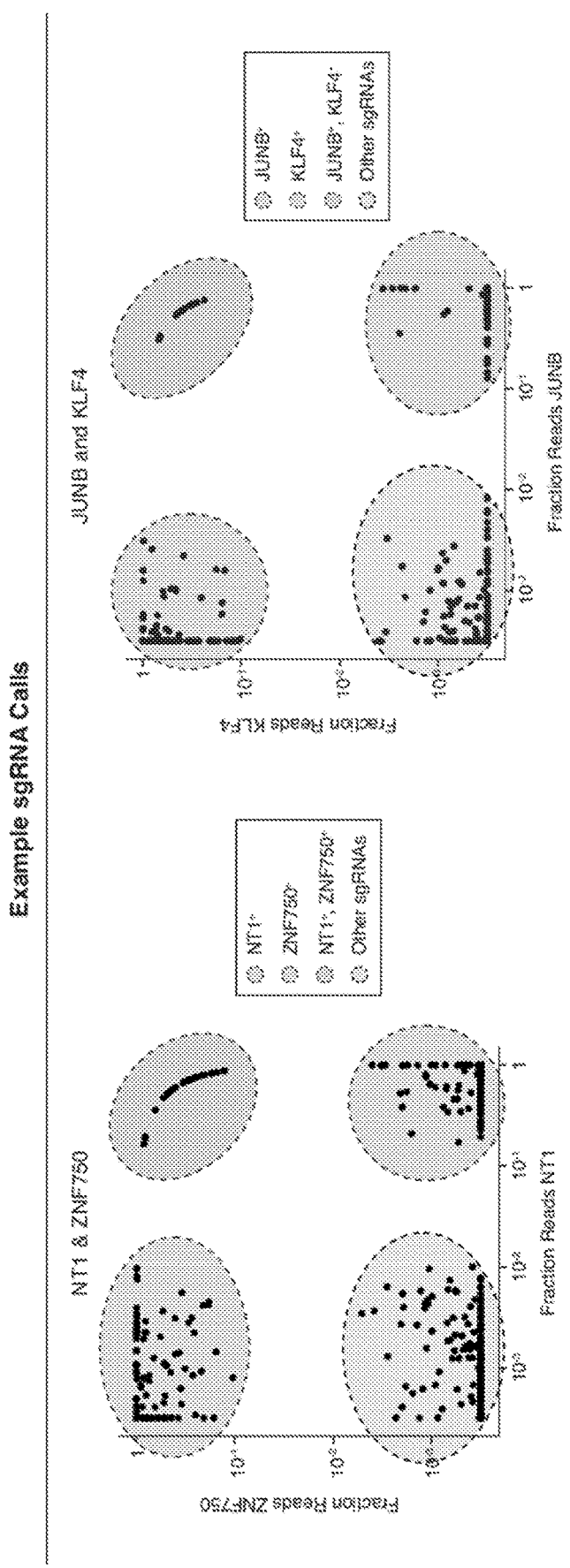

FIG. 145 shows scatter plots of proportion of reads associated with two guide sequences for all cells passing final filters.

Figure 146:
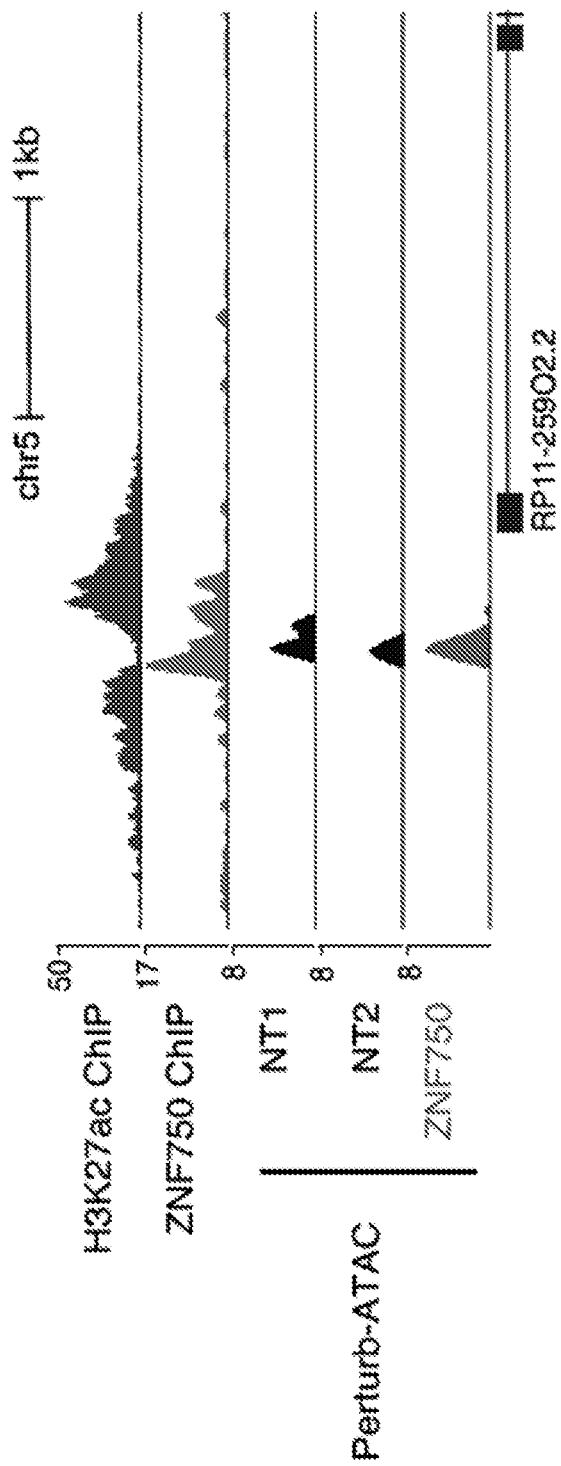

FIG. 146 shows a signal track indicating a ZNF750 binding site that gains accessibility in targeted cells, indicating repressive activity of ZNF750.

Figure 147:
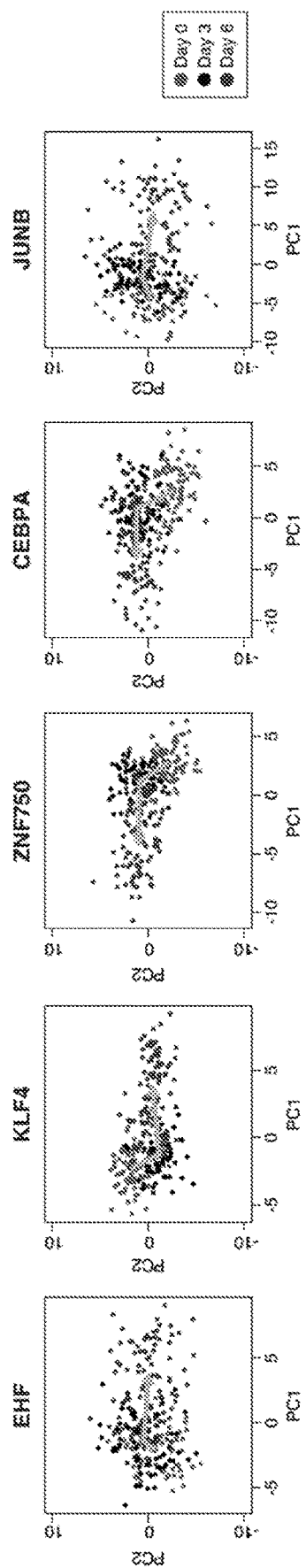

FIG. 147 shows a scatter plot of principal component (PC) values for unperturbed keratinocytes.

Figure 148:
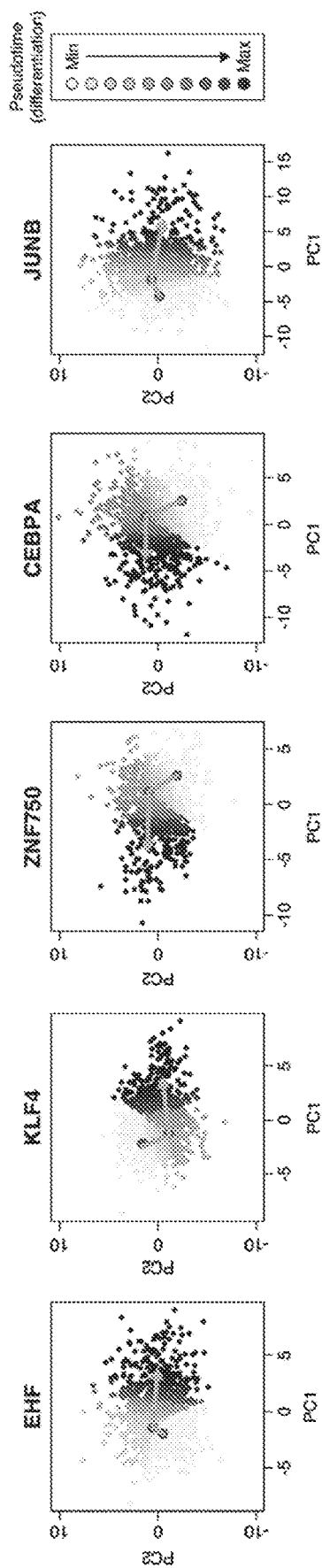
Figure 149:
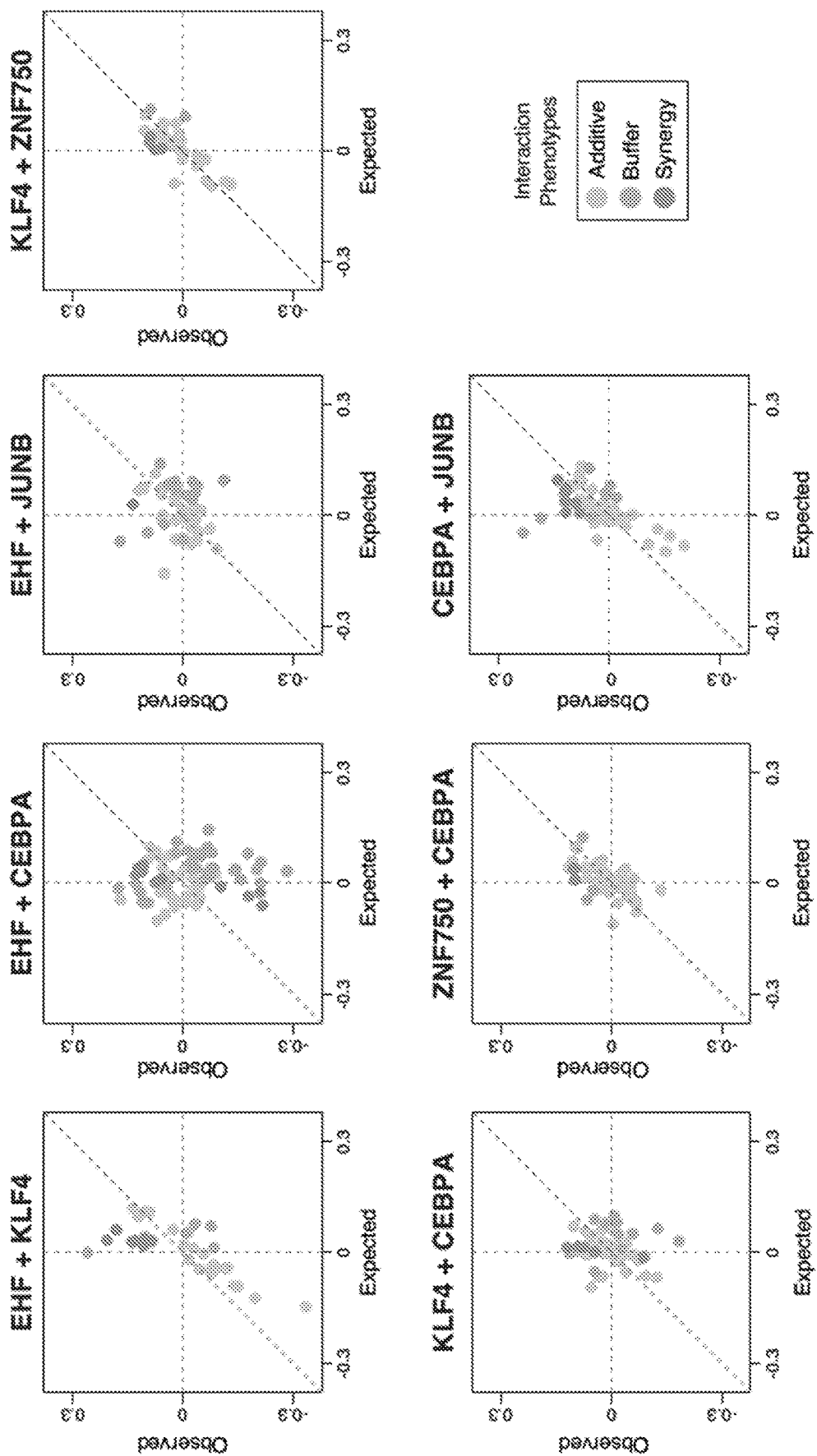

FIG. 148 shows a scatter plot of 1397 PC values for all perturbed and non-targeting cells embedded in PC space FIG. 149 shows scatter plots of observed versus expected (based on additive model) accessibility in double knockout cells.

Figure 150:
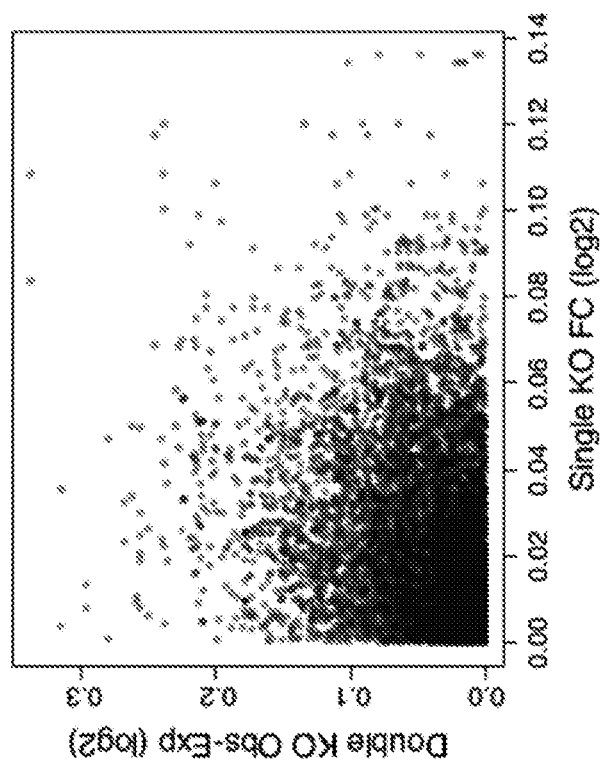

FIG. 150 shows a scatter plot of absolute log 2 fold changes of features in single knockout cells versus double knockouts (r~0.18).

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated. The terms "about" or "approximately," as used herein, mean within an acceptable error range for the particular value as determined by those skilled in the art, which will depend in part on how the value is measured or determined, i.e., the limitations of the measurement system. For example, "about" can mean within 1 or more than 1 standard deviation, per the practice in the relevant field. Alternatively, "about" can mean a range of up to 20%, up to 10%, up to 5%, or up to 1% of a given value.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N. Y. (1991) provide one of skill with the general meaning of many of the terms used herein. Still, certain terms are defined below for the sake of clarity and ease of reference.

The term "sample," as used herein, generally refers to a biological sample of a subject. The biological sample may comprise any number of macromolecules, for example, cellular macromolecules. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "nucleic acid sample," as used herein, generally refers to a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acid, e.g., genomic DNA from tissue culture cells or a sample of tissue, may be employed herein.

The term "mixture," as used herein, generally refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide," as used herein, generally includes those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "nucleic acid," "oligonucleotide," and "polynucleotide," as used interchangeably herein, generally refers to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "primer," as used herein, generally refers to an oligonucleotide molecule, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process may be determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis. A primer be sequence-specific and may hybridize to a unique sequence in messenger RNA (mRNA) or a target RNA.

The terms "hybridization" or "hybridizes," as used herein, generally refer to a process in which a region of nucleic acid strand anneals to and forms a stable duplex, either a homo-duplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A "selectively hybridizable" nucleic acid, as used herein, generally refers to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, generally refers to two complementary polynucleotide regions that are base-paired, i.e., hybridized together.

The terms "amplifying," or "amplification," as used herein, generally refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein.

The terms "determining," "measuring," "evaluating," "assessing," "assaying," and "analyzing," are used interchangeably herein to generally refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" as used herein, generally refers to its conventional meaning, and, as such, may mean employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "ligating," as used herein, generally refers to the enzymatically catalyzed joining of the terminal nucleotide at the 5' end of a first DNA molecule to the terminal nucleotide at the 3' end of a second DNA molecule.

A "plurality," as used herein, generally refers to containing at least 2 members. In certain cases, a plurality may have at least 2, at least 5, at least 10, at least 100, at least 100, at least 10,000, at least 100,000, at least 106, at least 107, at least 108 or at least 109 or more members.

If two nucleic acids are "complementary," generally, they can hybridize with one another under high stringency conditions. The term "perfectly complementary" is generally used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site," as used herein, generally refers to a site to which an oligonucleotide hybridizes in a target polynucleotide. If an oligonucleotide "provides" a binding site for a primer, then the primer may hybridize to that oligonucleotide or its complement.

The term "strand," as used herein, generally refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, generally refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "sequencing," as used herein, generally refers to a method by which the identity of consecutive nucleotides (e.g., the identity of at least 10, of at least 20, at least 50, at least 100 or at least 200 or more consecutive nucleotides) of a polynucleotide is obtained.

The terms "next-generation sequencing" or "high-throughput sequencing," as used herein, generally refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences.

The term "barcode," "barcode sequence," or "molecular barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "in vitro," as used herein, generally refers to a reaction that occurs in a vessel with isolated components, not in cells.

The term "distributed," as used herein, in the context of cleavage sites that are distributed along the length of a target nucleic acid molecule, generally refers to insertions that are spaced from another along the length of the target nucleic acid molecule. There is no requirement that all of the insertions are spaced by the same amount. Rather, spacing between insertions may be random, semi-random, or not random.

The term "chromatin," as used herein, generally refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

The term "treating," as used herein, generally refers to combining under conditions (e.g., a suitable temperature, time and conditions) that result in a reaction, e.g., cleavage.

The term "chromatin isolated from a population of cells," as used herein, generally refers to a source of chromatin that is caused to be made available. Isolated nuclei (which can be lysed to produce chromatin) as well as isolated chromatin (i.e., the product of lysed nuclei) are both considered types of chromatin isolated from a population of cells.

The term "transcription factor," as used herein, generally refers to any polypeptide that may act by itself or in combination with at least one other polypeptide to regulate gene expression levels. The term includes, but is not limited to, polypeptides that directly bind DNA sequences. Transcription factors can either increases or suppress expression levels. Examples of transcription factors include, but are not limited to Myc/Max, AP-1 (Jun, Fos, ATF), CREB, SMAD, HIF, ETS, ERG, ELK, STAT, estrogen receptor (ER), androgen receptor (AR), glucocorticoid receptor (GR), progesterone receptor (PR), NFκB, p53, OCT, SOX and PAX. The transcription factor may be a transcription factor identified by sequence analysis or a naturally-occurring reading frame sequence that has not been previously characterized as a transcription factor. The polypeptide may also be an artificially generated or chemically or enzymatically modified polypeptide.

The term "insertional enzyme complex," as used herein, generally refers to a complex comprising an insertional enzyme and two adaptor molecules (the "transposon tags") that are combined with polynucleotides to fragment and add adaptors to the polynucleotides. Such a system is described in a variety of publications, including Caruccio (Methods Mol. Biol. 2011 733:241-55) and US20100120098, which are incorporated by reference herein.

The term "tagged fragments," as used herein, generally refers to polynucleotide fragments that are attached to tags.

The term "region," as used herein, generally refers to a contiguous length of nucleotides in a genome of an organism. A chromosomal region may be in the range of 1 bp to the length of an entire chromosome. In some instances, a region may have a length of at least 200 bp, at least 500 bp, at least 1 kb, at least 10 kb or at least 100 kb or more (e.g., up to 1 Mb or 10 Mb or more). The genome may be from any eukaryotic organism, e.g., an animal or plant genome such as the genome of a human, monkey, rat, fish or insect.

Figure 7A:
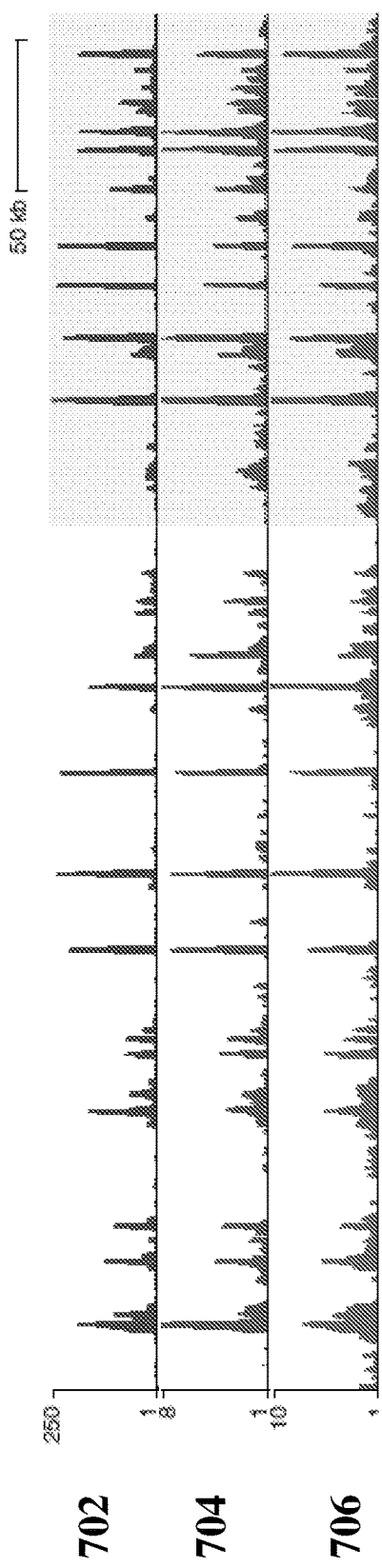
FIG. 7A show plots generated from T-ATAC-seq, identifying epigenomic signatures.

The term "epigenetic map," as used herein, generally refers to any representation of epigenetic features, e.g., sites of nucleosomes, nucleosome-free regions, binding sites for transcription factors, etc. A map can be physically displayed, e.g., on a computer monitor. Exemplary epigenetic maps are shown in FIG. 7A. 9, 13, 20, among others.

The term "mapping information," as used herein, generally refers to assembling experimentally-obtained information about an area to a physical map of the area.

The term "sequence read abundance," as used herein, generally refers to the number of times a particular sequence or nucleotide is observed in a collection of sequence reads.

The term "nucleosome-free fragments," as used herein, generally refers to fragments of genomic DNA that are relatively depleted or devoid of nucleosomes, i.e., between nucleosomes.

The term "chromatin accessibility," as used herein, generally refers to how accessible a nucleic acid site is within a polynucleotide, such as in genomic DNA, i.e., how "open" the chromatin is. A nucleic acid site associated with a polypeptide, such as with genomic DNA in nucleosomes, is usually inaccessible. A nucleic acid site not complexed with a polypeptide is generally accessible, such as with genomic DNA between nucleosomes (with the exception of nucleic acid sites complexed with transcription factors and other DNA binding proteins).

The term "DNA binding protein occupancy," as used herein, generally refers to whether a binding site for a sequence specific DNA binding protein (e.g., a binding site for a transcription factor) is occupied by the DNA binding protein. DNA binding protein occupancy can be measured quantitatively or qualitatively.

The term "global occupancy," as used herein, generally refers to whether a plurality of different binding sites for a DNA binding protein that are distributed throughout the genome (e.g., a binding sites for a transcription factor) are bound by the DNA binding protein. DNA binding protein occupancy can be measured quantitatively or qualitatively.

The term "diagnosis," as used herein, generally refers to a determination of whether a subject has a particular disease or condition.

The term "prognosis," as used herein, generally refers to prediction of a clinical outcome, e.g., disease recurrence, recovery from a disease, death, as well as a prediction of how a subject that has a particular disease or condition will respond to a particular treatment.

The term "cDNA copy," as used herein, generally refers to a DNA molecule that has the reverse complement of an RNA molecule (i.e., first strand cDNA) or a DNA molecule that has the same sequence as an RNA molecule except that the Us are T's (i.e., second strand cDNA).

The term "real time," as used herein, can generally refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)," "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single-stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be a sol-gel. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), short hairpin RNA (shRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity or selectivity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

The term "analyte," as used herein, generally refers to a substance or one or more constituents thereof that is capable of identification, such as by detection (e.g., detection via sequencing). Examples of analytes include, without limitation, DNA, RNA, synthetic oligonucleotides, the labelling agents described herein, antibodies, and proteins. An analyte may be a cell or one or more constituents of a cell.

Analytes may be of different types. In some examples, in a plurality of analytes, a given analyte is of a different structural or functional class from other analytes of the plurality. Examples of different types of analytes include DNA and RNA; a nucleic acid molecule and a labelling agent; a transcript and genomic nucleic acid; a plurality of nucleic acid molecules, where each nucleic acid molecule has a different function, such as a different cellular function. A sample may have a plurality of analytes of different types, such as a mixture of DNA and RNA molecules, or a mixture of nucleic acid molecules and labelling agents.

The term "epitope binding fragment" or "antibody fragment," as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')2 fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

Provided are systems and methods that can combine T cell receptor sequencing (TCR-seq) and Assay for Transposase Accessible Chromatin using sequencing (ATAC-seq), and/or respective aspects thereof. Such methods may generally be referred to herein as Transcript-indexed Assay for Transposase Accessible Chromatin using Sequencing (T-ATAC-Seq). Further provided are systems and methods that can combine ATAC-seq and perturbation sequencing (Perturb-seq), and/or respective aspects thereof. Such methods may generally be referred to herein as Perturbation-indexed Assay for Transposase Accessible Chromatin using Sequencing (Perturb-ATAC-Seq).

The methods described herein may compartmentalize (e.g., partition) the analysis of individual cells or small populations of cells, including analytes of individual cells or small groups of cells, and then allow that analysis to be attributed back to the individual cell or small group of cells from which the analytes were derived. Unique identifiers, e.g., barcodes (e.g., carrying barcode sequences), may be previously, subsequently, or concurrently delivered to the partitions that hold the compartmentalized or partitioned cells, in order to allow for the later attribution of the characteristics of the individual cells to the particular compartment. Further, unique identifiers, e.g., barcodes, may be coupled or attached to the analytes and previously, subsequently, or concurrently delivered to the partitions that hold the compartmentalized or partitioned cells, in order to allow for the later attribution of the characteristics of the individual cells to the particular compartment. Barcodes may be delivered, for example on an oligonucleotide, to a partition via any suitable mechanism (e.g., attached to a gel bead as described elsewhere herein, in solution, etc.). In some aspects, the unique identifiers are provided in the form of oligonucleotides that comprise nucleic acid barcode sequences that may be attached to or otherwise associated with the nucleic acid contents of individual cells, or to other components of the cells, and particularly to fragments of those nucleic acids.

Transcript-Indexed Assay for Transposase Accessible Chromatin Using Sequencing (T-ATAC-Seg)

Chromatin accessibility may be assessed in conjunction with other protein-encoding genes. In some cases, the assessment may comprise sequencing of polynucleotides and/or other nucleic acid molecules. Provided herein are systems and methods for processing and profiling immune cells, such as T lymphocytes, by sequencing cell receptor-encoding genes together with transposase accessible chromatin. The methods described herein may combine T cell receptor sequencing (TCR-seq) and Assay for Transposase Accessible Chromatin using sequencing (ATAC-seq), and/or respective aspects thereof. Such methods may generally be referred to herein as Transcript-indexed Assay for Transposase Accessible Chromatin using Sequencing (T-ATAC-Seq). Systems and methods relating to T-ATAC-Seq are described in Ansuman T. Satpathy et al., *Transcript-indexed ATAC-seq for precision immune profiling*, 24 Nature Medicine 580-90 (2018), which is entirely incorporated herein by reference.

Analytes of particular interest are immune cells. In particular, conventional analytical techniques, such as some ensemble sequencing processes, may not yield information on how epigenomic landscapes in clonal T cells can phenotypically result in T cell malignancy, immunity, and/or effectiveness in immunotherapy. Beneficially, the epigenetic landscape (e.g., epigenomic state of individual T cells) and T cell specificity may be analyzed simultaneously at the single-cell level. Beneficially, such analysis may facilitate discovery of antigens that drive a certain T cell fate, and/or cis and trans regulators that drive the expansion of a T cell clone. For example, the methods described herein may enable the identification of cancer-clone-specific epigenomic signatures, which was otherwise not apparent from some ensemble measurements.

In some cases, T-ATAC-seq comprises systems and methods to amplify and sequence the TRA and TRB loci, which may encode the TCR-alpha and TCR-beta chains, respectively, of single cells. T-ATAC-seq may also comprise measurements of epigenetic changes genome wide e.g., ATAC-seq or scATAC-seq, which enables measurement of regulatory DNA elements by direct transposition of sequencing adaptors into regions of accessible chromatin. In some cases, scATAC-seq identifies cell-to-cell variation in cis and trans regulator elements and factors that influence epigenetic cell states. ATAC-seq may also provide insight into epigenetic regulation, e.g., through identification of enhancer and promoter sequences with basepair resolution, positioning of nucleosomes, accessibility of cis-regulatory DNA elements, and the interference of transcription factors bound to each site through DNA foot-printing of transposase-inaccessible regions. Beneficially, a correlation between accessible genomic DNA and sequences that correspond to V(D)J regions of the genome of the immune cells may be determined. Such correlations may be mapped based on sequencing reads associated with the accessible genomic DNA and sequencing reads associated with the sequences corresponding to V(D)J regions of the genome.

Provided herein is a method of processing immune cells. The method can comprise capturing an immune cell, wherein the immune cell comprises genomic deoxyribonucleic acid (gDNA) and messenger ribonucleic acid (mRNA) molecules, contacting gDNA from the immune cell with a transposase to generate tagged gDNA fragments in a tagmentation reaction, and generating complementary DNA (cDNA) molecules from the mRNA molecules, wherein the cDNA molecules comprise sequences that correspond to a V (D) J region of a genome of the immune cell.

Non-limiting examples of immune cells which can be analyzed utilizing the methods described herein include B cells, T cells (e.g., cytotoxic T cells, natural killer T cells, regulatory T cells, and T helper cells, etc.), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cell, thrombocytes/megakaryocytes, and dendritic cells.

In some instances, individual T cells are analyzed using the methods disclosed herein. In some instances, individual B cells are analyzed using the methods disclosed herein. While some methods described herein describe the processing of T cells, with reference to T-ATAC-Seq, it will be appreciated that the methods may be applicable to, and/or adapted for, other types of immune cells, such as B cells. For example, as sequences encoding T cell receptors (TCRs) can be sequenced together with transposase accessible chromatin for processing T cells, sequences encoding B cell receptors (BCRs) may be sequenced together with transposase accessible chromatin for processing B cells.

In some instances, the immune cell may be isolated and/or captured from a plurality of immune cells. In some instances, the immune cell may be one of a subset of immune cells isolated and/or captured from the plurality of immune cells. The isolation and/or capturing can be in one or more stages. For example, in a stage, a plurality of immune cells may be sorted for types of immune cells. For example, T cells may be sorted from the immune cells. In another example, B cells may be sorted from the immune cells. A subset comprising T cells and a subset comprising B cells may be isolated from the same population of immune cells. In some instances, in a next stage, upon isolating by cell type, in a further isolation operation, cell subtypes may be isolated. For example, a subset of T cells comprising one or more TCRs may be isolated and/or captured from a plurality of T cells. Alternatively, a subset of T cells may be isolated and/or captured from a plurality of immune cells.

In some instances, the isolation can comprise magnetic cell sorting. In some instances, the isolation can comprise flow cytometry sorting. In some cases, the cell sample may be sorted based on the molecular tags (e.g. fluorescence tags). For example, cells may be sorted, isolated, and/or captured by magnetic-activated cell sorting (MACS) or fluorescence activated cell sorting (FACS) from a heterogeneous population of cells, e.g., blood, by known methods using labeled antibodies to cell surface markers. For example, using FACS or MACS, T cells and/or B cells can be isolated from a cell sample. Subsets of these cells can be isolated using antibodies for cell surface markers.

The capturing of the immune cell may comprise partitioning the immune cell in a partition. A partition may be any partition described elsewhere herein, such as a chamber, well, microwell, or droplet. The partition may contain the immune cell within a set of defined boundaries (closed or partially closed), and/or distinguish a space or volume inside the partition from other partitions or any space or volume external to the partition. In some instances, the partition may prevent its contents from escaping the partition under one or more conditions. In some instances, the partition may prevent external objects from entering the partition under one or more conditions. The partition may be an individual partition, such as an individual well or individual chamber or individual droplet. The partition may be one of a plurality of partitions, such as in an integral device, such as a fluidic chip.

Methods for ATAC-seq can generally be performed on the partitioned immune cell, such as according to one or more methods and systems outlined in U.S. Patent Pub. No. 2016/0060691 and PCT Patent Pub. No. WO 2018/218226A1 (hereinafter "Belhocine"), each of which is entirely incorporated herein by reference. Such methods may comprise fragmenting a polynucleotide (e.g., gDNA) into a plurality of fragments during the insertion of molecular tags. The polynucleotide can be bound to a plurality of association molecules. The association molecules can be, for example, proteins, nucleic acids or saccharides. In some cases, the association molecules can comprise histones. In other cases, the association molecules can comprise aptamers. In some cases, the fragments may be amplified and sequenced to generate sequencing reads. Such reads may be used to determine the accessibility of the polynucleotide at any given site. The fragments may be sequenced using a high-throughput sequencing technique, as described elsewhere herein. In some cases, the sequencing reads can be normalized based on the sequence insertion preference of the insertional enzyme. The length of the sequenced reads can be used to determine a chromatin state annotation. In some cases, ATAC-seq may further identify one or more proteins, such as a transcription factor, that are bound to the polynucleotide at the site. In some instances, the molecular tags can be used to generate an accessibility map of the polynucleotide.

In the partition, the immune cell can be subject to lysing conditions prior to fragmentation of the gDNA. The lysing conditions may lyse the immune cell and release the chromatin while maintaining chromatin organization, and fragment the released chromatin. Alternatively, cells (or nuclei) may be permeabilized or be permeable such as to allow transposase-nucleic acid complexes to enter the nucleus to generate nucleic acid fragments, and subsequently lysed to release the fragments into the partition. The permeabilization can be performed in a way to minimally perturb the nuclei in the cell sample. In some instances, the cell sample can be permeabilized using a permeabilization agent. Examples of permeabilization agents include, but are not limited to, NP40, digitonin, tween, streptolysin, and cationic lipids. In other instances, the cell sample can be permeabilized using hypotonic shock and/or ultrasonication. In other cases, the insertional enzyme can be highly charged, which may allow it to permeabilize through cell membranes.

In some cases, the cells may be subjected to lysing conditions that maintain the nucleus intact. The nuclei pellets may then be recollected and resuspended in transposition buffer comprising one or more types of transposases. The chromatin used in the method may be made by any suitable method. In some instances, nuclei may be isolated, lysed, and the chromatin may be further purified, e.g., from the nuclear envelope. In other instances, the chromatin may be isolated by contacting isolated nuclei with reaction buffer (which comprises insertional enzyme complexes and other necessary reagents). In these embodiments, the isolated nuclei may lyse when it makes contact with the reaction buffer, which allows the insertional enzyme complexes access to the chromatin.

The gDNA may be fragmented and tagged in a tagmentation reaction. A chromatin may be treated with an insertional enzyme complex to generate tagged fragments of genomic DNA. In this step, the chromatin may be tagmented (i.e., cleaved and tagged in the same reaction) using an insertional enzyme such as Tn5 or MuA that cleaves the genomic DNA in open regions (e.g., accessible regions) in the chromatin and adds adaptors to both ends of the fragments. Methods for tagmenting isolated genomic DNA are known in the art (see, e.g., Caruccio Methods Mol. Biol. 2011 733:241-55; Kaper et al, Proc. Natl. Acad. Sci. 2013 110:5552-7; Marine et al, Appl. Environ. Microbiol. 2011 77:8071-9 and US20100120098) and are commercially available from Illumina (San Diego, CA) and other vendors. Such systems may be readily adapted for use herein. In some cases, the conditions may be adjusted to obtain a desirable level of insertion in the chromatin (e.g., an insertion that occurs, on average, every 50 to 200 base pairs in open regions). Where nuclei are isolated, they may combine with the transposase and adaptors, wherein the combining results in both lysis of the nuclei to release the chromatin and production of the adaptor-tagged fragments of genomic DNA.

The insertional enzyme can be any enzyme capable of inserting a nucleic acid sequence into a polynucleotide. In some cases, the insertional enzyme can insert the nucleic acid sequence into the polynucleotide in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnIO, Tyl, any prokaryotic transposase, or any transposase related to and/or derived from those listed above. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$.

In some cases, the insertional enzyme can comprise two or more enzymatic moieties, which may be optionally linked together. The enzymatic moieties can be linked by using any suitable chemical synthesis or bioconjugation methods. For example, the enzymatic moieties can be linked via an ester/amide bond, a thiol addition into a maleimide, Native Chemical Ligation (NCL) techniques, Click Chemistry (i.e. an alkyne-azide pair), or a biotin-streptavidin pair. In some cases, each of the enzymatic moieties can insert a common sequence into the polynucleotide. The common sequence can comprise a common barcode. In some embodiments, the polynucleotide may be fragmented into a plurality of fragments during the insertion. The fragments comprising the common barcode can be determined to be in proximity in the three-dimensional structure of the polynucleotide.

In some instances, the insertional enzyme can further comprise an affinity tag. In some cases, the affinity tag can be an antibody. The antibody can bind to, for example, a transcription factor, a modified nucleosome or a modified nucleic acid. Examples of modified nucleic acids include, but are not limited to, methylated or hydroxymethylated DNA. In other cases, the affinity tag can be a single-stranded nucleic acid (e.g. ssDNA, ssRNA). In some examples, the single-stranded nucleic acid can bind to a target nucleic acid. In further cases, the insertional enzyme can further comprise a nuclear localization signal.

The tagged gDNA fragments may comprise one or more adapters. The one or more adapters may be attached to the gDNA fragments. An adapter may be attached to both ends of each fragment. A first adapter attached to a first end and a second adapter attached to a second end, where the first adapter and second adapter are different. The adapters can comprise sequencing adaptors, locked nucleic acids (LNAs), zip nucleic acids (ZNAs), RNAs, affinity reactive molecules (e.g. biotin, dig), self-complementary molecules, phosphorothioate modifications, azide or alkyne groups. In some cases, the adaptors can further comprise a barcode molecule. The barcode molecule may comprise a unique sequence, in some instances. Such unique sequences can be used to identify the individual insertion events. The adapters can further comprise fluorescence tags (e.g. fluorescein, rhodamine, Cy3, Cy5, thiazole orange, etc.). The adapters may comprise one or more adapter sequences. In non-limiting examples, for example, the adapters may each comprise one or more of a transposon end sequence (mosaic end sequence), a barcode sequence, a sequencing primer sequence, a primer sequence, an index sequence, a P5 sequence, a P7 sequence, or other sequences. Possible adapter configurations and components are described in further detail in Belhocine.

After generating the tagged gDNA fragments, and prior to initiating a reverse transcription reaction using the mRNA molecules, the tagmentation reaction may be inhibited or quenched, such as using magnesium chloride, or otherwise terminated. In some instances, the tagmenting operation can comprise using a detergent, an insertional enzyme complex (e.g., a transposase complex), and a divalent metal ion to the cell. In some instances, the detergent can be a non-ionic surfactant, e.g., an ethoxylated nonylphenol such as NP-40. In some instances, the terminating can be done by chelating the divalent metal ion required by the insertional enzyme complex (e.g., a transposase complex), thereby terminating the reaction and releasing the insertional enzyme complex (e.g., the transposase complex) from the tagged DNA. In some instances, the chelating can be done by ethylenediamine tetraacetatic acid (EDTA), nitriloacetic acid (NTA), or diethylenetriamine pentaacetic acid (DTPA), or other chelating agents. The termination can be facilitated by any other reaction terminator. The tagmentation reaction (and/or termination thereof) and reverse transcription reaction may happen in the same partition or in different partitions. For example, tagmentation (and/or termination thereof) may happen in a first partition and the reverse transcription in a different second partition. In another example, tagmentation (and/or termination thereof) may happen in a first partition and the reverse transcription in the same first partition.

After the chromatin has been fragmented and tagged to produce tagged fragments of genomic DNA, at least some of the adaptor tagged fragments, or derivatives thereof (e.g., amplicons) may be sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLID platform) or Life Technologies' Ion Torrent platform. Examples of such methods are described in the following references: Margulies et al (Nature 2005 437:376-80); Ronaghi et al (Analytical Biochemistry 1996 242:84-9); Shendure et al (Science 2005 309:1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, methods for library preparation, reagents, and final products for each of the steps. Forward and reverse sequencing primer sites that are compatible with a selected next generation sequencing platform can be added to the ends of the fragments during an amplification step.

The tagged gDNA fragments may be amplified using primers (e.g., polymerase chain reaction (PCR) primers). In some instances, the primers may hybridize to one or more adapter sequences in the tagged gDNA fragments. In some instances, the primer used for PCR can have 5' tails that are compatible with a particular sequencing platform. In certain cases, the primers used may comprise a cell-specific barcode sequence so that different pools (e.g., of amplicons) can be pooled together before sequencing, and the sequence reads can be traced to a particular sample using the cell-specific barcode sequence.

ATAC-Seq, and/or aspects thereof, may be performed in conjunction with TCR-seq, and/or aspects thereof. For example, after the tagmentation reaction is quenched or otherwise terminated, the mRNA molecules may be subject to reverse transcription reaction to generate cDNA molecules. The method may comprise using primers and reverse transcriptase to generate the cDNA molecules.

In T cells, the mRNA molecules from which the cDNA molecules are generated from can comprise T cell receptor alpha (TRA) and/or T cell receptor beta (TRB) RNA molecules. In some instances, at least a subset of the primers may comprise a sequence specific to or targeted for a sequence encoding a constant region of the TRA and/or TRB RNA molecules. Thus, at least a subset of the cDNA generated may correspond to a V(D)J region of a genome of the immune cell. In some cases, such cDNA may be barcoded. Methods and compositions suitable for barcoding cDNA generated from mRNA transcripts including those encoding V(D)J regions of an immune cell receptor and/or barcoding methods and composition including a template switch oligonucleotide are described in PCT Patent Pub. No. WO/2018/075693 and U.S. Patent Pub. No. 2018/0105808, each of which applications are herein incorporated by reference in their entireties.

Provided herein are beads suitable for processing a nucleic acid sequence (e.g., mRNA, complementary DNA derived from reverse transcription of mRNA) encoding at least a portion of a V(D)J sequence of an immune cell receptor (e.g., a TCR or BCR). A bead may be a gel bead. A barcoded primer may be coupled or otherwise attached to the gel bead. In some instances, the barcoded primer may be releasably attached to the gel bead. Accordingly, a first barcode molecule may comprise a priming sequence that can prime such a nucleic acid sequence encoding at least a portion of a V(D)J sequence of an immune cell receptor. In some cases, the nucleic acid molecule with such nucleic acid sequence is cDNA that is generated from reverse transcription of the corresponding mRNA, such as using a poly-T containing primer. The cDNA that is generated can then be barcoded using a primer, comprising a barcode sequence (and optionally, a unique molecular identifier (UMI) sequence) that hybridizes with at least a portion of the cDNA that is generated. In some cases, a template switching oligonucleotide in conjunction with a terminal transferase or a reverse transcriptase having terminal transferase activity may be employed to generate a priming region on the cDNA to which a barcoded primer can hybridize during cDNA generation. Terminal transferase activity can, for example, add a poly-C tail to a 3' end of the cDNA such that the template switching oligonucleotide can bind via a poly-G priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated.

The cDNA and/or the tagged gDNA fragments may be amplified in a PCR reaction, for example by contacting them with a plurality of primers and a polymerase to generate cDNA molecule amplicons and/or tagged gDNA fragment amplicons. In some instances, at least a subset of the plurality of primers may comprise a sequence specific to or targeted for a sequence encoding a constant region and/or a variable region of a TCR. In some instances, amplicons of the cDNA and amplicons of the tagged gDNA fragments may comprise a cell-specific barcode sequence that identifies the immune cell. In some instances, such cell-specific barcode sequence-containing amplicons may be generated from other amplicons of the tagged gDNA fragments and cDNA molecules. Sequencing reads may be associated with the immune cell based at least in part on the cell-specific barcode sequence. Barcode molecules may be delivered prior to, concurrently with, or subsequent to partitioning of the cell. In some instances, the barcode molecule may be delivered via a bead (e.g., gel bead), as described elsewhere herein.

The cDNA, tagged gDNA, and/or amplicons thereof may be sequenced to generate sequencing reads. Such sequencing reads may be used to determine, in the immune cell, a correlation between accessible gDNA and the sequences that correspond to the V(D)J region. The correlation may be mapped. In some instances, the cDNA, tagged gDNA, and/or amplicons thereof may be removed from the partition prior to sequencing, pooled, and sequenced. The cell-specific barcode sequence may associate sequencing reads generated from products or derivatives of the partition that partitioned the immune cell to the immune cell.

In some embodiments, T cells may be analyzed for chromatin and T-cell receptors (e.g., ATAC-seq and/or T-ATAC-seq). T cells may be collected, partitioned, lysed, and subjected to transposition. Following treatment of transposase and reaction quenching, samples may be subjected to reverse transcription and PCR using a mix of primers that include multiple V-alpha and V-beta region primers and C-alpha and C-beta primers. These processes may be conducted in a microfluidic chip. For example, Fluidigm, an automated microfluidic platform, may be used for single-cell capture, lysis, and downstream processing.

Harvested libraries may be further amplified. For example, when examining T cells, T-cell receptor (TCR) primers may be used. Thereafter, an aliquot of this sample may be used as a template for a subsequent PCR reaction. The subsequent PCR reaction may be a nested PCR reaction, using, for example, primers for TCRV-alpha, TCRV-beta, TCRC-alpha, and TCRC-beta primers. The product of these reactions may be used subsequently as a template for a PCR reaction, which incorporates barcodes and enables sequencing.

Purification of libraries may be obtained by selecting a nucleotide fragment of choice. A nucleotide fragment may be selected by its size, isoelectric point, or other biochemical or biophysical properties. For example, a nucleotide fragment may be purified by size by using polyacrylamide gel electrophoresis and selecting fragments of a desired size.

Following barcoding, amplicons from PCR may be purified and sequenced to form a library. Libraries may be additionally amplified, and/or quantified prior to sequencing.

Various applications of T-ATAC-seq data may be envisioned. In one non-limiting example, epigenomic signatures in immortalized leukemic T cells may be compared to that of primary human T cells from a healthy patient and primary human T cells from leukemic patients. The data arising from T-ATAC-seq may be used, for example, to identify leukemic and nonleukemic regulatory pathways in T cells. In some cases, T-ATAC-seq may enable the identification of cancer-clone-specific epigenomic signatures that are not readily apparent from ensemble or bulk measurements. In another application, the heterogeneity of T cells within a population may be characterized, e.g., via identification of cis and trans regulators of naive versus memory T cell states. The cell-to-cell variability and intermediate epigenomic phenotypes may also be characterized in single cells, which are often obscured by bulk measurements. Identification of TCR-alpha-beta-encoding sequences may also aid in the understanding of the identity of single T cells and in discovery of clonal gene regulatory pathways. Similarly, T-ATAC-seq may be used to separate clonal and nonclonal regulatory pathways in cells from the same individual. It is thus apparent to those skilled in the art that T-ATAC-seq may enable analysis of epigenomic landscapes in clonal T cells and can be valuable in studies pertaining to T cell malignancy, immunity, and immunotherapy.

Figure 1:
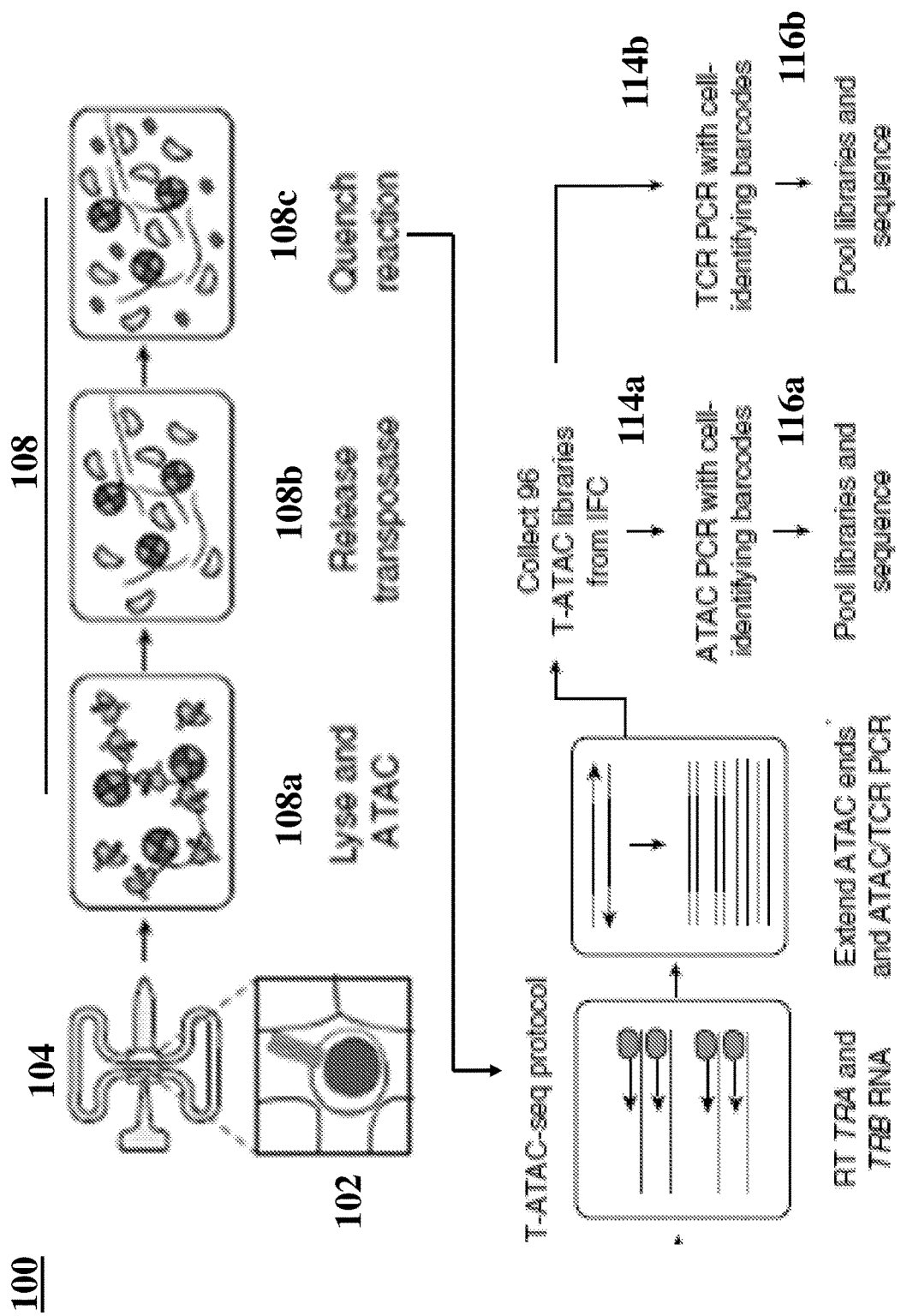
FIG. 1 illustrates an example protocol and/or workflow for transcript-indexed assay for transposase-accessible chromatin using sequencing (T-ATAC-seq).

FIG. 1 illustrates an example protocol and/or workflow 100 for T-ATAC-seq. Individual T cells 102 are isolated in a microfluidic chip using a microfluidic single-cell capture mechanism 104, such as those found in an integrated fluidics circuit or partitioning mechanisms described elsewhere herein. The chip may comprise multiple chambers. T cells are sequentially subjected to operations 108 relating to ATAC-seq, including lysing 108a (or isolating nuclei), releasing 108b transposase, initiating a tagmentation reaction to generate tagged gDNA fragments, and quenching 108c of the tagmentation reaction. Subsequent to quenching, reverse transcription 110 is performed on TRA and TRB transcripts. The tagged gDNA fragments and cDNA, and/or amplicons thereof (e.g., ATAC-seq and TCR-seq amplicons) are thereafter amplified 112. Optionally, single-cell libraries are then amplified with cell-identifying barcodes 114a, b, and pooled 116a, b. The amplicons are analyzed by high-throughput sequencing.

Some embodiments of the methods may involve making an epigenetic map of a region of the genome of the cells. This operation may be done by mapping information obtained from the sequence reads to the region. In these cases, the sequence reads may be analyzed computationally to produce a number of numerical outputs that are mapped to a representation (e.g., a graphical representation) of a region of interest. As will be explained in greater detail below, many types of information may be mapped, including, but not limited to: (i) cleavage sites for the transposase; (ii) the sizes of the fragments produced in step a); (iii) fragment length; (iv) the positions of sequence reads of a defined range in length; (v) sequence read abundance; and (vi) transcription factor deviation.

Figure 10:
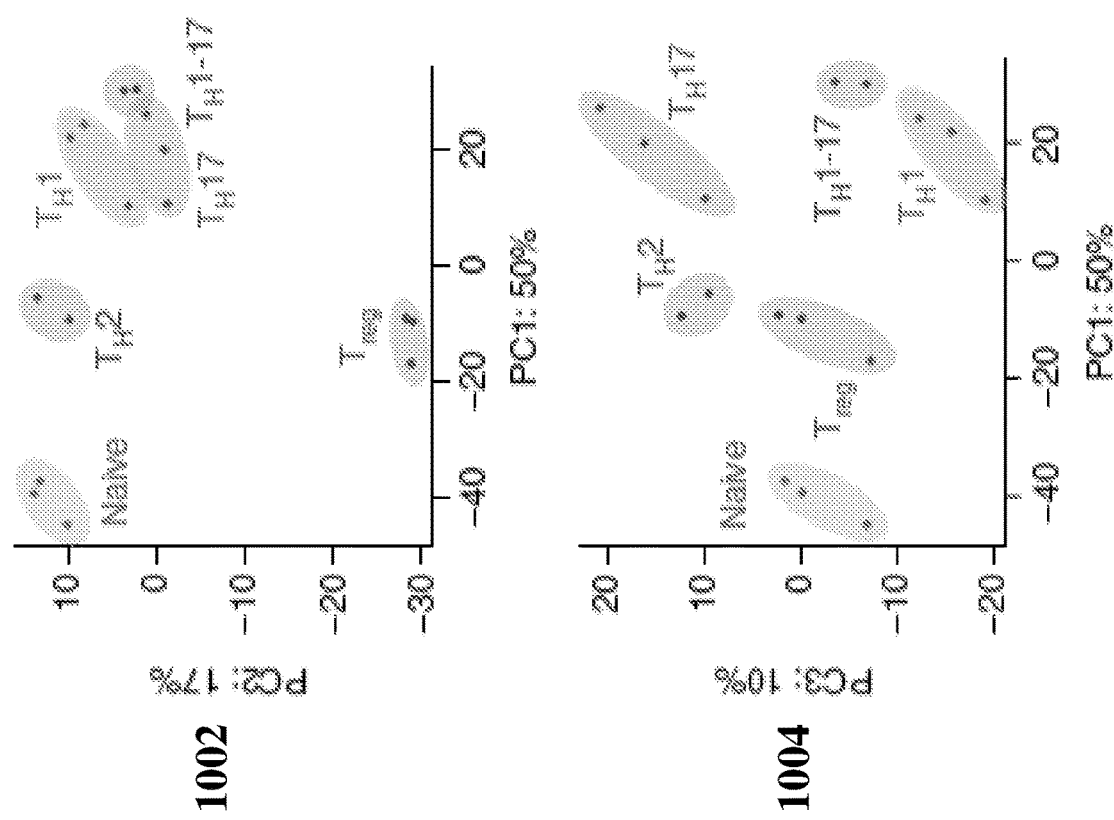
FIG. 10 shows plots of the epigenomic landscape of ensemble T cell subtypes.

In some cases, data obtained from T-ATAC-seq may be used to distinguish cell subtypes. For example, FIG. 10 shows plots of the epigenomic landscape of ensemble T cell subtypes. FIG. 10 demonstrates principal component analysis (PCA) showing distinct chromatin states for T cell subsets, e.g., naive and memory T cell subtypes. Percentages (1002, 1004) of variance explained by each PC are listed. Principal components may then be trained on ensemble ATAC-seq data to remove contaminating non-T cells that may remain after sorting. PCA of ensemble ATAC-seq profiles from CD4+ T cell subtypes are shown.

The sequence reads may be analyzed computationally to identify the ends of the fragments (from which the transposon cleavage sites can be inferred). In these embodiments, one end of a fragment can be defined by a sequence that is at the beginning of a sequencing read and the other end of the fragment can be defined by a sequence that is at the beginning of a second sequencing read, where the first and second sequencing reads were obtained by paired end sequencing (e.g., using Illumina's sequencing platform). The same information can be obtained from examining the beginning and end of longer sequence reads (which should, in theory, have the sequence of both adaptors; one at one end and the other at the other end). In these embodiments, a single sequence read may contain both adaptor sequences, in which case both ends of a fragment (which correspond to two cleavage sites for the two separate transposases) can be inferred from a single sequence read. The lengths of the fragments can be calculated by, e.g., mapping the fragment ends onto the nucleotide sequence of the region of interest, and counting the number of base pairs between those positions. The information used may be obtained using the nucleotide sequences at the beginning and/or the end of a sequence read.

In certain cases, the sequence reads can be placed into groups by length. In some embodiments, some sequences can be annotated as being a nucleosome-free sequence (i.e., a sequence from a fragment that is predicted to be between nucleosomes) based on its size. Reads that are associated with mononucleosomes, dinucleosomes and trinucleosomes can also be identified. These cutoffs can be determined using the data shown in FIG. 4. Fragment lengths (which provide the same information as sequence read lengths) can also be processed in the same way. In certain cases, sequence read abundance, i.e., the number of times a particular sequence in a genomic region is represented in the sequence reads, may be calculated.

The resultant epigenetic map can provide an analysis of the chromatin in the region of interest. For example, depending on which information is mapped, the map can show one or more of the following: a profile of chromatin accessibility along the region; DNA binding protein (e.g., transcription factor) occupancy for a site in the region; nucleosome-free DNA in the region; positioning of nucleosomes along the region; and a profile of chromatin states along the region. In some embodiments, the method may further comprise measuring global occupancy of a binding site for the DNA binding protein by, e.g., aggregating data for one DNA binding protein over a plurality of sites to which that protein binds. In certain instances, the map can also be annotated with sequence information, and information about the sequence (e.g., the positions of promoters, introns, exons, known enhancers, transcriptional start sites, untranslated regions, terminators, etc.) so that the epigenetic information can be viewed in context with the annotation.

In some cases, the epigenetic map may comprise representation(s) of calculation(s) of transcription factor (TF) deviation. TF deviation may be performed by calculating raw accessibility deviations, i.e., subtracting the expected number of ATAC-seq reads in peaks for a given motif from the observed number of ATAC-seq reads in peaks for each single cell. Expected reads may then be calculated from the population average of all cells for the experiment. The deviation value may be bias-corrected (e.g., subtracting the mean deviation calculated with similar accessibility and GC content). In some cases, the deviation value may be divided by the standard deviation of the background to obtain a Z-score. Other methods of data analysis, peak processing, peak sorting and data processing are envisioned.

In certain embodiments, the epigenetic map can provide information regarding active regulatory regions and/or the transcription factors that are bound to the regulatory regions. For example, nucleosome positions can be inferred from the lengths of sequencing reads generated. Alternatively, transcription factor binding sites can be inferred from the size, distribution and/or position of the sequencing reads generated. In some cases, novel transcription factor binding sites can be inferred from sequencing reads generated. In other cases, novel transcription factors can be inferred from sequencing reads generated.

Provided herein are some embodiments of methods for processing cells. In an aspect, provided is a method comprising: (a) tagmenting accessible genomic DNA in a nucleus of one or more cells to produce tagged genomic DNA, (b) terminating the tagmentation reaction, and (c), after operation (b), adding a primer, reverse transcriptase, and dNTPs to the one or more cells to reverse transcribe RNA in the one or more cells to produce cDNA.

In some embodiments, the method is performed in a single vessel or partition. In some embodiments, operation (b) is done my mixing a reaction terminator to the reaction of operation (a), and operation (c) is done by adding a primer, reverse transcriptase and dNTPs to the reaction of operation (b), without transferring any of the reactions to second vessel or partition.

In some embodiments, the tagmenting operation (a) is done by combining the one or more cells with a detergent, an insertional enzyme complex (e.g., a transposase complex) and a divalent metal ion. In some embodiments, the detergent is a non-ionic surfactant, e.g., an ethoxylated nonylphenol such as NP-40. In some embodiments, the terminating operation (b) is done by chelating the divalent metal ion required by the insertional enzyme complex (e.g., a transposase complex), thereby terminating the reaction and releasing the insertional enzyme complex (e.g., the transposase complex) from the tagged DNA. In some embodiments, the chelating is done by ethylenediamine tetraacetic acid (EDTA), nitriloacetic acid (NTA), or diethylenetriamine pentaacetic acid (DTPA). In some embodiments, the reverse transcription operation (c) comprises adding an excess of the divalent metal ion to the reaction. The termination can be facilitated by any other reaction terminator. The tagmentation reaction (and/or termination thereof) and reverse transcription reaction may happen in the same partition or in different partitions.

In some embodiments, the one or more cells are mammalian cells. In some embodiments, the one or more cells is a single cell. In some embodiments, the one or more cells is a plurality of cells.

In some embodiments, the primer of (c) is an oligo (d) T primer, a random primer, or a gene-specific primer.

In some embodiments, the method comprises amplifying the tagged genomic DNA and the cDNA from the cells, after operation (c). In some embodiments, the amplifying is done by PCR. In some embodiments, the tagged genomic DNA and the cDNA are amplified separately. In some embodiments, the method further comprises sequencing the amplified tagged genomic DNA and the amplified cDNA from the cells. In some embodiments, the method further comprises identifying a correlation between chromatin structure and gene expression.

Figure 2:
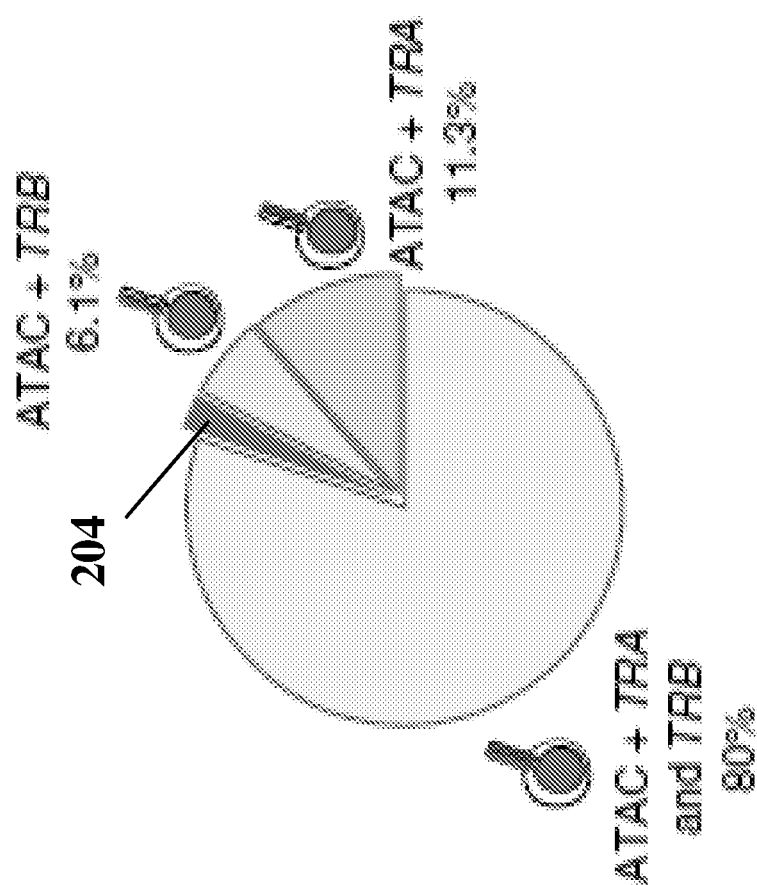
FIG. 2 shows a pie chart indicating the overlap of T cell receptor sequencing (TCR-seq) and ATAC-seq data from T cells.

FIG. 2 shows a pie chart indicating the overlap of TCR-seq and ATAC-seq data from single Jurkat cells (n=231 single cells) that passed quality-control filters. The pie chart shows the proportion of cells that generated ATAC-seq profiles in which TRA or TRB sequence was also obtained. 204 shows the portion of cells in which ATAC-seq data were obtained but in which TRA or TRB data were not obtained.

Figure 3:
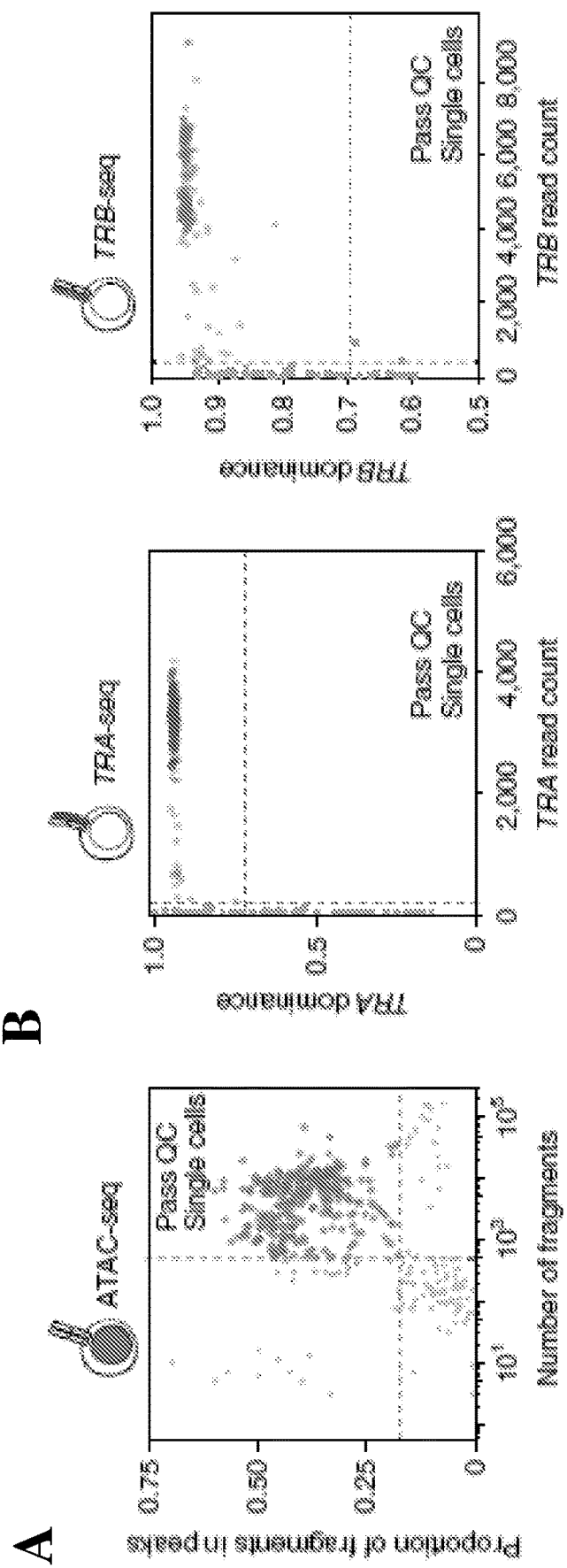
FIG. 3 shows plots following quality-control filters.

FIG. 3 shows plots following quality-control filters. In panel A, the number of unique ATAC-seq nuclear fragments in each cell is plotted, compared to the percentage of fragments in ATAC-seq peaks derived from ensemble ATAC-seq profiles. Panel B shows the read counts from TRA or TRB paired-end sequencing, as compared to the TCR dominance of the top clone for each cell.

Figure 4:
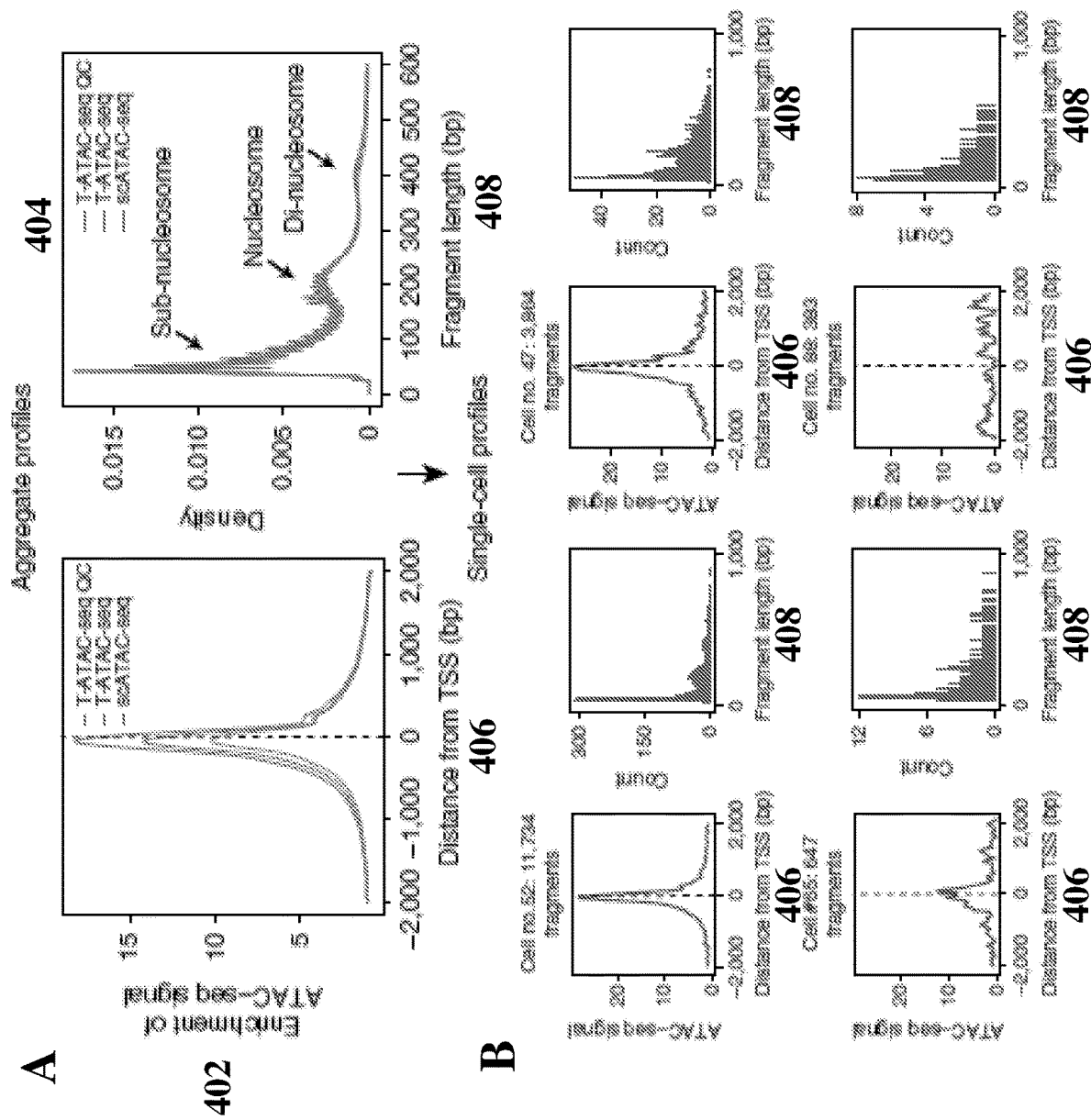
FIG. 4 illustrates a comparison of aggregate (panel A) and single-cell T-ATAC-seq (panel B) profile characteristics.

FIG. 4 illustrates a comparison of aggregate (panel A) and single-cell T-ATAC-seq (panel B) profile characteristics. Shown are the enrichments 402 of ATAC-seq Tn5 insertions around TSSs and nucleosomal periodicity 404 of ATAC-seq fragment lengths. In panel B, plots of distance from TSS 406 of single cells are shown, as well as frequency (counts) of fragment length 408. Fragment length 408 indicates the genomic distance between two Tn5 insertion sites, as determined by paired-end sequencing of ATAC fragments.

Figure 5:
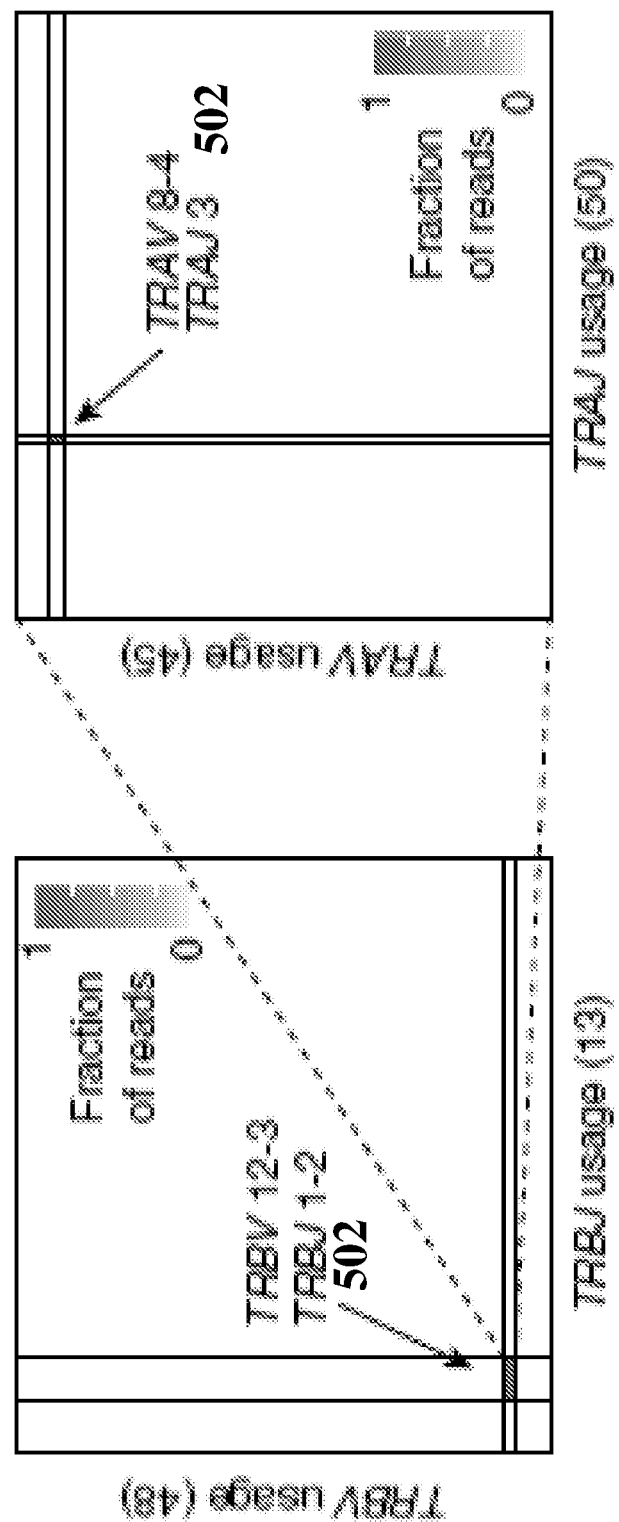
FIG. 5 shows heat maps of the T cell Receptor Alpha (TRA) or T cell Receptor Beta (TRB) rearrangements in cells.

FIG. 5 shows heat maps of the TRA or TRB rearrangements in cells. Each axis represents all possible genes within the indicated TRA or TRB locus. Labeled genes 502 indicate the sequences identified using T-ATAC-seq.

Figure 6:
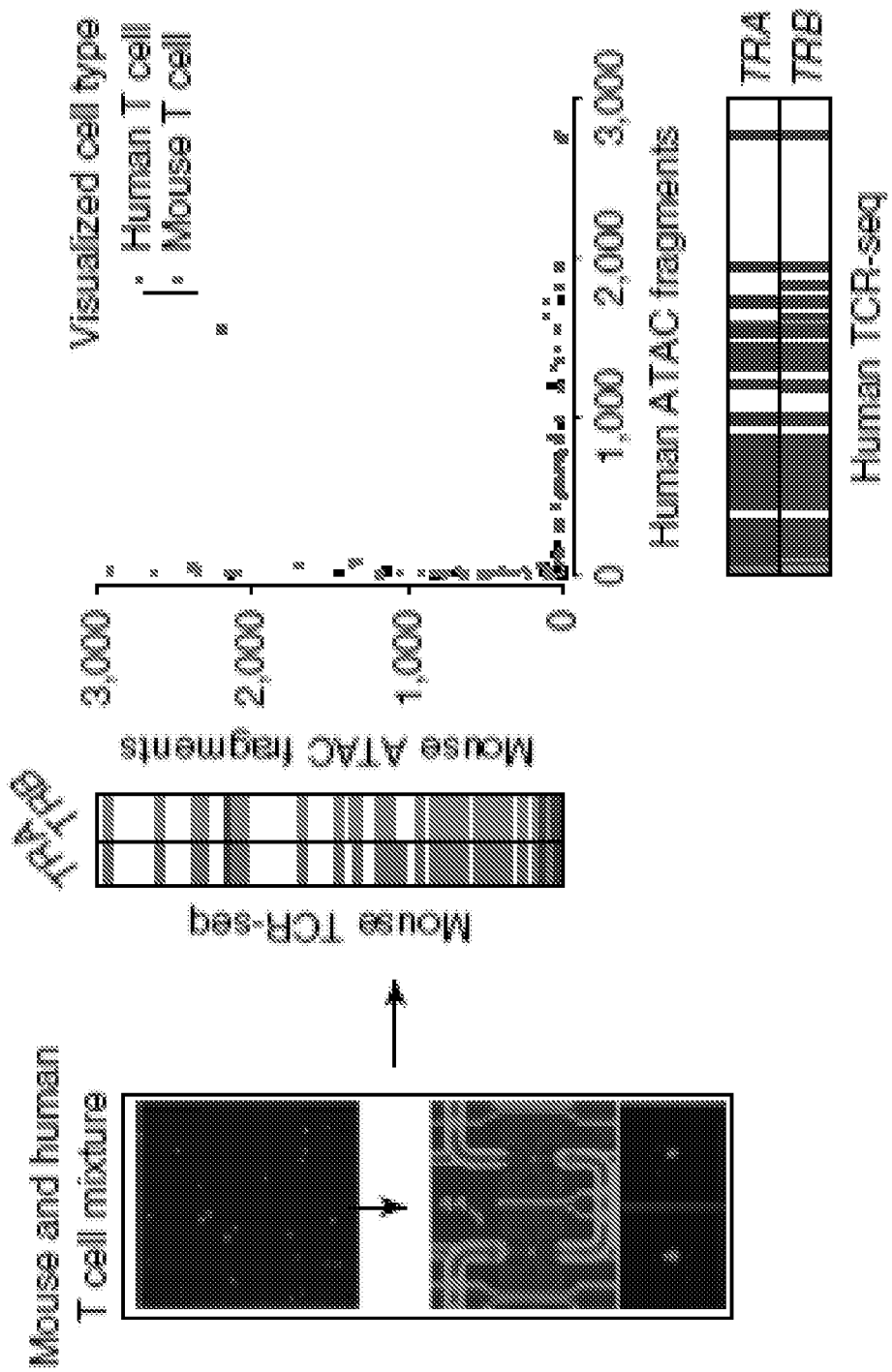
FIG. 6 demonstrates identification of mouse or human genomes using TCR-Seq clones.

FIG. 6 demonstrates identification of mouse or human genomes using TCR-Seq clones.

Figure 7B:
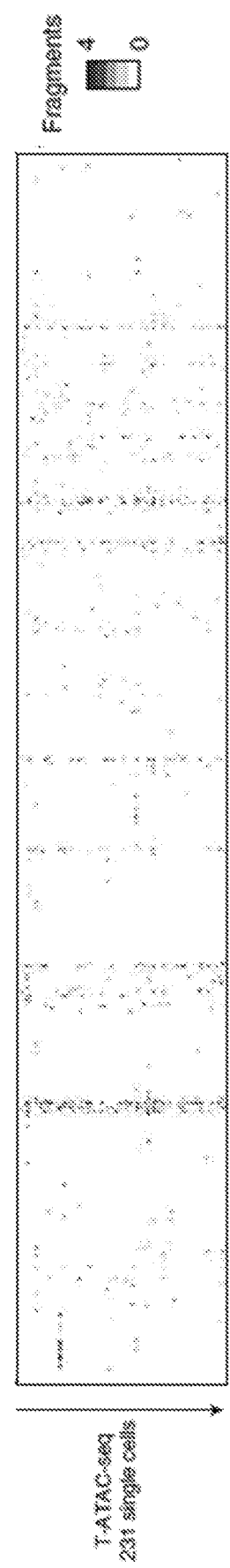
FIG. 7B shows a magnified view of the genome track of FIG. 7A.

FIG. 7A show plots generated from T-ATAC-seq, identifying epigenomic signatures. Genome tracks compare aggregate T-ATAC-seq profiles 706 to ensemble ATAC-Seq 704 and DHS-seq 702 profiles. FIG. 7B shows a magnified view of the genome track of FIG. 7A.

Figure 8:
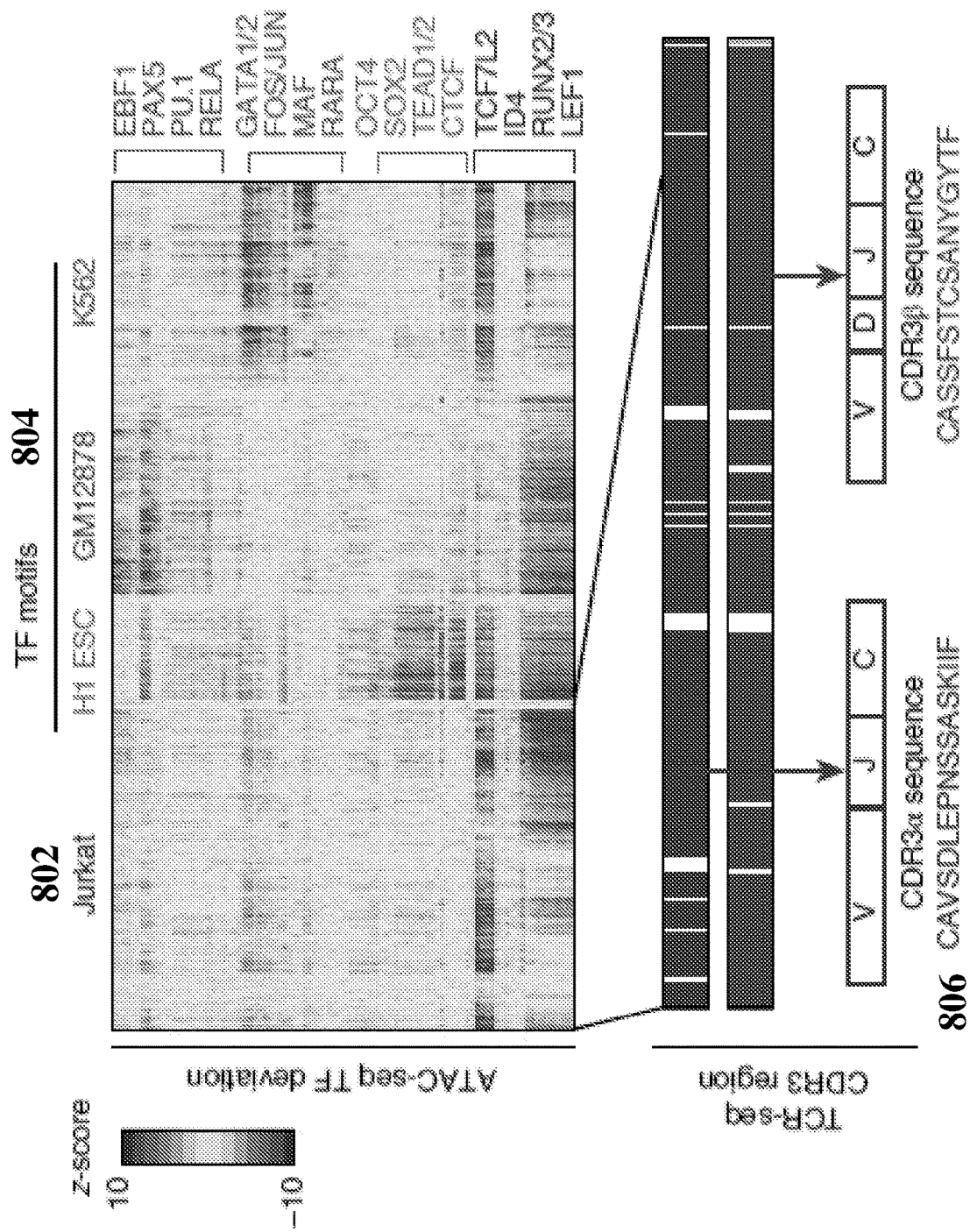
FIG. 8 shows a heat map of transcription factor (TF) deviation z-scores of Jurkat cells compared to other cell types.

FIG. 8 shows a heat map of transcription factor (TF) deviation z-scores of Jurkat cells 802 obtained using T-ATAC-seq, compared to other cell types 804, as previously published. Example single-letter amino acid sequences 806 are represented for the identified CDR3 region.

Figure 9:
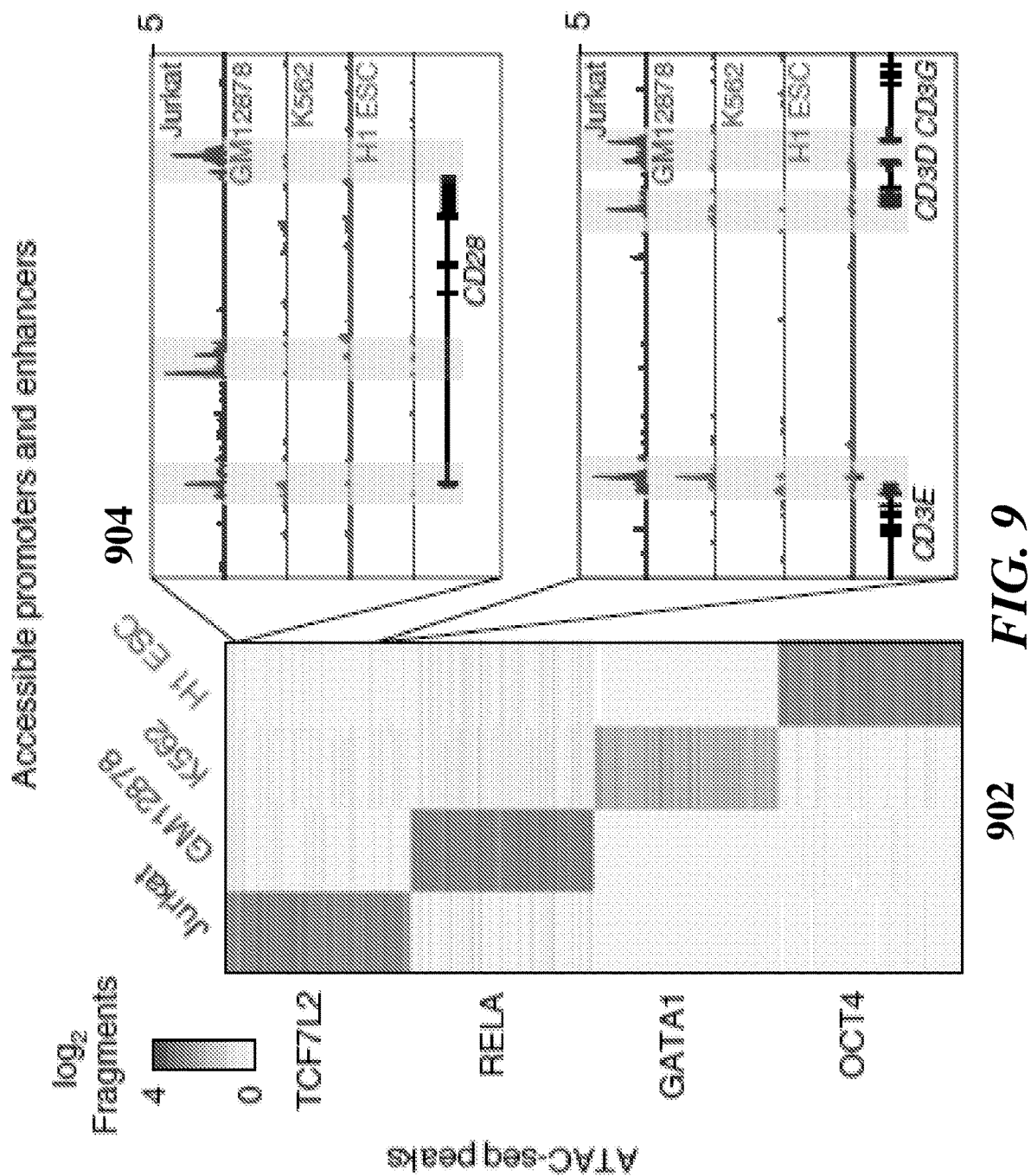
FIG. 9 shows a heat map of ATAC-seq fragment counts.

FIG. 9 shows a heat map 902 showing ATAC_seq fragment counts in peaks (rows) containing the indicated motifs from aggregated single cells. 904 shows genome tracks for aggregated T-ATAC-seq data.

FIG. 10 shows plots of the epigenomic landscape of ensemble T cell subtypes. PCA of ensemble ATAC-seq profiles from CD4+ T cell subtypes are shown. Percentages (1002, 1004) of variance explained by each PC are listed.

Figure 11:
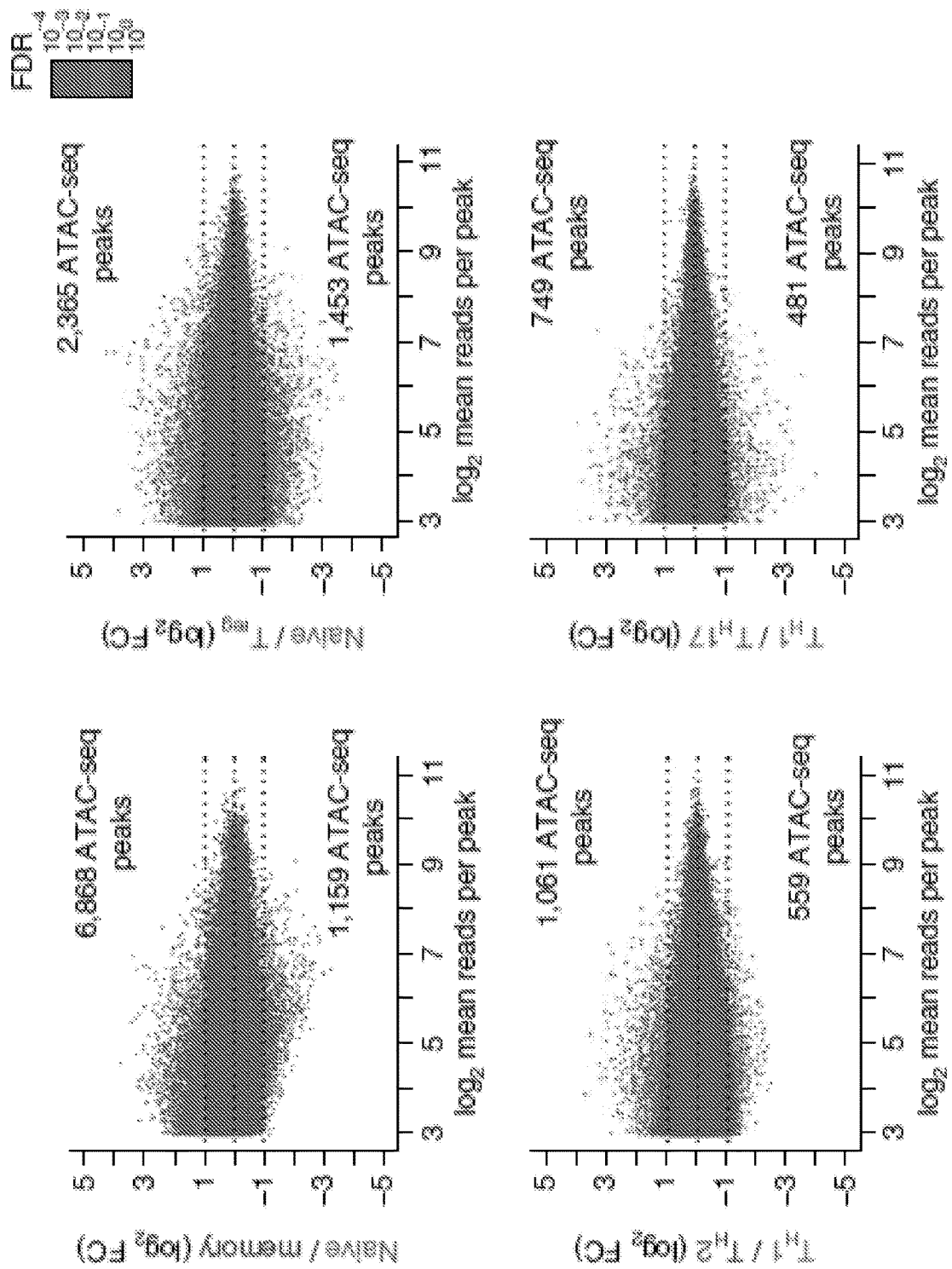
FIG. 11 show plots of epigenomic landscape of ensemble T cell subtypes.

FIG. 11 show plots of epigenomic landscape of ensemble T cell subtypes. Plots show differential ATAC-seq peaks for the different T cell subtypes.

Figure 12:
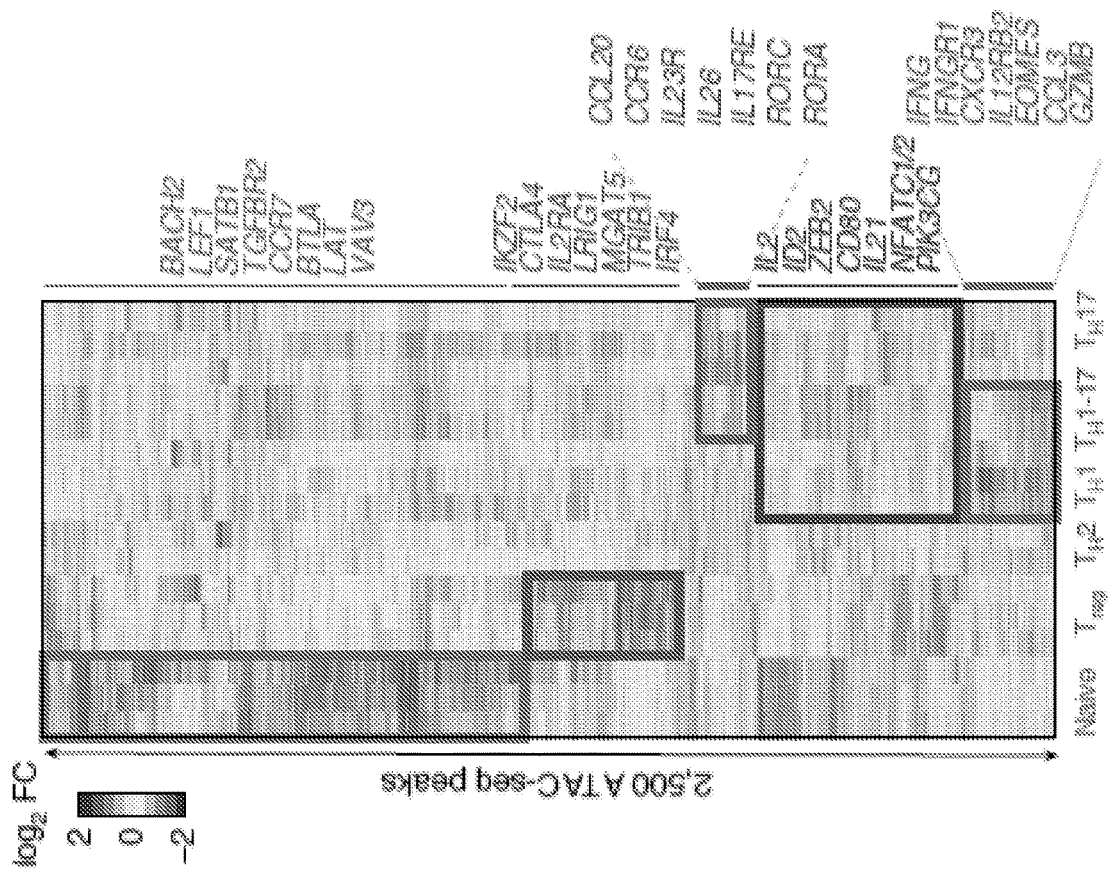
FIG. 12 is a heat map demonstrating clusters for the top varying ATAC-seq peaks.

FIG. 12 is a heat map demonstrating clusters for the top varying ATAC-seq peaks.

Figure 13:
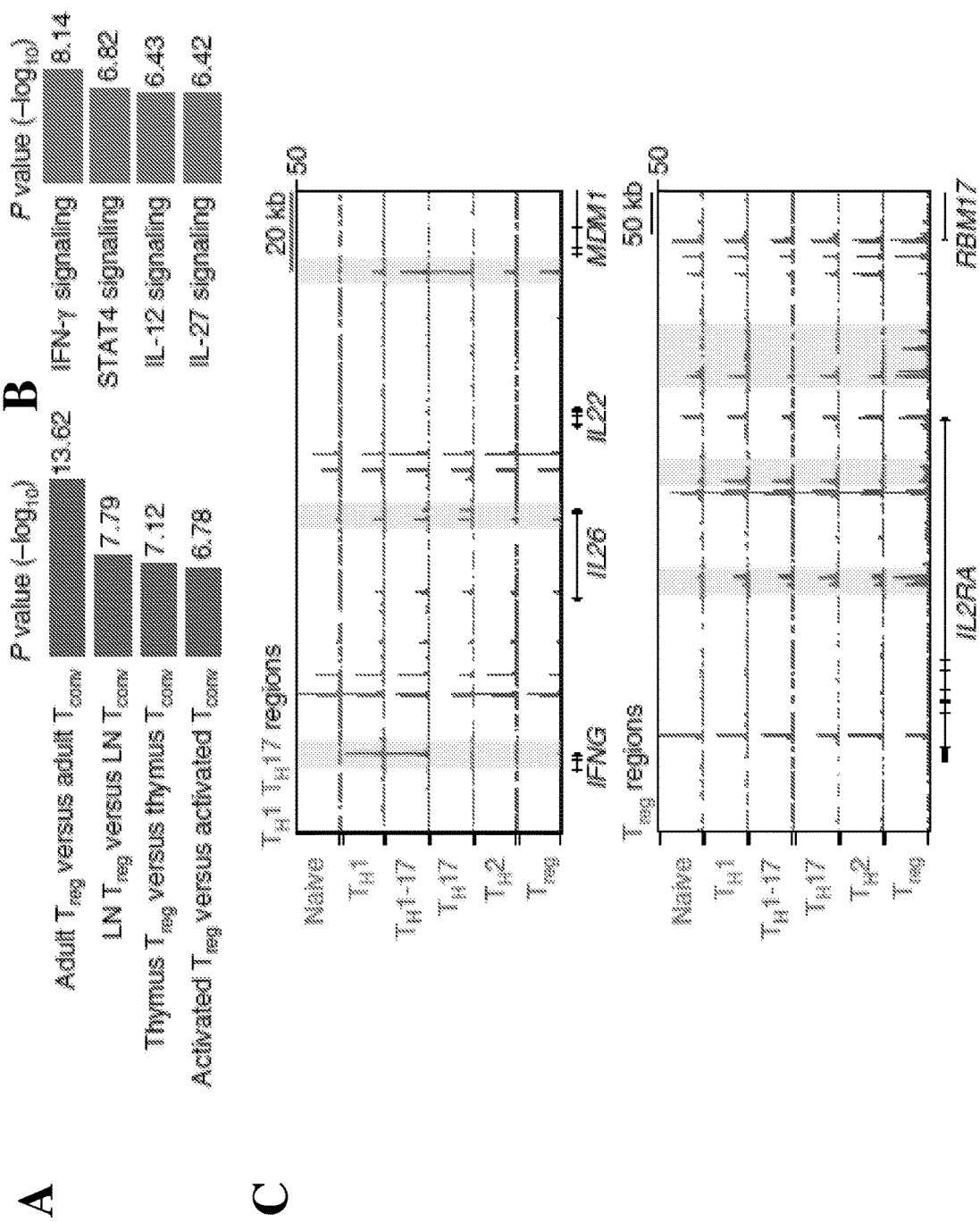
FIG. 13 shows immunologic signatures obtained from ATAC-seq.

FIG. 13 shows immunologic signatures obtained from ATAC-se. In panel A, MsigDB immunologic signatures of regulatory T cells-specific ATAC-seq are shown, as obtained from GREAT analysis. In panel B, MsigDB pathway signatures of TH1-specific ATAC-seq peaks are shown. In panel C, ensemble ATAC-seq genome track data are shown.

FIG. 14 shows plots of Pearson correlation of PC scores of ensemble ATAC-seq profiles 1402 and of ensemble ATAC-seq profiles after downsampling to 10,000 1404 or 1,000 1406 fragments. Heat maps demonstrate that CD4+ T cell subtype profiles can be distinguished from one another.

Figure 15:
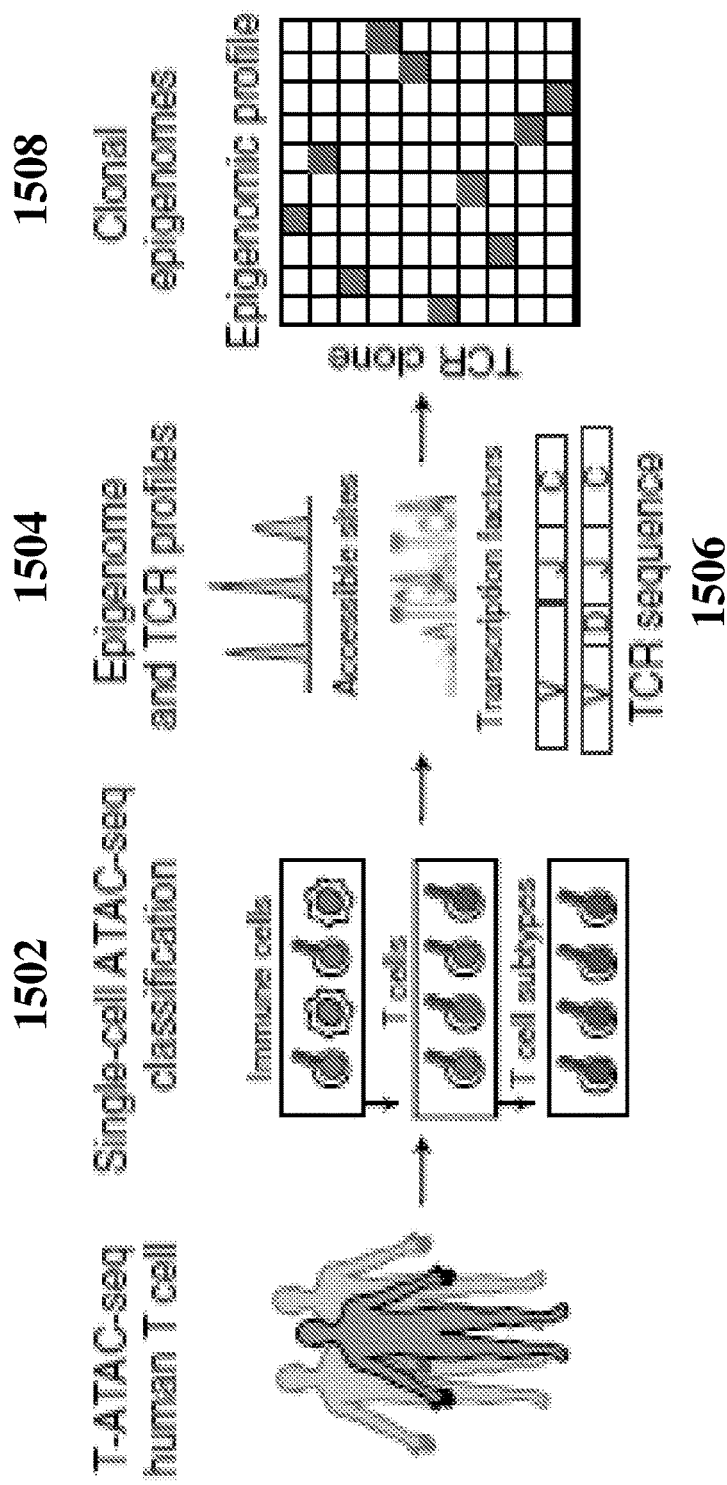
FIG. 15 shows the workflow for T-ATAC-seq analysis in primary human T cells.

FIG. 15 shows the workflow for T-ATAC-seq analysis in primary human T cells. Single cells are sequentially classified 1502 to major blood lineages and then to T cell subsets, by similarity to ensemble reference ATAC-seq profiles. T-ATAC-seq data from classified single T cells 1504 are analyzed for accessibility at regulatory DNA elements and TF activity using ATAC-seq data, as well as for TCR (TRA and TRB) sequence identity 1506. Integrative analysis is then performed to identify genomic signatures 1508 in T cell clones.

Figure 16:
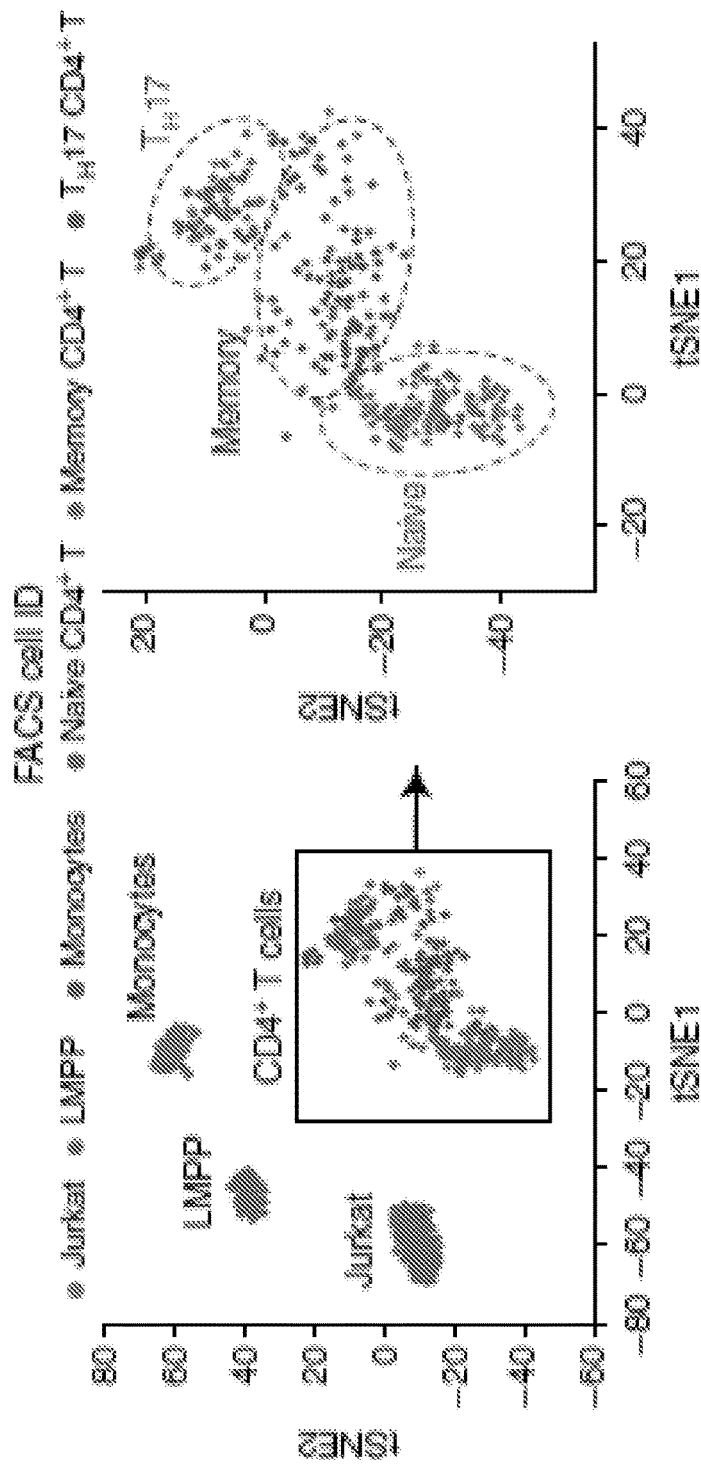
FIG. 16 shows t-SNE projections of various T cells.

FIG. 16 shows t-SNE projections of various T cells.

Figure 17:
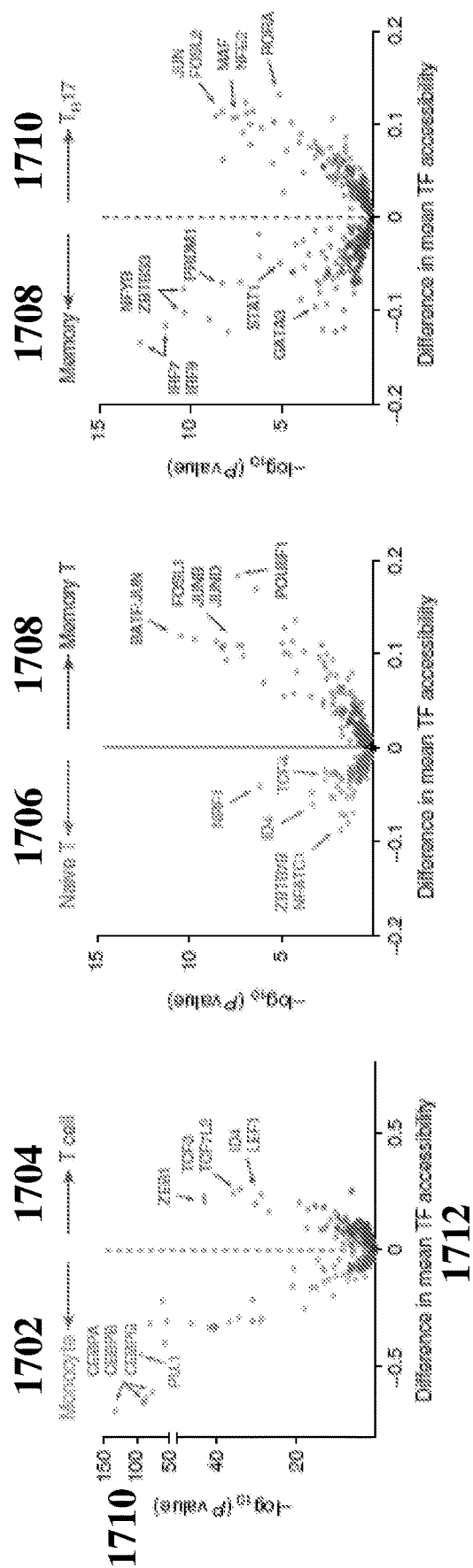
FIG. 17 shows a plot of TF bias-corrected deviation enrichments in aggregated single-cell populations.

FIG. 17 shows a plot of TF bias-corrected deviation enrichments in aggregated single-cell populations. TF enrichments were calculated as the difference in mean TF motif accessibility between two populations of single cells. Shown are enrichments for all T cells 1704 as compared to monocytes 1702, for memory T cells 1708 compared to naive T cells 1706, and for $T_H17$ 1710 cells compared to memory T cells 1708. The axes depict-log (P value) 1710 and difference in mean TF accessibility 1712.

Figure 18:
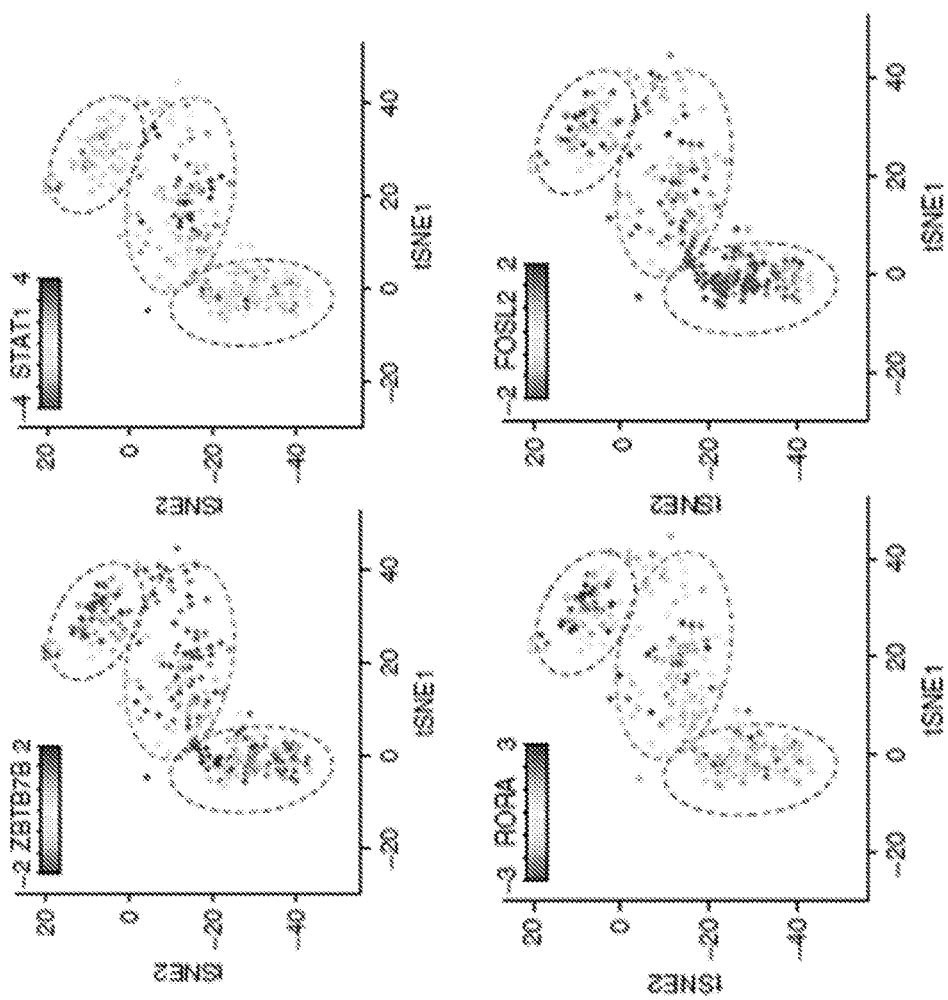
FIG. 18 shows a plot of t-SNE projections of single T cells highlighting motif accessibility.

FIG. 18 shows a plot of t-SNE projections of single T cells highlighting motif accessibility TF z-scores for ZBTB7B, STAT1, RORA, and FOSL2.

Figure 19:
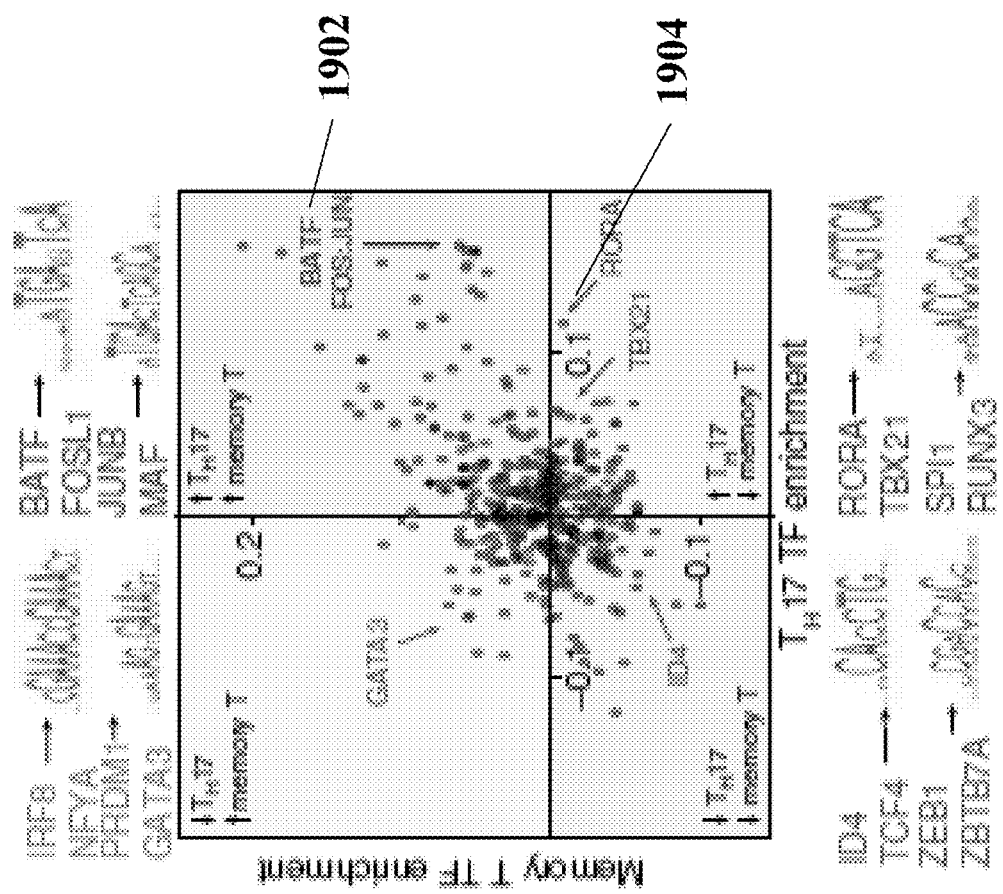
FIG. 19 shows mean bias-corrected deviations ranked for difference in aggregated TH17cells versus aggregated naive cells and for aggregated memory cells versus aggregated naive cells.

FIG. 19 shows mean bias-corrected deviations ranked for difference in aggregated $T_H17$cells versus aggregated naive cells and for aggregated memory cells versus aggregated naive cells. TF motifs for selected factors are shown in each quadrant. From these plots, it is apparent that BATF motifs 1902 show increased accessibility in memory T cells and $T_H17$cells. In contrast, RORA motifs 1904 show increased accessibility in $T_H17$cells but not in memory T cells.

Figure 20:
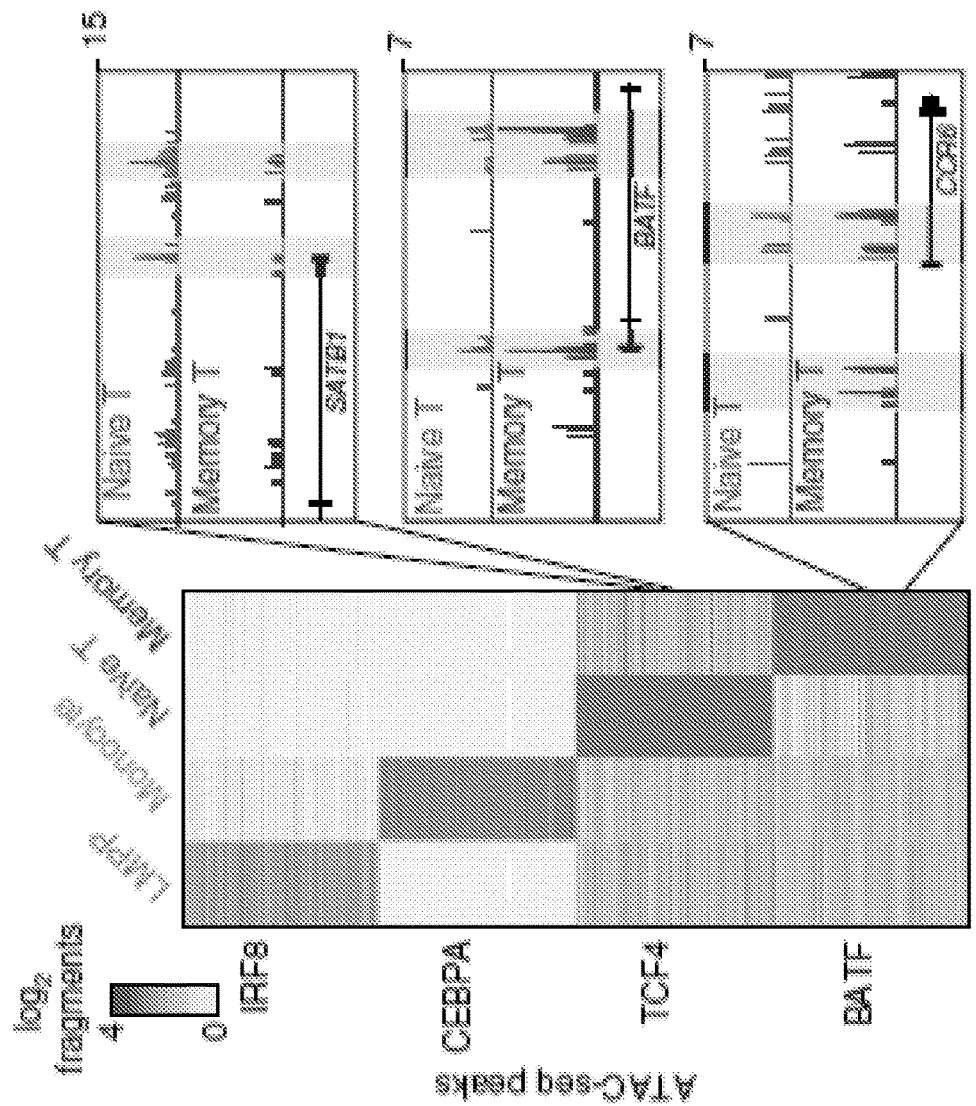
FIG. 20 shows a heat map showing ATAC-seq fragment counts in peaks containing the indicated motifs from aggregated single cells.

FIG. 20 shows a heat map showing ATAC-seq fragment counts in peaks containing the indicated motifs from aggregated single cells.

Figure 21:
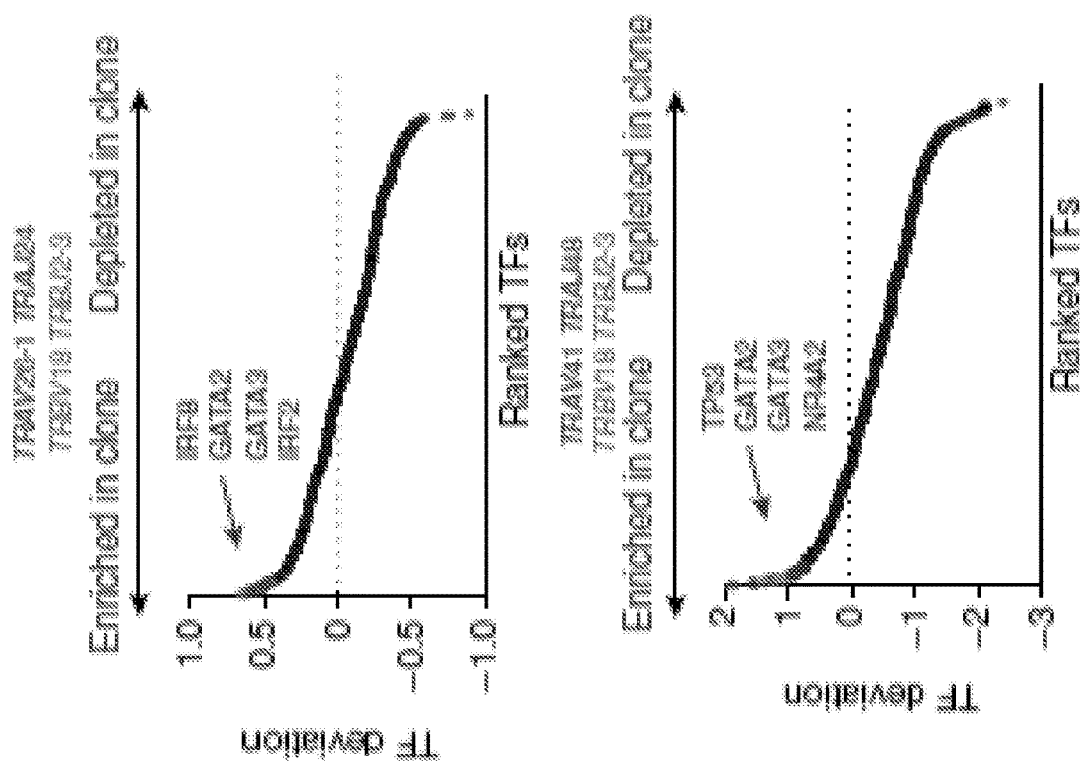
FIG. 21 shows TF deviation enrichments in clonal cells versus nonclonal memory T cells for two memory T cell clones (top and bottom).

FIG. 21 shows TF deviation enrichments in clonal cells versus nonclonal memory T cells for two memory T cell clones (top and bottom).

Figure 22:
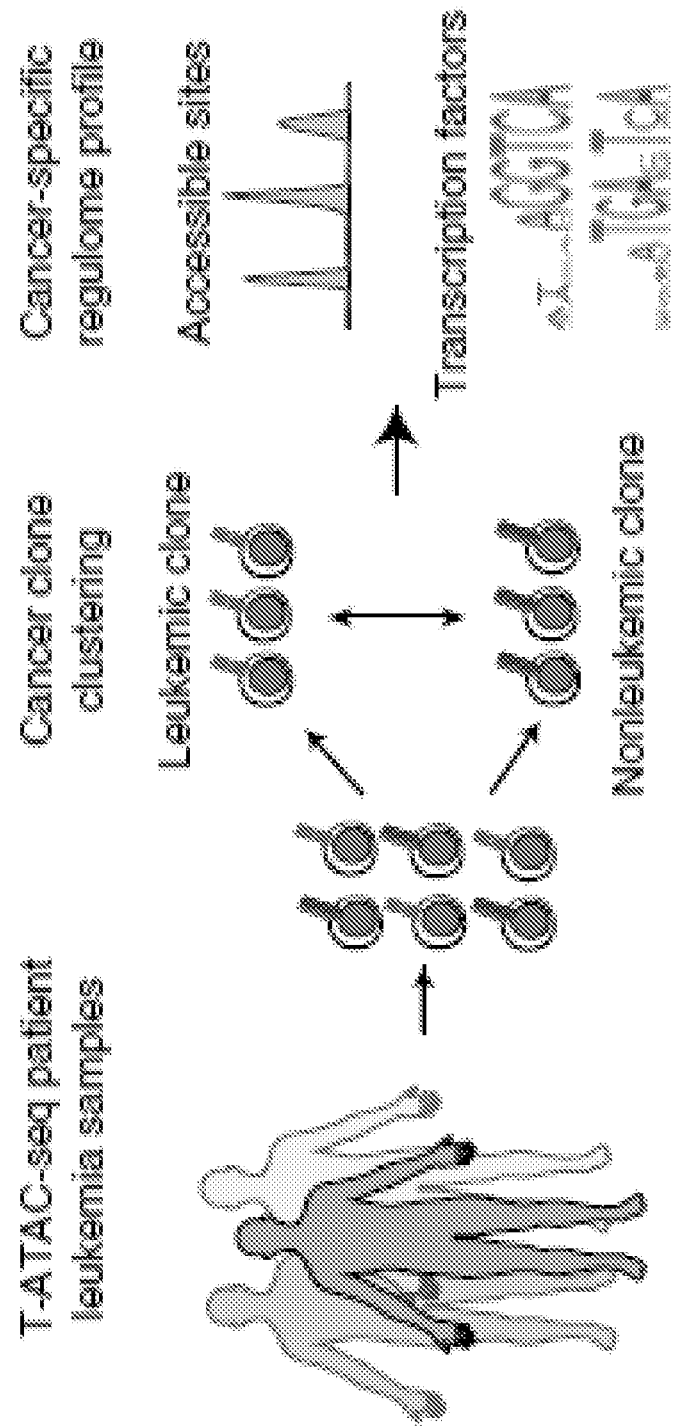
FIG. 22 shows the workflow for T-ATAC-seq analysis in T cell samples from patients with leukemia.

FIG. 22 shows the workflow for T-ATAC-seq analysis in T cell samples from patients with leukemia. Single cells are first classified according to TCR sequence identity as leukemic cells or nonleukemic cells. ATAC-seq data from classified single T cells are then analyzed for accessibility at regulatory DNA elements and TF activity.

Figure 23:
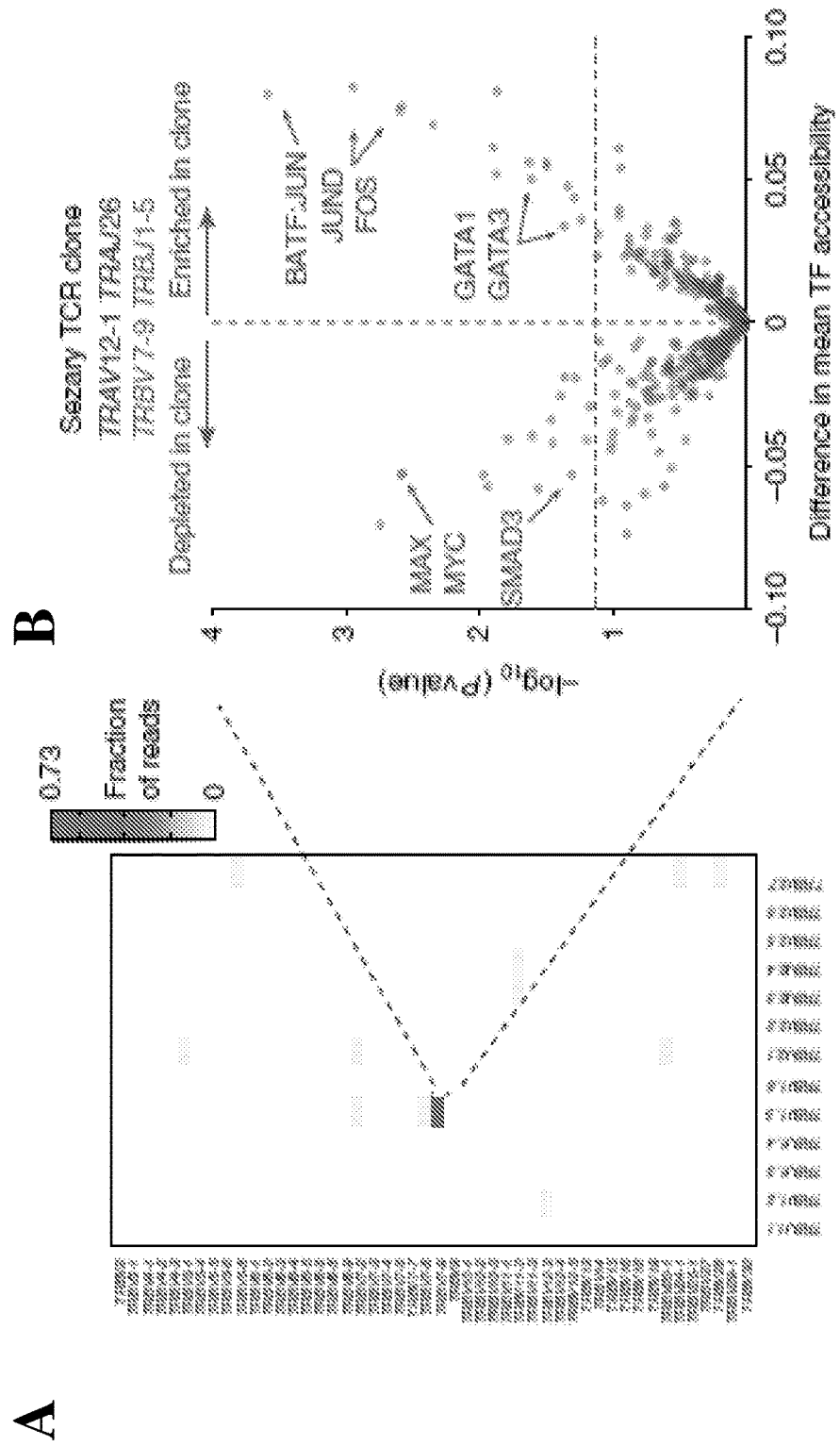
FIG. 23 shows a heatmap of TRB rearrangements in peripheral blood samples from a patient with a disease condition.

FIG. 23 shows a heatmap of TRB rearrangements in peripheral blood samples from a patient with Sezary syndrome in panel A. Panel B shows TF bias-corrected deviation enrichments in aggregated clonal T cells as compared to all other T cells. Shown is the TCR (TRA and TRB) sequence identified in the putative leukemic T cell clone (top). TF enrichments (bottom) were calculated as the difference in mean TF motif accessibility between aggregated leukemic T cell clone profiles and nonclonal T cell profiles in the same patient. Selected TF motifs that were enriched or depleted in the T cell clone are indicated. P values were calculated using a two-tailed t-test (n=139 cells, n=3 independent experiments).

Figure 24:
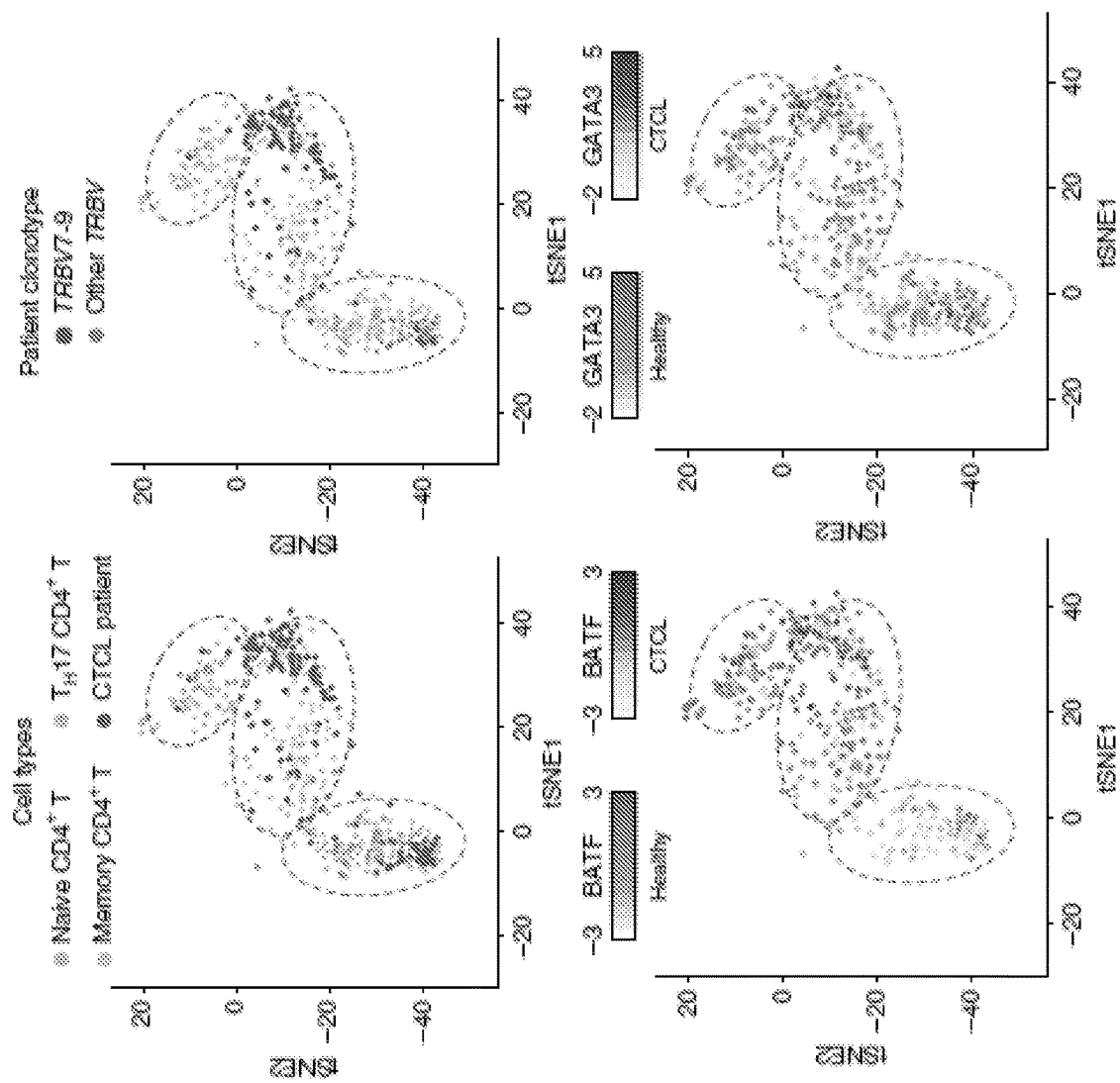
FIG. 24 shows a t-SNE projection of naive and memory T cells from healthy and diseased patient samples.

FIG. 24 t-SNE projection of naive and memory T cells from healthy individuals (n=320 cells, n=6 independent experiments) and patient cells (n=139 cells, n=3 independent experiments), as colored by cell ID, clonal versus non-clonal cells, BATF TF score and GATA3 TF score. Scale bars indicate range of TF z-scores.

Figure 25:
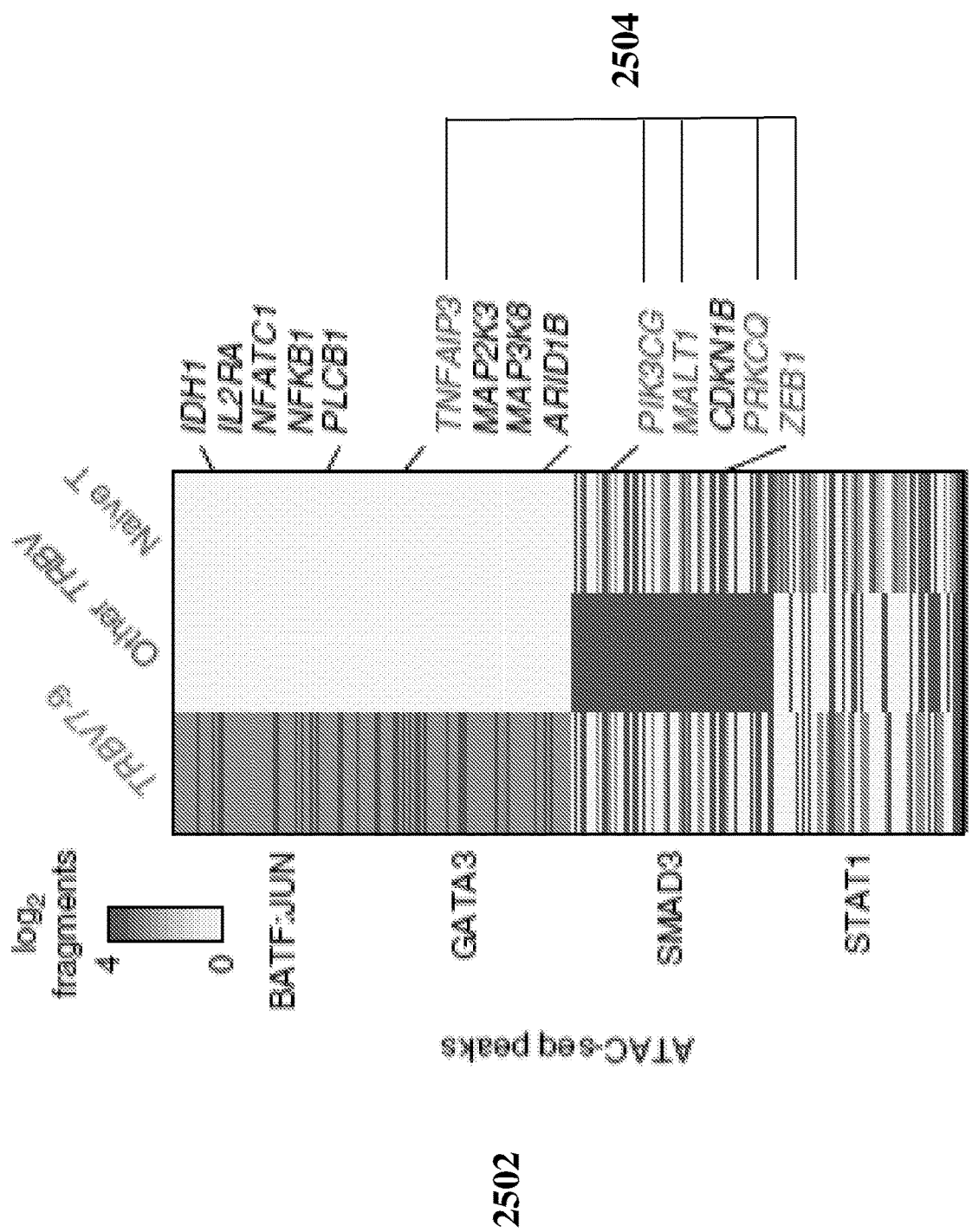
FIG. 25 shows a heat map of ATAC-seq fragment counts in peaks.

FIG. 25 shows a heat map of ATAC-seq fragment counts in peaks containing the indicated motifs 2502. Labels indicate genes associated with differential peaks, including genes previously shown to be mutated in individuals with CTCL 2504.

Figure 26:
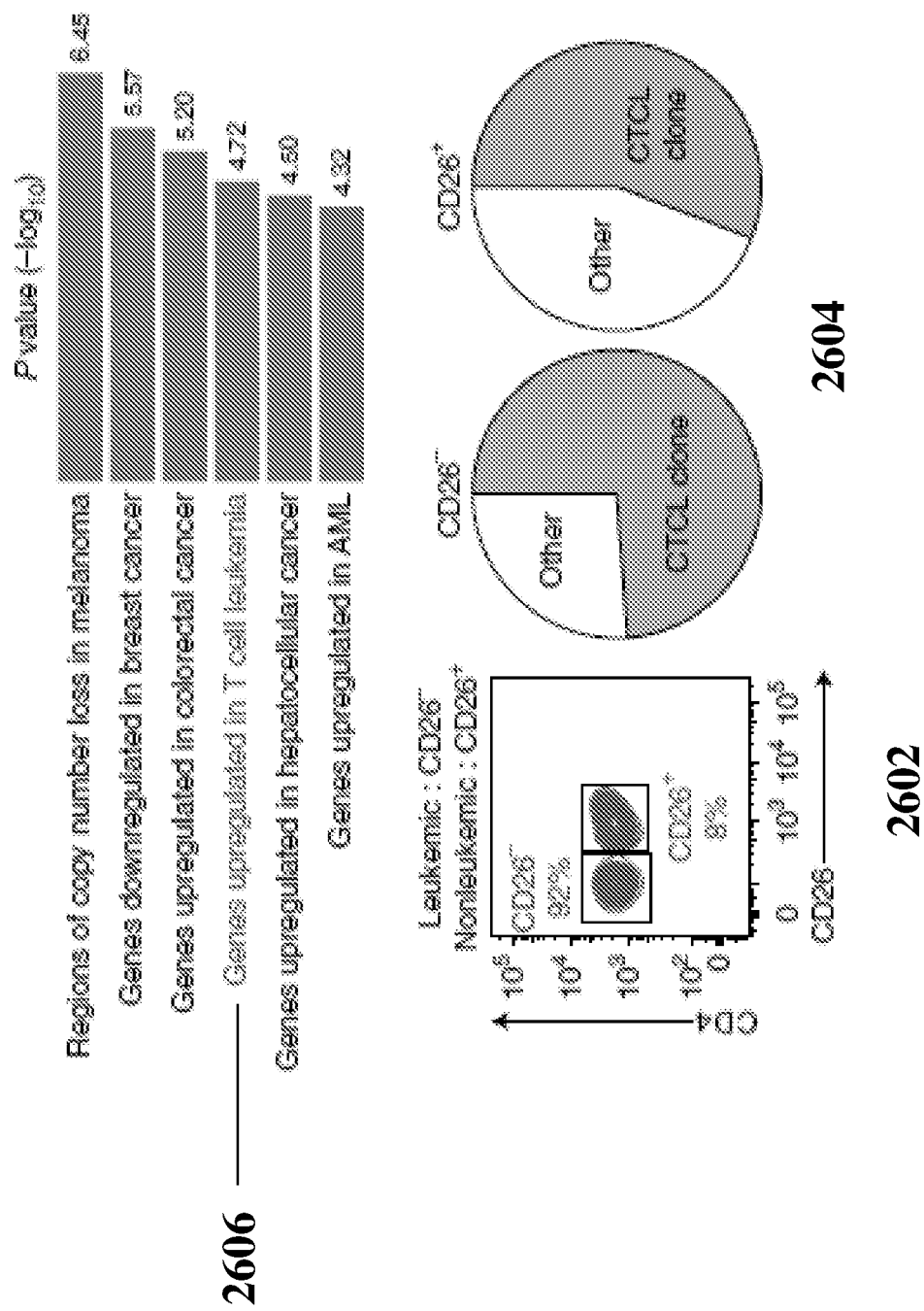
FIG. 26 shows MSigDB perturbation signatures of TRB7-9-specific ATAC-seq peaks, as obtained from GREAT analysis.

FIG. 26 shows MSigDB perturbation signatures of TRB7-9-specific ATAC-seq peaks, as obtained from GREAT analysis. Cells were sorted for CD26+ and CD26− CD4+ T cells 2602, and clonal TCR profiles in each population 2604. The lack of CD26 expression has been previously used to distinguish leukemic cells from non-leukemic cells. TF bias-corrected deviation enrichments in aggregated CD26− cells (n=56 single cells) relative to CD26+ cells (n=49 single cells). P values were calculated using a two-tailed t-test. TFs identified above the dashed line in FIG. 23B are labeled 2606.

Figure 27:
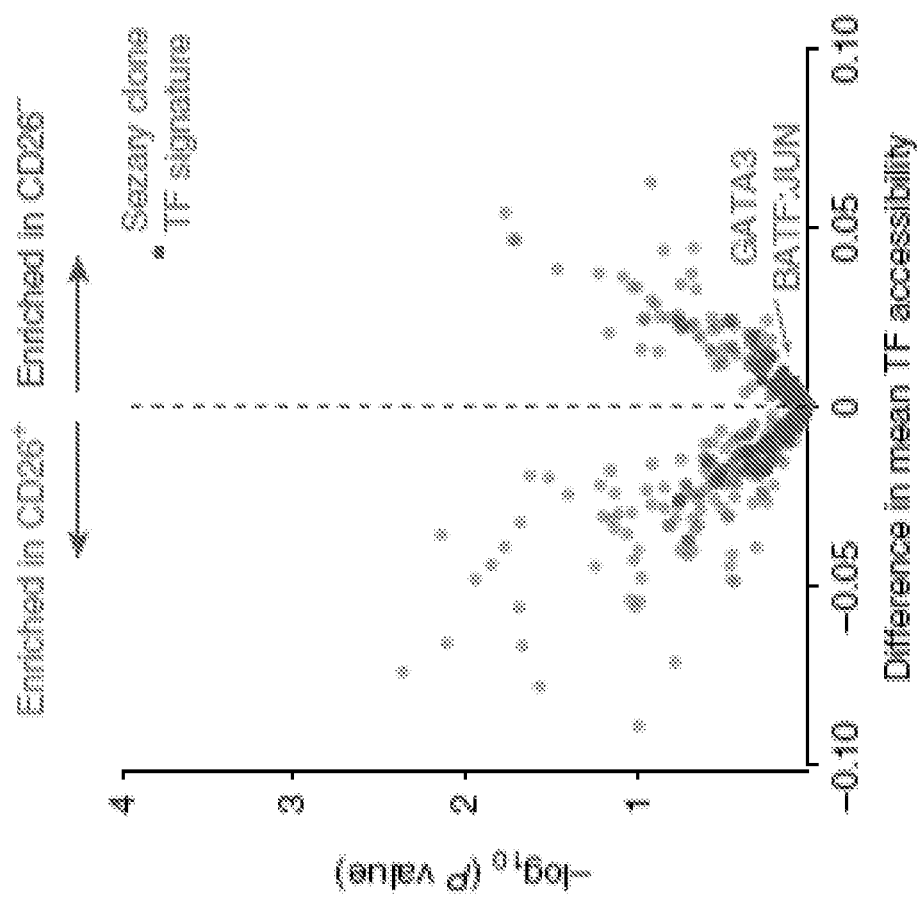
FIG. 27 shows TF bias-corrected deviation enrichments in aggregated CD26− cells relative to CD26+ cells.

FIG. 27 shows TF bias-corrected deviation enrichments in aggregated CD26− cells (n=56 single cells) relative to CD26+ cells (n=49 single cells). P values were calculated using a two-tailed t-test.

Figure 28:
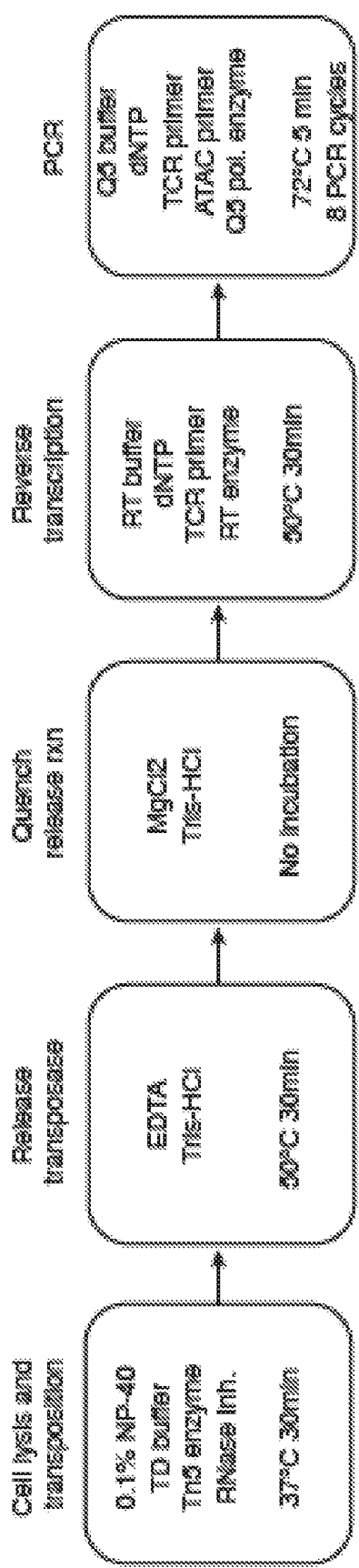
FIG. 28 shows the T-ATAC-seq protocol outlining biochemical reactions occurring in each microfluidic chamber in the IFC.

FIG. 28 shows the T-ATAC-seq protocol outlining biochemical reactions occurring in each microfluidic chamber in the IFC. Microfluidic chambers are indicated as boxes.

Figure 29:
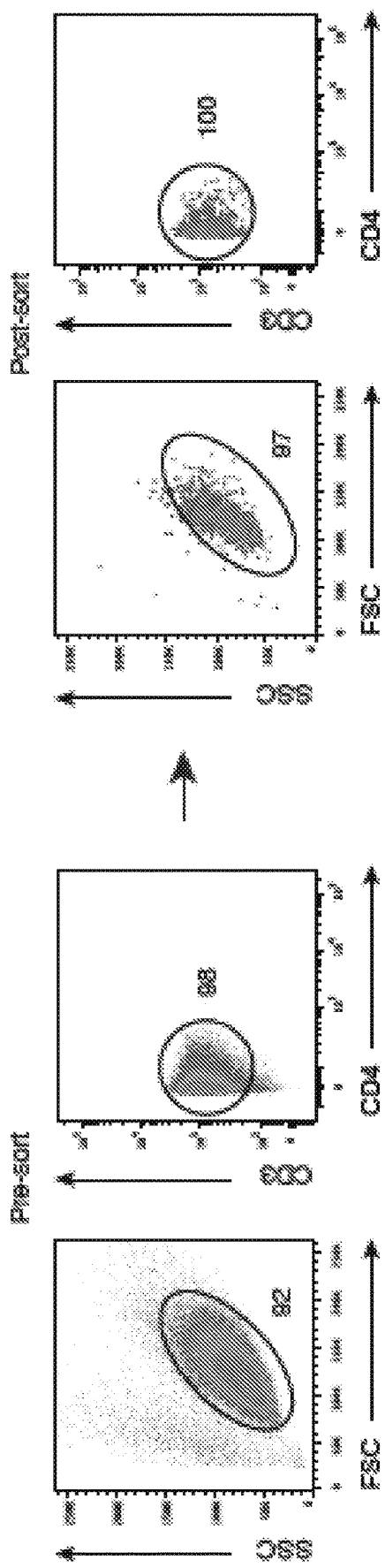
FIG. 29 shows a FACS analysis of Jurkat cells.

FIG. 29 FACS analysis of Jurkat cells pre-sort 2902 and post-sort 2904. Cells were sorted for single live cells prior to loading in the IFC. Numbers represent the percentage of cells within the indicated gate.

Figure 30:
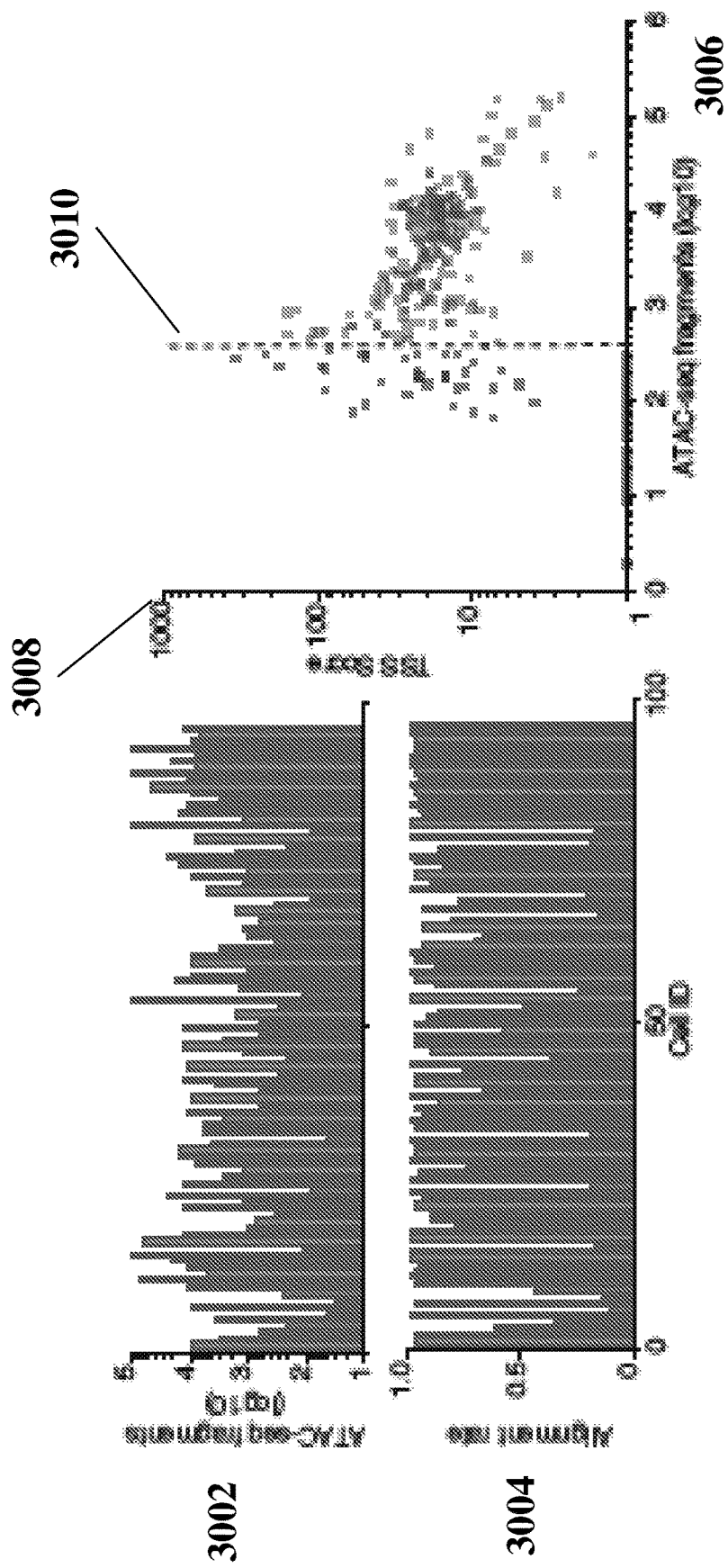
FIG. 30 shows ATAC-seq quality measurements for single Jurkat cells in a single experiment.

FIG. 30 shows ATAC-seq quality measurements for single Jurkat cells in a single experiment (96 cells). Plots show unique nuclear ATAC-seq fragments 3002 and read alignment rate 3004 for each single cell. Single cells from three independent T-ATAC-seq experiments on Jurkat cells are compared for ATAC-seq fragment number 3006 vs TSS enrichment rate 3008. Dashed line 3010 indicates quality filter of 500 unique nuclear fragments per cell.

Figure 31:
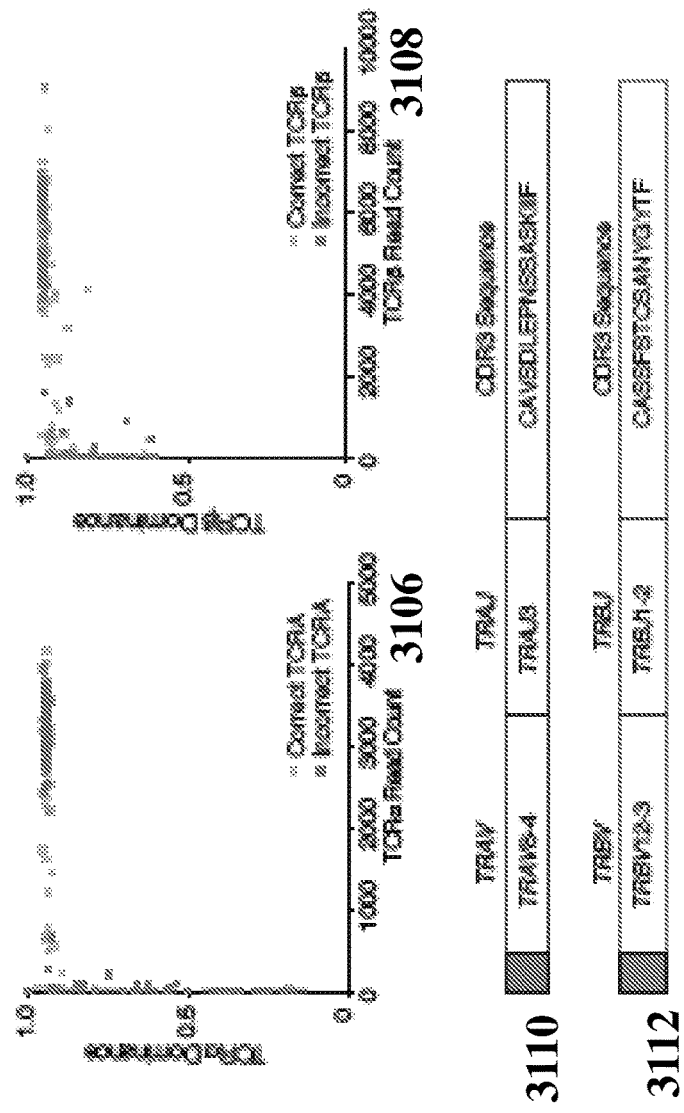
FIG. 31 shows a comparison of ATAC-seq fragments 3102 and TCR-seq paired-end reads in single Jurkat cells. Figure discloses SEQ ID NOS 18-19, respectively, in order of appearance.

FIG. 31 Panel A shows a comparison of ATAC-seq fragments 3102 and TCR-seq paired-end reads 3104 in single Jurkat cells from three individual T-ATAC-seq experiments. Dashed lines indicate quality filters of 500 unique nuclear fragments for ATAC-seq data and 100 reads for TCR-seq data. Panel B shows TCR-seq quality control measurements in Jurkat cells. Shown are TCRα reads 3106 or TCRβ reads 3108 in single cells and associated dominance of the major TCR clone. CDR3 sequences and gene usage of the Jurkat TCR are shown in the bottom panels 3110, 3112.

Figure 32:
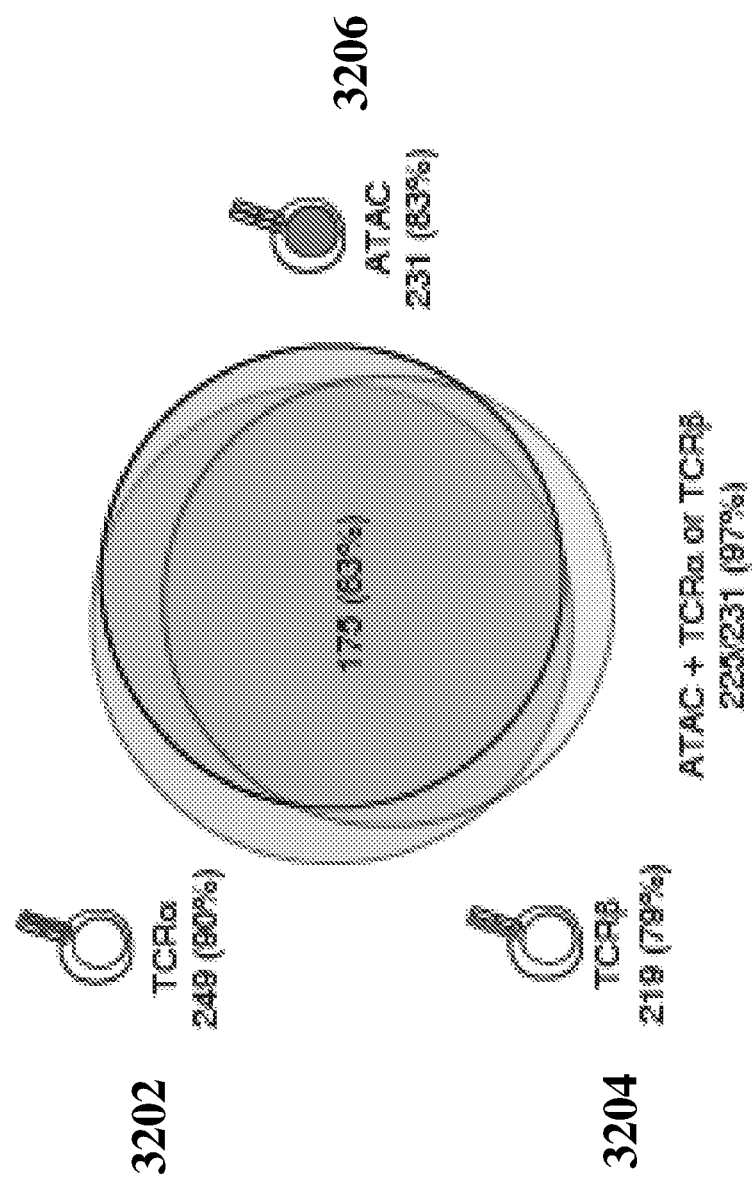
FIG. 32 shows overlap of single-cell TCR-seq and ATAC-seq data.

FIG. 32 Overlap of single-cell TCR-seq and ATAC-seq data in all cells in which TCRα 3202, TCRβ 3204, or ATAC 3206 sequence was obtained.

Figure 33:
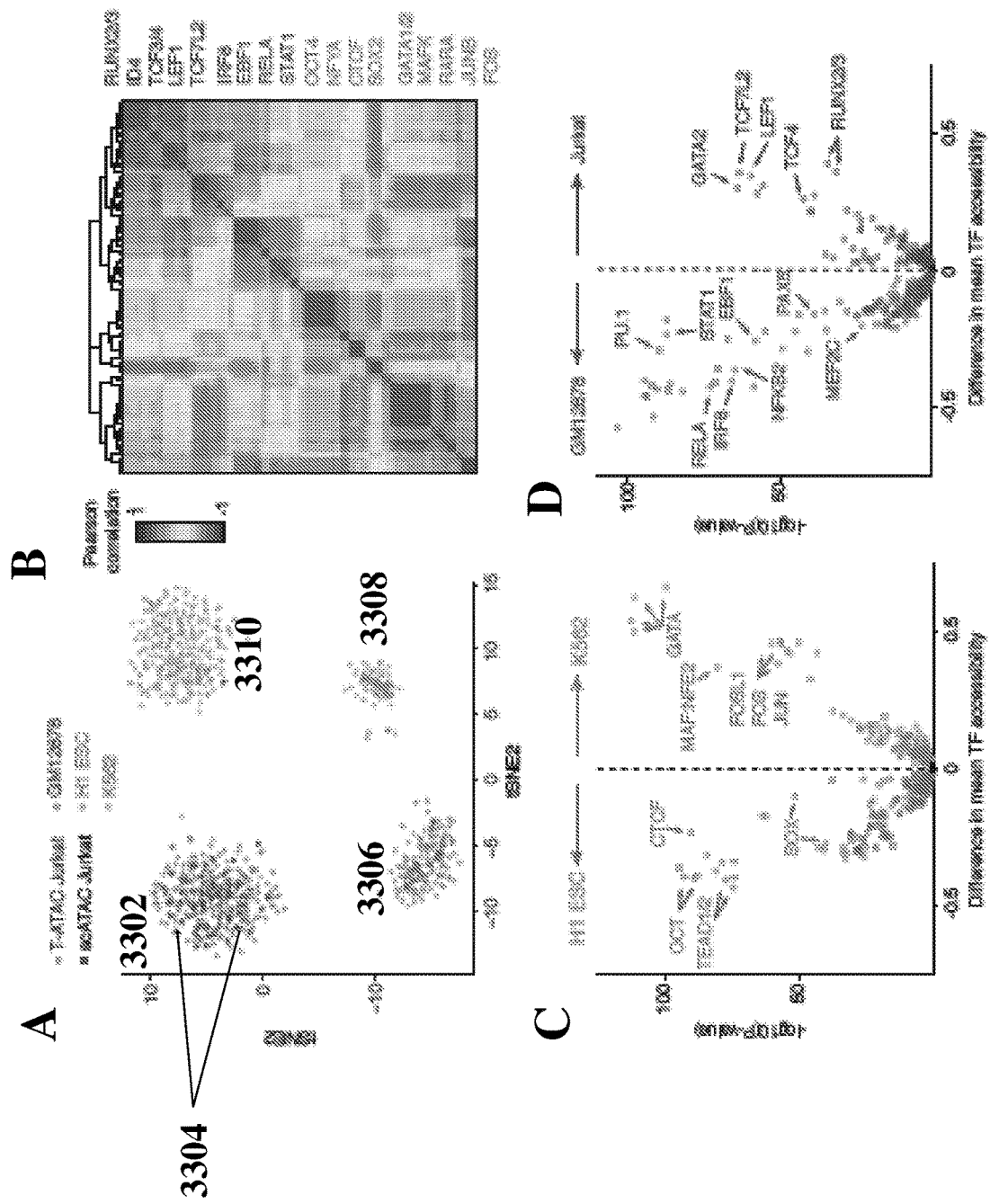
FIG. 33 Panel A shows t-SNE projection of T-ATAC-seq data from single Jurkat cells.

FIG. 33 Panel A shows t-SNE projection of T-ATAC-seq data 3302 from single Jurkat cells, scATAC-seq 3304 data from single Jurkat cells, and scATAC-seq data from previously published single GM12878 3306, H1 ESC 3308, and K562 cells 3310. Panel B shows Pearson correlation of TF deviation z-scores in single cells described in panel A. Panel C shows TF bias-corrected deviation enrichments in aggregated single-cell populations described in panel A. TF bias-corrected deviation enrichments in K562 cells compared to H1 ESCs and in Panel D, Jurkat cells compared to GM12878 cells. TF enrichments are calculated as the difference in mean TF motif accessibility between two populations of single cells. P-values were calculated using a two-tailed t-test.

Figure 34:
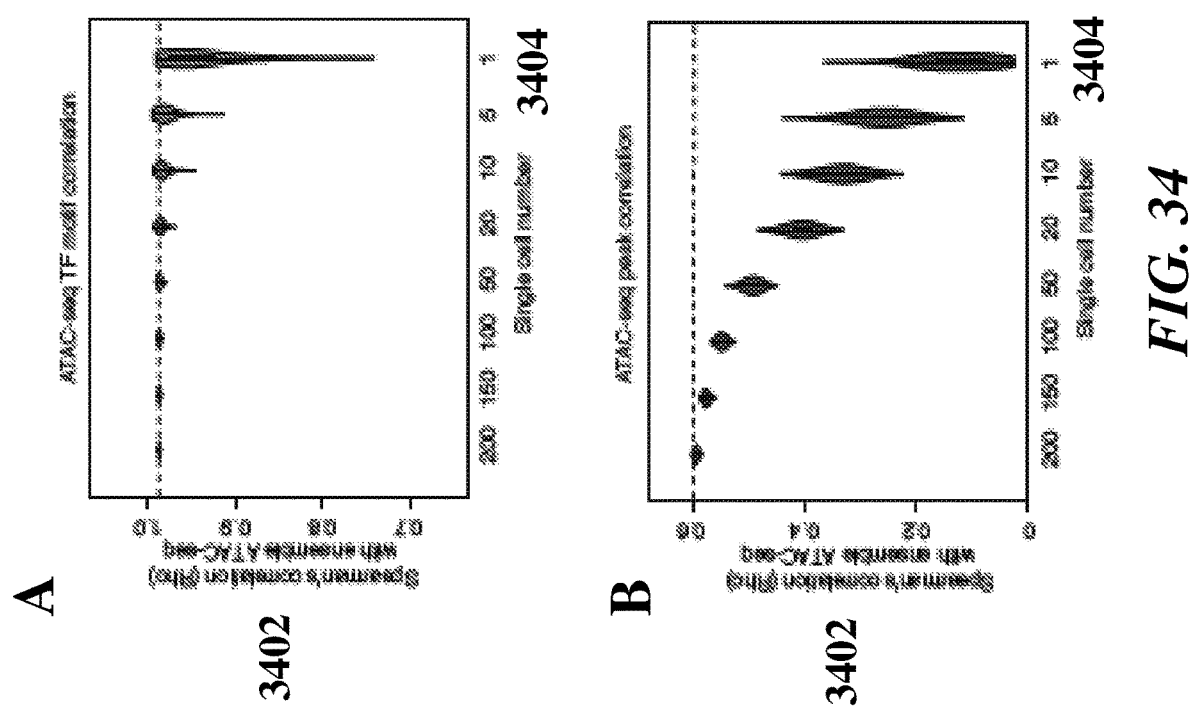
FIG. 34 shows plots of Spearman's correlation of TF z-score in ensemble ATAC-seq data in Jurkat cells compared to aggregated single cells.

FIG. 34 Panel A shows plots of Spearman's correlation 3402 of TF z-score in ensemble ATAC-seq data in Jurkat cells compared to aggregated single cells. The number of aggregated single cells 3404 in each comparison is noted on the x-axis. Cells were obtained from 3 independent experiments. Thick black boxes within the violin plots extend from the 25th to the 75th percentile, and boundaries of the violin are max and min values. Panel B shows Spearman's correlation of fragment counts in ATAC-seq peaks in ensemble ATAC-seq data in Jurkat cells compared to fragment counts in aggregated single cells. The number of aggregated single cells in each comparison is noted on the x-axis. Cells were obtained from 3 independent experiments. Thick black boxes within the violin plots extend from the 25th to the 75th percentile, and boundaries of the violin are max and min values.

Figure 35:
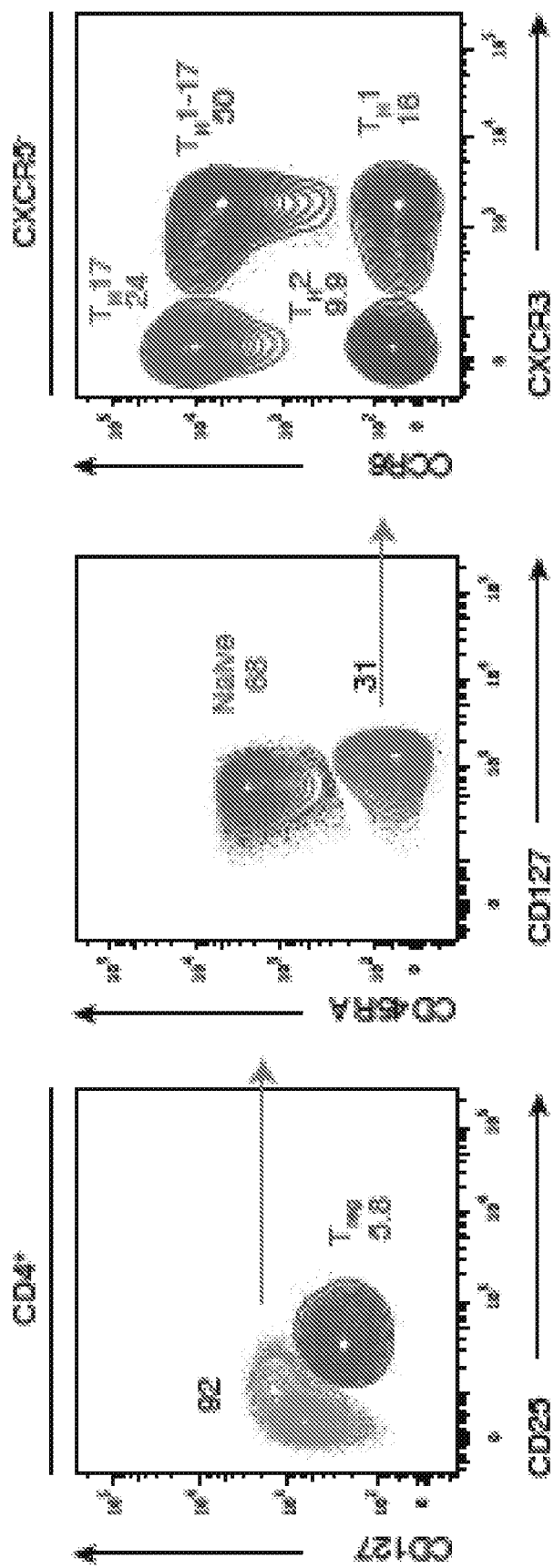
FIG. 35 shows histograms for live cells that are pre-gated.

FIG. 35 shows histograms for live cells that are pre-gated. Numbers represent the percentage of cells within the indicated gate.

Figure 36:
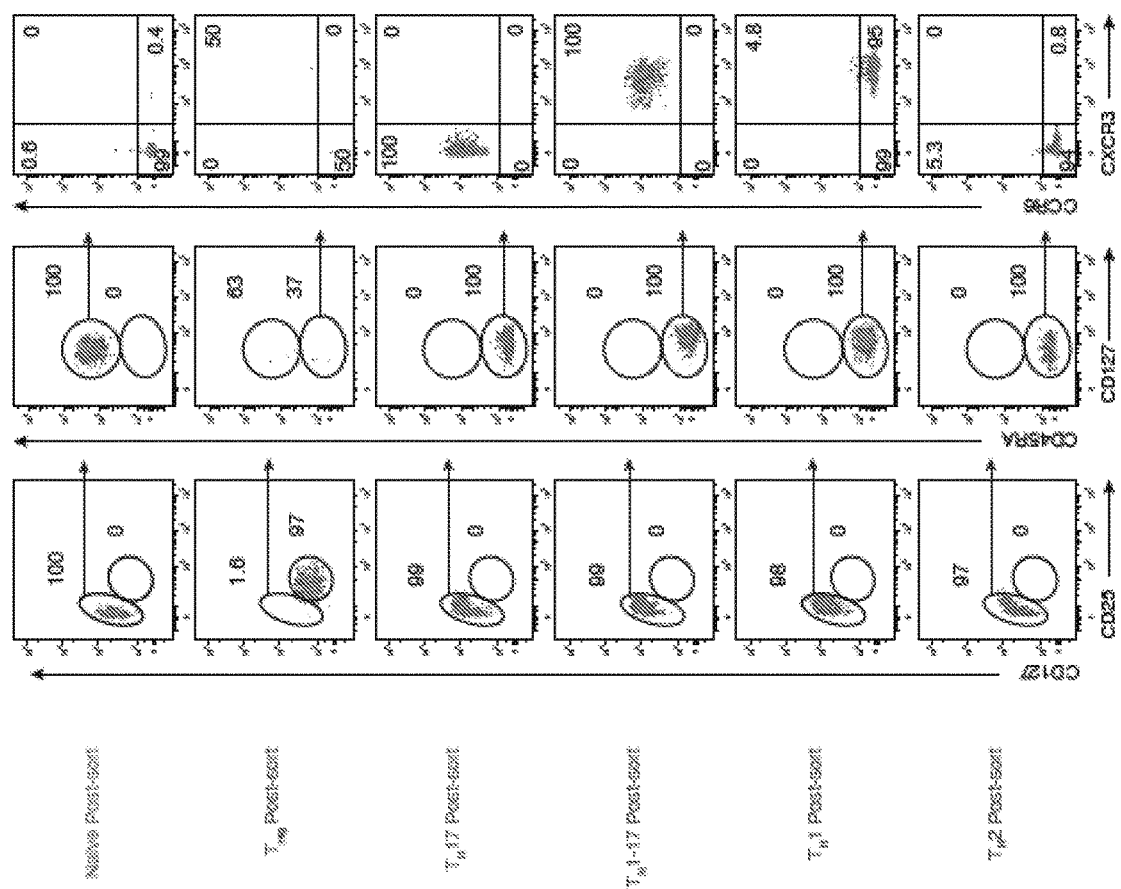
FIG. 36 show plots of post-sort purities for CD4+ T cell subtypes.

FIG. 36 show plots of post-sort purities for CD4+ T cell subtypes. Numbers represent the percentage of cells within the indicated gate.

Figure 37:
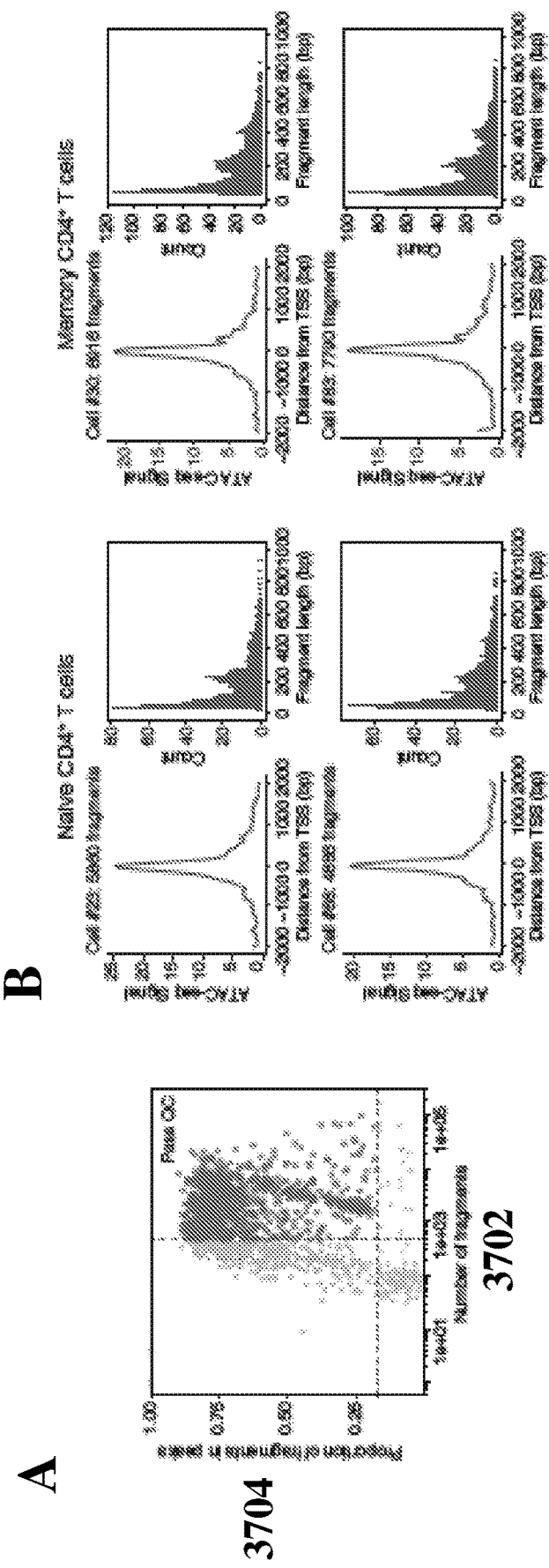
FIG. 37 shows T-ATAC-seq data quality control filters.

FIG. 37 shows T-ATAC-seq data quality control filters. Shown are the number of unique ATAC-seq nuclear fragments 3702 in each single primary T cell compared to the percentage of fragments in ATAC-seq peaks 3704 derived from ensemble T cell ATAC-seq data (panel A). Panel B shows individual single-cell profiles for four cells. Single cells show enrichment at transcription start sites (TSS) and nucleosomal periodicity of ATAC-seq fragment lengths. Fragment length indicates the genomic distance between two Tn5 insertion sites, as determined by paired-end sequencing of ATAC fragments.

Figure 38:
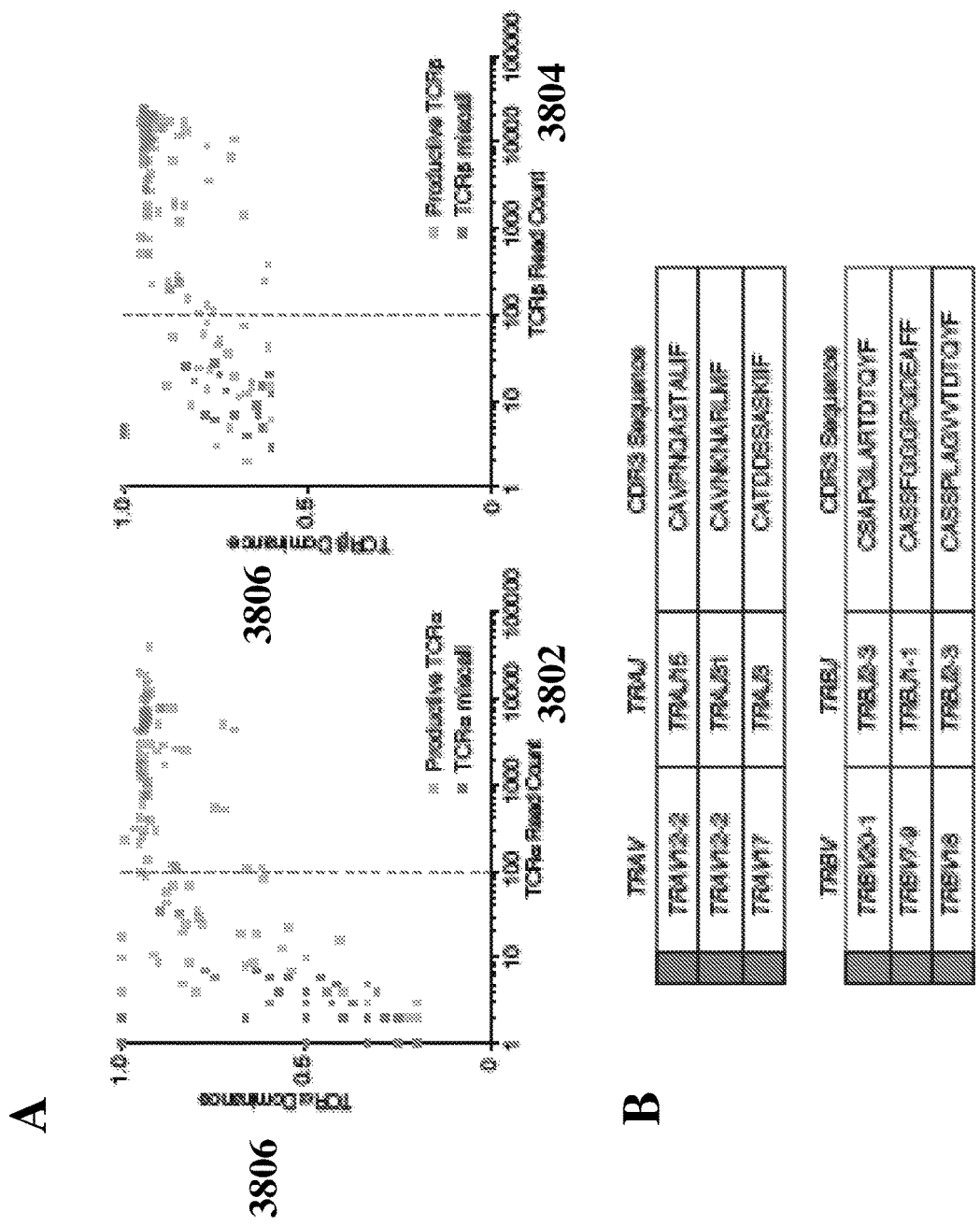
FIG. 38 shows a plot of quality measurements of TCR-seq profiles from T-ATAC-seq in single cells. Figure discloses SEQ ID NOS 1-6, respectively, in order of appearance.

FIG. 38 Panel A shows a plot of quality measurements of TCR-seq profiles from T-ATAC-seq in single cells. Shown are TCRα reads 3802 and TCRβ reads 3804 in each single cell compared to TCR read dominance 3806 in each cell. Panel B shows example sequences for productive TCR data are shown.

Figure 39:
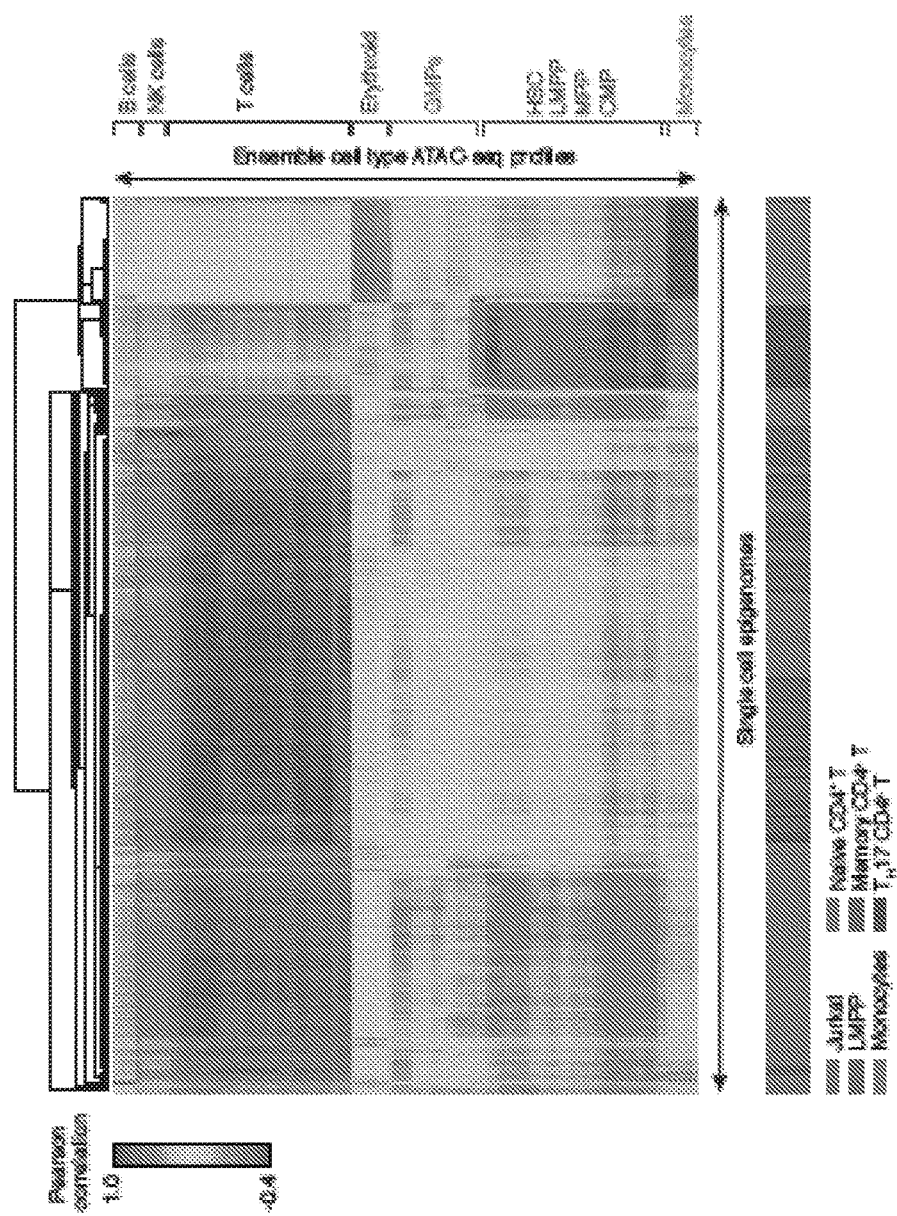
FIG. 39 shows Pearson correlation of PC scores of single cells and ensemble cells.

FIG. 39 shows Pearson correlation of PC scores of single cells (x-axis; 879 single cells) and ensemble cells (y-axis; 93 ensemble cell types). Ensemble cell types are derived from data generated in this study (T cell subtypes, 3 independent experiments) and from Corces et al. (2016) 9.

Figure 40:
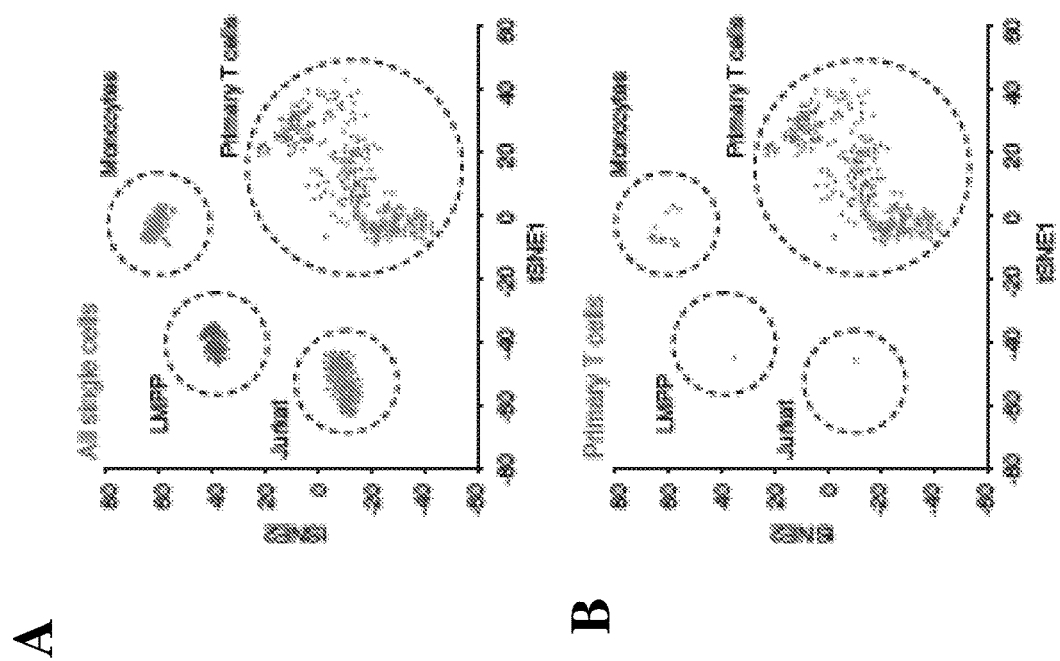
FIG. 40 shows t-SNE projection of PCA scores for all cells (panel A) or primary human T cells (panel B).

FIG. 40 shows t-SNE projection of PCA scores for all cells (panel A) or primary human T cells (panel B).

FIG. 41 Panel A shows a heat map of TF deviation z-scores for ensemble T cell ATAC-seq profiles. Panel B shows Ranked TF motif z-scores for each T cell subtype compared to the average TF z-score calculated in all other subtypes.

Figure 42:
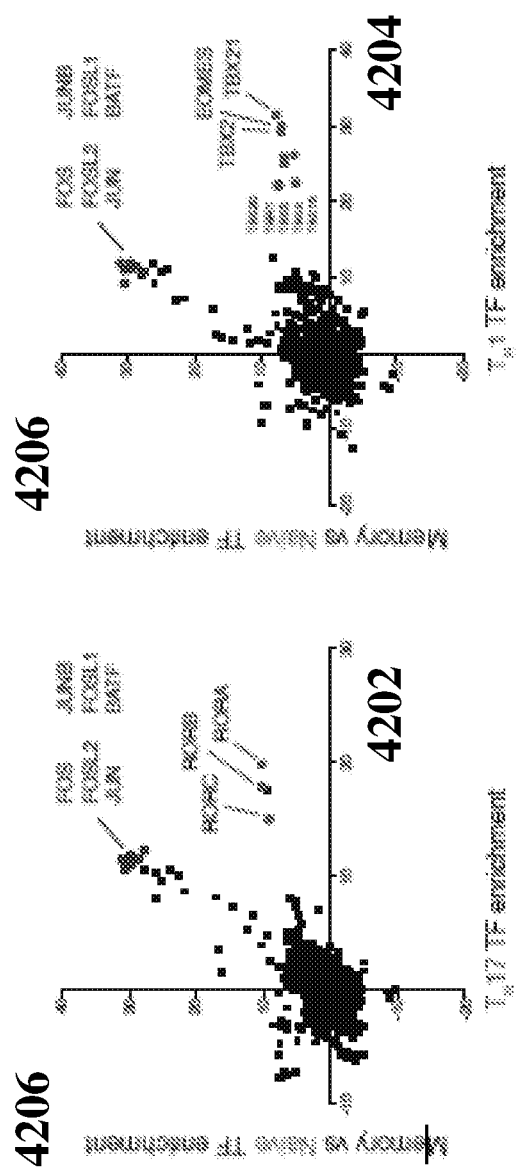
FIG. 42 shows a comparison of TF deviation z-score enrichment (mean difference) in cell subtypes.

FIG. 42 shows a comparison of TF deviation z-score enrichment (mean difference) in TH17 cells vs all other T cell subtypes 4202 and in TH1 cells vs all other T cell subtypes 4204. The enrichment of TFs in each subtype is compared to their enrichment in all T cell memory subtypes compared to naive cells 4206.

Figure 43:
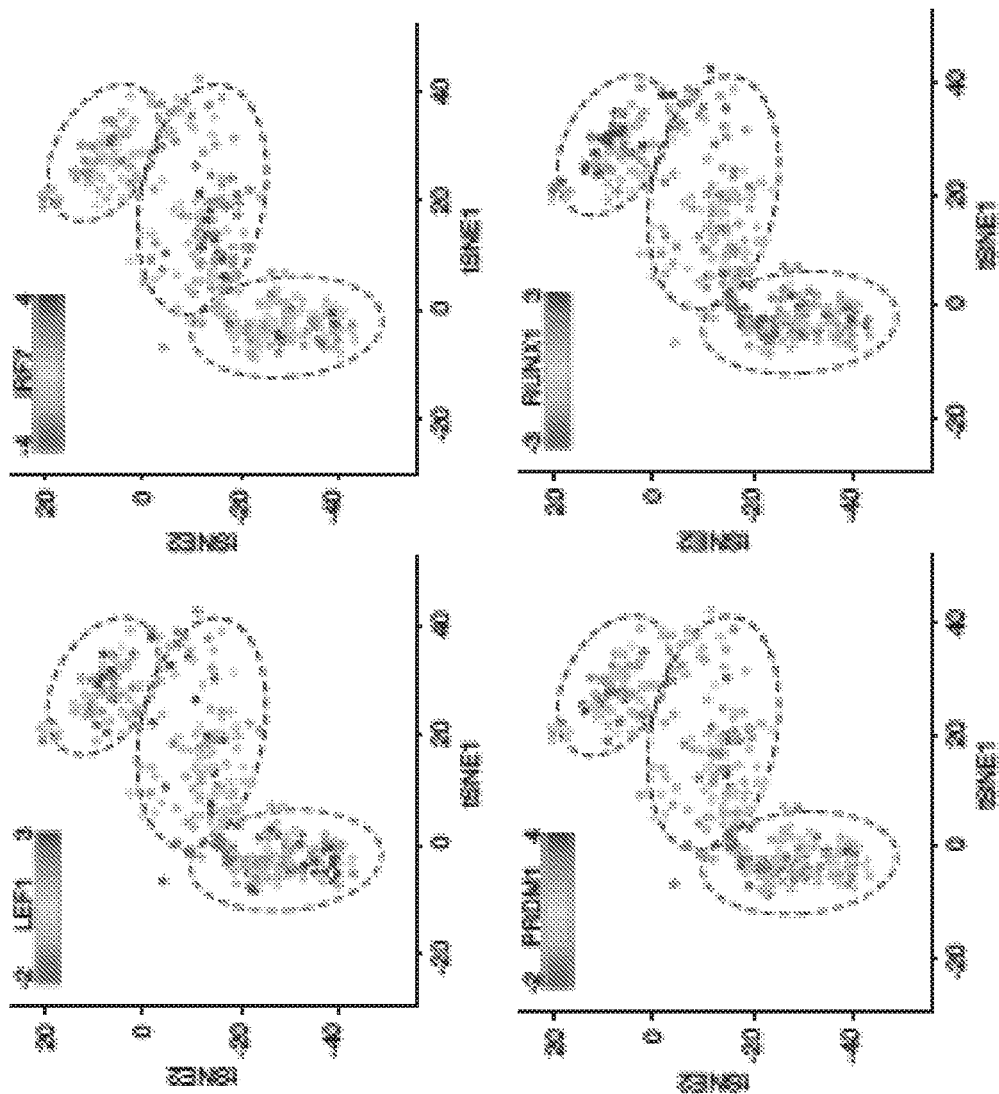
FIG. 43 shows a t-SNE projection of sorted single cell subtypes.

FIG. 43 shows a t-SNE projection of sorted single naïve, memory, and TH17 T cells. Cells are colored by LEF1, IRF7, PRDM1, and RUNX1 motif accessibility TF scores. Scale bars indicate range of TF z-scores.

Figure 44:
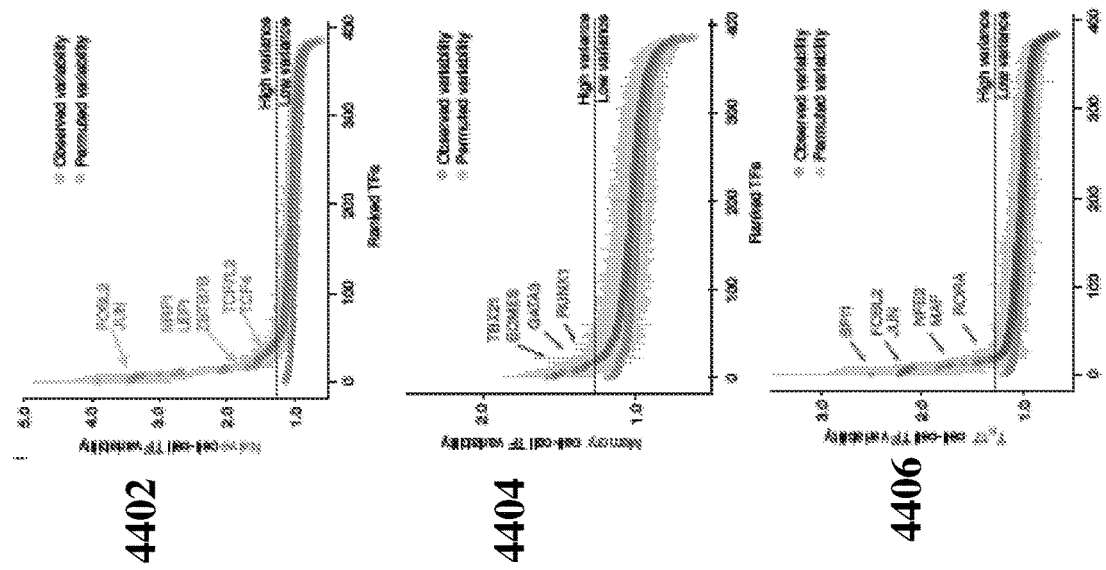
FIG. 44 shows cell-to-cell variability of TF motif accessibility in cell subtypes.

FIG. 44 show cell-to-cell variability of TF motif accessibility in single naive 4402, memory 4404 and $T_H17$ 4406 cells. Shown is the observed TF variability in sorted T cell populations and error estimates (gray shading). Variability measured from a permuted background is shown in gray dots for comparison (see Methods for details of background calculations). Selected high variance TFs are indicated by arrows.

Figure 45:
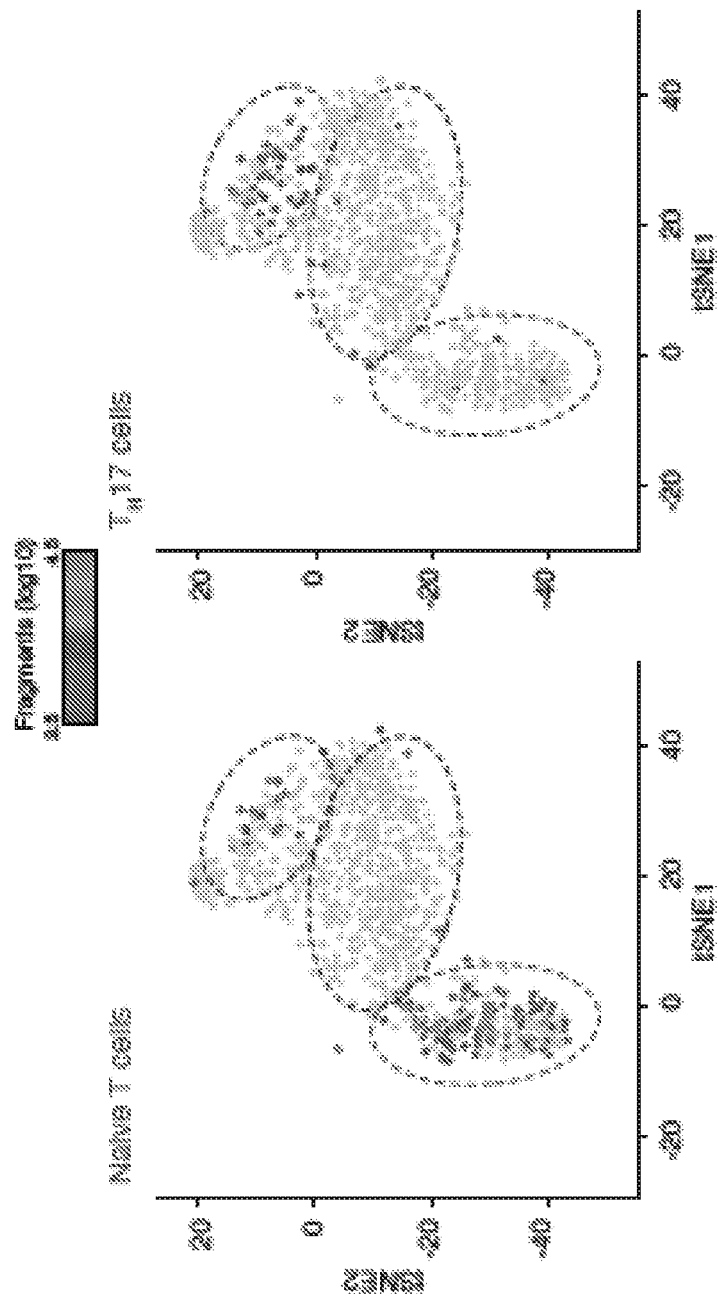
FIG. 45 shows a t-SNE projection of single T cells.

FIG. 45 shows a t-SNE projection of single T cells. Naive T cells (left) or TH17 cells (right) are shaded by the number of unique nuclear ATAC-seq fragments obtained in that cell. Light gray cells are additional populations of T cells (including Memory T and CTCL cells). These plots demonstrate that distinct clusters of naive T cells are not a byproduct of differences in ATAC-seq fragments obtained per cell. Highlighted cells were obtained from 2 independent experiments for each subtype.

Figure 46:
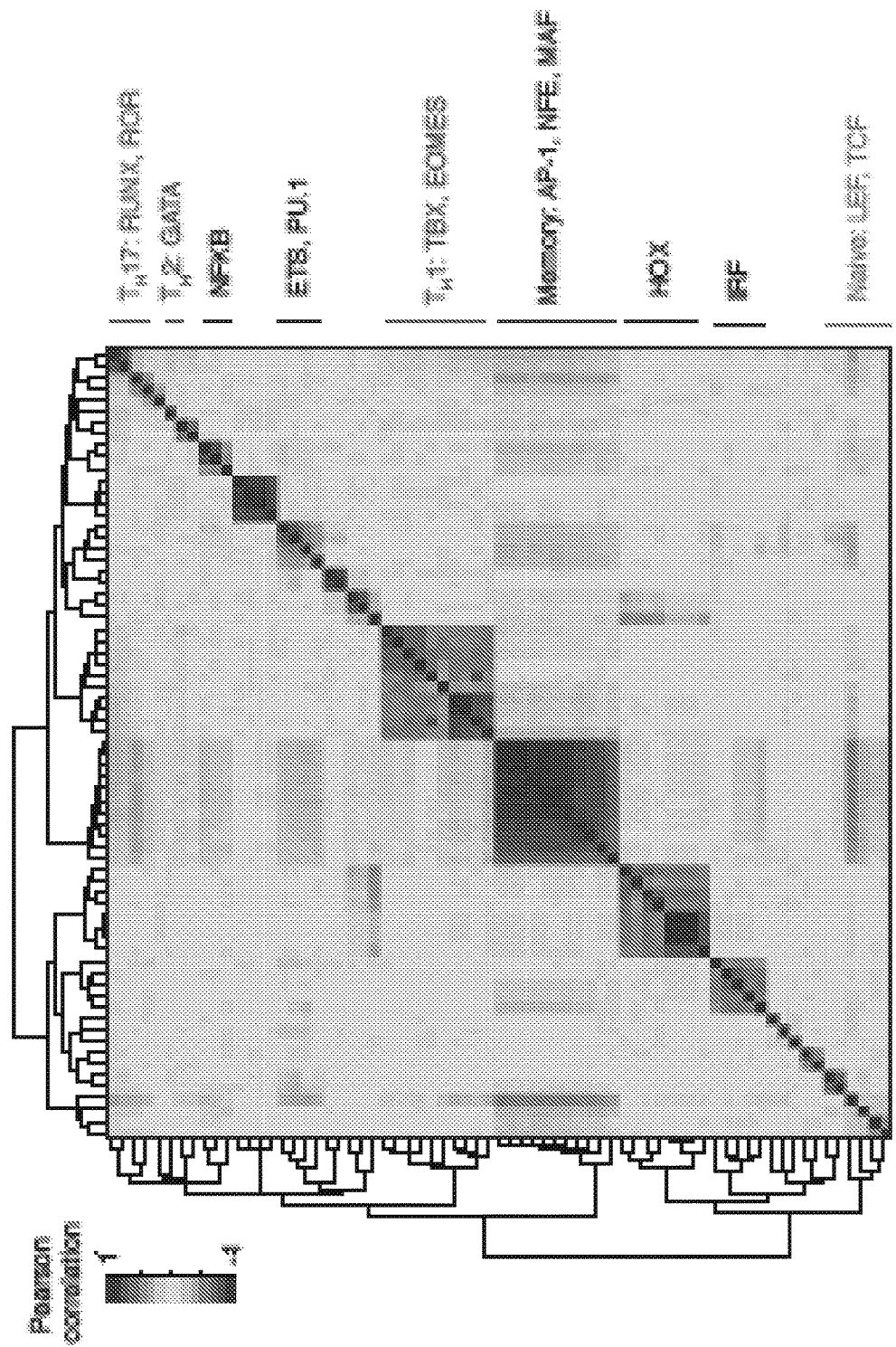
FIG. 46 shows a Pearson correlation of TF deviation z-scores for single naive, memory, and TH17 cells.

FIG. 46 shows a Pearson correlation of TF deviation z-scores for single naive, memory, and TH17 cells. TF modules associated with canonical T helper cell phenotypes are indicated on the right.

Figure 47:
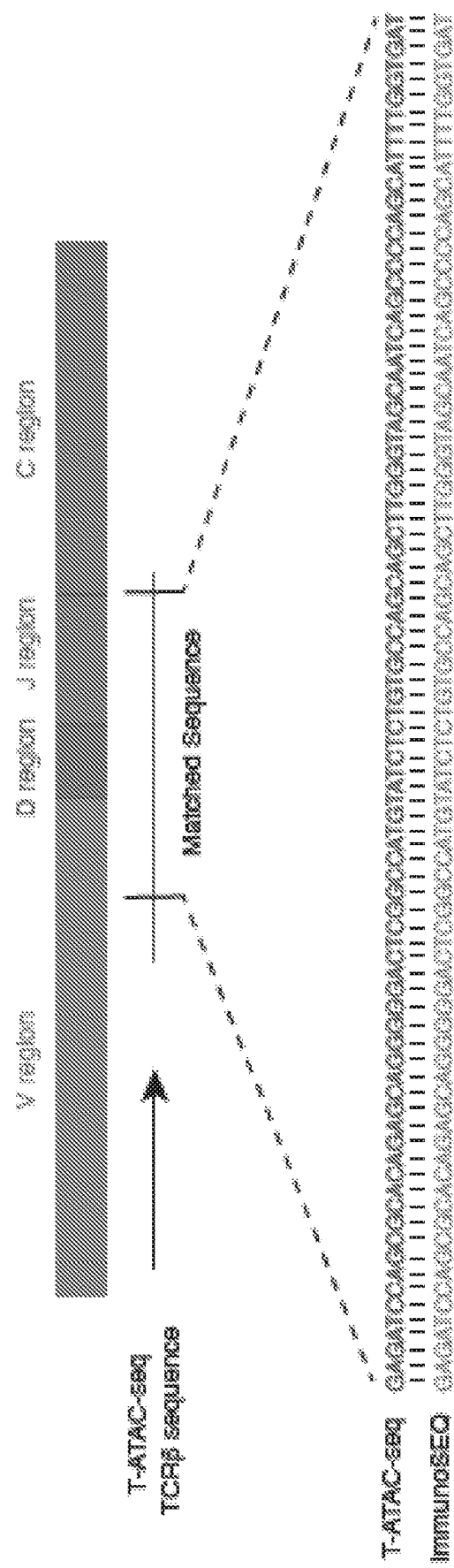
FIG. 47 shows confirmation of TCRβ sequence obtained in clonal CTCL cells using T-ATAC-seq with immunoSEQ profiling. Figure discloses SEQ ID NOS 7 and 7, respectively in order of appearance.

FIG. 47 shows confirmation of TCRβ sequence obtained in clonal CTCL cells using T-ATAC-seq with immunoSEQ profiling from the same sample (Adaptive Biotechnologies).

Figure 48:
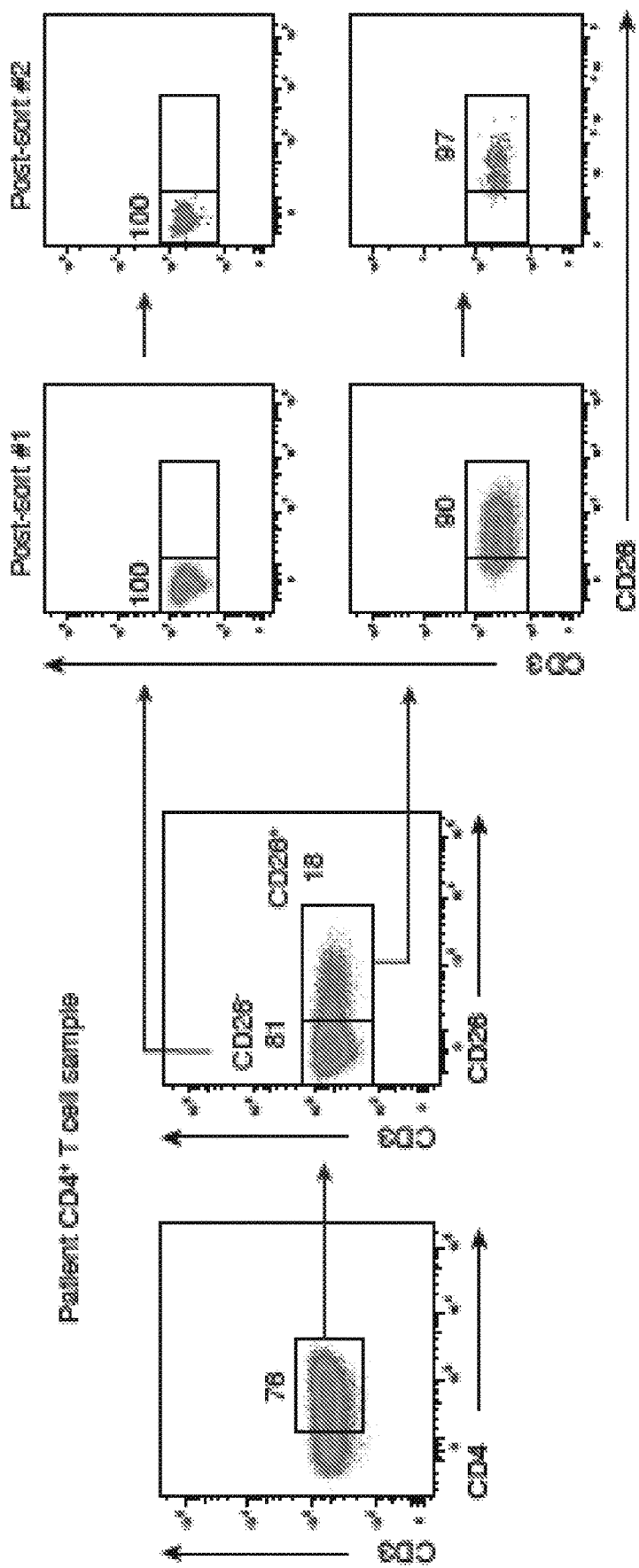
FIG. 48 shows representative FACS strategy and post-sort purities for CD26+ and CD26− CTCL cells.

FIG. 48 shows representative FACS strategy and post-sort purities for CD26+ and CD26− CTCL cells. Peripheral CD4+ blood cells were stained for expression of the indicated markers. Numbers represent the percentage of cells within the indicated gate. Cells were double-sorted to ensure high purity of the desired populations. Data are representative of 3 independent experiments. (c) Expanded TCR clones are present in CD26+ and CD26− CD4+ T cell populations in CTCL patients #2 and #3.

Figure 49:
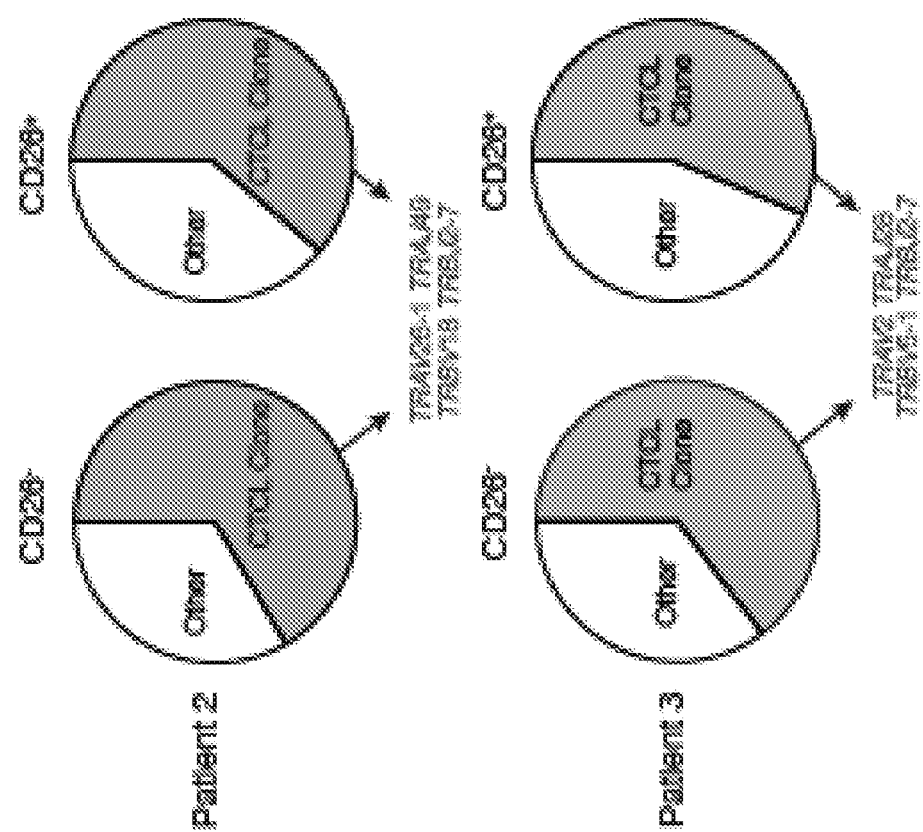
FIG. 49 shows expanded TCR clones are present in CD26+ and CD26− CD4+ T cell populations in CTCL patients #2 and #3.

FIG. 49 shows expanded TCR clones are present in CD26+ and CD26− CD4+ T cell populations in CTCL patients #2 and #3.

Figure 50:
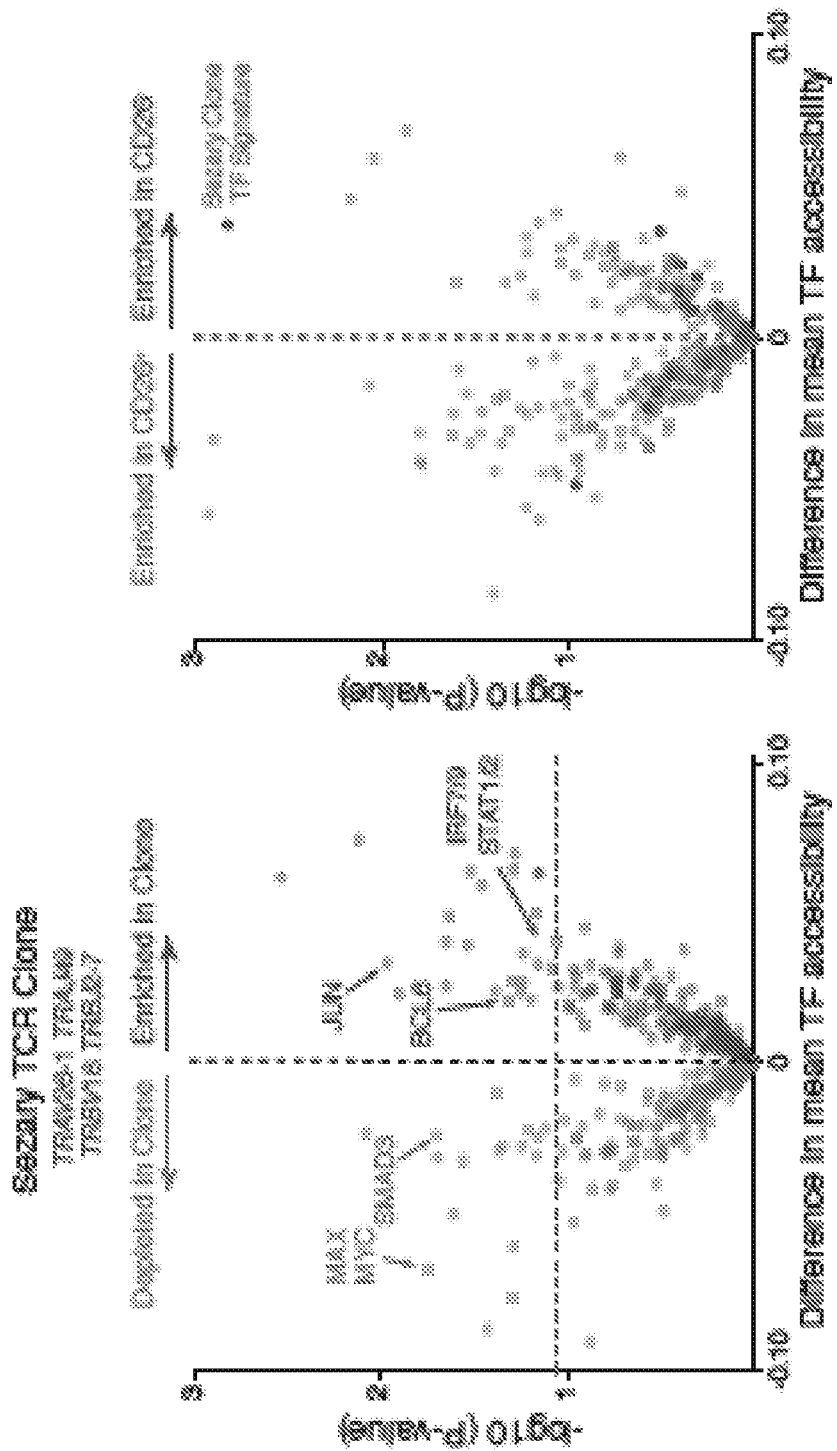
FIG. 50 shows TF bias-corrected deviation enrichments in aggregated clonal T cells compared to all other T cells.

FIG. 50 TF bias-corrected deviation enrichments in aggregated clonal T cells from patient #2 compared to all other T cells (left). TF deviations enrichments in aggregated clonal cells are not enriched in CD26− cells compared to CD26+ cells (right).

Figure 51:
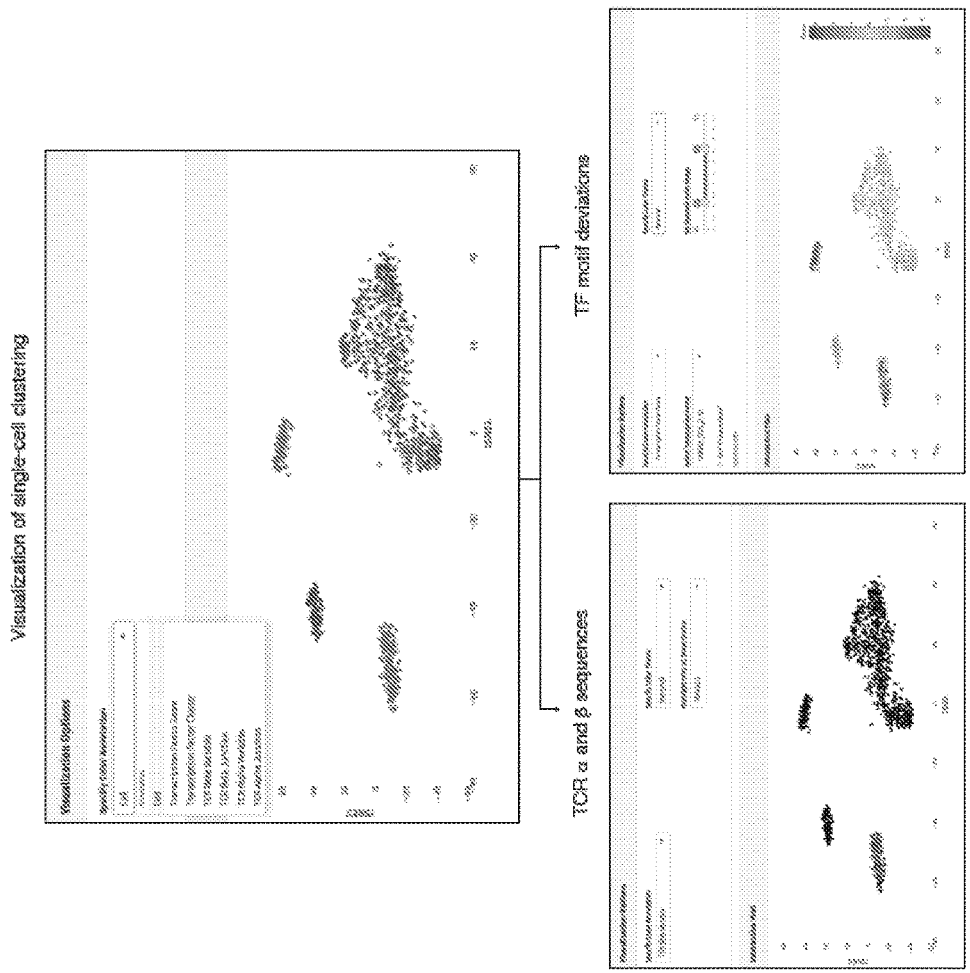
FIG. 51 shows browser screenshot from tcr.buenrostro-lab.com software showing drop-down menu options to navigate single-cell TF deviation scores and TCR sequences.

FIG. 51 Panel A shows browser screenshot from tcr.buenrostrolab.com showing drop-down menu options to navigate single-cell TF deviation scores and TCR sequences. Panel B shows example screenshots showing single cells with TRBV12-3 identity (left) and colored by TCF4 TF deviation z-score (right).

Figure 52:
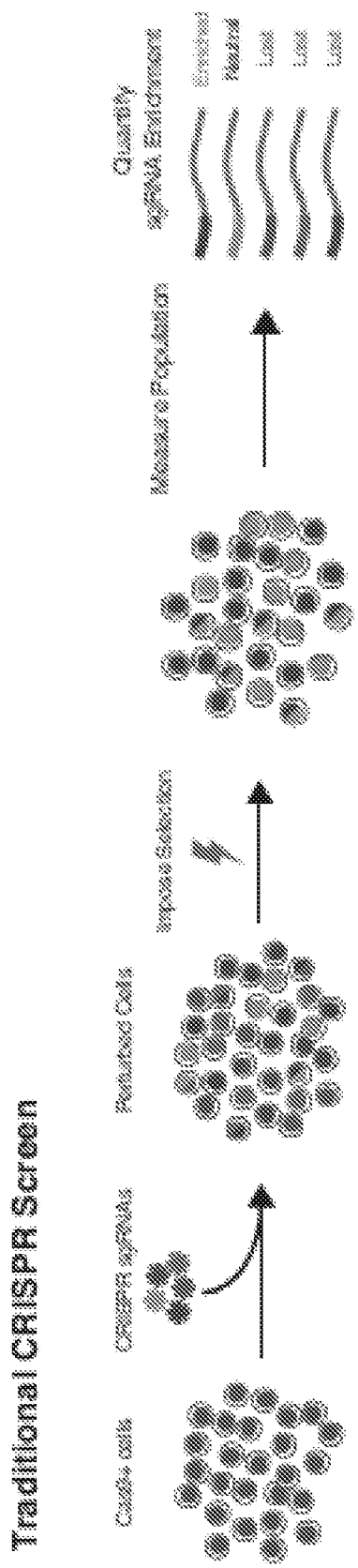
FIG. 52 shows a schematic describing traditional Clustered Regularly Interspaced Short Palindromic Repeats (CRISPR) screens.

FIG. 52 shows a schematic describing traditional CRISPR screens.

Perturbation-Indexed Single-Cell ATAC-Seq (Perturb-ATAC-Seg)

Another aspect of the present disclosure provides systems, methods, and compositions for high-throughput, simultaneous measurement of CRISPR perturbations and chromatin state in single cells. The methods and systems described herein can combine ATAC-seq and perturbation sequencing (Perturb-seq), and/or respective aspects thereof. Such methods may generally be referred to herein as Perturbation-indexed Assay for Transposase Accessible Chromatin using Sequencing (Perturb-ATAC-seq or Perturb-ATAC). In some cases, Perturb-ATAC is employed, wherein a cell sample comprising one or more cells is perturbed by introduction of CRISPR guide RNAs and then profiled for simultaneous detection of CRISPR guide RNAs and open chromatin sites by ATAC-seq. Beneficially, Perturb-ATAC may reveal regulatory factors that control epigenomic state. In some cases, Perturb-ATAC may reveal regulatory factors that control cis-element accessibility and/or trans-factor occupancy. In some cases, Perturb-ATAC may reveal nucleosome positioning. In some cases, Perturb-ATAC may reveal regulatory modules of coordinated activity in a cell type, e.g., coordinated trans-factor activities, synergistic activities of co-binding TFs on cis-elements, etc. In some cases, Perturb-ATAC is performed in a high-throughput manner, and single cell data, including epigenomic variability, may be obtained.

In some embodiments, select perturbations (i.e., CRISPR inhibition) are applied to a cell or population of cells. In other embodiments, unbiased perturbation may be performed to uncover distinct trans-factor activities that occur during a biological process such as cell differentiation, metastasis, migration, etc. A global analysis of perturbed factors and their corresponding target regions may reveal a inter-connected network of regulation that yields information otherwise not accessible from single-target perturbations.

Perturb-ATAC may be used to infer a variety of genotype-phenotype relationships. In some cases, Perturb-ATAC is applied to transcription factors. Perturb-ATAC may also be applied to, in non-limiting examples, chromatin-modifying factors, and noncoding RNAs. Combinations of factors may be assayed using Perturb-ATAC.

In some cases, Perturb-ATAC may be used to uncover hierarchical organization of TFs that govern cell behavior. For example, cell state, cell variation, cell fate, cell pathology (e.g., disease-associated cis-regulatory elements), epistatic relationships of TFs, genomic co-localization of TFs, and/or synergistic and/or inhibitory interactions of TFs may be inferred from Perturb-ATAC. Gene regulatory networks in development and disease may also be analyzed using Perturb-ATAC. In some cases, Perturb-ATAC may uncover epigenetic interactions that establish gene expression patterns that underlie development, differentiation, cell-cell and/or cell-matrix interactions, and cell-environmental responses. In some cases, Perturb-ATAC may be used to identify gene targets, gene signatures, transcription factors, regulatory factors, and/or cell states that are impacted by perturbations to a given cell and/or drive distinct cell states.

Provided are methods for processing cells. The method may comprise capturing a cell, wherein the cell comprises genomic deoxyribonucleic acid (gDNA) and guide ribonucleic acid (gRNA) molecules, or gRNA identifying barcodes thereof, contacting accessible gDNA from the cell with a transposase to generate tagged gDNA fragments in a tagmentation reaction, and generating complementary DNA (cDNA) molecules from the gRNA molecules, or gRNA identifying barcodes thereof.

The cell may be any type of cell described herein. For example, the cell may be an immune cell, as described elsewhere herein. The cell may not be an immune cell. While some methods described herein describe the processing of B cells, with reference to Perturb-ATAC, it will be appreciated that the methods may be applicable to, and/or adapted for, other types of cells, including other immune cells and non-immune cells. The cell can be from any source, as described elsewhere herein.

In some instances, the cell may be isolated and/or captured from a plurality of cells. In some instances, the cell may be one of a subset of cells isolated and/or captured from the plurality of cells. The isolation and/or capturing can be in one or more stages. For example, in a stage, a plurality of cells may be sorted for types of cells. In a next stage, a sub-type of a type of cell may be isolated. In some instances, the isolation can comprise magnetic cell sorting. In some instances, the isolation can comprise flow cytometry sorting. For example, such methods may be used to sort between at least two or more of the following types of cells: stem cells, cancer stem cells, blood cells, T cells, dendritic cells, NK cells, precursor cells, granulocytes, platelets, erythrocytes, endothelial cells, epithelial cells, or subsets thereof. Subsets of cells can be further isolated using antibodies for cell surface markers.

In some embodiments, cells are pre-sorted based on a transduced marker prior to analysis (e.g., t-ATAC-seq, Perturb-ATAC) by FACS or MACS. For example, cells may be transduced with a fluorescent protein (e.g., GFP, YFP, CFP, mCherry, mRuby, etc.). In some cases, the fluorescent protein may be transduced with a sgRNA cassette. Selection for cells expressing the sgRNA cassette may be done by a pre-sorting mechanism. In some cases, one or more selection markers may be used. For example, cells may be transduced with a drug-resistance (e.g., puromycin, blasticidin resistance) gene to select for the sgRNA vector.

The plurality of cells may comprise any number of cells, e.g., about 500 to about $10^6$ or more cells, about 500 to about 100,000 cells, about 500 to about 50,000 cells, about 500 to about 10,000 cells, about 50 to 1000 cells, about 1 to 500 cells, about 1 to 100 cells, about 1 to 50 cells, or a single cell. In some cases, the plurality of cells can consist of less than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells. In other cases, the plurality of cells can comprise of more than about 1000, about 2000, about 3000, about 4000, about 5000, about 6000, about 7000, about 8000, about 9000, about 10,000, about 15,000, about 20,000, about 25,000, about 30,000, about 40,000, about 50,000, about 60,000, about 70,000, about 80,000, about 90,000, about 100,000, about 120,000, about 140,000, about 160,000, about 180,000, about 200,000, about 250,000, about 300,000, about 350,000, about 400,000, about 450,000, about 500,000, about 600,000, about 700,000, about 800,000, about 900,000, or about 1,000,000 cells.

The capturing of the cell may comprise partitioning the cell in a partition. A partition may be any partition described elsewhere herein, such as a chamber, well, microwell, or droplet. The partition may contain the cell within a set of defined boundaries (closed or partially closed), and/or distinguish a space or volume inside the partition from other partitions or any space or volume external to the partition. In some instances, the partition may prevent its contents from escaping the partition under one or more conditions. In some instances, the partition may prevent external objects from entering the partition under one or more conditions. The partition may be an individual partition, such as an individual well or individual chamber or individual droplet. The partition may be one of a plurality of partitions, such as in an integral device, such as a fluidic chip.

Methods for ATAC-seq can generally be performed on the partitioned cell, such as according to one or more methods described elsewhere herein, to generate tagged gDNA fragments.

After generating the tagged gDNA fragments, and prior to initiating a reverse transcription reaction using the gRNA molecules, the tagmentation reaction may be inhibited or quenched, such as using magnesium chloride, or otherwise terminated. In some instances, the tagmenting operation can comprise using a detergent, an insertional enzyme complex (e.g., a transposase complex), and a divalent metal ion to the cell. In some instances, the detergent can be a non-ionic surfactant, e.g., an ethoxylated nonylphenol such as NP-40. In some instances, the terminating can be done by chelating the divalent metal ion required by the insertional enzyme complex (e.g., a transposase complex), thereby terminating the reaction and releasing the insertional enzyme complex (e.g., the transposase complex) from the tagged DNA. In some instances, the chelating can be done by ethylenediamine tetraacetic acid (EDTA), nitriloacetic acid (NTA), or diethylenetriamine pentaacetic acid (DTPA), or other chelating agents. The termination can be facilitated by any other reaction terminator. The tagmentation reaction (and/or termination thereof) and reverse transcription reaction may happen in the same partition or in different partitions.

After the chromatin has been fragmented and tagged to produce tagged fragments of genomic DNA, at least some of the adaptor tagged fragments, or derivatives thereof (e.g., amplicons) may be sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLID platform) or Life Technologies' Ion Torrent platform. Examples of such methods are described in the following references: Margulies et al (Nature 2005 437:376-80); Ronaghi et al (Analytical Biochemistry 1996 242:84-9); Shendure et al (Science 2005 309:1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, methods for library preparation, reagents, and final products for each of the steps. Forward and reverse sequencing primer sites that are compatible with a selected next generation sequencing platform can be added to the ends of the fragments during an amplification step.

The tagged gDNA fragments may be amplified using primers (e.g., polymerase chain reaction (PCR) primers). In some instances, the primers may hybridize to one or more adapter sequences in the tagged gDNA fragments. In some instances, the primer used for PCR can have 5' tails that are compatible with a particular sequencing platform. In certain cases, the primers used may comprise a cell-specific barcode sequence so that different pools (e.g., of amplicons) can be pooled together before sequencing, and the sequence reads can be traced to a particular sample using the cell-specific barcode sequence.

ATAC-Seq, and/or aspects thereof, may be performed in conjunction with Perturb-seq, and/or aspects thereof. For example, after the tagmentation reaction is quenched or otherwise terminated, the gRNA molecules may be subject to reverse transcription reaction to generate cDNA molecules. The method may comprise using primers and reverse transcriptase to generate the cDNA molecules.

Perturbations to cells may be achieved by transducing cells with a Perturb-ATAC vector, i.e., Clustered Regularly Interspaced Short Palindromic Repeats (CRISPR) guide RNAs (gRNAs, also referred to as single gRNAs (sgRNAs) as used herein). gRNAs may be designed per target gene and may target a different region between the transcriptional start side and the gene body. The vectors may be cloned, amplified, and assembled into a lentiviral vector. gRNA sequences may be sequenced to confirm the identity. Generation of gRNAs are known, and described in, for example Adamson, B. et al., A Multiplexed Single-Cell CRISPR Screening Platform Enables Systematic Dissection of the Unfolded Protein Response. 167 Cell 1867-82.e21 (2016); and S. W. Cho et al. *Promoter of lncRNA Gene PVT1 Is a Tumor-Suppressor DNA Boundary Element*, 173 Cell 1398-1412.e22 (2018), each of which is entirely incorporated herein by reference.

A barcode may be added to a gRNA vector. The barcode may be a gRNA-identifying barcode that comprises a barcode sequence. Such barcode sequence may correspond to the identity of a gRNAs encoded by the vector, e.g., for identification of gRNAs in individual cells after mixing populations of gRNA-targeted cells for high-throughput analysis. The barcode sequence may be any length. For example, the barcode sequence can have a length of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30 or more basepairs (bp). Alternatively or in addition, the barcode sequence can have a length of at most about 60, 50, 40, 30, 20, 10 or fewer bp. In some cases, non-human-genome-targeting gRNAs may be transduced in a subset of the cells. In some cases, cells may be transduced to stably express dCas9-KRAB along with one or more gRNAs. Cells may then be pooled post-transduction for Perturb-ATAC analysis. In some cases, the fidelity of pairing barcode detection with the measurement of epigenetic phenotypes may be assessed.

The gRNA molecule may be attached to a barcode. The barcode may comprise a barcode sequence that may identify the identity of the gRNA molecule it is attached to. Each gRNA having a different target sequence may have a unique barcode sequence as between other gRNAs having different target sequences. In some instances, the gRNA molecules may comprise a target sequence that is configured to target a sequence associated with a transcription factor, a chromatin modifier, noncoding RNA, or other complex. In some instances, the gRNA molecules introduced in the cell may comprise the same target sequence. In other instances, the gRNA molecules introduced in the cell may comprise different target sequences. For example, a first gRNA molecule may comprise a first target sequence, and a second gRNA molecule may comprise a second target sequence.

After introduction of the gRNAs into the cell, the cell may be subjected to lysis and DNA transposition using a transposase (e.g., Tn5). Following transposition, Tn5 may be released from the open chromatin fragments, and CRISPR guide RNAs (gRNAs) or gRNA-identifying barcodes thereof may be subjected to reverse transcription. Reverse transcription may be performed on the gRNA (e.g., directly) and/or the gRNA-identifying barcode thereof to generate cDNA molecules. Reverse transcription may be performed on the gRNA and/or the gRNA-identifying barcode thereof to generate cDNA molecules. Sequencing reads generated from cDNA generated from the gRNA-identifying barcodes may be processed against a known list or table of gRNA-identifying barcodes. Sequencing reads generated from cDNA generated directly from the gRNAs may be processed against may be processed against a known list or table of gRNA (e.g., sequences thereof). Such methods may be used, for example, where the vector construct used does not include gRNA-identifying barcodes. The reverse transcription may be performed using primer sequences targeting sequences flanking (or otherwise adjacent to) the gRNA or the gRNA-identifying barcode, respectively.

Figure 92:
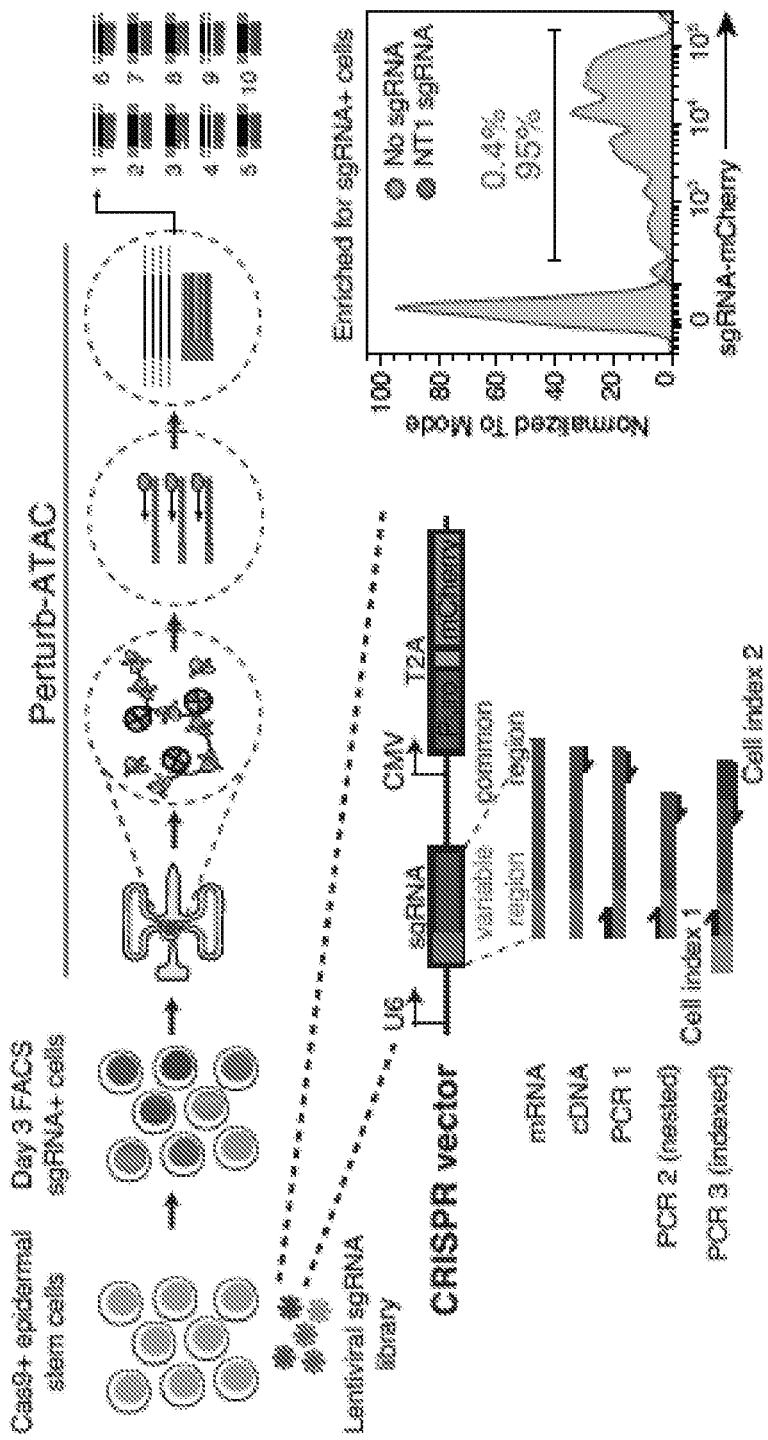
FIG. 92 shows a schematic of sgRNA expression vector and library amplification for direct sequencing readout of guide RNA identity.

For example, where reverse transcription is performed on the gRNA directly, reverse transcription may be performed using a reverse primer that matches the common 3' end of the gRNA. After, the ATAC-seq fragments may be extended. Contents of the chamber may then be amplified by PCR. In some cases, the PCR amplification may comprise forward primers that match the variable 5' ends of the gRNAs used in the experiment. Single-cell libraries may then be collected and gRNA and/or ATAC amplicons may be further amplified with cell-identifying barcoded primers, pooled, and sequenced. FIG. 92, for example, shows a schematic of a sgRNA expression vector and library amplification for the direct sequencing readout of guide RNA identity. As shown in FIG. 92, a cDNA may be generated from a mRNA molecule comprising the variable region and the common region of the gRNA, where the reverse transcription reaction uses a reverse primer corresponding to the common 3' end of the gRNA. Then, during PCR amplification (e.g., "PCR 1"), forward primers that correspond to the variable 5' ends of the gRNAs can be used. Further extension reactions (e.g., via polymerase chain reaction (PCR)) can be performed (e.g., "PCR 2"; "PCR 3"), such as to generate derivative products comprising cell-identifying barcode sequences.

Figure 55:
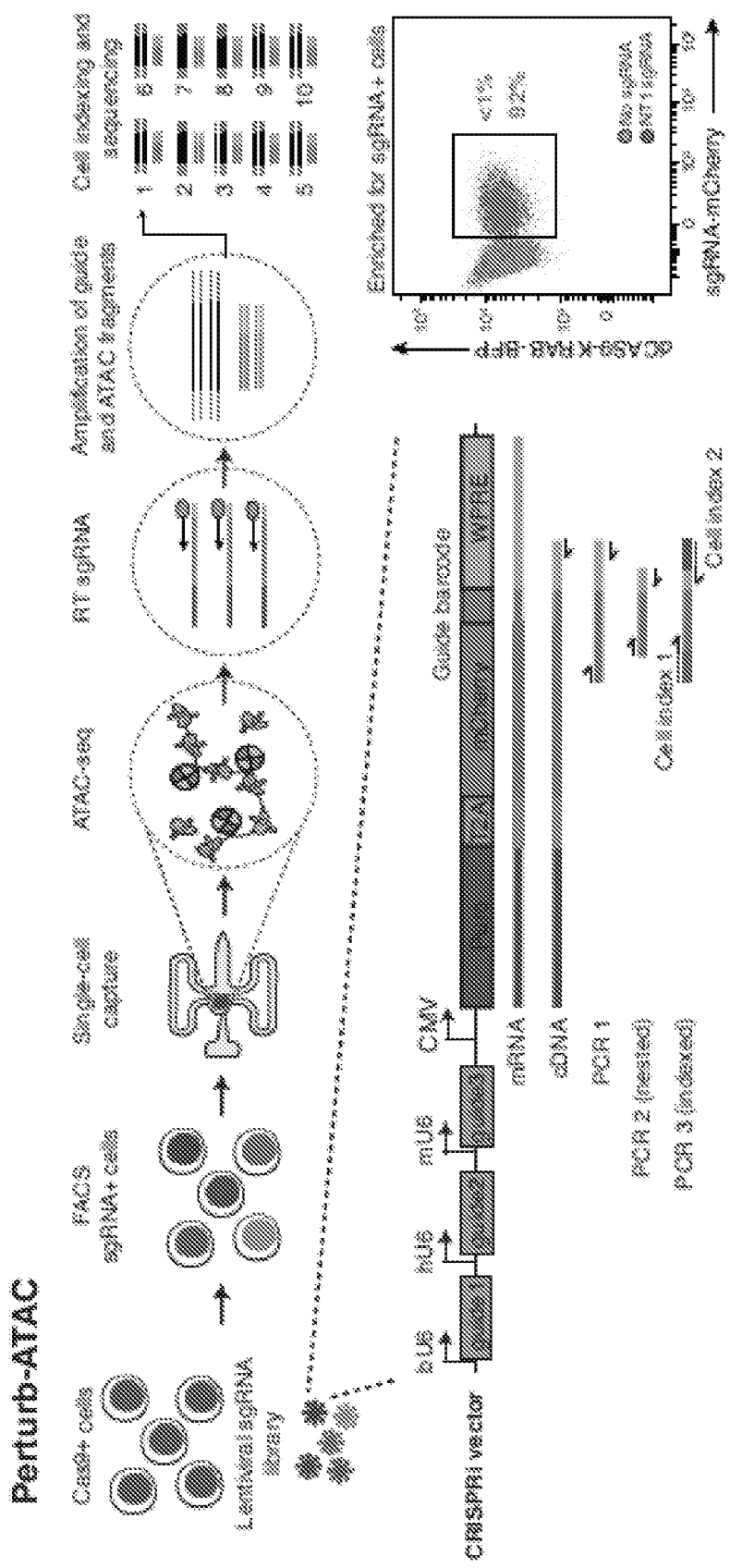
FIG. 55 shows a schematic of Perturb-ATAC protocol, lentiviral construct, and generation of sequencing library for guide RNA detection.

In another example, where reverse transcription is performed on the gRNA-identifying barcode, the primers used in the reverse transcription reaction can correspond to (and/or be targeted to) sequences flanking the gRNA-identifying barcode. FIG. 55, for example, shows a schematic for generating sequencing reads corresponding to the gRNA-identifying barcode. As shown in FIG. 55, a cDNA may be generated from a mRNA molecule comprising the gRNA-identifying barcode, where the reverse transcription reaction uses a primer targeted to a sequence flanking the 3' end of the barcode. Then, during PCR amplification (e.g., "PCR 1"), forward primers that correspond to a sequence flanking the 5' end of the barcode can be used. Further extension reactions (e.g., via PCR) can be performed (e.g., "PCR 2"; "PCR 3"), such as to generate derivative products comprising cell-identifying barcode sequences.

The cDNA (e.g., from the gRNA and/or the gRNA identifying barcode thereof) and/or the tagged gDNA fragments may be amplified in a PCR reaction, for example by contacting them with a plurality of primers and a polymerase to generate cDNA molecule amplicons and/or tagged gDNA fragment amplicons. In some instances, amplicons of the cDNA and amplicons of the tagged gDNA fragments may comprise a cell-specific barcode sequence that identifies the cell. In some instances, such cell-specific barcode sequence-containing amplicons may be generated from other amplicons of the tagged gDNA fragments and cDNA molecules. Sequencing reads may be associated with the cell based at least in part on the cell-specific barcode sequence. Barcode molecules may be delivered prior to, concurrently with, or subsequent to partitioning of the cell. In some instances, the barcode molecule may be delivered via a bead (e.g., gel bead), as described elsewhere herein.

The cDNA (e.g., from the gRNA and/or the gRNA identifying barcode thereof), tagged gDNA, and/or amplicons thereof may be sequenced to generate sequencing reads. Such sequencing reads may be used to determine, in the cell, a correlation between accessible gDNA and the sequences that correspond to the V(D)J region. The correlation may be mapped. In some instances, the cDNA, tagged gDNA, and/or amplicons thereof may be removed from the partition prior to sequencing, pooled, and sequenced. The cell-specific barcode sequence may associate sequencing reads generated from products or derivatives of the partition that partitioned the cell to the cell.

Figure 53:
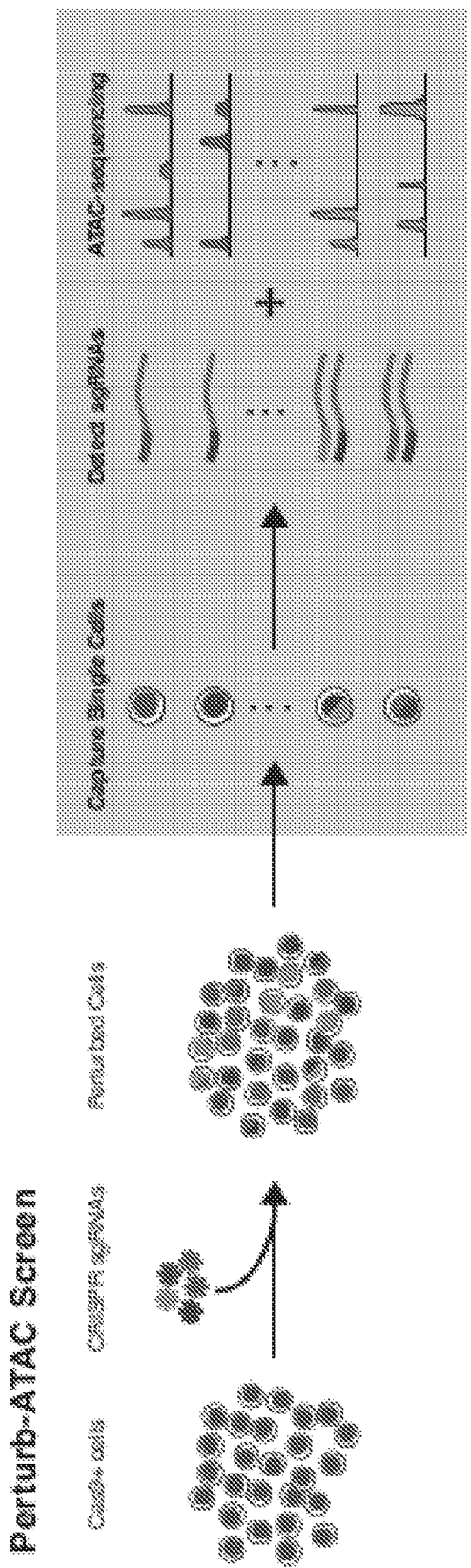
FIG. 53 shows a schematic of workflow for Perturb-ATAC.

FIG. 53 shows a schematic of workflow for Perturb-ATAC and FIG. 55 shows a schematic of Perturb-ATAC protocol, lentiviral construct, and generation of sequencing library for guide RNA detection. As shown in FIG. 55, sgRNA molecules are introduced to a plurality of cells, the cells comprising the sgRNA molecules are sorted (e.g., using FACS), a single cell captured in a partition, an ATAC-seq transposition of chromatin is performed to generate tagged gDNA fragments, sgRNA molecules are subjected to reverse transcription to generate corresponding cDNA molecules, and the cDNA molecules and tagged gDNA fragments are then amplified and sequenced.

In some embodiments, cells may be analyzed for chromatin accessibility following perturbations (i.e., Perturb-ATAC). For example, cells (e.g., B cells) may be collected, partitioned, lysed, and subjected to a transposition reaction. Following treatment of transposase and reaction quenching, samples may be subjected to reverse transcription and optionally PCR using a mix of primers. These processes may be conducted in a microfluidic chip. For example, Fluidigm, an automated microfluidic platform, may be used for single-cell capture, lysis, and downstream processing.

Harvested libraries may be further amplified. For example, PCR may be used to incorporate barcodes and enable sequencing. Following barcoding, amplicons from PCR may be purified and sequenced to form a library of barcoded gDNA and (sgRNA or sgRNA-identifying) cDNA sequences. Libraries may be additionally amplified, and/or quantified prior to sequencing.

Purification of libraries may be obtained by selecting a nucleotide fragment of choice. A nucleotide fragment may be selected by its size, isoelectric point, or other biochemical or biophysical properties. For example, a nucleotide fragment may be purified by size by using polyacrylamide gel electrophoresis and selecting fragments of a desired size.

In some embodiments, the presence or absence of a barcode in a given cell may be assessed. In some cases, cutoffs may be assigned to assign the presence or absence of a barcode in a given cell. In one non-limiting example, the number of reads for each possible barcode in every cell may be counted and then adjusted for sequencing depth, e.g., to account for variation during library preparation or sequencing. In another example, a minimum read cutoff of 1,000 barcode reads per cell may be applied to remove cells with low coverage. Cells with high background reads may also be removed. In addition, a cutoff based on the percent of barcode reads aligning to the second-most common barcode may also be used as a cutoff.

As will be apparent to those skilled in the art, Perturb-ATAC may be used for a variety of applications in biological discovery. For example, Perturb-ATAC may identify epigenomic functions of chromatin regulators, transcription factors and noncoding RNAs. Performing a Perturb-ATAC screen may be used to compare how broadly-expressed and lineage-specific trans-factors shape the chromatin landscape of a cell type. Perturb-ATAC may also identify epigenomic phenotypes associated with genetic perturbations of diverse categories of trans-factors. For example, as a control experiment, an analysis of aggregate ATAC-seq profiles of cells receiving non-human-genome-targeting barcodes may be expected to result in little to no change in chromatin accessibility; however, a selective perturbation with gRNA targeted to, for example, DNMT3a, may result in changes in the accessibility.

In some cases, more than one perturbation (i.e., application of more than one gRNA) may be applied to cells. Combinations of perturbations, followed by ATAC-seq may reveal how, for example, transcription factors function together to establish chromatin landscape in cells. Perturb-ATAC may also be useful, in non-limiting examples, in identifying co-varying regulatory networks across single cells, measuring the effects of perturbation on one or more regulatory networks, and/or inferring regulatory relationships between perturbed factor and the constituent factors in the regulatory network. In one example, dual perturbations in single cells for a subset of factors followed by Perturb-ATAC may determine the degree of genetic interaction across all genomic features. Perturb-ATAC on cells that with more than one perturbation may be used to characterize trans-factor relationships as "expected" (i.e., based on the combination of the effects of each perturbation alone) or "unexpected" (i.e., non-additive, suggesting interaction between the perturbations). The "unexpected" relationships may be trans-factors that act synergistically, have a canceling effect, or interact in a non-additive way. Epistatic interactions analyzed from more than one perturbation may also be useful in screening for disease-related transcription factors and mapping interactions of epigenomic networks.

In some cases, the occupancy and positioning of nucleosomes genome-wide may be inferred by the fragment sizes obtained from ATAC-seq. Assessment of trans factors, which may control accessibility of a locus by regulating the binding of TFs in pre-established nucleosome-free regions and/or by altering the positions or occupancy of local nucleosomes, may yield additional information. In some cases, ATAC-seq data may determine whether changes in ATAC-seq signal at genomic regions are associated with alterations in nucleosome structure rather than exchange of TF binding within a stable nucleosome scaffold.

In some cases, Perturb-ATAC analysis may inform of pathological processes. For example, Perturb-ATAC may inform regulators of noncoding regions that contain genetic variants associated with human disease. Selective perturbation of candidate factors may reveal disease-specific activities of several TFs.

In some instances, the method can be used to compare two samples. A first epigenetic map may be generated by analyzing a first cell or a first population of cells. A second epigenetic map may be generated by analyzing a second cell or a second population of cells. The two epigenetic maps may be compared, consolidated, or otherwise processed against or with each other. For example, the first epigenetic map may be mapped to the second epigenetic map, such as to determine or characterize accessibility of chromatin (e.g., chromatin openness) or transcription factor occupancy, optionally for quality control, optionally in response to perturbation of target genes, and/or changes thereof. In some instances, the first input (first cell or first population of cell) may be a clone of the second input (second cell or second population of cell), or vice versa. In some instances, the first input and the second input may be obtained from a same source at different times. In some instances, the first input and the second input may be obtained from different sources. In some instances, the first input and the second input may be obtained from different locations or regions of the same source (e.g., individual). In some instances, the first input may be a pre-treated input and the second input may be a post-treated input, such as by treatment with an agent (e.g., test agent), a drug, a perturbation agent, and the like. In such cases, the first input and the second input may be clones or identical populations, and the second input may be incubated with the treatment before the assays and/or methods described herein are performed. In some instances, these methods can be used to determine the mode of action of a test agent, to identify changes in chromatin structure or transcription factor occupancy in response to the drug, for example. In some instances, one of the two samples may be a control sample.

The method described above may also be used to provide a diagnosis and/or prognosis, such as based on one or more epigenetic maps, such as for a patient.

The method set forth herein may be used to provide a reliable diagnostic to any condition associated with altered chromatin or DNA binding protein occupancy. The method can be applied to the characterization, classification, differentiation, grading, staging, diagnosis, or prognosis of a condition characterized by an epigenetic pattern (e.g., a pattern of chromatin accessibility or DNA binding protein occupancy). For example, the method can be used to determine whether the epigenetic map of a sample from an individual suspected of being affected by a disease or condition is the same or different compared to a sample that is considered "normal" with respect to the disease or condition. In particular embodiments, the method can be directed to diagnosing an individual with a condition that is characterized by an epigenetic pattern at a particular locus in a test sample, where the pattern is correlated with the condition. The methods can also be used for predicting the susceptibility of an individual to a condition.

Exemplary conditions that are suitable for analysis using the methods set forth herein can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

In some instances, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The method can also be used to determining a proper course of treatment for a patient having a disease or condition, e.g., a patient that has cancer. A course of treatment refers to the therapeutic measures taken for a patient after diagnosis or after treatment. For example, a determination of the likelihood for recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

FIG. 54 shows an overview of classes of biological questions that can be interrogated from Perturb-ATAC data. These include, but are not limited to, nucleosome positioning 5402, enhancer accessibility 5404, promoter accessibility 5406, and transcription factor accessibility 5408.

Figure 56:
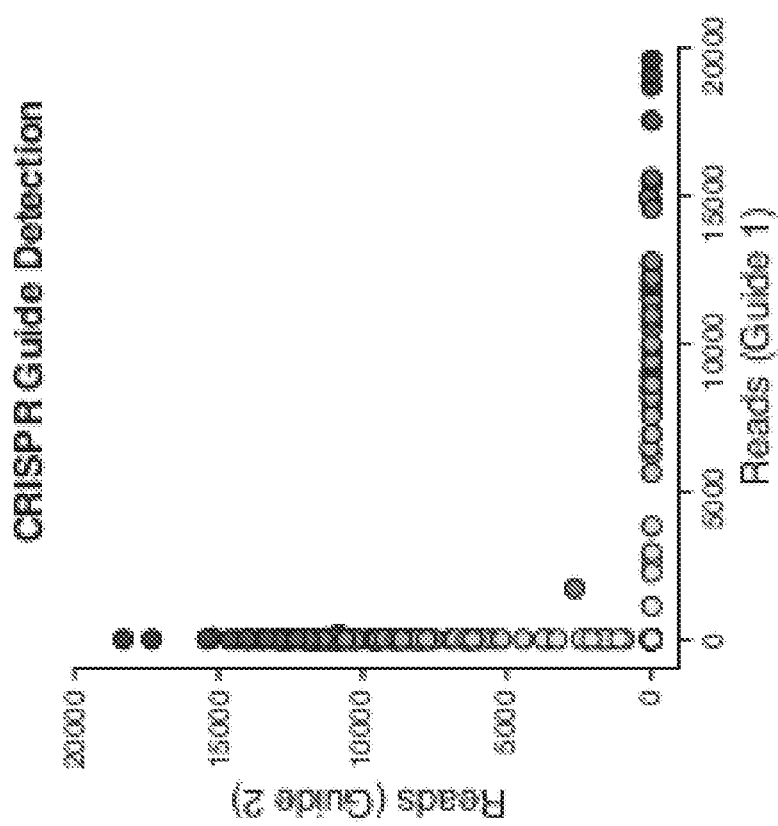
FIG. 56 shows a scatter plot of guide barcode reads from pool of cells transduced with one of two guide constructs.

FIG. 56 shows a scatter plot of guide barcode reads from pool of cells transduced with one of two guide constructs.

Figure 57:
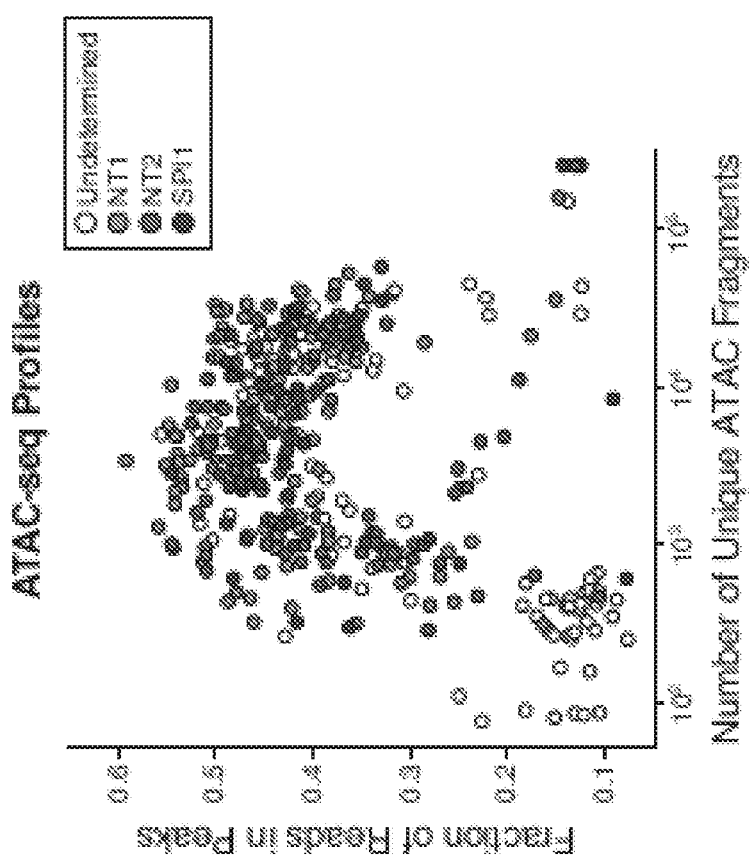
FIG. 57 shows a scatter plot of ATAC fragments and the fraction of ATAC fragments in peak regions for each cell.

FIG. 57 shows a scatter plot of ATAC fragments and the fraction of ATAC fragments in peak regions for each cell. Labels indicating guide barcode detection in each cell are shown.

Figure 58:
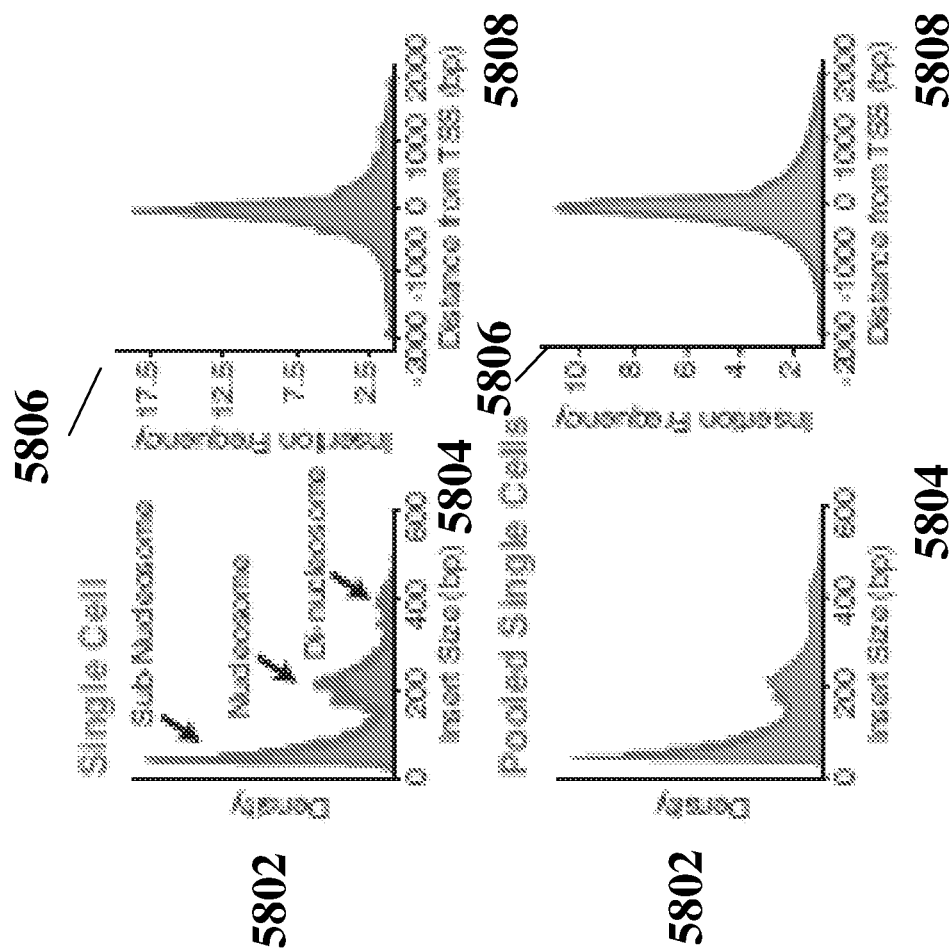
FIG. 58 shows density histograms of ATAC fragment size distribution indicating expected nucleosome phasing and relative frequency of ATAC insertions surrounding transcription start sites in merged single cells and bulk cells.

FIG. 58 shows density 5802 histograms of ATAC fragment size 5804 distribution indicating expected nucleosome phasing and relative frequency 5806 of ATAC insertions surrounding transcription start sites 5808 in merged single cells (top) and bulk cells (bottom).

Figure 59:
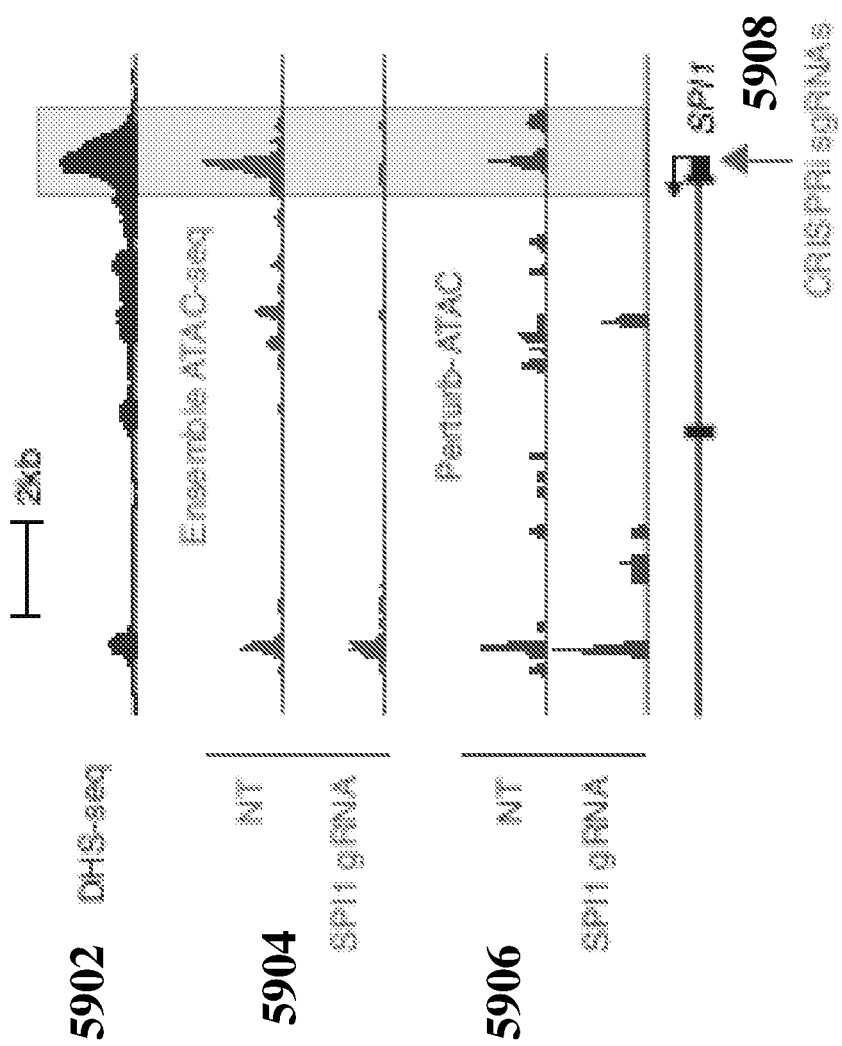
FIG. 59 show plots of genomic locus of SPI1 gene.

FIG. 59 show plots of genomic locus of SPI1 gene, indicating DNase I hypersensitivity 5902 sequencing, bulk ATAC-seq 5904, and Perturb-ATAC-seq 5906. The SPI1 promoter region exhibits selective loss of accessibility in cells expressing SPI1sgRNA 5908.

Figure 60:
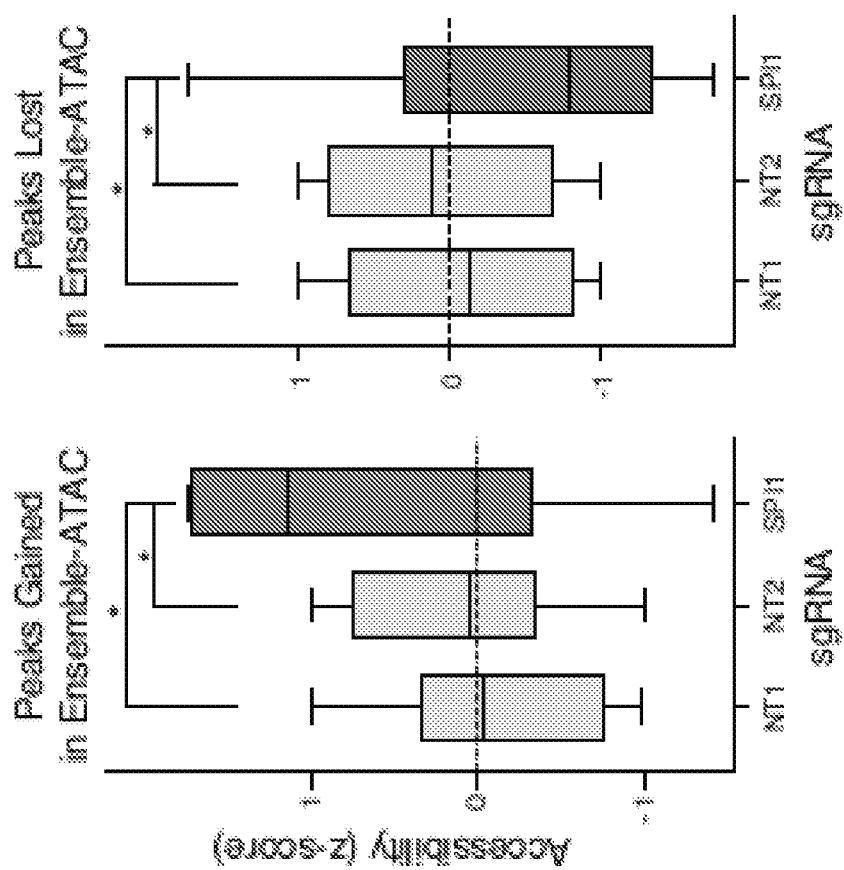
FIG. 60 show box plots of accessibility from merged single cells of individual genomic regions identified as altered in bulk ATAC-seq.

FIG. 60 show box plots of accessibility from merged single cells of individual genomic regions identified as altered in bulk ATAC-seq. * indicates p-value <1e-3 by KS1173 test.

Figure 61:
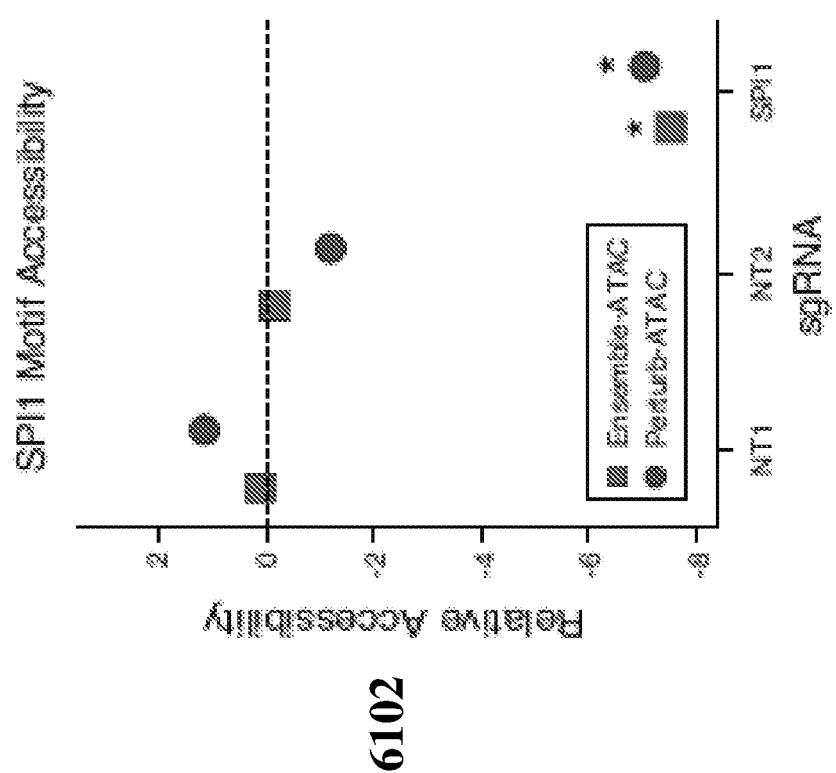
FIG. 61 shows a plot of relative accessibility of SPI1 motif-containing regions.

FIG. 61 shows a plot of relative accessibility 6102 of SPI1 motif-containing regions (z-score of relative activity of SPI1 motif versus all other genomic features). * indicates false discovery rate <1e-3 by permutation test.

Figure 62:
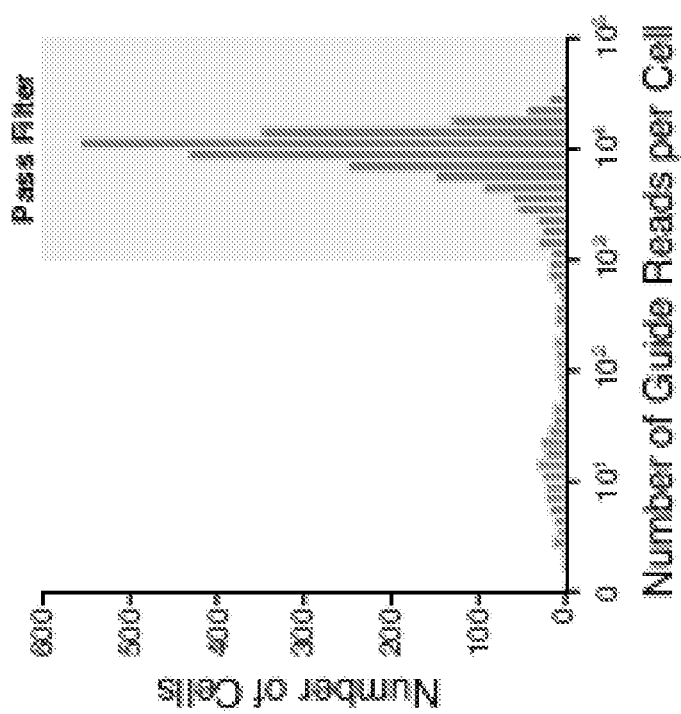
FIG. 62 shows a histogram of total guide barcode sequencing reads per cell.

FIG. 62 shows a histogram of total guide barcode sequencing reads per cell.

Figure 63:
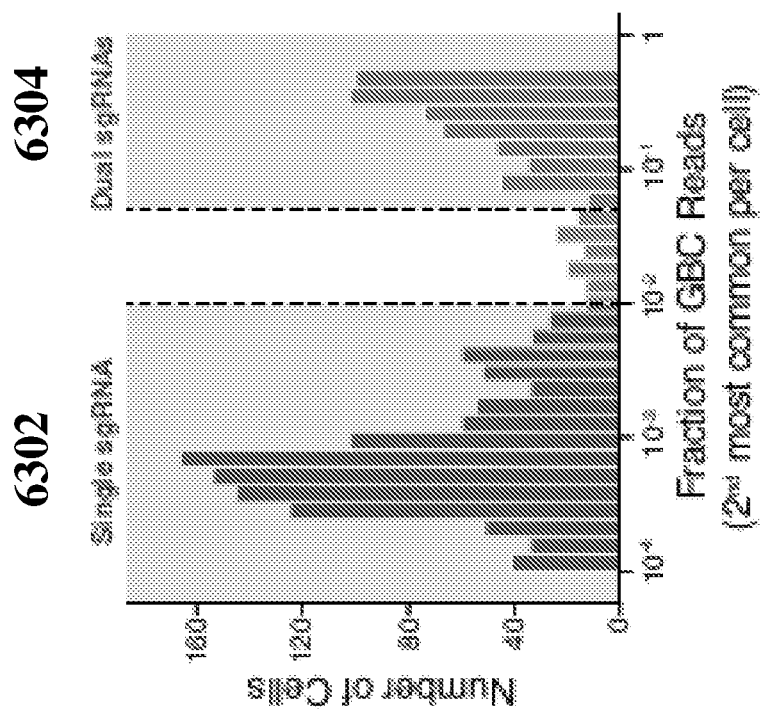
FIG. 63 shows a histogram of the second most common guide barcode identified in each cell.

FIG. 63 shows a histogram of the second most common guide barcode identified in each cell. Cells on the low end of the distribution express a single guide RNA 6302, while cells on the high end of the distribution express two guide RNAs 6304.

Figure 64:
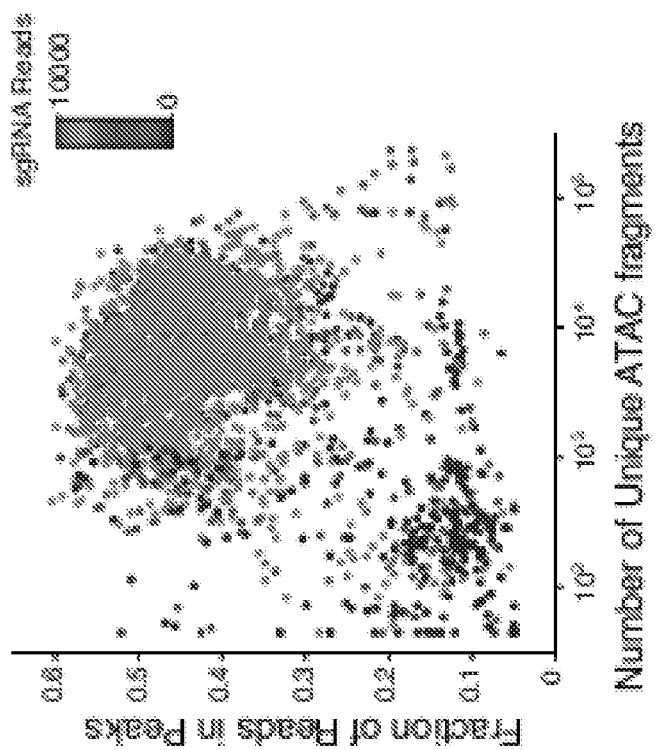
FIG. 64 shows a scatter plot of ATAC fragments and fraction of fragments in peak regions.

FIG. 64 shows a scatter plot of ATAC fragments and fraction of fragments in peak regions. Cells are shaded by total guide barcode reads.

Figure 65:
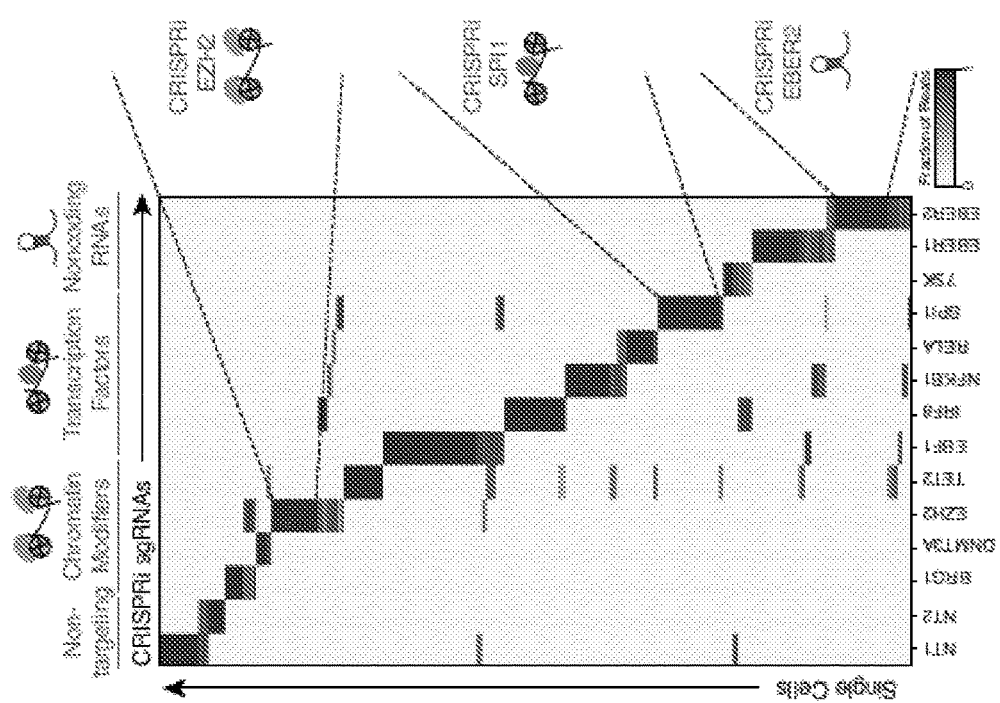
FIG. 65 shows a heatmap of cells (rows) versus guide barcodes (columns) indicating proportion of total reads associated with each barcode.

FIG. 65 shows a heatmap of cells (rows) versus guide barcodes (columns) indicating proportion of total reads associated with each barcode.

Figure 66:
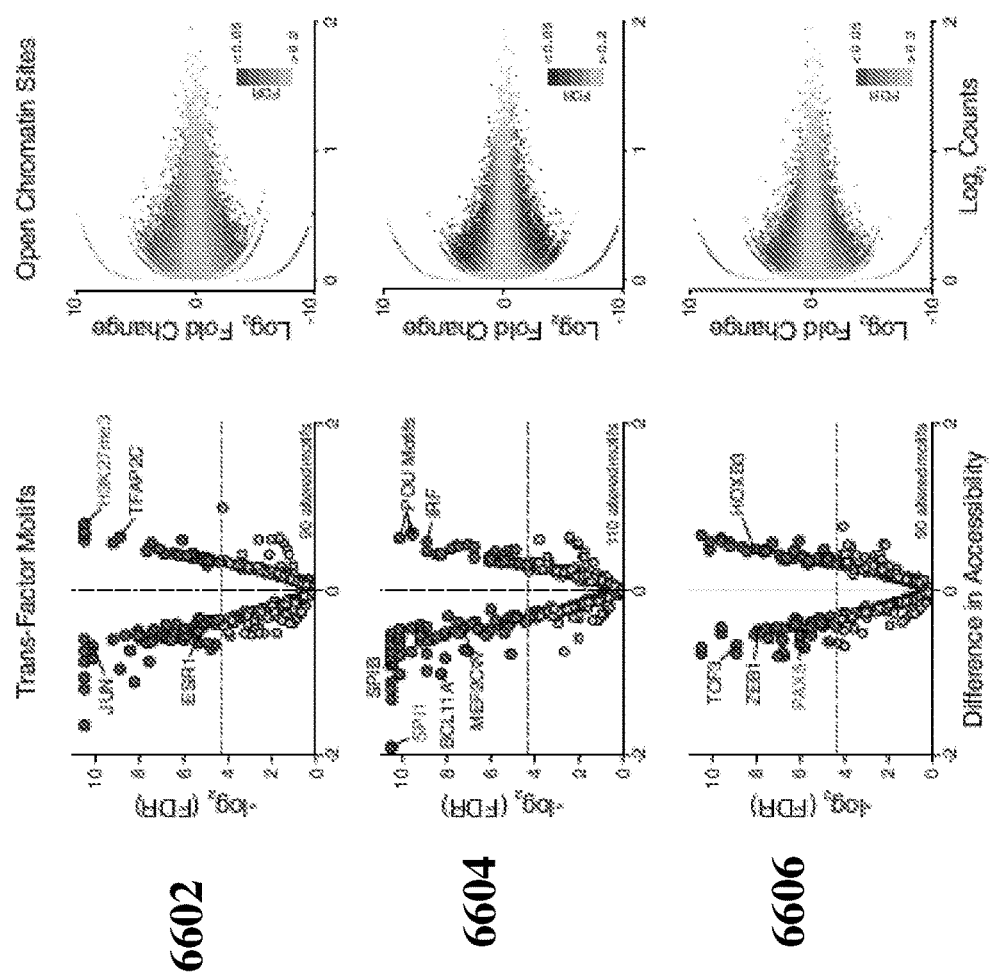
FIG. 66 shows volcano plots to identify significantly altered genomic features between cells carrying non-targeting guides and guides targeting various genes.

FIG. 66 shows volcano plots to identify significantly altered genomic features between cells carrying non-targeting guides and guides targeting EZH2 6602, SPI1 6604, and EBER2 6606 (FDR <=0.025). Right: scatter plots of mean accessibility versus fold change of accessibility of individual genomic peaks.

Figure 67:
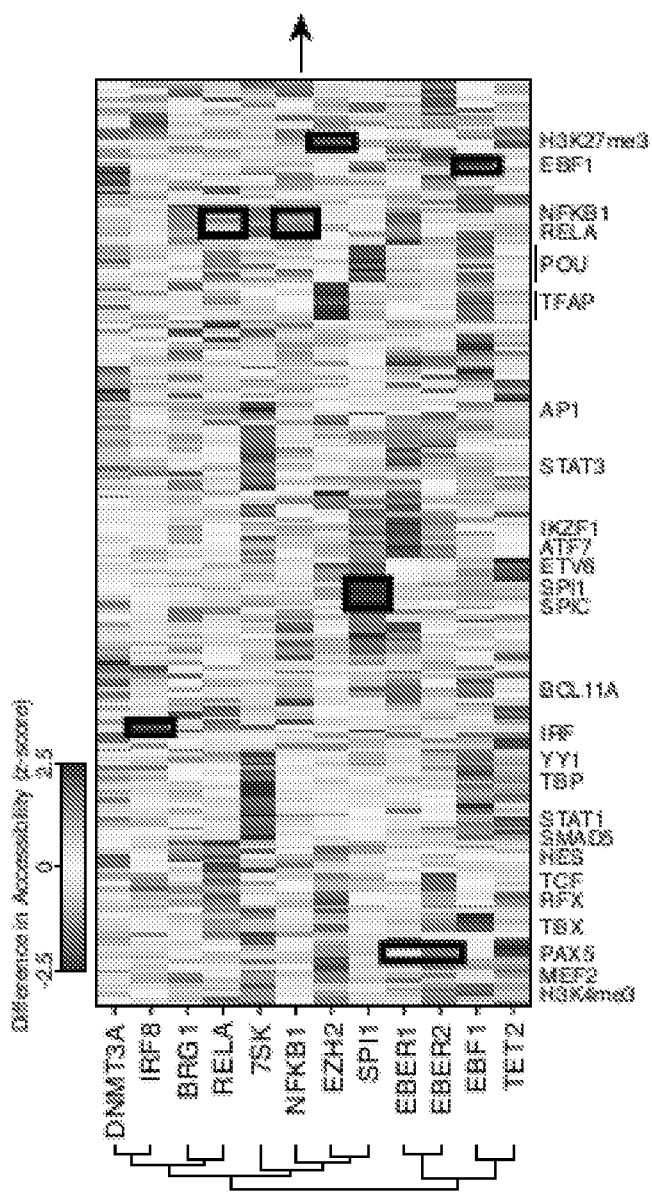
FIG. 67 shows a heatmap of perturbed factors versus genomic annotations.

FIG. 67 shows a heatmap of perturbed factors (rows) versus genomic annotations (columns) indicating difference in accessibility between perturbed cells and non-targeting control cells. Only annotations significantly altered in at least one perturbation are shown.

Figure 68:
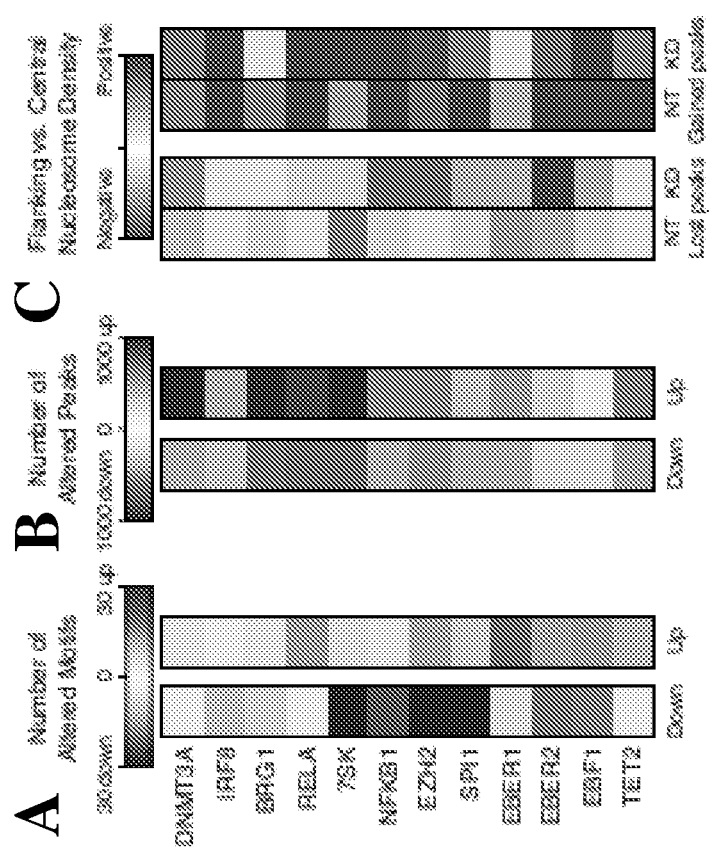
FIG. 68 Panel A shows heatmaps indicating number of significantly altered features, genomic regions, or quantification of the ratio of flanking to central nucleosome occupancy at altered peaks for single perturbations.

FIG. 68 Panel A shows heatmpas indicating number of significantly altered features (absolute log 2FC>=1.5, mean reads/cell>=0.4), panel B shows number of altered genomic regions (middle, absolute chromVAR deviation Z>=0.75, FDR<=.05), or quantification of the ratio of flanking to central nucleosome occupancy at altered peaks for each single perturbation (panel C).

Figure 69:
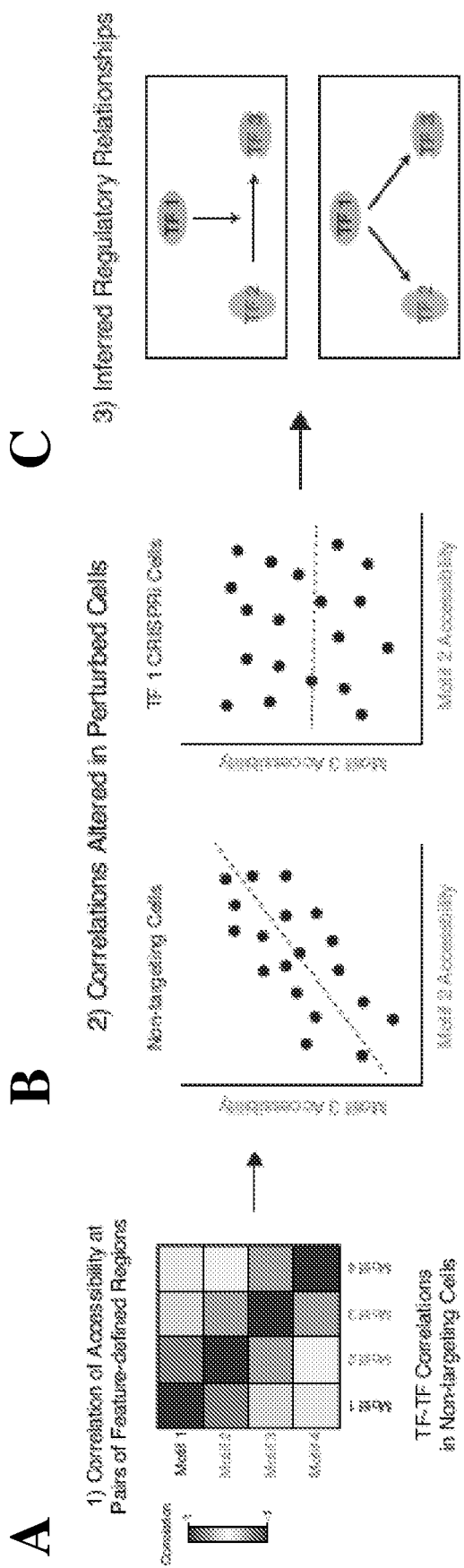
FIG. 69 shows an example workflow identifying genomic features exhibiting correlated activity across cells.

FIG. 69 shows an example workflow identifying genomic features exhibiting correlated activity across cells. Panel A shows a heat map indicating correlation of motif activity across cells for a group of motifs. Panel B shows a comparison of non-targeting control cells to perturbed cells identifying motif pairs that change in correlation as a result of perturbation. Panel C shows functional relationships constrain hypothetical regulatory networks.

Figure 70:
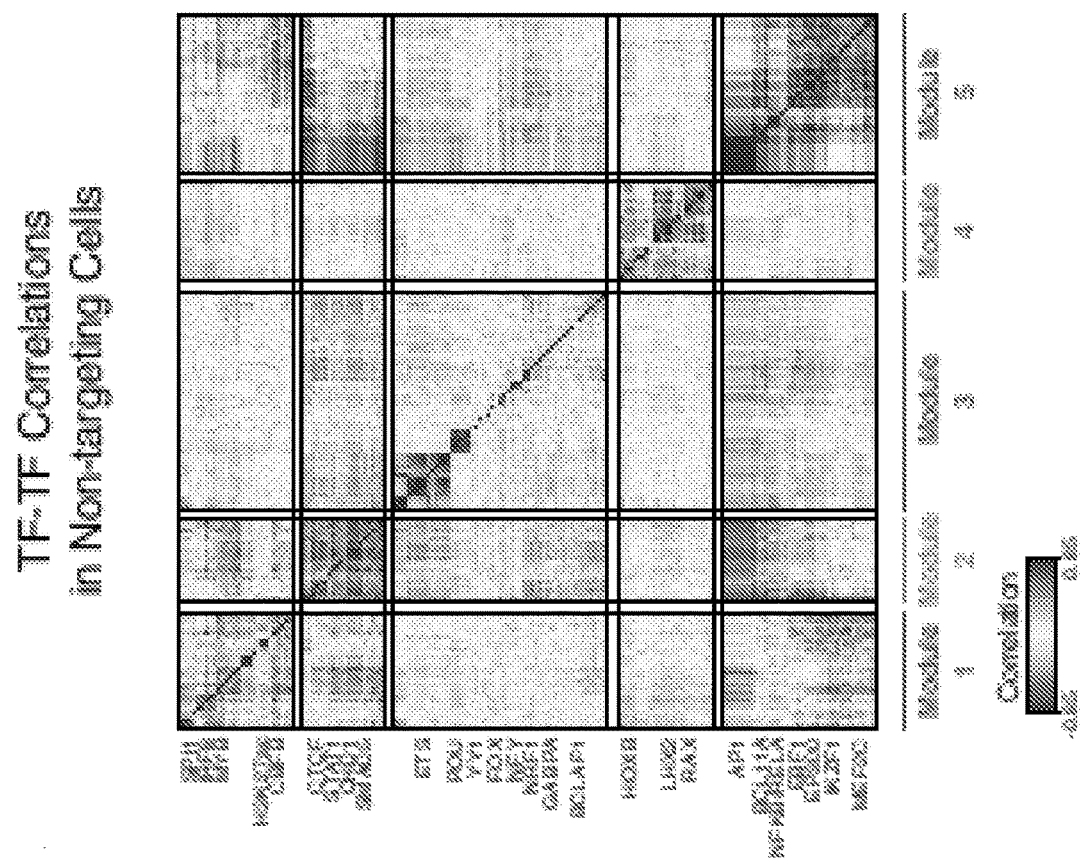
FIG. 70 shows a heatmap of Pearson correlations between features across non-targeting cells.

FIG. 70 shows a heatmap of Pearson correlations between features across non-targeting cells.

Figure 71:
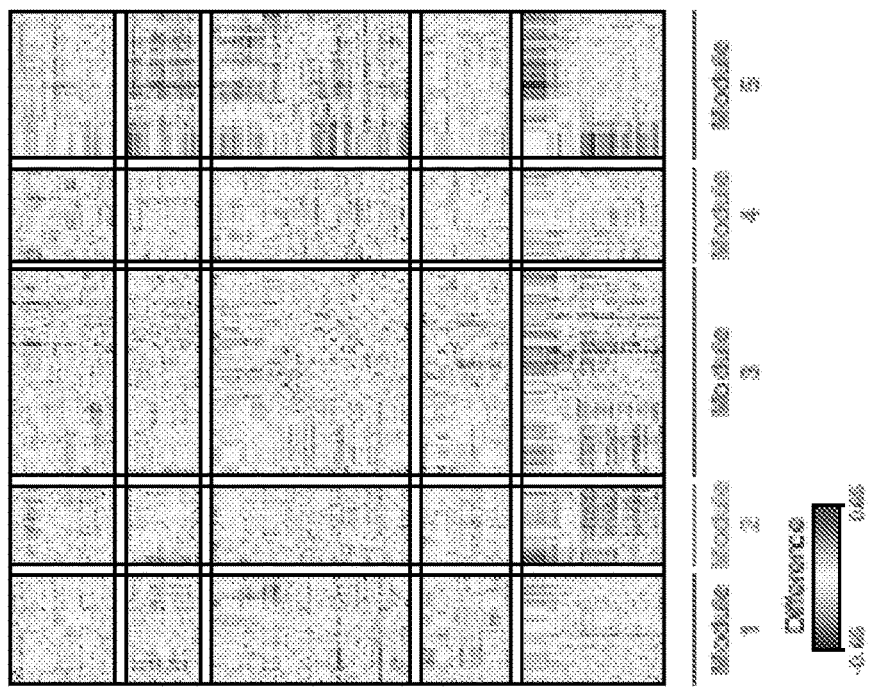
FIG. 71 shows a heatmap displaying the difference in correlations between non-targeting cells and IRF8 knockdown cells.

FIG. 71 shows a heatmap displaying the difference in correlations between non-targeting cells and IRF8 knockdown cells.

Figure 72:
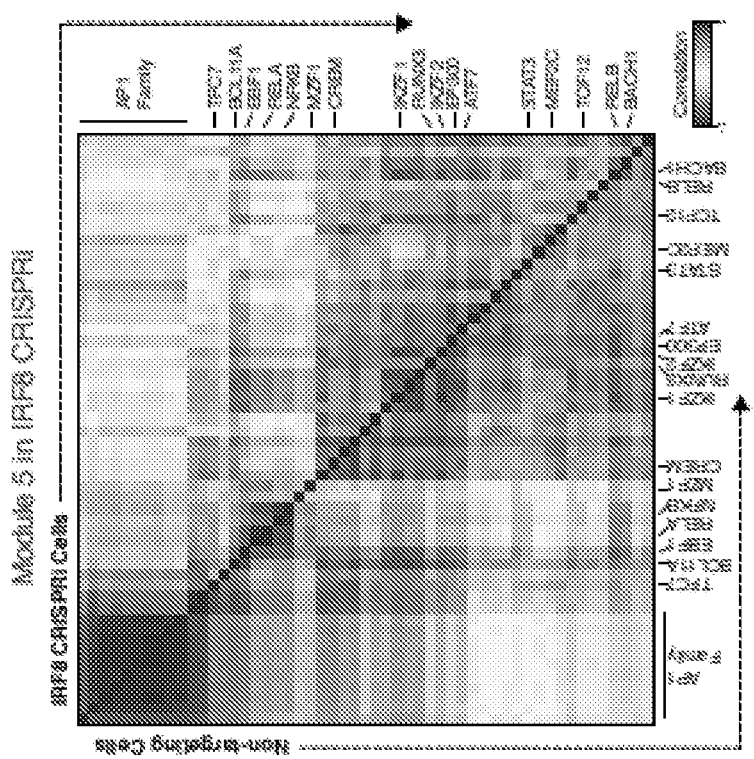
FIG. 72 shows a heatmap displaying Module 5 feature correlations in non-targeting cells (bottom half) and IRF8 (top half) knockdown cells.

FIG. 72 shows a heatmap displaying Module 5 feature correlations in non-targeting cells (bottom half) and IRF8 (top half) knockdown cells.

Figure 73:
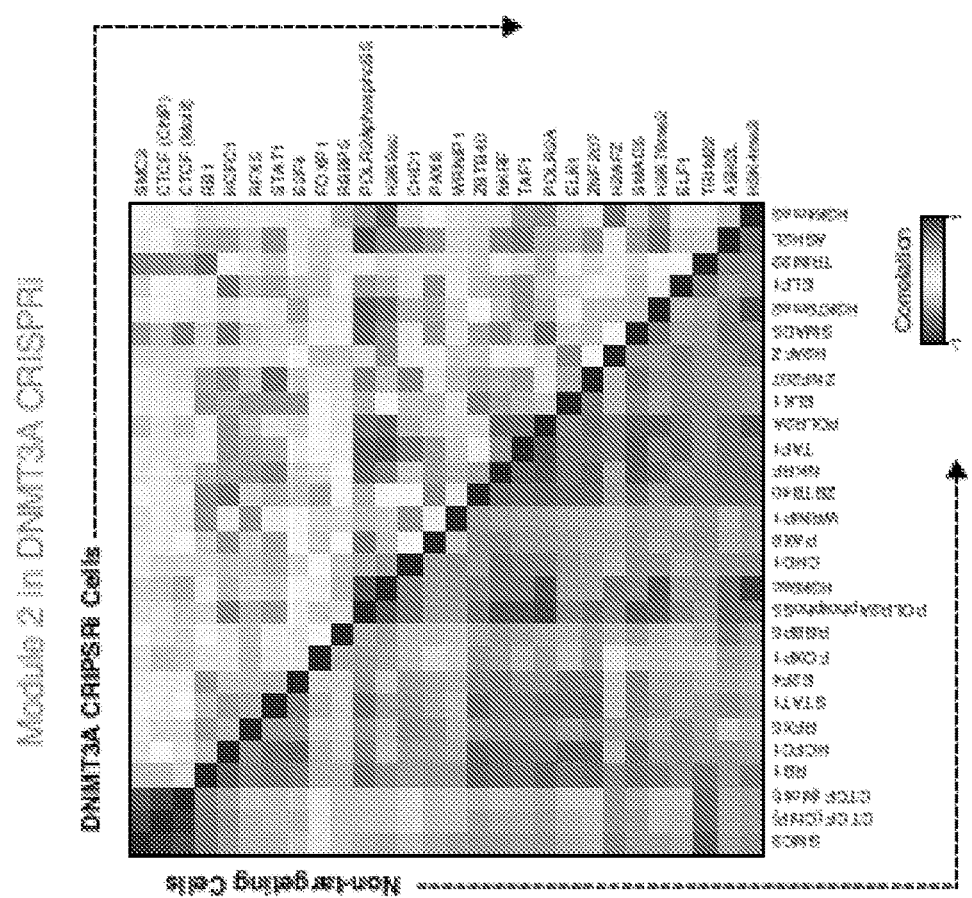
FIG. 73 shows a heatmap displaying Module 2 feature correlations in non-targeting cells (bottom half) and DNMT3A (top half) knockdown cells.

FIG. 73 shows a heatmap displaying Module 2 feature correlations in non-targeting cells (bottom half) and DNMT3A (top half) knockdown cells.

Figure 74:
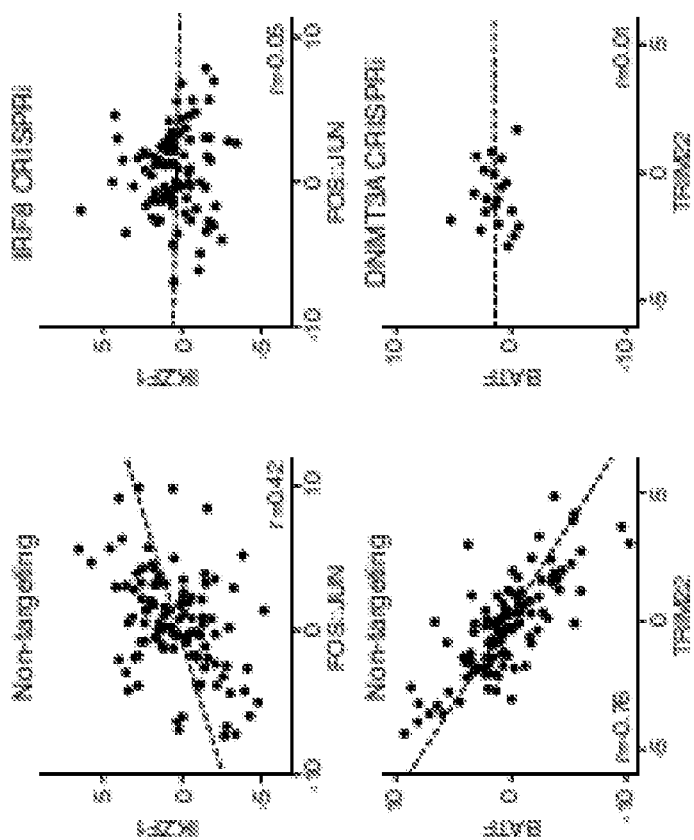
FIG. 74 shows scatter plots of accessibility for cells with line of linear best fit demonstrating correlation in specific conditions.

FIG. 74 shows scatter plots of accessibility for cells with line of linear best fit demonstrating correlation in specific conditions.

Figure 75:
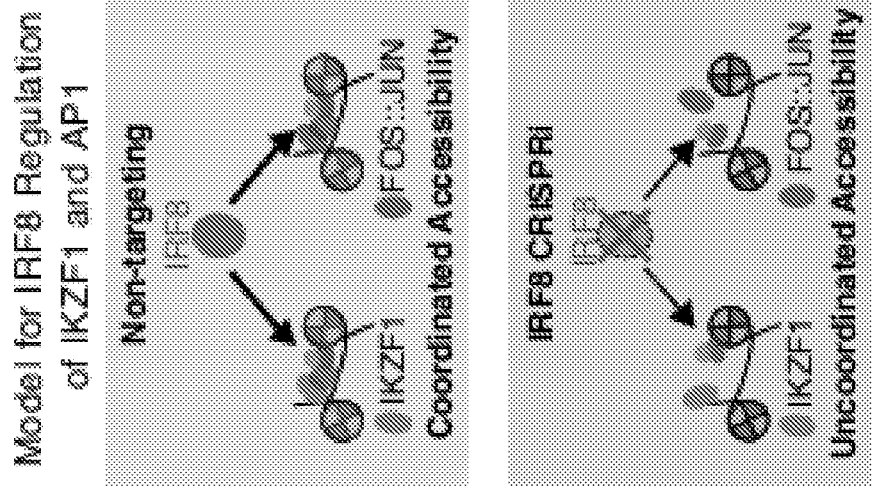
FIG. 75 shows a hypothetical model of IRF8 co-factor activity with AP1 and IKZF1.

FIG. 75 shows a hypothetical model of IRF8 co-factor activity with AP1 and IKZF1.

Figure 76:
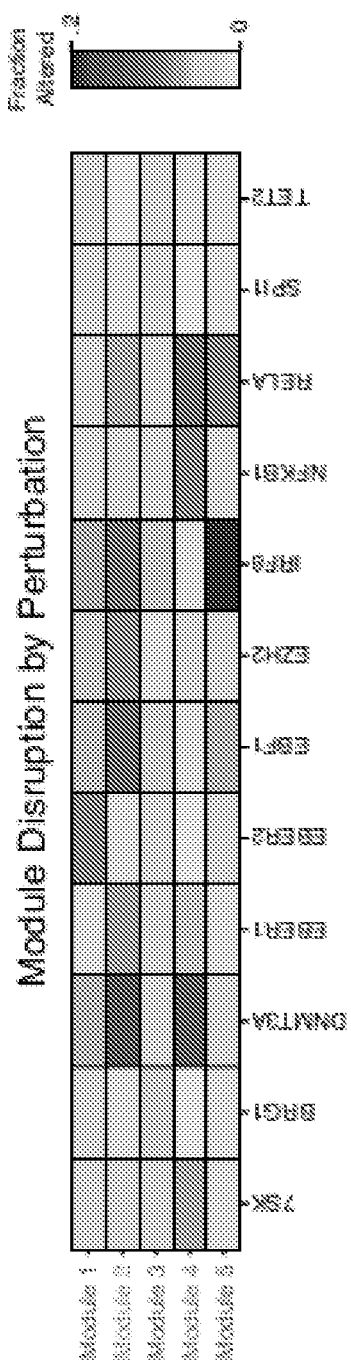
FIG. 76 shows a heatmap of the fraction of altered feature-feature correlations within modules by perturbation, showing specific effects on particular modules in different perturbations.

FIG. 76 shows a heatmap of the fraction of altered feature-feature correlations within modules by perturbation, showing specific effects on particular modules in different perturbations.

Figure 77:
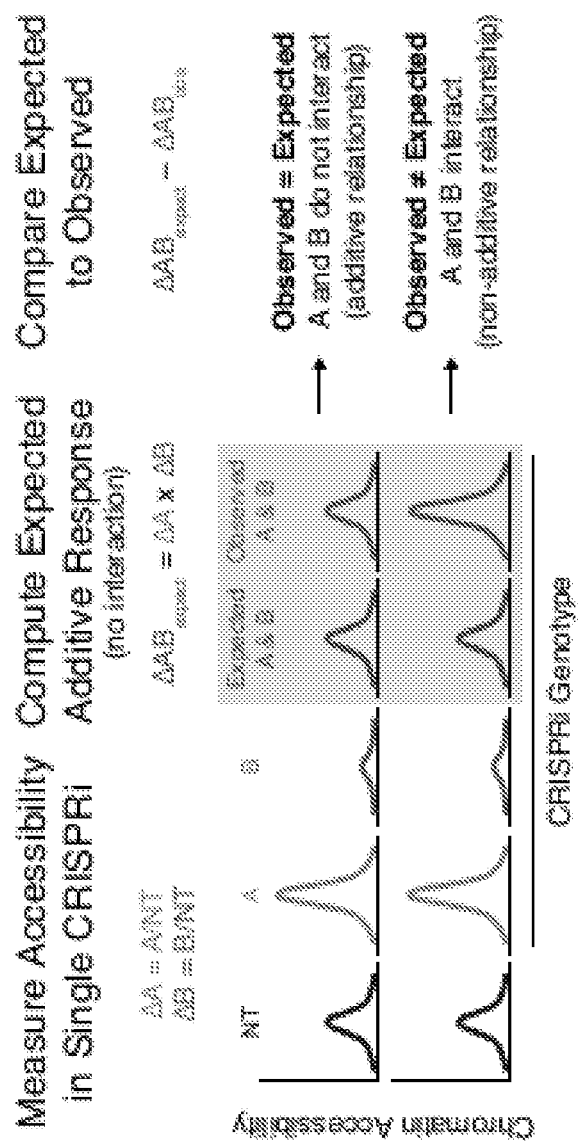
FIG. 77 shows a schematic of calculation of expected accessibility in double knockdown context based on additive model integrating accessibility in each single knockdown condition FIG. 78 show box plots representing the distribution of SPI1 binding sites (left) and IKZF1 binding sites (right) accessibility for 1221 individual cells in respective single or double knockdown conditions.
Figure 78:
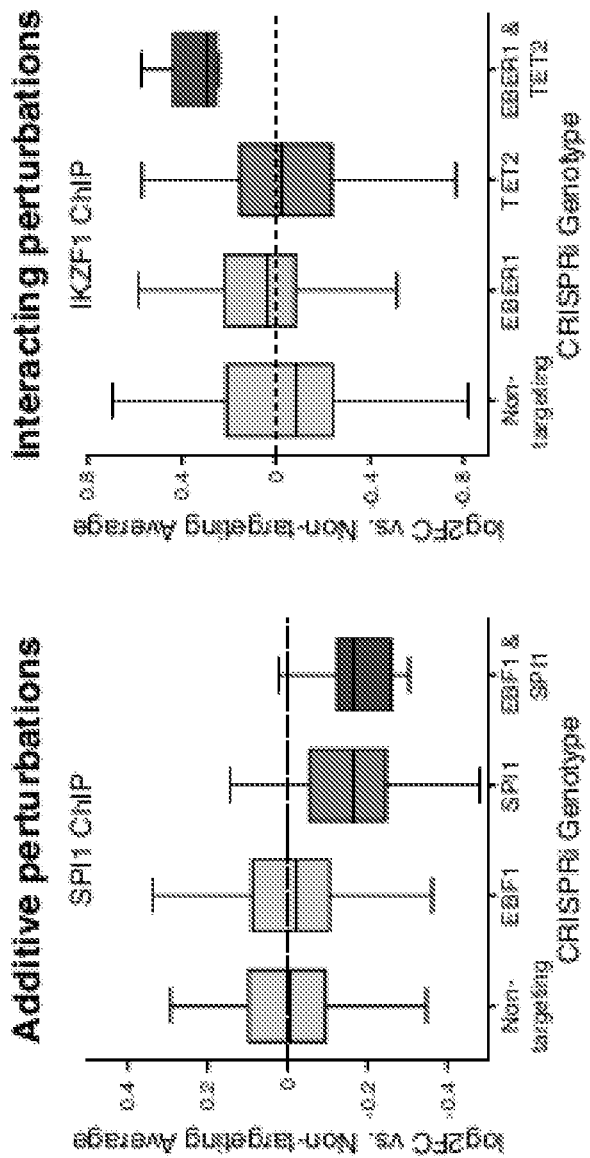

FIG. 77 shows a schematic of calculation of expected accessibility in double knockdown context based on additive model integrating accessibility in each single knockdown condition FIG. 78 show box plots representing the distribution of SPI1 binding sites (left) and IKZF1 binding sites (right) accessibility for 1221 individual cells in respective single or double knockdown conditions.

Figure 79:
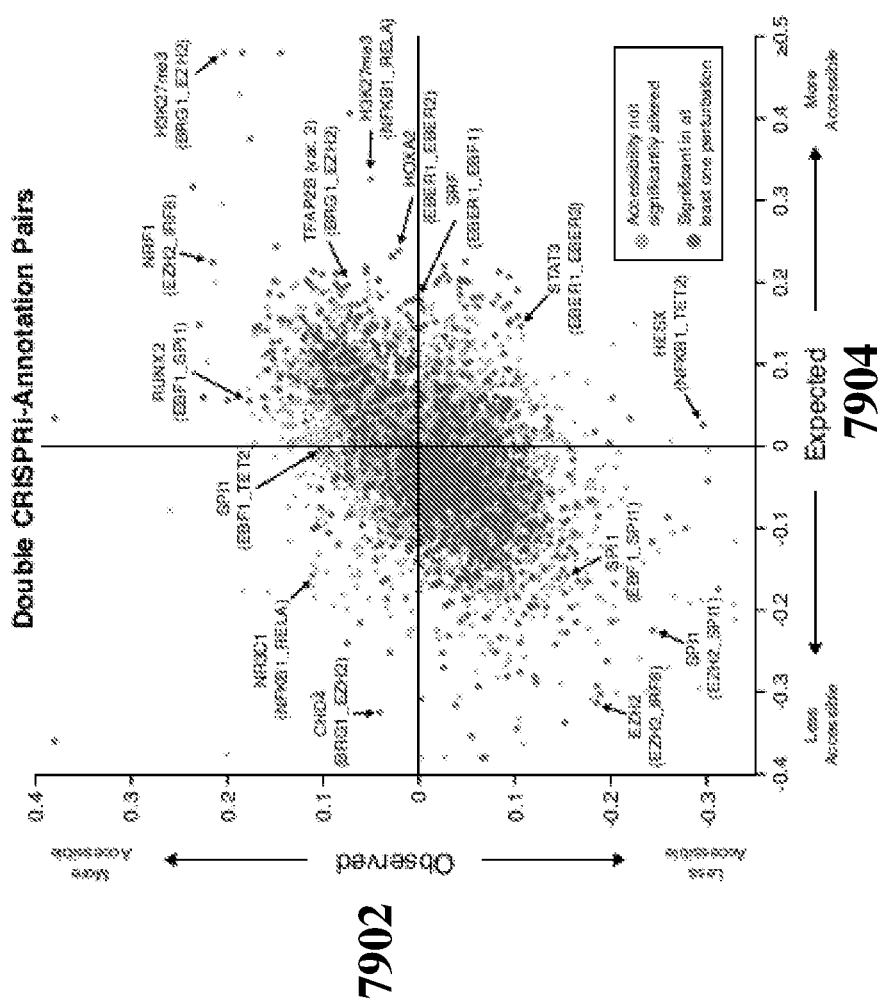
FIG. 79 shows a scatter plot of observed 7902 versus expected 7904 accessibility for epistatic interactions. Each dot represents a single annotation in the pairing of two perturbed factors.

FIG. 79 shows a scatter plot of observed 7902 versus expected 7904 accessibility for epistatic interactions. Each dot represents a single annotation in the pairing of two perturbed factors. Darker dots indicate significantly altered activity in either single perturbation or double perturbation.

Figure 80:
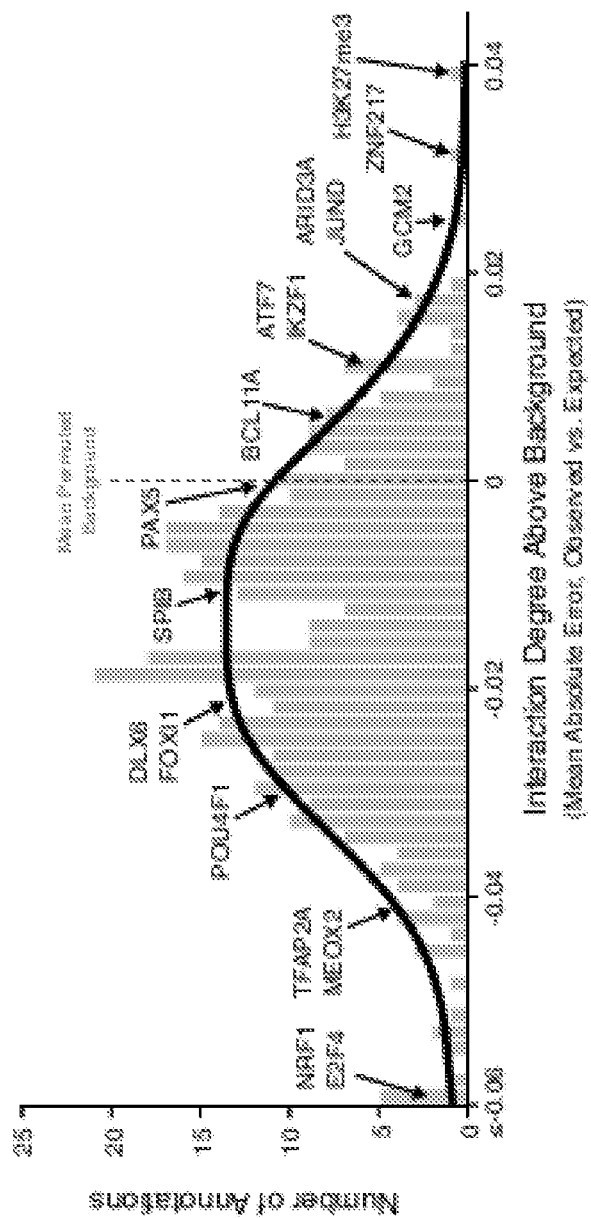
FIG. 80 shows a histogram of background-corrected interaction degree for each feature.

FIG. 80 shows a histogram of background-corrected interaction degree for each feature. Background distribution calculated by permuting single and double knockdown associations.

Figure 81:
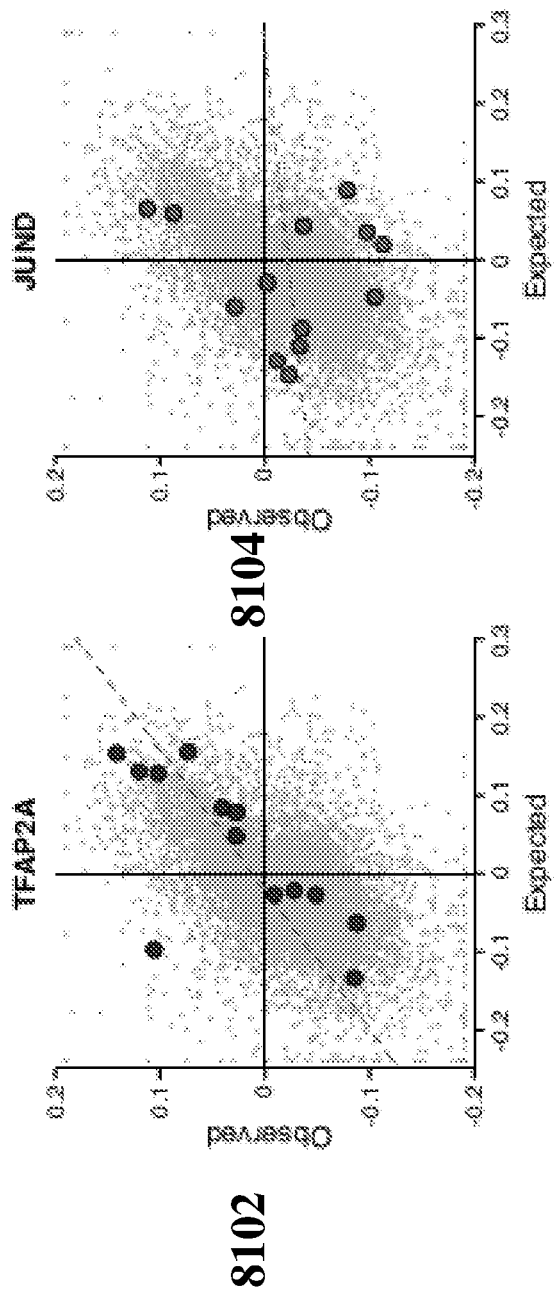
FIG. 81 demonstrate scatter plots of observed versus expected interactions.

FIG. 81 demonstrate scatter plots of observed 8102 versus expected 8104 interactions, highlighting TFAP2A (relatively low interaction degree) and JUND (relatively high interaction degree).

Figure 82:
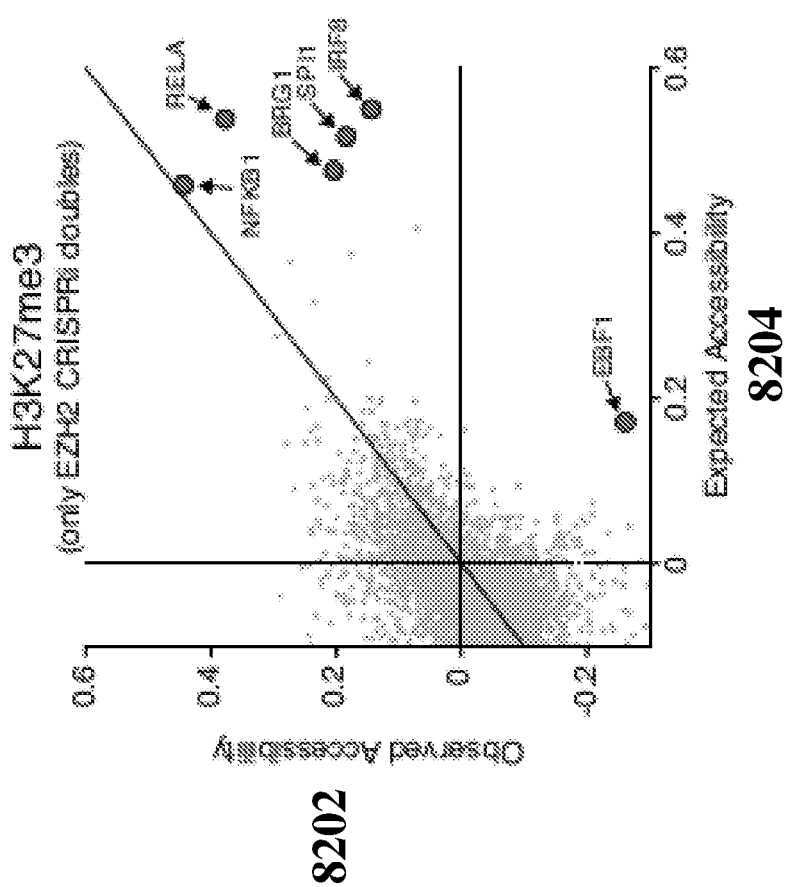
FIG. 82 shows a scatter plot of observed 8202 versus expected 8204 change in accessibility at H3K27me3-marked regions in cells depleted of EZH2 and one other factor.

FIG. 82 shows a scatter plot of observed 8202 versus expected 8204 change in accessibility at H3K27me3-marked regions in cells depleted of EZH2 and one other factor.

Figure 83:
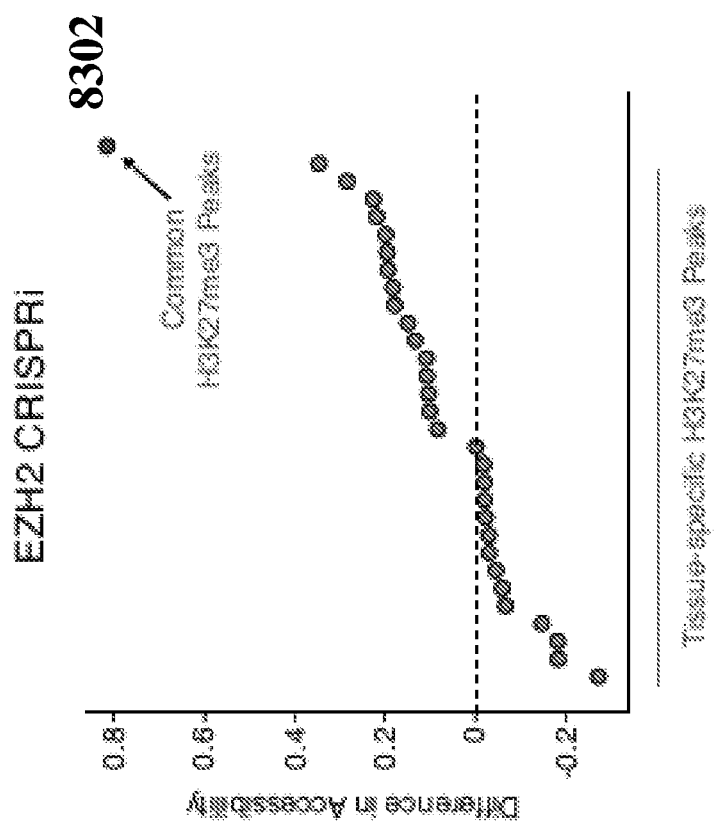
FIG. 83 shows a scatter plot of relative accessibility in EZH2 knockdown cells compared to control cells for various subsets of H3K27me3 peaks.

FIG. 83 shows a scatter plot of relative accessibility in EZH2 knockdown cells compared to control cells for various subsets of H3K27me3 peaks. Common peaks 8302 refer to regions exhibiting H3K27me3 status across a majority of cell types.

Figure 84:
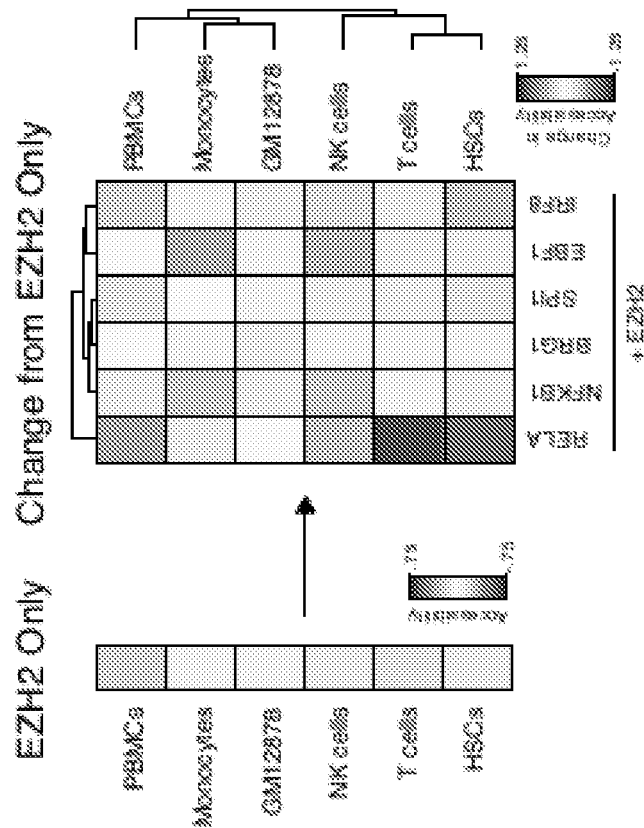
FIG. 84 shows heatmaps indicating change in accessibility due to EZH2 depletion at regions marked by H3K27me3 in GM12878 and exhibiting H3K27ac mark in each specific other cell type.

FIG. 84 Left: heatmap indicating change in accessibility due to EZH2 depletion at regions marked by H3K27me3 in GM12878 and exhibiting H3K27ac mark in each specific other cell type. Right: heatmap indicating change in accessibility in same sets of regions included in the left heatmap, for cells simultaneously depleted of EZH2 and a TF.

Figure 85:
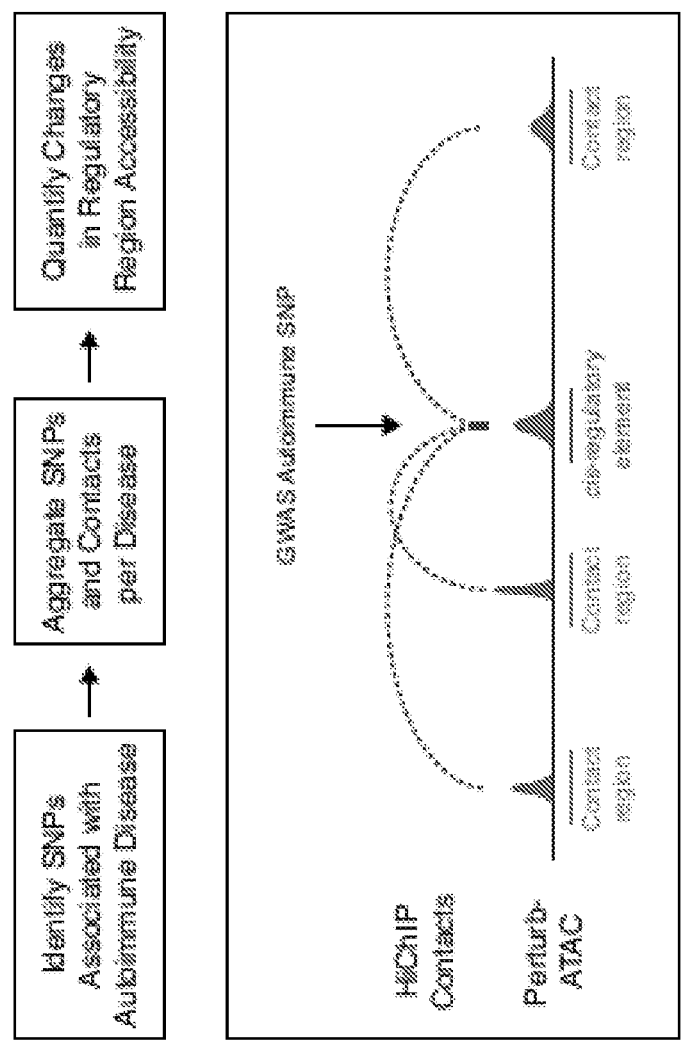
FIG. 85 shows a schematic indicating the workflow to aggregate SNPs associated with autoimmune diseases with 3D chromatin contact regions.

FIG. 85 shows a schematic indicating the workflow to aggregate SNPs associated with autoimmune diseases with 3D chromatin contact regions.

Figure 86:
FIG. 86 shows a heatmap of the absolute change in accessibility for the SNP-contact feature set of each autoimmune disease and perturbation.

FIG. 86 shows a heatmap of the absolute change in accessibility for the SNP-contact feature set of each autoimmune disease and perturbation.

Figure 87:
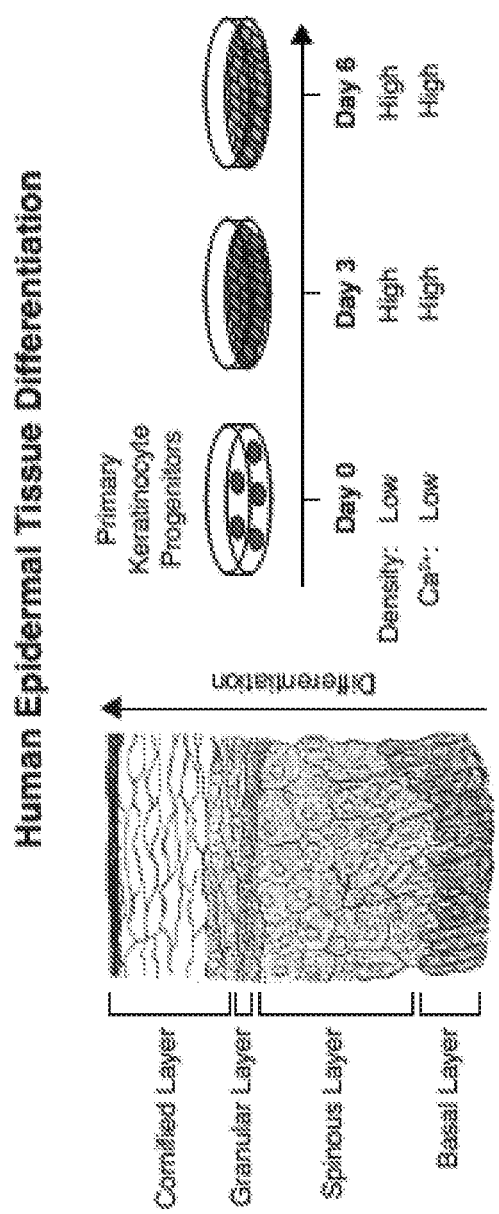
FIG. 87 shows a schematic of human epidermis and cell culture model system of epidermal differentiation
Figure 88:
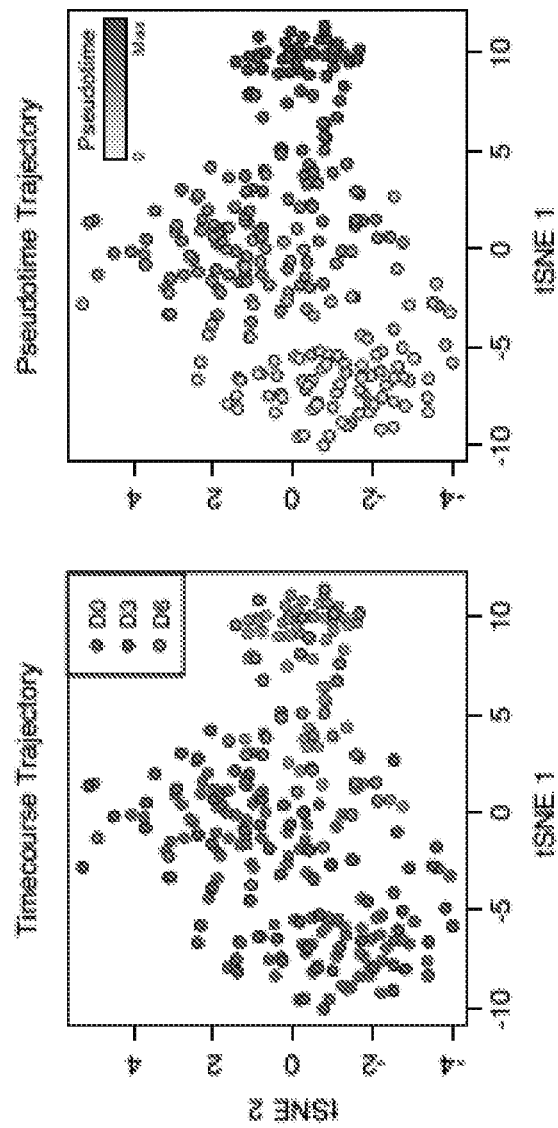
FIG. 88 shows a tSNE projection of TF feature activity for epidermal cells.

FIG. 87 shows a schematic of human epidermis and cell culture model system of epidermal differentiation FIG. 88 shows a tSNE projection of TF feature activity for epidermal cells labeled by differentiation day (left) or pseudotime (right).

Figure 89:
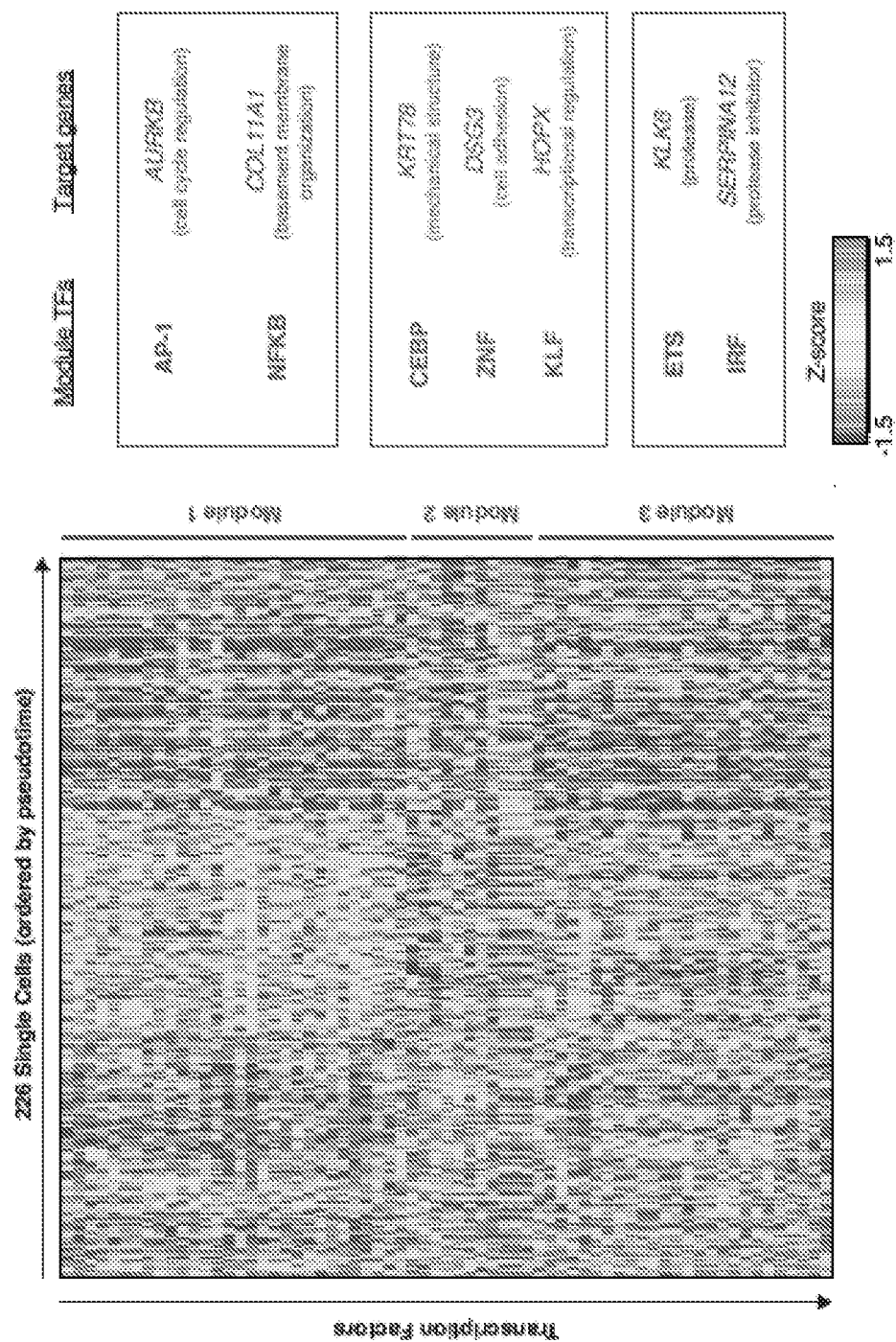
FIG. 89 shows a heatmap of cells ordered by pseudotime versus TF feature activity.

FIG. 89 shows a heatmap of cells ordered by pseudotime (columns) versus TF feature activity (filtered for motifs with dynamic activity). Modules represent collections of TF features with similar temporal profiles. Genes listed next to heat map were found proximal to (<50 kb) from genomic regions exhibiting accessibility kinetics associated with that module.

Figure 90:
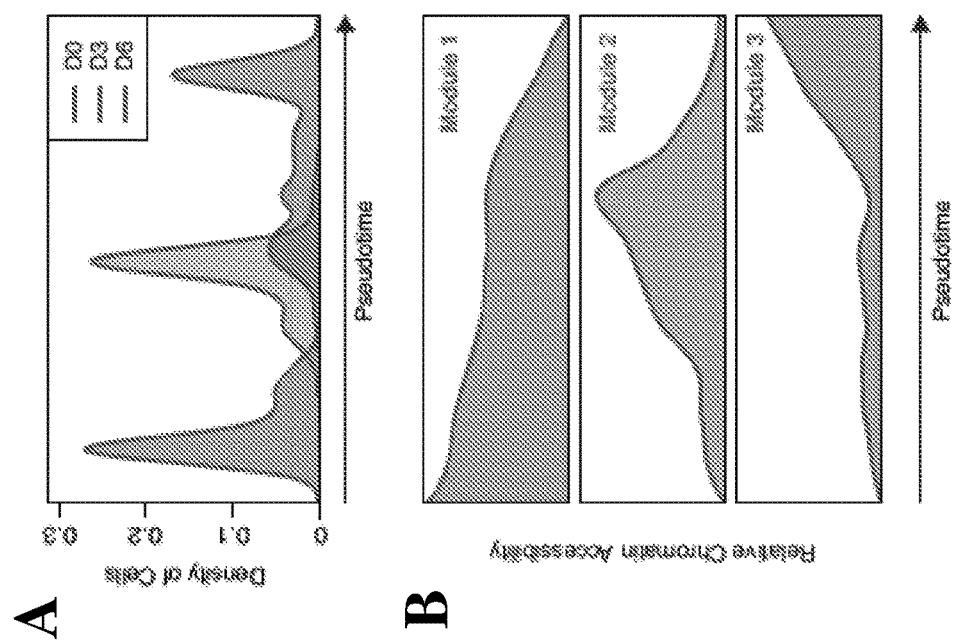
FIG. 90 shows a density histogram of pseudotime values for cells from each day of differentiation.

FIG. 90 Panel A shows a density histogram of pseudotime values for cells from each day of differentiation. Panel B shows the average accessibility profiles for each module identified in FIG. 89.

Figure 91:
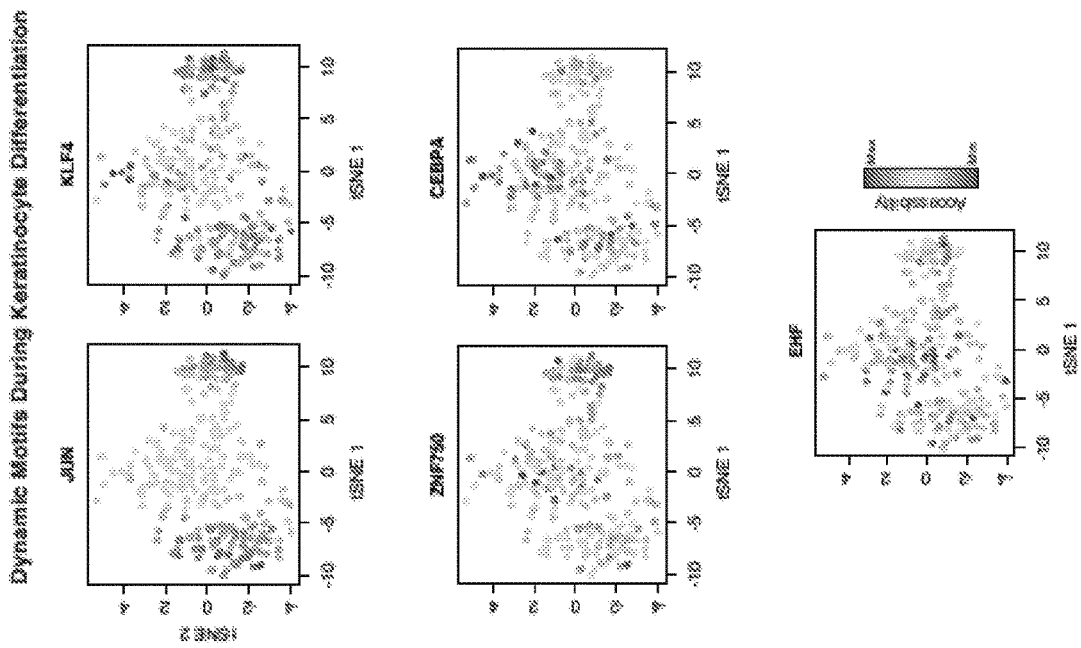
FIG. 91 shows tSNE projections of TF activity.

FIG. 91 shows tSNE projections of TF activity, cells are labeled by relative activity of individual motifs for each plot.

FIG. 92 shows a schematic of sgRNA expression vector and library amplification for direct sequencing readout of guide RNA identity.

Figure 93:
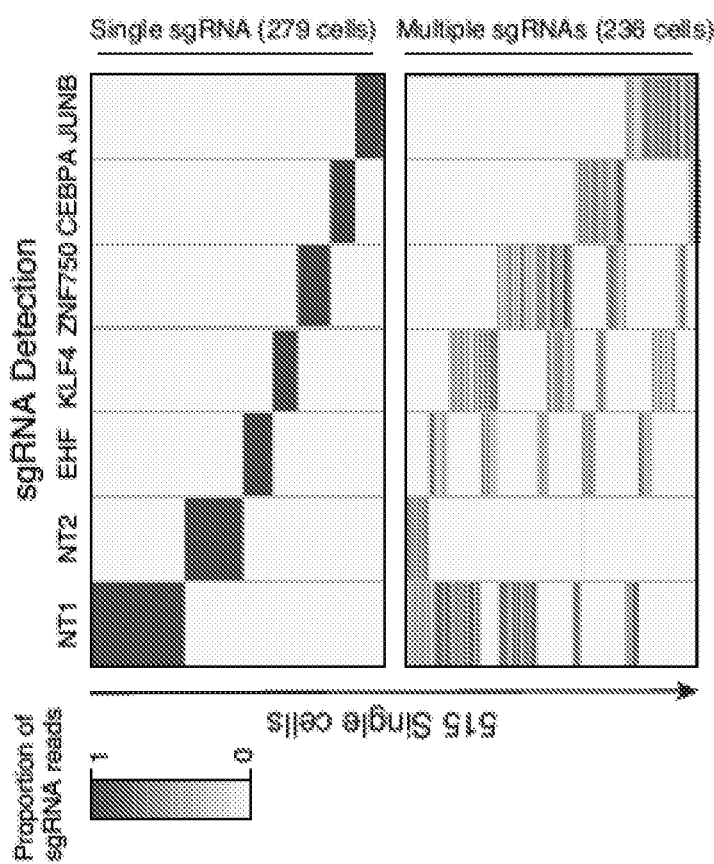
FIG. 93 shows a heatmap of sgRNA identities (columns) versus single cells (rows) indicating the proportion of all reads associated with each sgRNA.

FIG. 93 shows a heatmap of sgRNA identities (columns) versus single cells (rows) indicating the proportion of all reads associated with each sgRNA.

Figure 94:
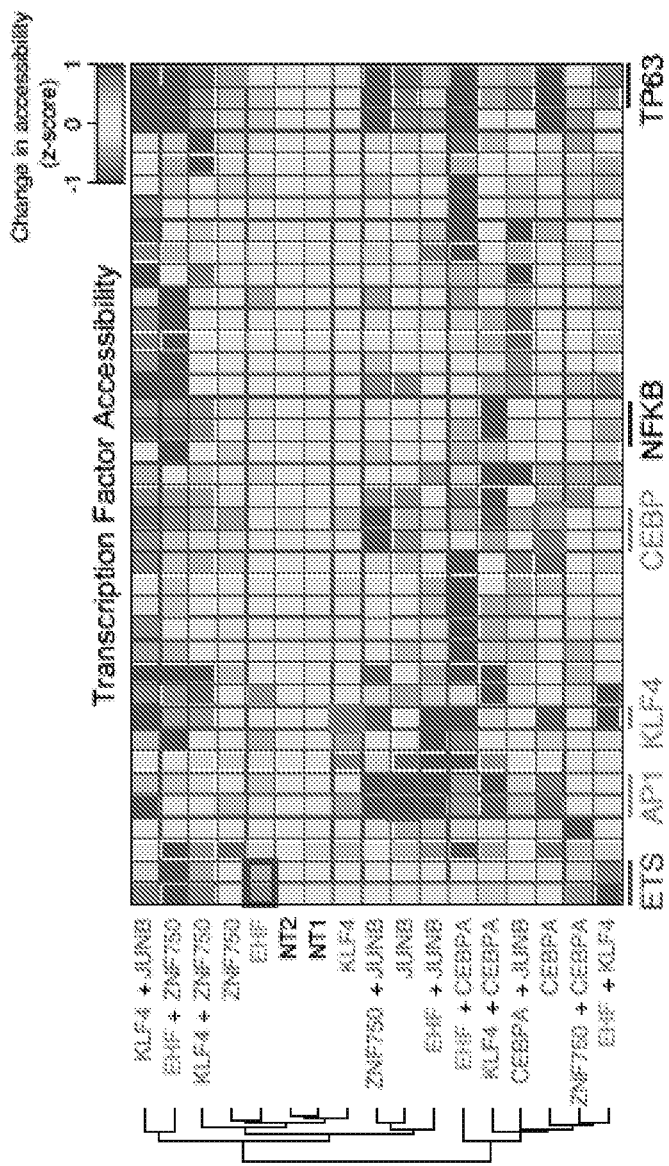
FIG. 94 shows a heatmap of genetic perturbations versus TF features indicating activity of TF feature in perturbed cells relative to non-targeting (NT) cells.

FIG. 94 shows a heatmap of genetic perturbations (noted by target gene) versus TF features indicating activity of TF feature in perturbed cells relative to non-targeting (NT) cells. Similar motif features from AP1, FOX, and ETS families were merged.

Figure 95:
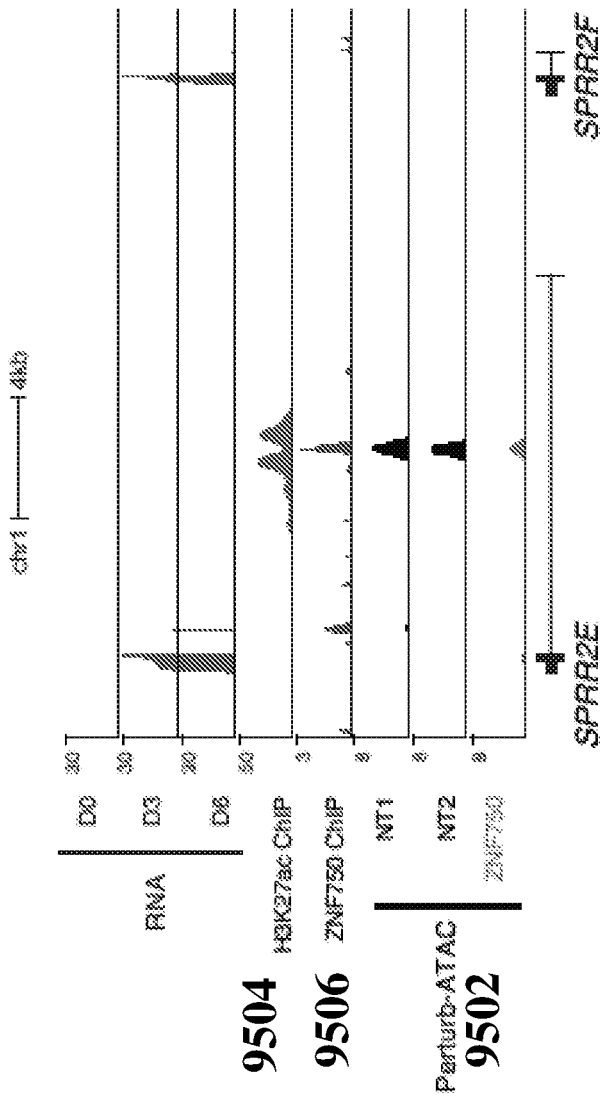
FIG. 95 shows a map of genomic locus of SPRR2E gene.

FIG. 95 shows a map of genomic locus of SPRR2E gene. Perturb-ATAC tracks 9502 represent signal from merged single cells identified for each sgRNA. H3K27ac 9504 and ZNF750 9506 ChIP-seq tracks (from Day 3 differentiating keratinocytes, normalized to 10m reads, from Rubin et al. 2017) are also displayed.

Figure 96:
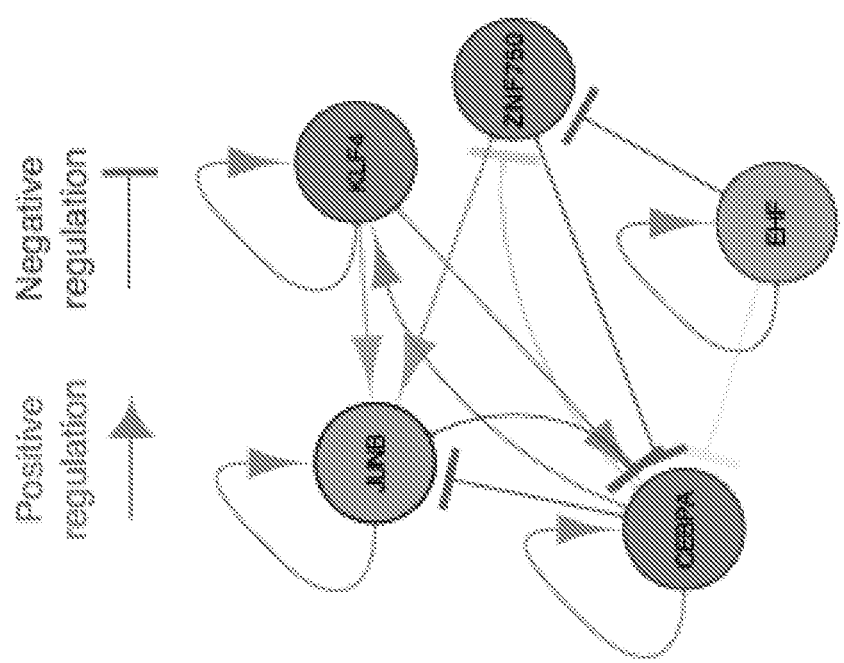
FIG. 96 shows a representation of positive and negative regulation between targeted genes (factors) and sets of genomic regions (features).

FIG. 96 shows a representation of positive and negative regulation between targeted genes (factors) and sets of genomic regions (features). Arrows are shown for regulation with FDR <0.25 and decreasing transparency is associated with lower FDR. Map was generated using Cytoscape 1271 v3.1.0.

Figure 97:
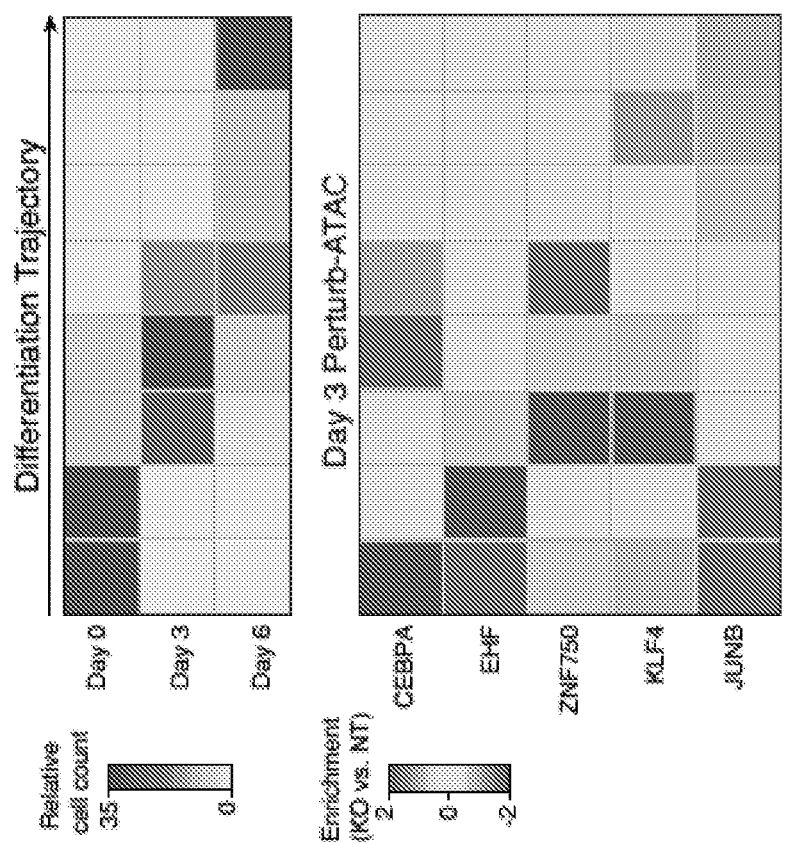
FIG. 97 shows a heatmap displaying the frequency of cells in each of eight bins representing progression along differentiation trajectory.

FIG. 97 Top: heatmap displaying the frequency of cells in each of eight bins representing progression along differentiation trajectory. Bottom: heatmap indicating the enrichment or depletion of cells in each differentiation bin compared to non-targeting control cells. For each perturbation, a custom reduced dimensionality space was created to highlight altered features.

Figure 98:
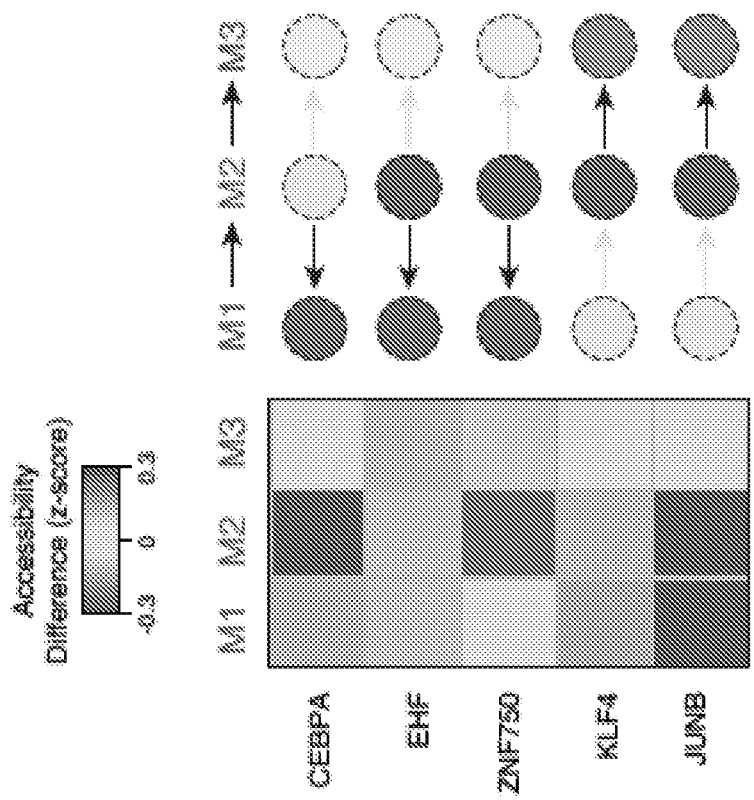
FIG. 98 shows a heatmap of perturbations versus modules of features.

FIG. 98 shows a heatmap of perturbations (targeted genes, rows) versus modules of features (columns). For each module, the mean change in feature activity is shown.

Figure 99:
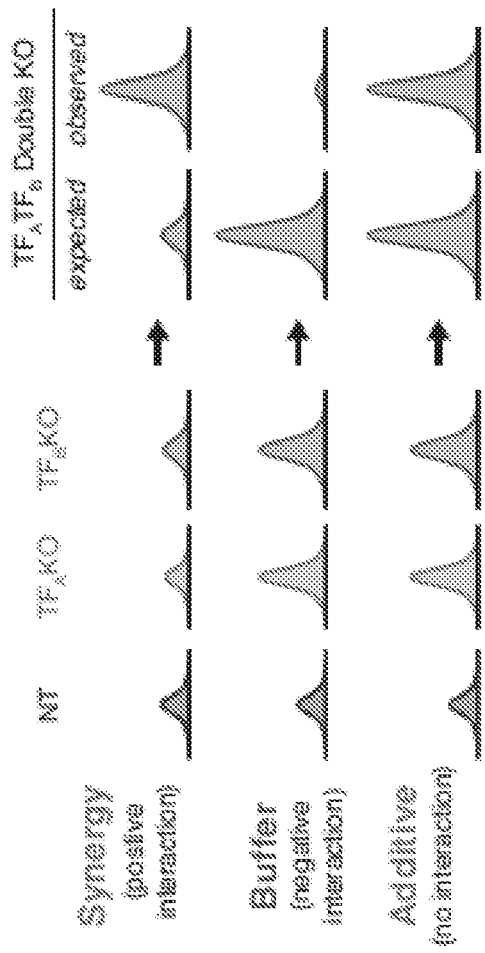
FIG. 99 shows a representative peak signal for each category of interaction.

FIG. 99 shows an example, representative peak signal for each category of interaction.

Figure 100:
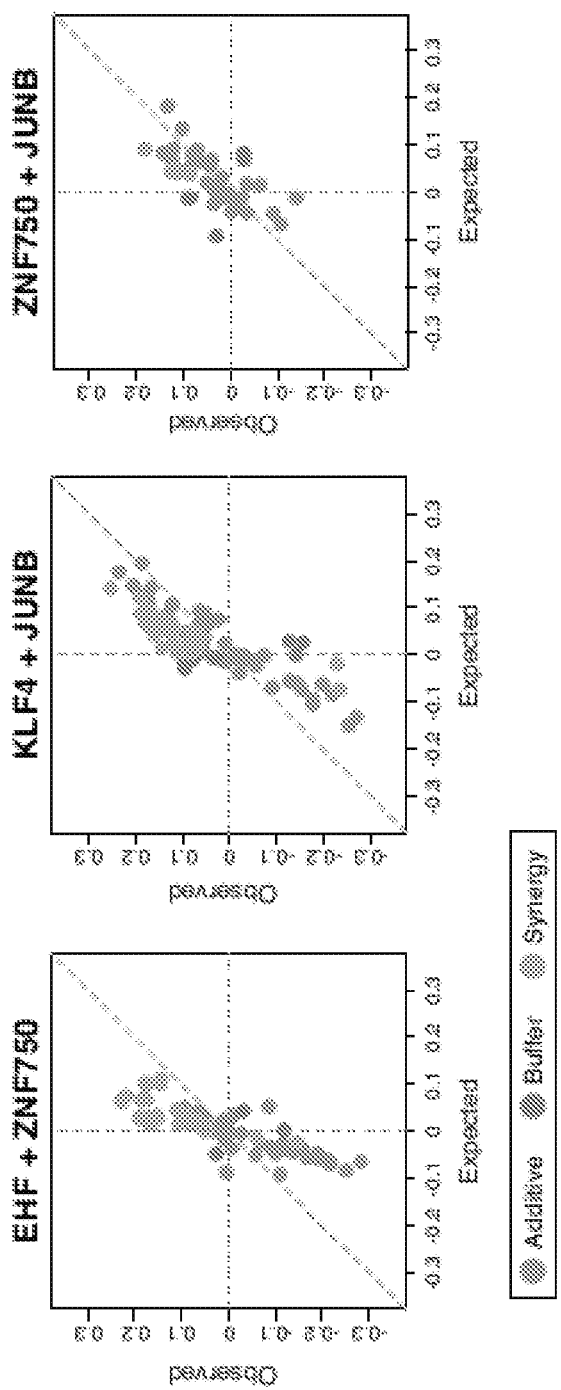
FIG. 100 shows scatter plots of observed versus expected accessibility in double knockout cells.

FIG. 100 shows scatter plots of observed versus expected (based on additive model) accessibility in double knockout cells. Only features significantly altered in either single knockout or double knockout condition are plotted, and feature colors indicate category of interaction.

Figure 101:
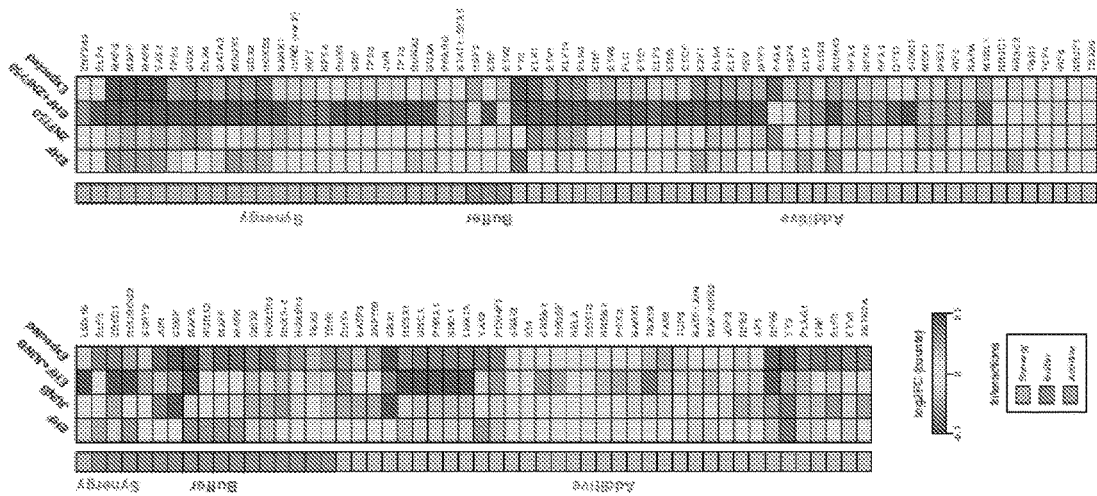
FIG. 101 shows heatmaps of altered activity of features (rows) in the condition of various knockouts in the same cell, along with their expected activity.

FIG. 101 shows heatmaps of altered activity of features (rows) in the condition of EHF knockout, JUNB knockout, or simultaneous EHF and JUNB knockouts in the same cell, along with their expected activity (left). Right: heatmaps of altered activity for EHF and ZNF750 knockouts.

Figure 102:
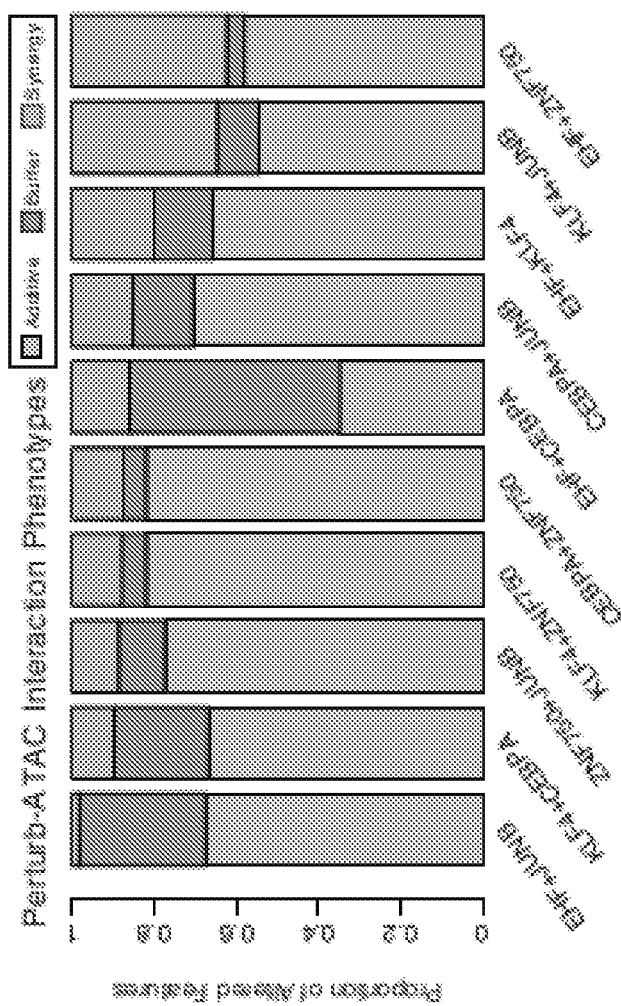
FIG. 102 shows a bar plot of the proportion of interacting features belonging to each category.

FIG. 102 shows a bar plot of the proportion of interacting features belonging to each category. Each column represents a particular pair of targeted genes. Only features altered in either single perturbation or the double perturbation condition are considered.

Figure 103:
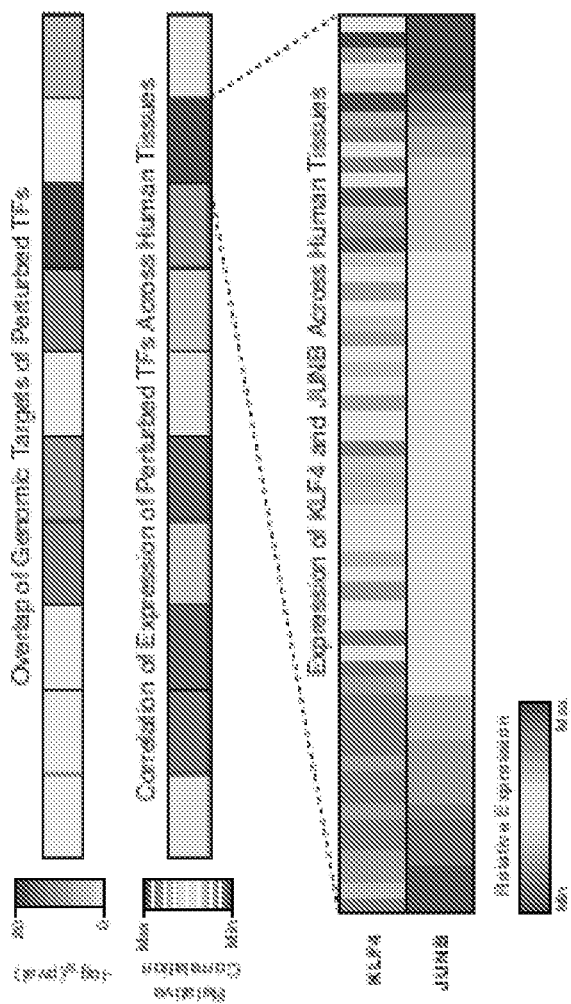
FIG. 103 shows a heatmap indicating significance of genomic overlap or correlation of gene expression for pairs of TF corresponding to pairs.

FIG. 103 shows a heatmap indicating significance of genomic overlap or correlation of gene expression for pairs of TF corresponding to pairs (top). Bottom: Heatmap displaying relative RNA expression of KLF4 and JUNB across tissues from the Roadmap Epigenomics Project.

Figure 104:
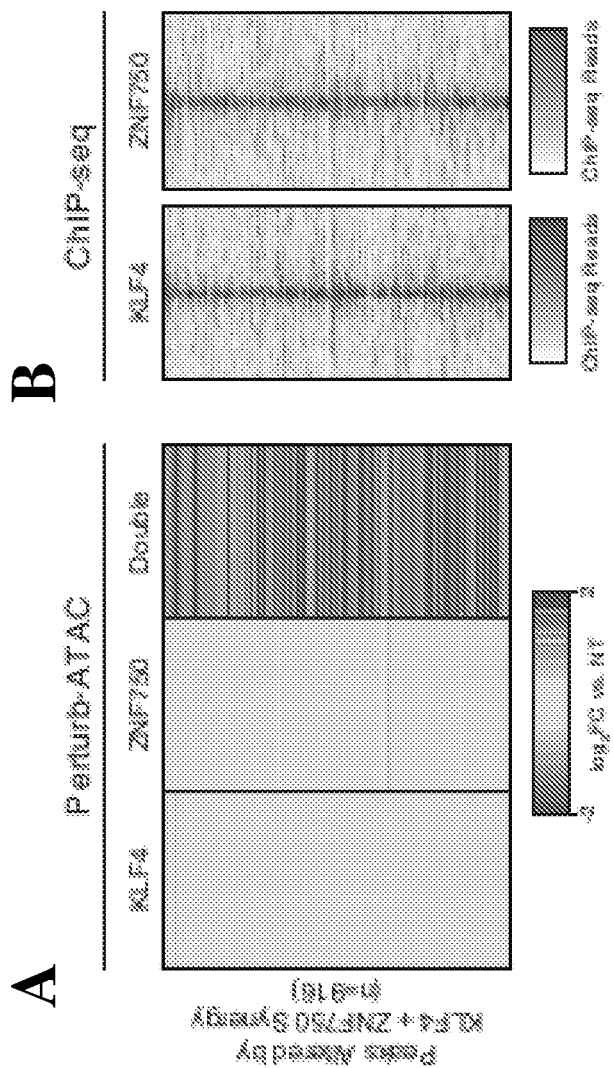
FIG. 104 shows a heatmap indicating relative accessibility of genomic regions exhibiting synergistic behavior in double knockout cells.

FIG. 104 panel A shows a heatmap indicating relative accessibility of genomic regions (rows) exhibiting synergistic behavior in KLF4 and ZNF750 double knockout cells. Panel B shows a heatmap with rows corresponding to regions displayed on left, displaying ChIP seq profiles for KLF4 and ZNF750.

Figure 105:
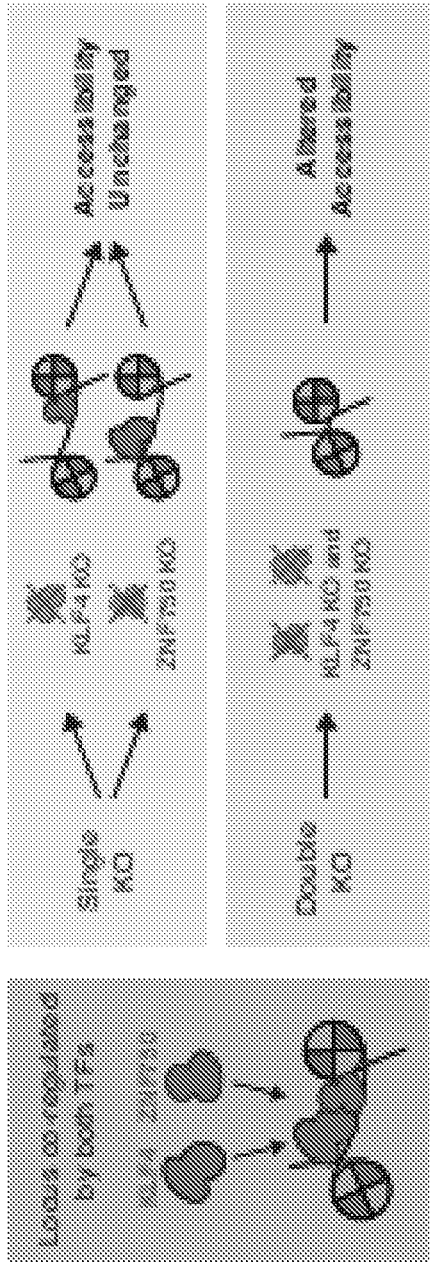
FIG. 105 shows a hypothetical model of KLF4 and ZNF750 redundancy for maintenance of accessibility at co-occupied loci.

FIG. 105 shows a hypothetical model of KLF4 and ZNF750 redundancy for maintenance of accessibility at co-occupied loci.

Figure 116:
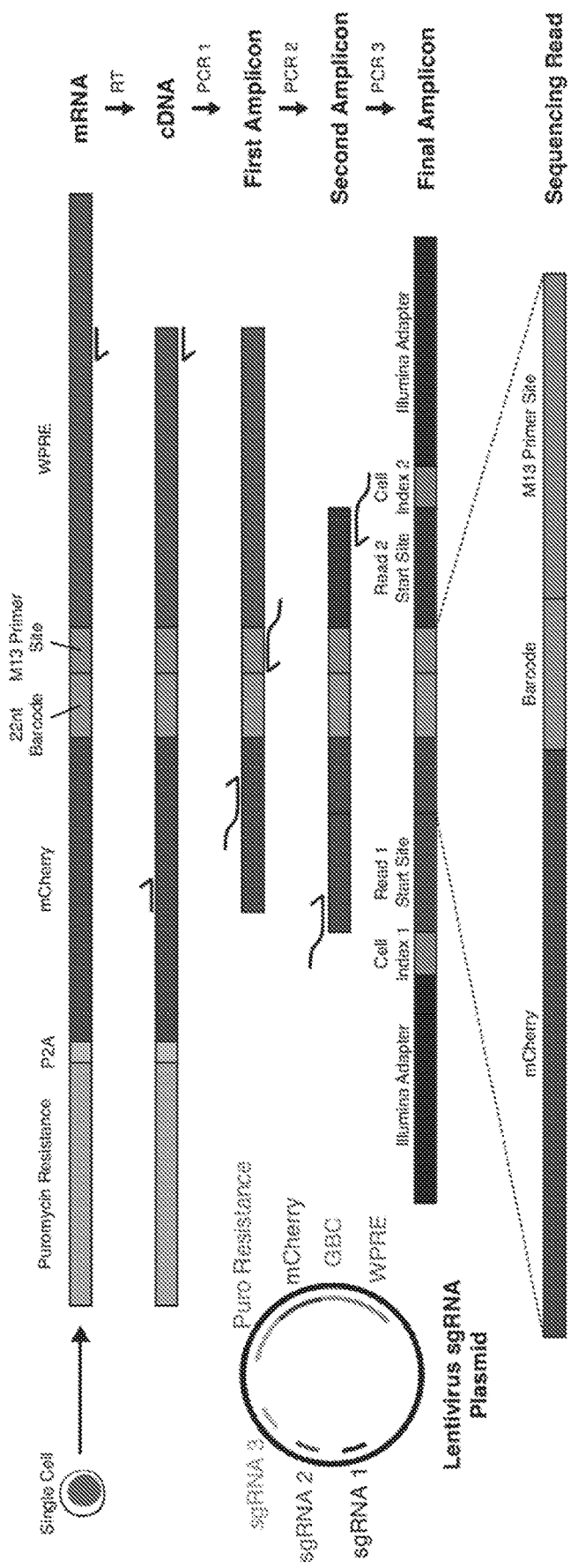
FIG. 116 shows a schematic of lentiviral plasmid encoding sgRNAs for CRISPRi as well as selection marker containing guide barcode.

FIG. 116 shows a schematic of lentiviral plasmid encoding sgRNAs for CRISPRi as well as selection marker containing guide barcode. Stepwise targeted reverse transcription and PCR steps are displayed from top to bottom.

Figure 117:
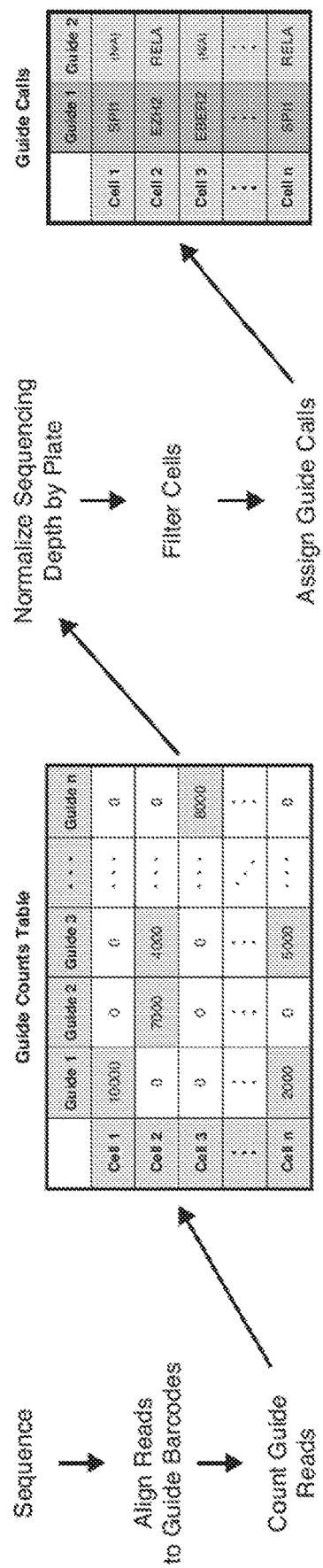
FIG. 117 shows an overview of computational pipeline taking sequencing reads for GBC and producing final table of guide calls for each cell.

FIG. 117 shows an overview of computational pipeline taking sequencing reads for GBC and producing final table of guide calls for each cell.

Figure 118:
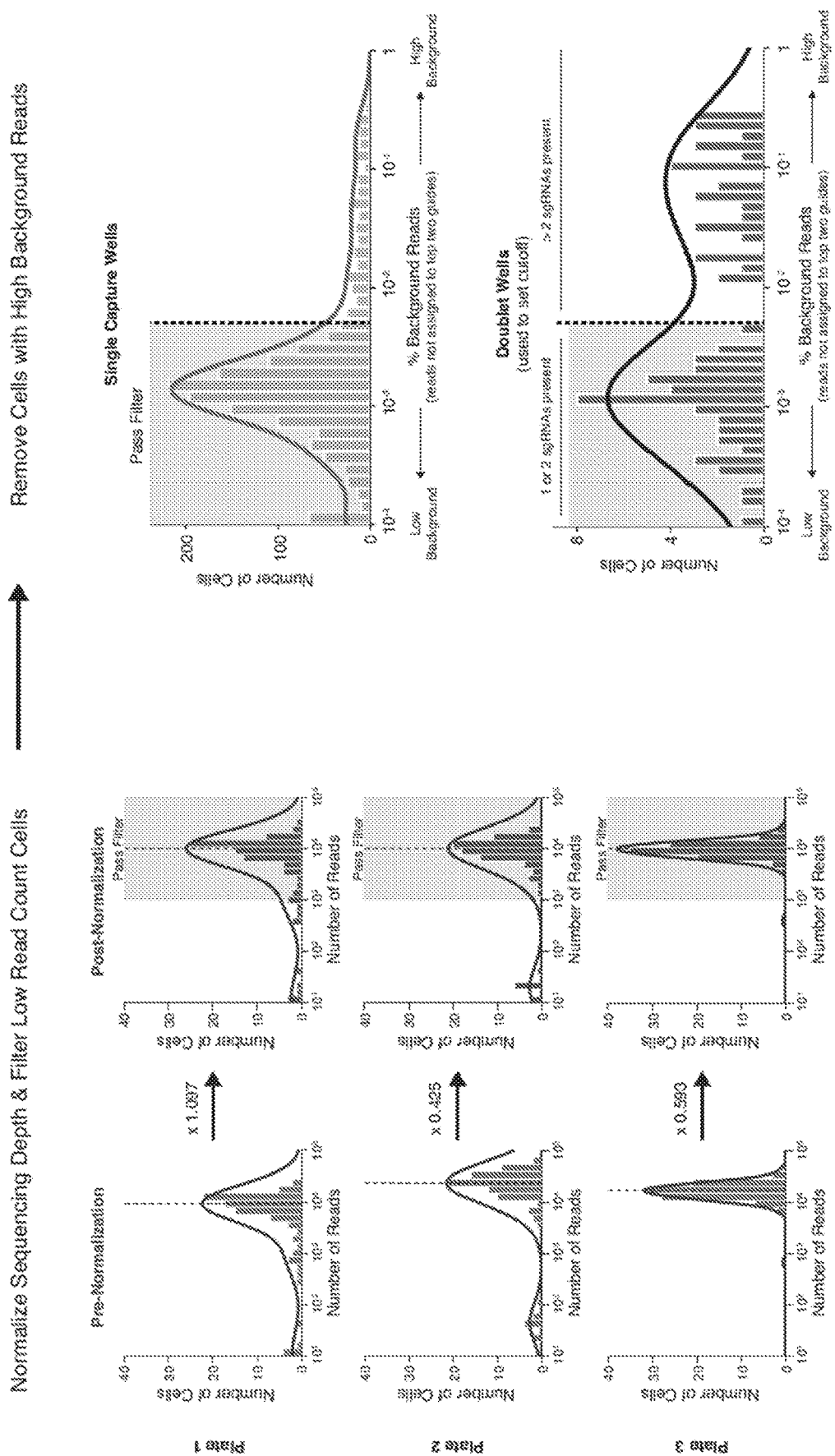
FIG. 118 shows detail on derivation of filtering parameters for per-cell sequencing depth and background reads.

FIG. 118 shows detail on derivation of filtering parameters for per-cell sequencing depth and background reads. Left: distribution of reads aligning to any guide barcode are displayed for each of three representative plates. Middle: distribution of reads after plate-specific depth adjustment for high mode, resulting in uniform median depth for high mode across plates and uniform filter threshold of 1,000 normalized reads per cell. Right: Distribution of reads per cell not assigned to two most abundant guides, for cells annotated as single cell or doublet capture. Doublet wells separate into two modes, allowing determination of threshold separating unexpected high background in single capture wells.

Figure 119:
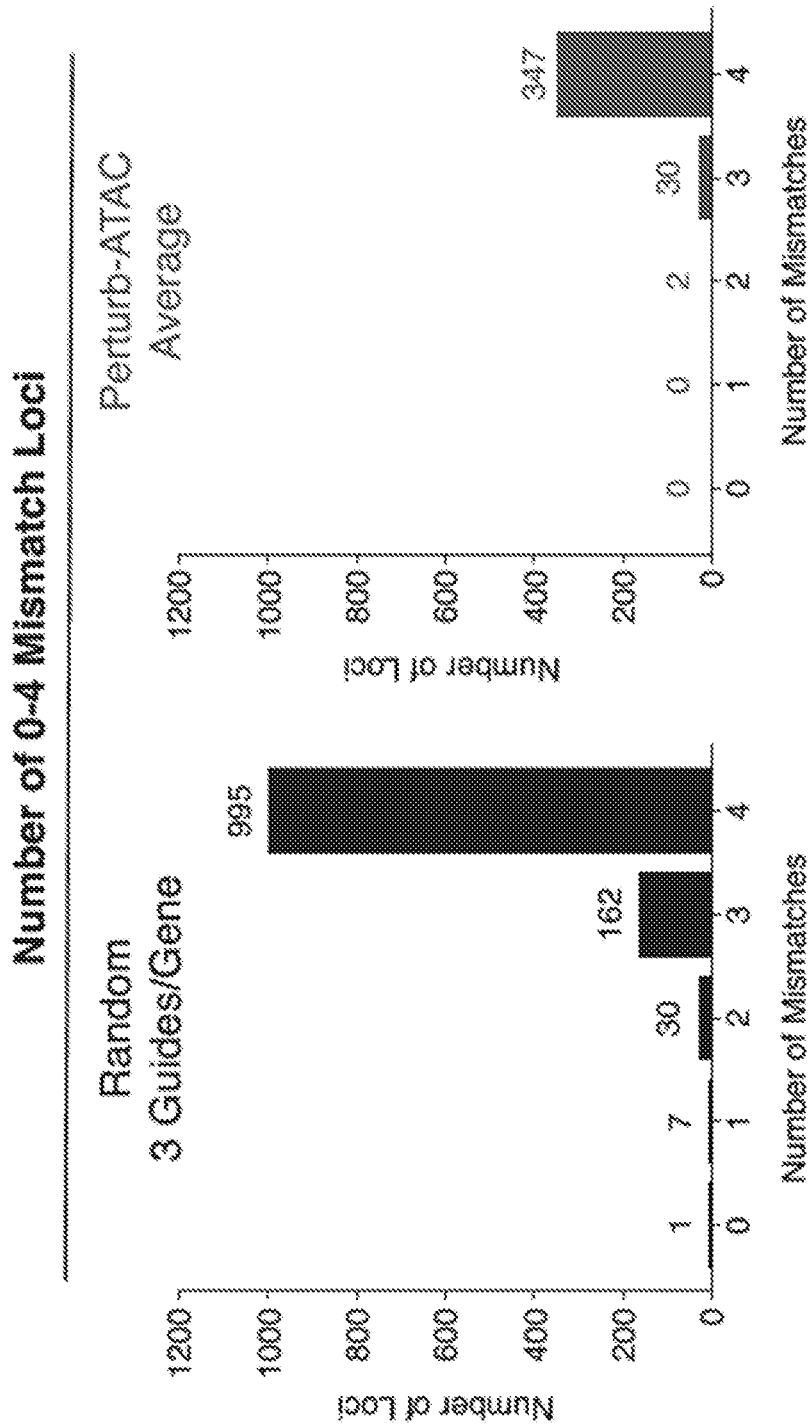
FIG. 119 show bar plots indicating the count of sgRNA sequence mismatch for random guide or guides selected for Perturb-ATAC.

FIG. 119 show bar plots indicating the count of sgRNA sequence mismatch for random guide or guides selected for Perturb-ATAC.

Figure 120:
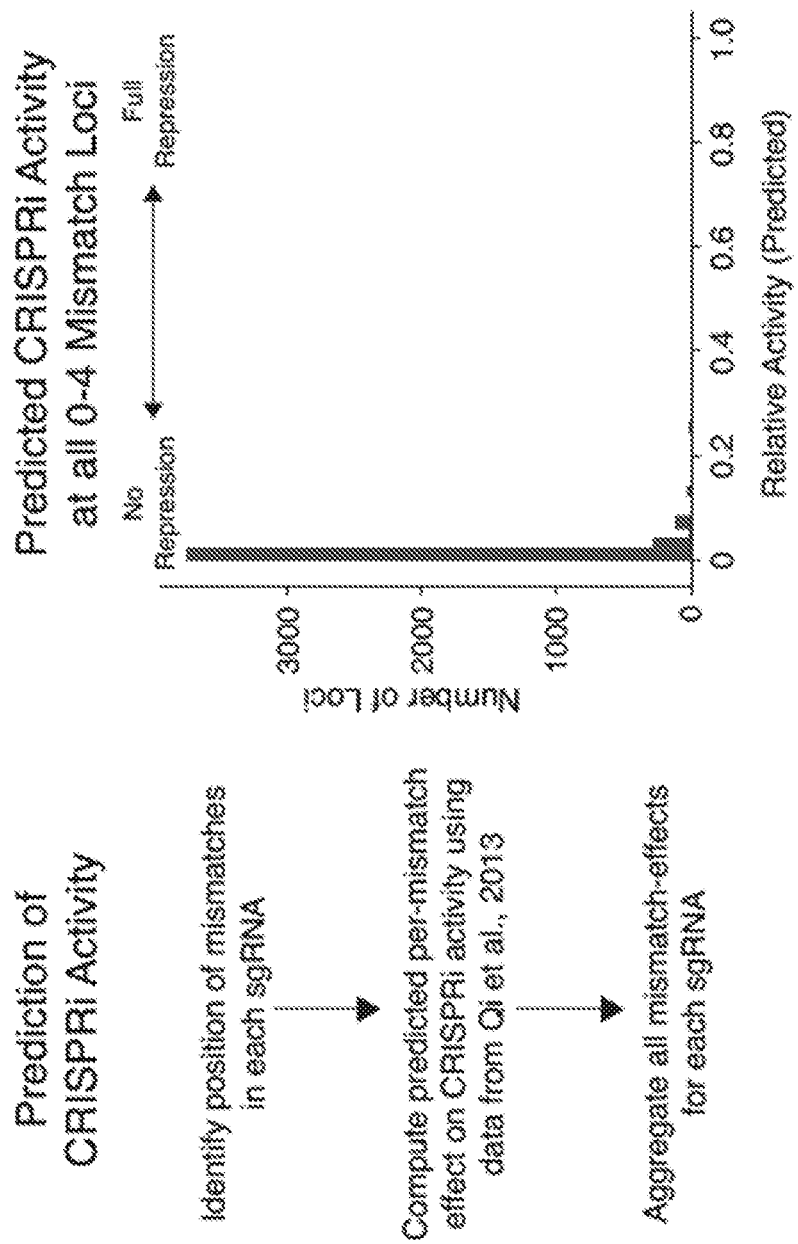
FIG. 120 shows the workflow to calculate predicted off-target CRISPRi activity based on contribution of mismatches.

FIG. 120 shows the workflow to calculate predicted off-target CRISPRi activity based on contribution of mismatches. Right: Histogram of predicted relative off-target activity for all sgRNAs used in this study, including up to 4 mismatches.

Figure 121:
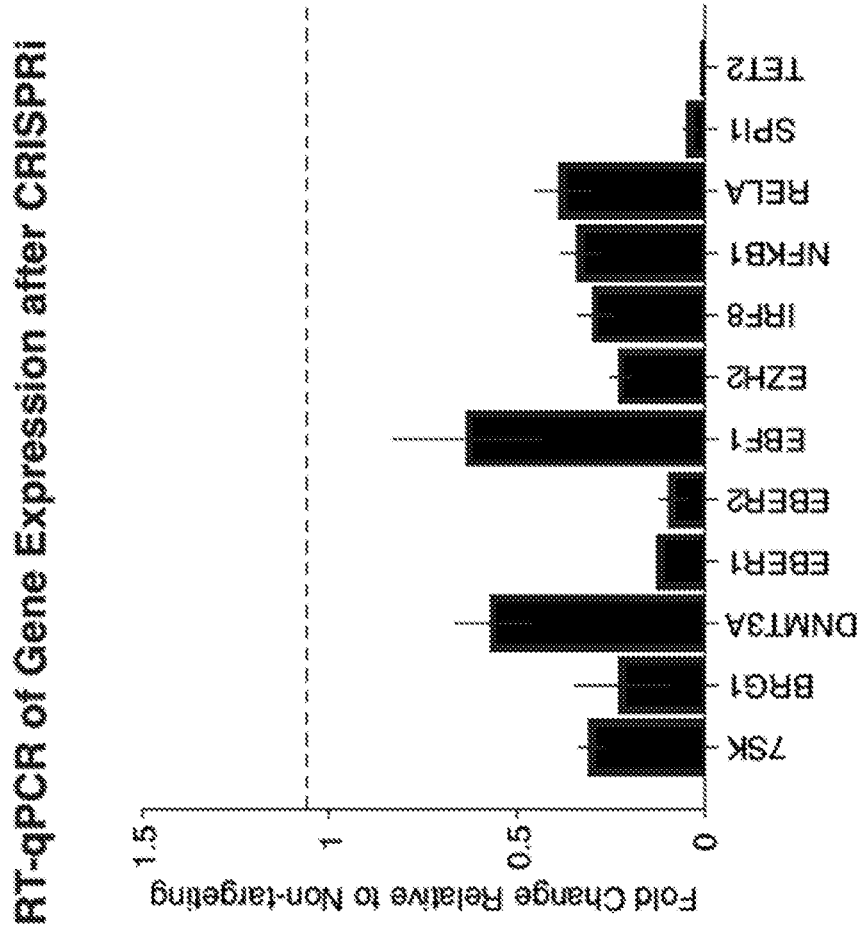
FIG. 121 shows qPCR validation of CRISPRi gene expression knockdown after transduction with sgRNAs targeting the specified gene.

FIG. 121 shows qPCR validation of CRISPRi gene expression knockdown after transduction with sgRNAs targeting the specified gene.

Figure 122:
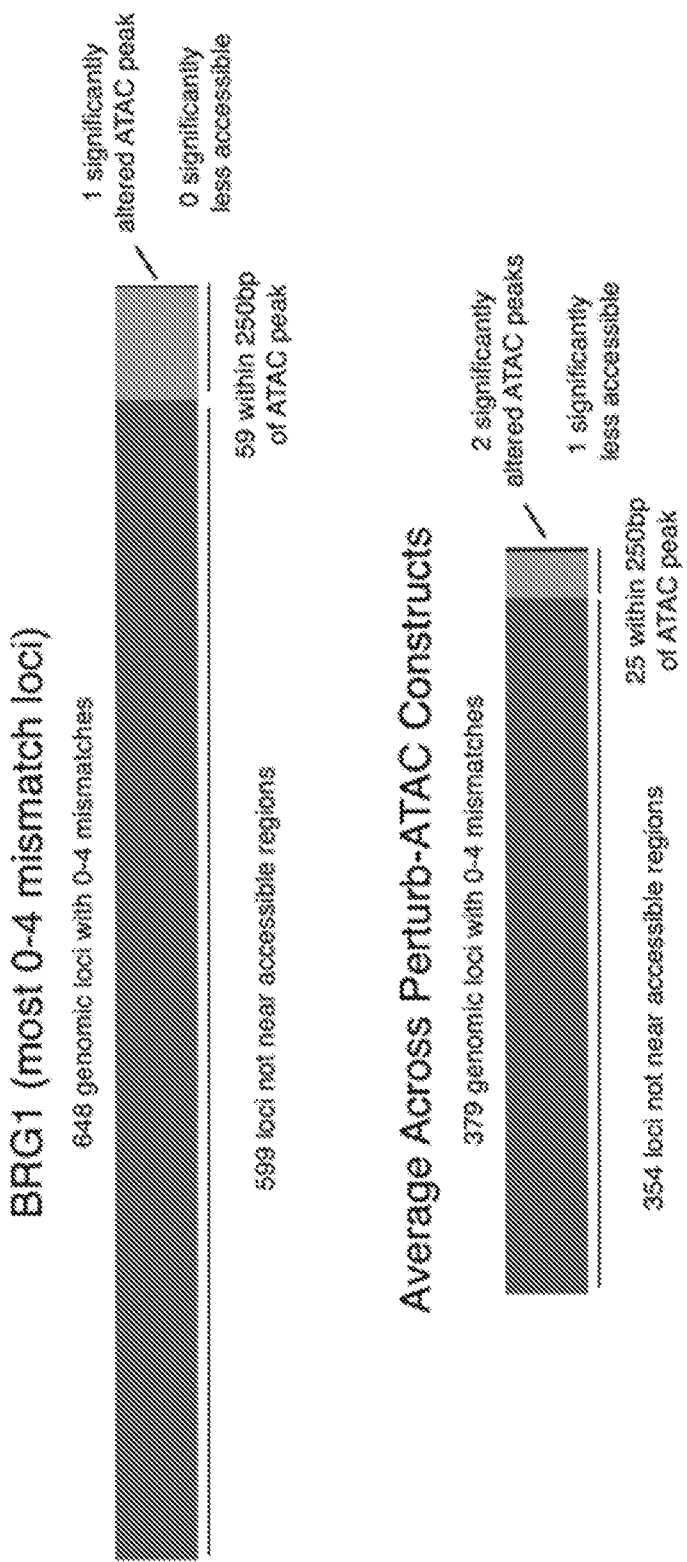

FIG. 122 shows bar plots indicating categories of sgRNA mismatch loci based on ATAC peak proximity and observed accessibility compared to non-targeting cells.

Figure 123:
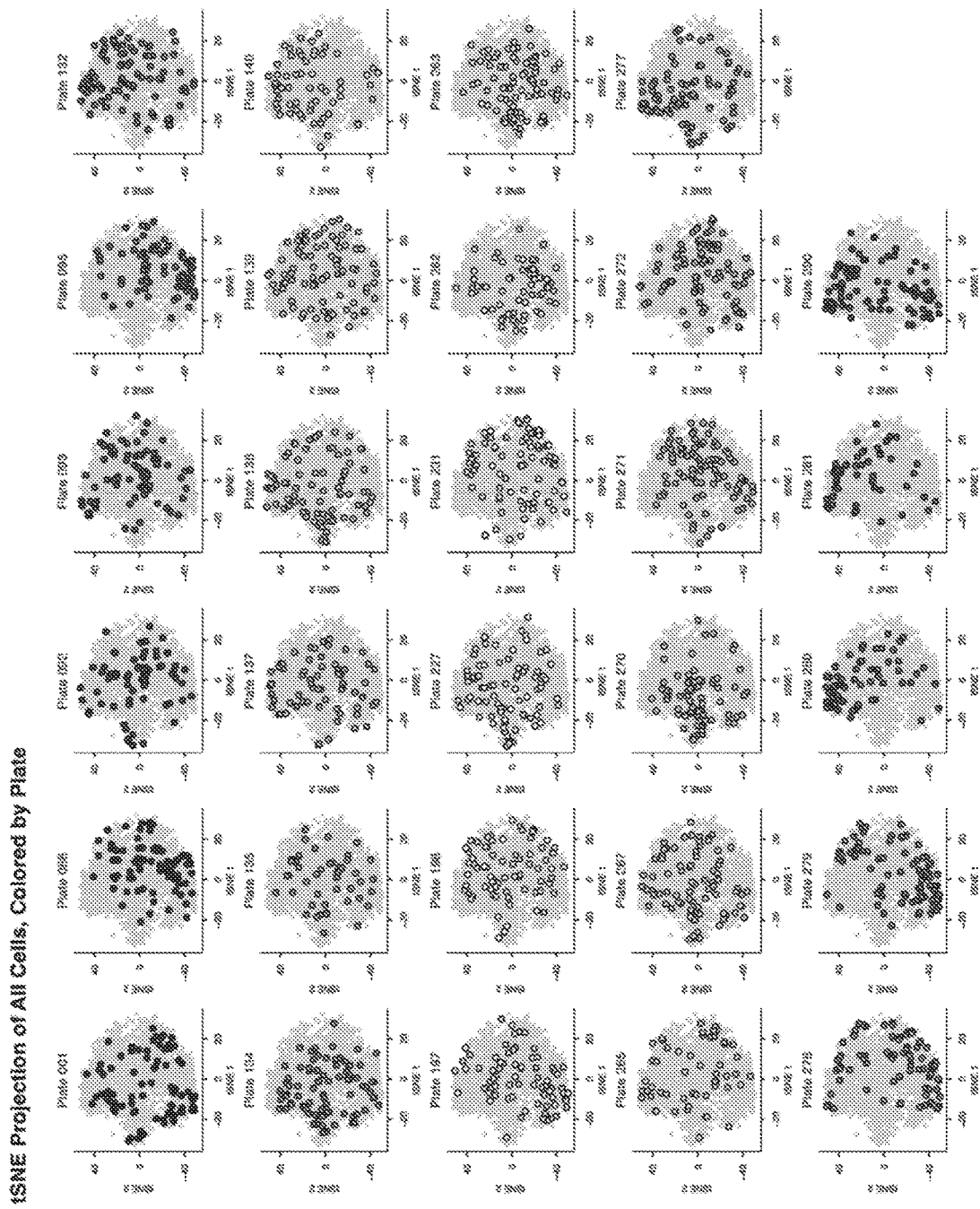

FIG. 123 shows tSNE plots of all cells assayed in GM12878 experiment based on chromVAR feature deviation z scores. For each plot, the cells assayed on a particular plate are highlighted.

Figure 124:
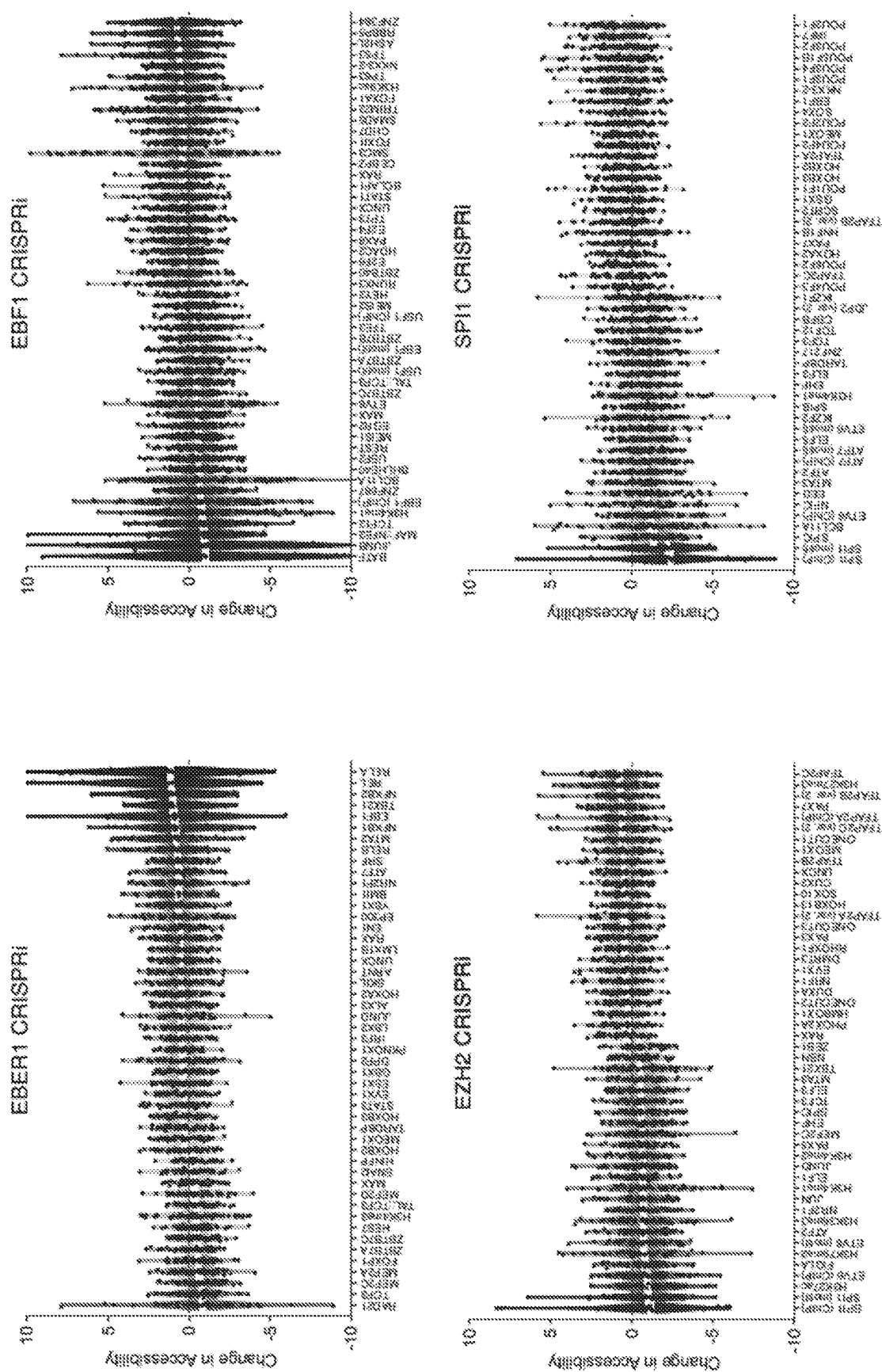

FIG. 124 shows violin plots of single cell accessibility relative to mean accessibility in non-targeting cells for significantly altered features in either EBER1, EBF1, EZH2, or SPI1 targeted cells. Each point represents an individual genomic feature (collection of genomic regions sharing an annotation such as a TF motif or ChIP-seq peak) in an individual cell. A maximum of 50 features are shown per genotype.

Figure 125:
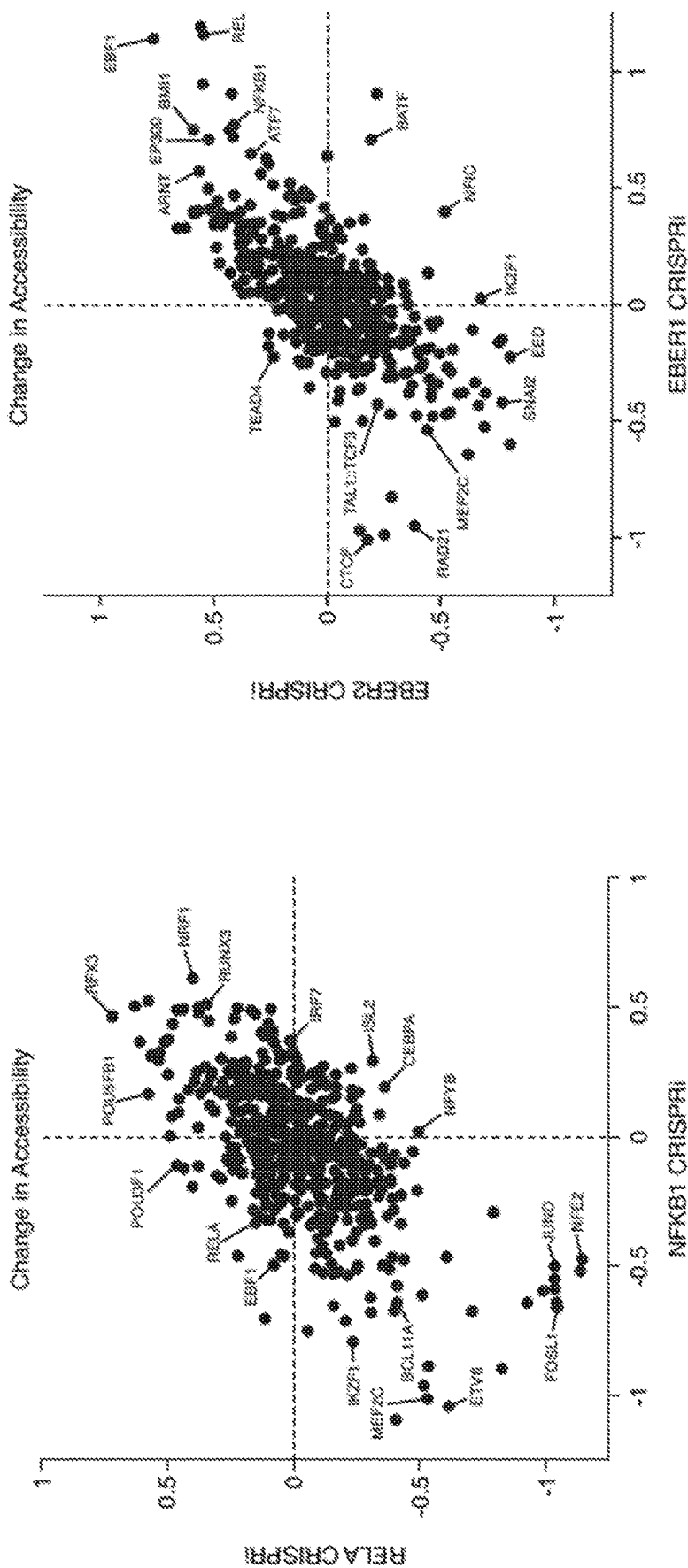

FIG. 125 shows scatter plots of accessibility in knockdown conditions, NFKB1 versus RELA (left) or EBER1 versus EBER1 (right).

Figure 126:
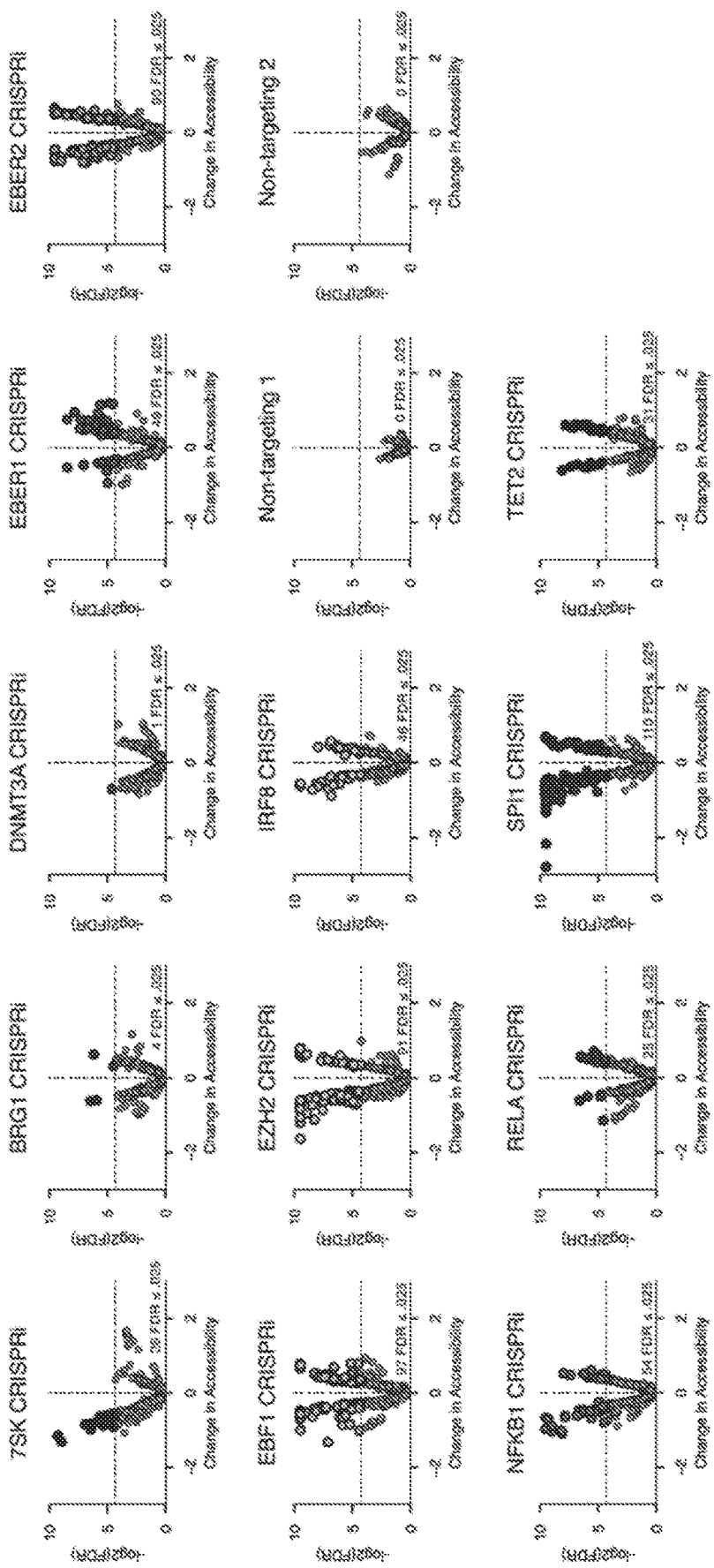

FIG. 126 shows volcano plots for each single perturbation condition comparing perturbed cells to non-targeting control cells. Each point represents a genomic feature; significance threshold of FDR <=0.025.

Figure 127:
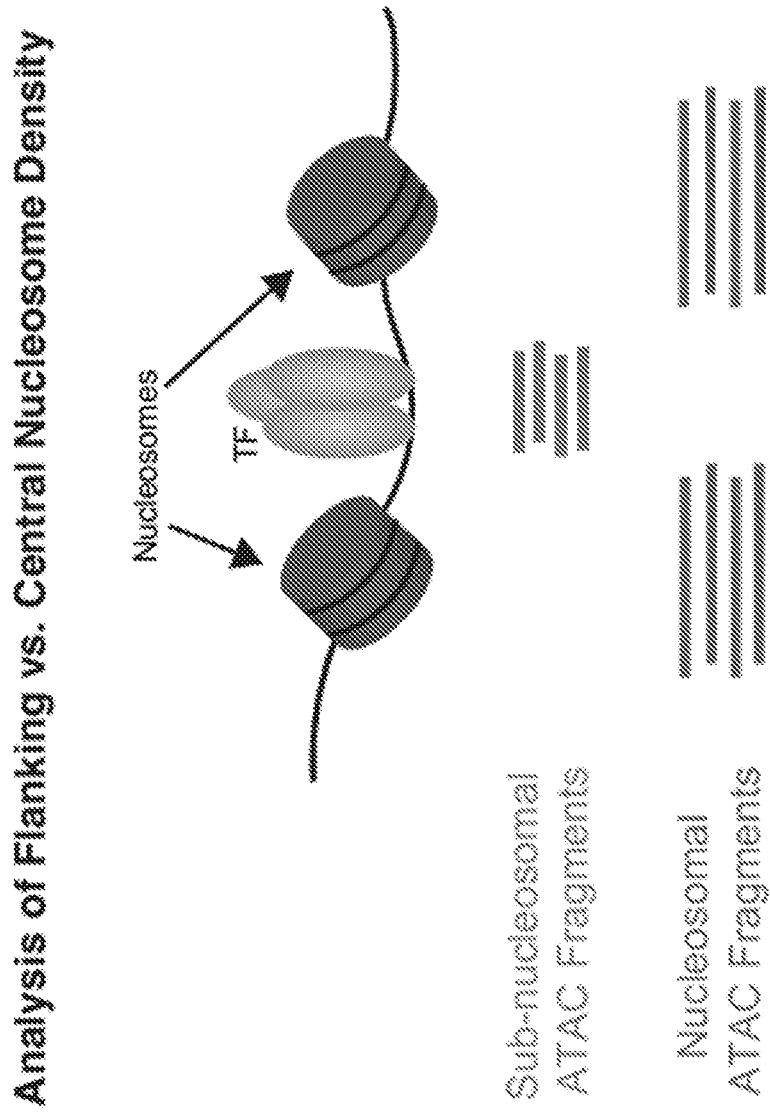

FIG. 127 shows a schematic depicting generation of short (<100 bp) ATAC fragments from sub-nucleosome regions and large fragments (180-247 bp) spanning nucleosome-protected regions.

Figure 128:
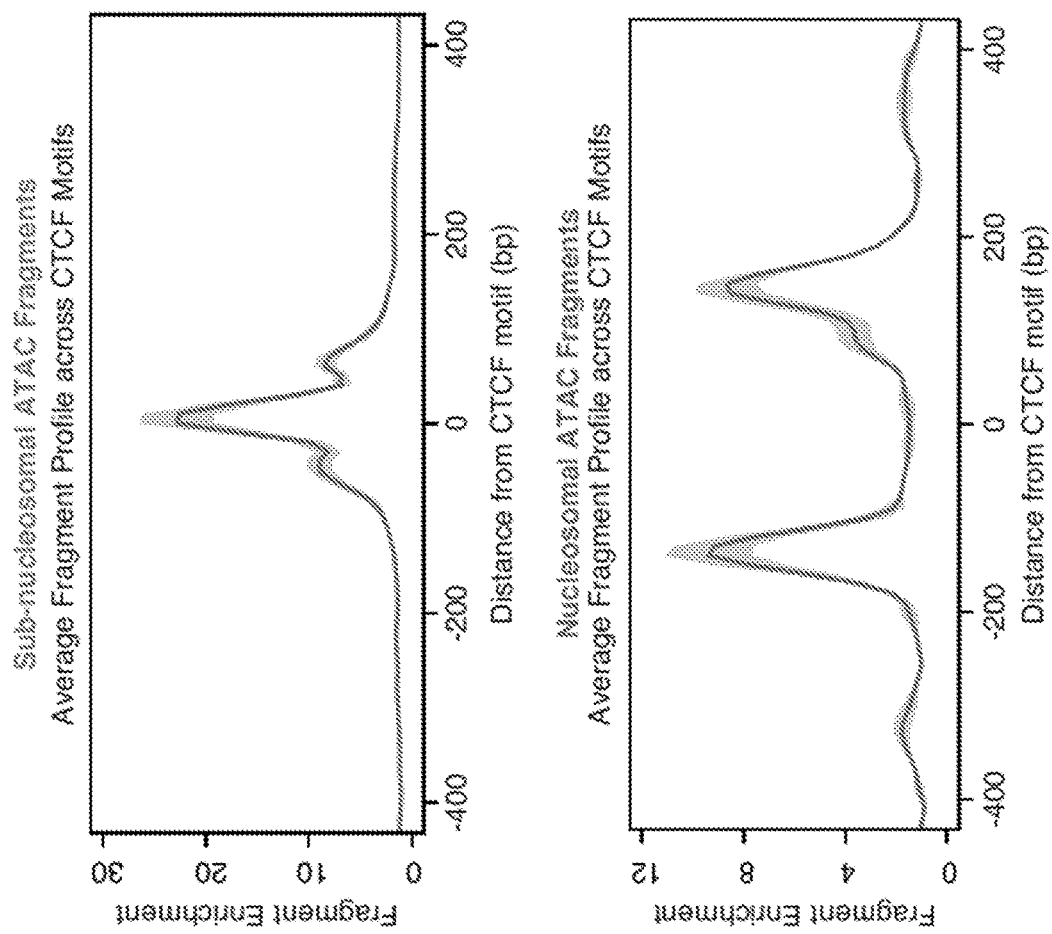

FIG. 128 shows metaplots of sub-nucleosome and nucleosome fragment signal at CTCF motif regions overlapping with CTCF ChIP seq peaks in GM12878. Signal represents average of two non-targeting cell populations, gray range represents standard deviation between samples.

Figure 129:
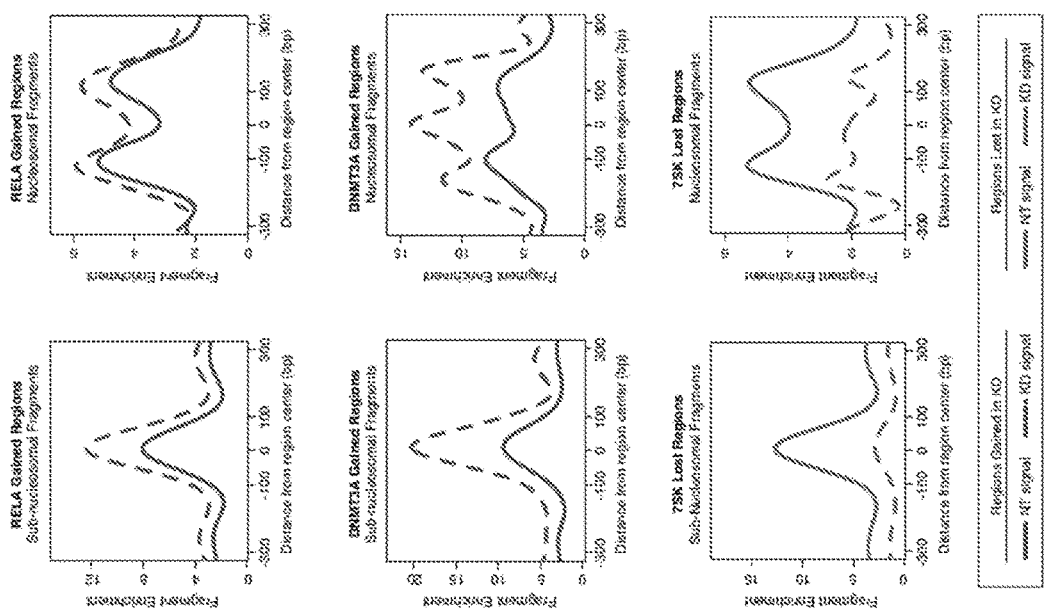

FIG. 129 shows metaplots of sub-nucleosome and nucleosome signal at differentially accessible regions.

Figure 130:
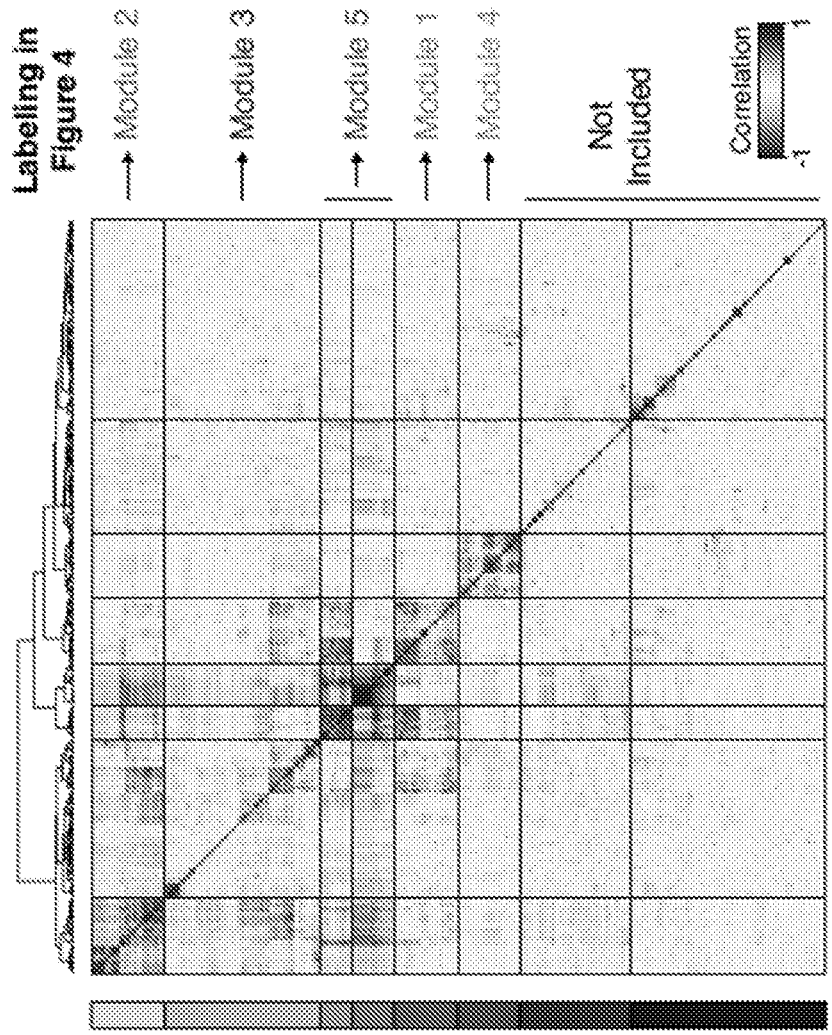

FIG. 130 shows a heatmap of correlation matrices for genomic features. Values indicate Pearson correlation across non-targeting cells for accessibility of two genomic features. Ward's hierarchical clustering was used to identify five modules with substantial intra-cluster correlation.

FIG. 131 shows a listing of key features in each module.

Figure 132:
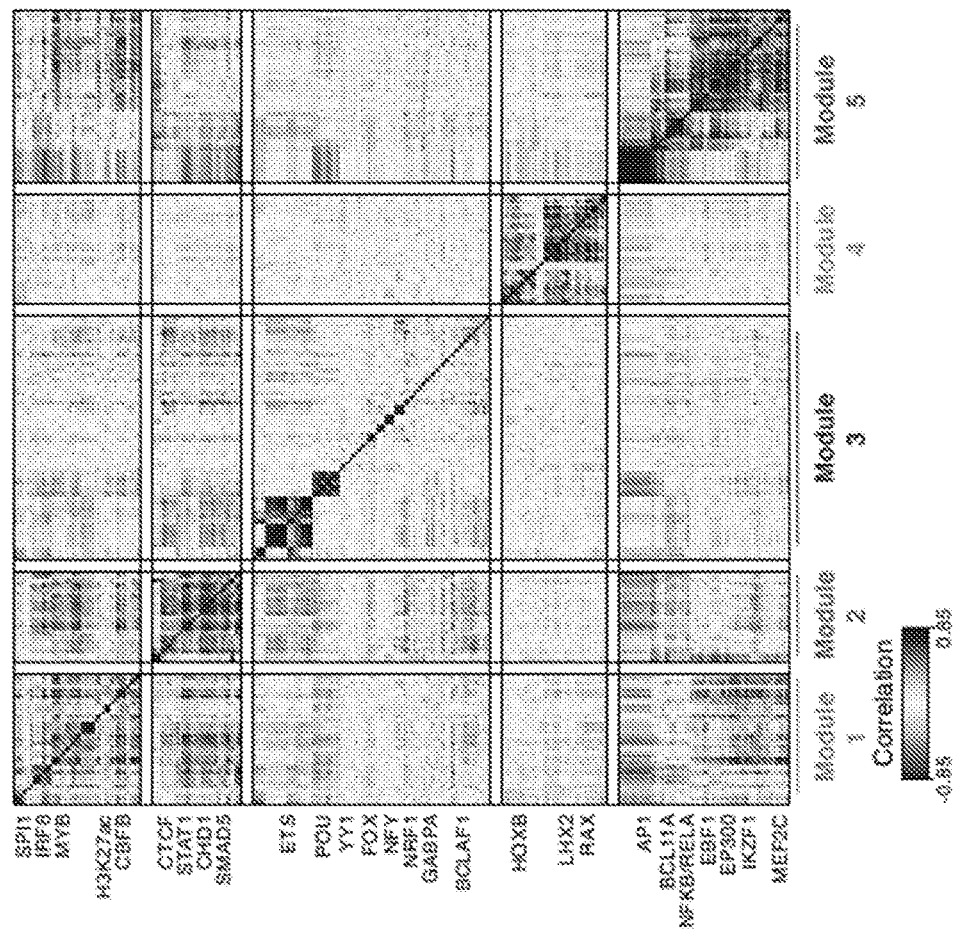

FIG. 132 shows a heatmap of correlation matrix for genomic features in IRF8 knockdown cells.

FIG. 133 shows box plots of single cell accessibility for CTCF and SMAD5 features in non-targeting and DNMT3A knockdown cells. Right: Histogram of z-score of number of altered correlations for each feature in DNMT3A knockdown cells.

FIG. 134 shows a heatmap of difference in feature correlations between NFKB1 knockdown cells (bottom) and RELA knockdown cells (top).

FIG. 135 shows heatmaps of feature correlations for Module 1 vs. Module 5 in non-targeting cells or EBER2 knockdown cells.

FIG. 136 shows a histogram of change in feature correlations for SPI1 knockdown versus non-targeting 1 cells, used to inform thresholds for designation of altered correlation.

FIG. 137 shows a table of counts and highlighted top altered-correlation features based on 5% FDR threshold FIG. 138 shows a schematic of lentiviral plasmids for sgRNA and Cas9 expression.

FIG. 139 shows Sanger sequencing traces of the 100 bp surrounding sgRNA 3' end for each target gene. Sequencing proceeded in forward direction (left to right), resulting in abrupt drop in sequencing alignment after sgRNA due to mixture of indels.

FIG. 140 shows a schematic of lentiviral plasmid encoding sgRNA for CRISPR knockout. Stepwise targeted reverse transcription and PCR steps are displayed from top to bottom FIG. 141 shows the distributions of reads per cell mapping to a sgRNA variable sequence. For each plate, a clear high mode of reads was identified and used to determine a depth cutoff.

FIG. 142 shows the distribution of proportion of all reads per cell mapping to known sgRNA sequence FIG. 143 shows the distribution of proportion of reads per cell associated with background (third most common) guide sequence. Cells in low mode passed filter.

FIG. 144 shows the distribution of proportion of reads associated with second most common guide. Cells were those that passed quality control, and those in the low mode of this distribution were considered to express a single guide, while cells in the high mode were considered to express two guides FIG. 145 shows scatter plots of proportion of reads associated with two guide sequences for all cells passing final filters.

FIG. 146 shows a signal track indicating a ZNF750 binding site that gains accessibility in targeted cells, indicating repressive activity of ZNF750.

FIG. 147 shows a scatter plot of principal component (PC) values for unperturbed keratinocytes. PC space was generated using altered features from specific single TF knockout cells. Yellow line represents pseudotime trajectory connecting centroids of cells from each differentiation day.

FIG. 148 shows a scatter plot of 1397 PC values for all perturbed and non-targeting cells embedded in PC space generated in (a). Cells are scored and colored by progression along pseudotime trajectory. These pseudotime values were used to assess the enrichment or depletion of knockout versus non-targeting cells.

FIG. 149 shows scatter plots of observed versus expected (based on additive model) accessibility in double knockout cells.

FIG. 150 shows a scatter plot of absolute log 2 fold changes of features in single knockout cells versus double knockouts (r~0.18).

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowed within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The single cell T-ATAC-seq and Perturb-ATAC protocols described above can be performed using (and/or aspects thereof in) droplets. For example, a cell (e.g., T cell, B cell, immune cell, other cell) being processed with T-ATAC-seq or Perturb-ATAC may be co-partitioned with a barcoded bead, as described elsewhere herein to facilitate one or more reactions described herein. For example, they may be co-partitioned with one or more reagents (e.g., lysis reagents) described herein to facilitate one or more reactions of these protocols. In some instances, one or more reactions may be performed using the bead as a solid support.

Figure 106:
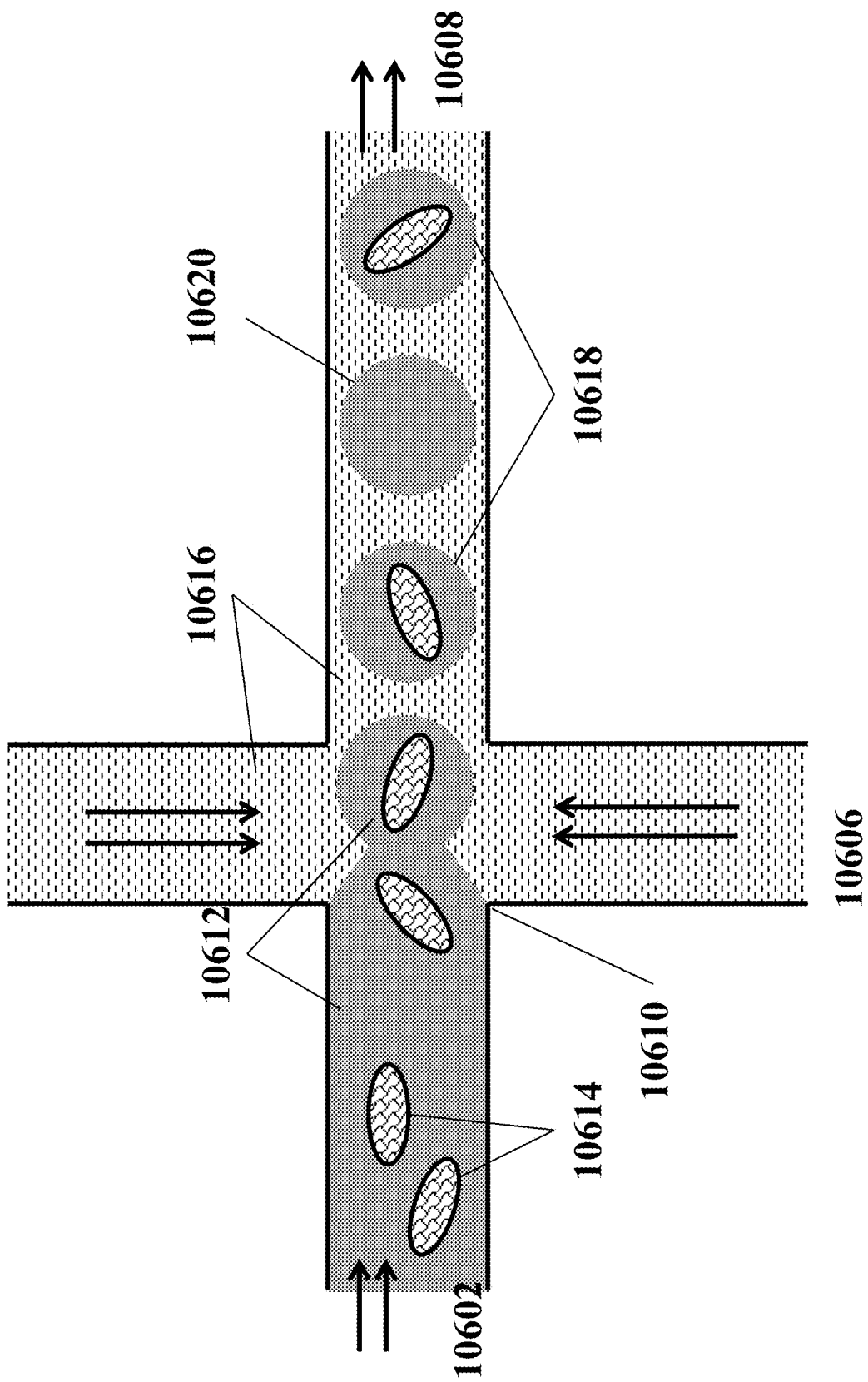
FIG. 106 shows an example of a microfluidic channel structure for partitioning individual biological particles.

FIG. 106 shows an example of a microfluidic channel structure 10600 for partitioning individual biological particles. The channel structure 10600 can include channel segments 10602, 10604, 10606 and 10608 communicating at a channel junction 10610. In operation, a first aqueous fluid 10612 that includes suspended biological particles (or cells) 10614 may be transported along channel segment 10602 into junction 10610, while a second fluid 10616 that is immiscible with the aqueous fluid 10612 is delivered to the junction 10610 from each of channel segments 10604 and 10606 to create discrete droplets 10618, 10620 of the first aqueous fluid 10612 flowing into channel segment 10608, and flowing away from junction 10610. The channel segment 10608 may be fluidically coupled to an outlet reservoir where the discrete droplets can be stored and/or harvested. A discrete droplet generated may include an individual biological particle 10614 (such as droplets 10618). A discrete droplet generated may include more than one individual biological particle 10614 (not shown in FIG. 106). A discrete droplet may contain no biological particle 10614 (such as droplet 10620). Each discrete partition may maintain separation of its own contents (e.g., individual biological particle 10614) from the contents of other partitions.

The second fluid 10616 can comprise an oil, such as a fluorinated oil, that includes a fluorosurfactant for stabilizing the resulting droplets, for example, inhibiting subsequent coalescence of the resulting droplets 10618, 10620. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 10600 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 10618, containing one or more biological particles 10614, and (2) unoccupied droplets 10620, not containing any biological particles 10614. Occupied droplets 10618 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 10614) at the partitioning junction 10610, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 10602), or other fluids directed into the partitioning junction (e.g., in channel segments 10604, 10606) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 107:
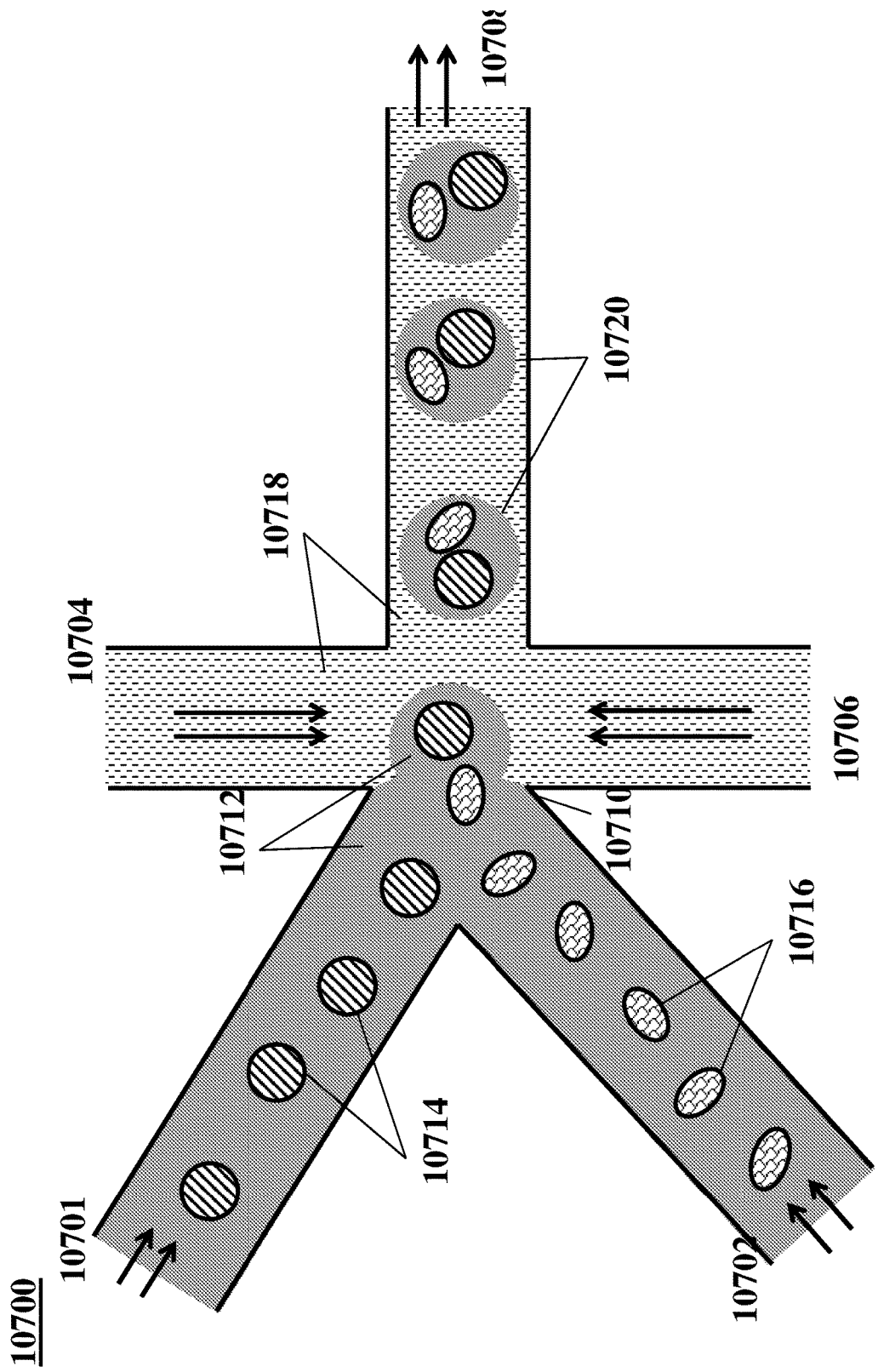
FIG. 107 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 107). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 106, may be readily used in encapsulating cells as described herein. In particular, and with reference to FIG. 106, the aqueous fluid 10612 comprising (i) the biological particles 10614 and (ii) the polymer precursor material (not shown) is flowed into channel junction 10610, where it is partitioned into droplets 10618, 10620 through the flow of non-aqueous fluid 10616. In the case of encapsulation methods, non-aqueous fluid 10616 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, agents such as ammonium persulfate (APS) and tetraethylmethylenediamine (TEMED) and may be provided within the second fluid streams 10616 in channel segments 10604 and 10606, which can initiate and catalyze the copolymerization of the acrylamide and BAC into a cross-linked polymer network, or hydrogel. Other non-limiting examples of initiators include azide-based reagents (e.g., VA-086) and lithium phenyl-trimethylbenzoylphosphinate.

Upon contact of the second fluid stream 10616 with the first fluid stream 10612 at junction 10610, during formation of droplets, the TEMED may diffuse from the second fluid 10616 into the aqueous fluid 10612 comprising the linear polyacrylamide, which will activate the crosslinking of the polyacrylamide within the droplets 10618, 10620, resulting in the formation of gel (e.g., hydrogel) microcapsules, as solid or semi-solid beads or particles entraining the cells 10614. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.). In another example, addition of a complementary nucleic acid (e.g., DNA) may be used to crosslink or un-crosslink nucleic acid molecules that are conjugated to a polymer network.

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline or acidic conditions or at elevated temperature. The polymer or gel may have mechanical properties similar to the mechanical properties of the bead. For instance, the polymer or gel may be of a similar size to the bead. The polymer or gel may have a mechanical strength (e.g., tensile strength, compressive strength, stiffness, toughness, etc.) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles, as described elsewhere herein.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 107 shows an example of a microfluidic channel structure 10700 for delivering barcode carrying beads to droplets. The channel structure 10700 can include channel segments 10701, 10702, 10704, 10706 and 10708 communicating at a channel junction 10710. In operation, the channel segment 201 may transport an aqueous fluid 10712 that includes a plurality of beads 10714 (e.g., with nucleic acid molecules, oligonucleotides, molecular tags) along the channel segment 10701 into junction 10710. The plurality of beads 10714 may be sourced from a suspension of beads. For example, the channel segment 10701 may be connected to a reservoir comprising an aqueous suspension of beads 10714. The channel segment 10702 may transport the aqueous fluid 10712 that includes a plurality of biological particles 10716 along the channel segment 10702 into junction 10710. The plurality of biological particles 10716 may be sourced from a suspension of biological particles. For example, the channel segment 10702 may be connected to a reservoir comprising an aqueous suspension of biological particles 10716. In some instances, the aqueous fluid 10712 in either the first channel segment 10701 or the second channel segment 10702, or in both segments, can include one or more reagents, as further described below. A second fluid 10718 that is immiscible with the aqueous fluid 10712 (e.g., oil) can be delivered to the junction 10710 from each of channel segments 10704 and 10706. Upon meeting of the aqueous fluid 10712 from each of channel segments 10701 and 10702 and the second fluid 10718 from each of channel segments 10704 and 10706 at the channel junction 10710, the aqueous fluid 10712 can be partitioned as discrete droplets 10720 in the second fluid 10718 and flow away from the junction 10710 along channel segment 10708. The channel segment 10708 may deliver the discrete droplets to an outlet reservoir fluidly coupled to the channel segment 10708, where they may be harvested.

As an alternative, the channel segments 10701 and 10702 may meet at another junction upstream of the junction 10710. At such junction, beads and biological particles may form a mixture that is directed along another channel to the junction 10710 to yield droplets 10720. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 10718 can comprise an oil, such as a fluorinated oil, that includes a fluorosurfactant for stabilizing the resulting droplets, for example, inhibiting subsequent coalescence of the resulting droplets 10720. Other surfactants such as Span80, Triton X-100, SDS, perfluorooctanol (PFO), perfluoropolyethers, etc. may also be employed to prevent coalescence of droplets.

A discrete droplet that is generated may include an individual biological particle 10716. A discrete droplet that is generated may include a barcode or other reagent carrying bead 10714. A discrete droplet generated may include both an individual biological particle and a barcode carrying bead, such as droplets 10720. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 10700 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer ($\mu$m), 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 250 $\mu$m, 500 $\mu$m, 1 mm, or greater. In some cases, a bead may have a diameter of less than about 10 nm, 100 nm, 500 nm, 1 $\mu$m, 5 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 250 $\mu$m, 500 $\mu$m, 1 mm, or less. In some cases, a bead may have a diameter in the range of about 40-75 $\mu$m, 30-75 $\mu$m, 20-75 $\mu$m, 40-85 $\mu$m, 40-95 $\mu$m, 20-100 $\mu$m, 10-100 $\mu$m, 1-100 $\mu$m, 20-250 $\mu$m, or 20-500 $\mu$m.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, liposomes, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using pre-polymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for mRNA) and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In aspects, provided herein are beads (e.g., barcoded beads) suitable for processing a nucleic acid sequence (e.g., mRNA, complementary DNA derived from reverse transcription of mRNA) encoding, for example, at least a portion of a V(D)J sequence of an immune cell receptor (e.g., a TCR or BCR), at least a portion of a guide RNA, and/or at least a portion of a guide RNA-identifying barcode. The bead may be a gel bead. A barcoded primer may be coupled or otherwise attached to the gel bead. In some instances, the barcoded primer may be releasably attached to the gel bead, as described herein. Accordingly, a first barcode molecule may comprise a priming sequence that can prime such a nucleic acid sequence encoding at least a portion of a V(D)J sequence of an immune cell receptor (e.g., a TCR or BCR), at least a portion of a guide RNA, and/or at least a portion of a guide RNA-identifying barcode. In some cases, the nucleic acid molecule with such nucleic acid sequence is cDNA that is generated from reverse transcription of the corresponding mRNA, such as using a poly-T containing primer (or other primer). The cDNA that is generated can then be barcoded using a primer, comprising a barcode sequence (and optionally, a unique molecular identifier (UMI) sequence) that hybridizes with at least a portion of the cDNA that is generated. In some cases, a template switching oligonucleotide in conjunction with a terminal transferase or a reverse transcriptase having terminal transferase activity may be employed to generate a priming region on the cDNA to which a barcoded primer can hybridize during cDNA generation. Terminal transferase activity can, for example, add a poly-C tail to a 3' end of the cDNA such that the template switching oligonucleotide can bind via a poly-G priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated.

In aspects, provided herein are beads (e.g., beads) suitable for processing gDNA or derivatives thereof. The bead may be a gel bead. The bead may be the same bead suitable for processing nucleic acid sequences (e.g., mRNA, cDNA, etc.) encoding, for example, at least a portion of a V(D)J sequence of an immune cell receptor (e.g., a TCR or BCR), at least a portion of a guide RNA, and/or at least a portion of a guide RNA-identifying barcode. For examples, the bead may comprise a plurality of different types of primers. A barcoded primer may be coupled or otherwise attached to the gel bead. In some instances, the barcoded primer may comprise a partially double-stranded adapter. In some instances, the adapter may be forked with single stranded regions (e.g., having a "Y" shape). In some instances, the adapter may not be forked. In some instances, the barcoded primer may be releasably attached to the gel bead, as described elsewhere herein. The barcoded primer may be capable of interacting with an enzyme, such as a transposase (e.g., to form a complex). In some instances, the bead may be coupled or otherwise attached to a transposase-primer complex.

Figure 113:
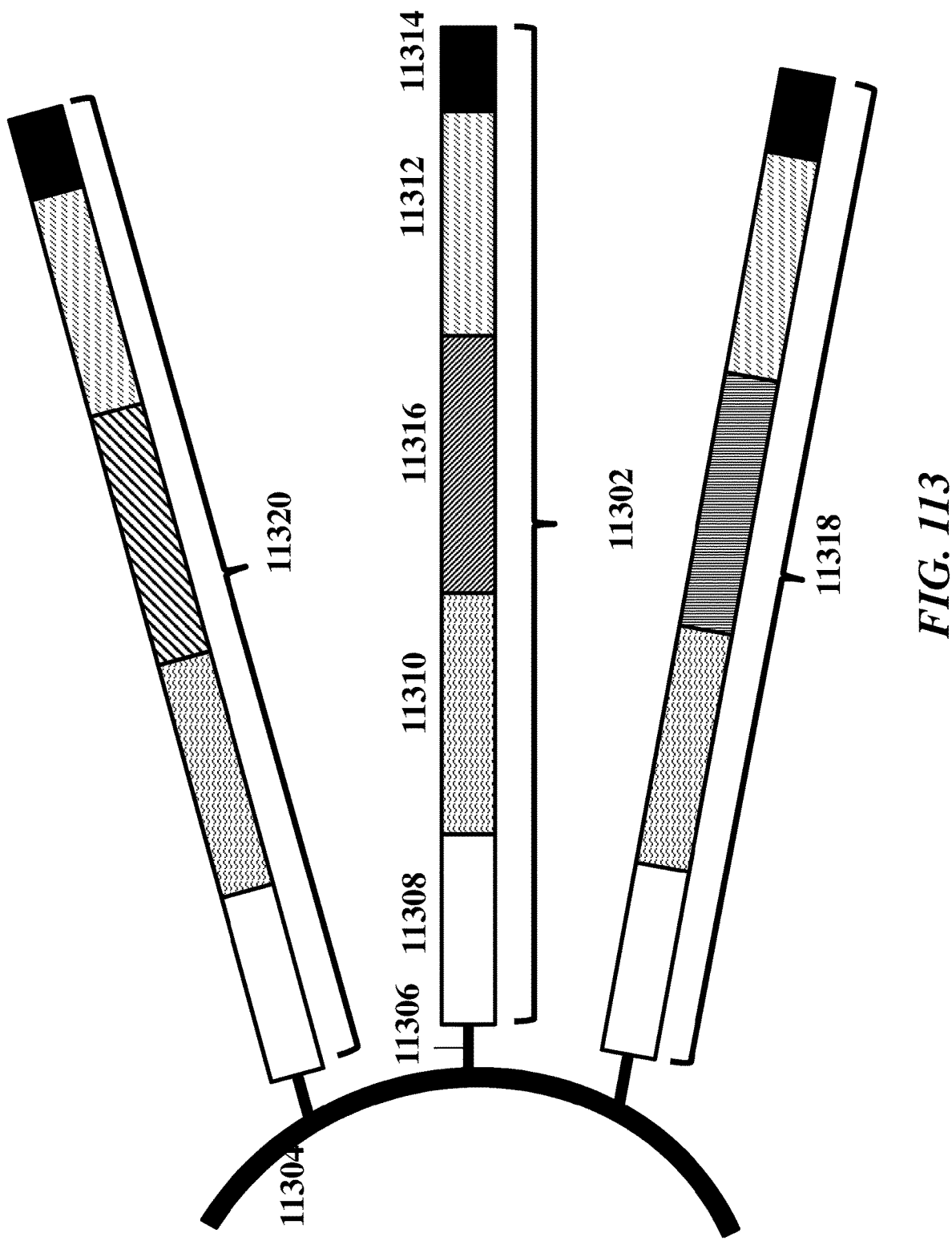
FIG. 113 illustrates an example of a barcode-carrying bead.

FIG. 113 illustrates an example of a barcode carrying bead. A nucleic acid molecule 11302, such as an oligonucleotide, can be coupled to a bead 11304 by a releasable linkage 11306, such as, for example, a disulfide linker. The same bead 11304 may be coupled (e.g., via releasable linkage) to one or more other nucleic acid molecules 11318, 11320. The nucleic acid molecule 11302 may be or comprise a barcode. As noted elsewhere herein, the structure of the barcode may comprise a number of sequence elements. The nucleic acid molecule 11302 may comprise a functional sequence 11308 that may be used in subsequent processing. For example, the functional sequence 11308 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 11302 may comprise a barcode sequence 11310 for use in barcoding the sample (e.g., DNA, RNA, protein, etc.). In some cases, the barcode sequence 11310 can be bead-specific such that the barcode sequence 11310 is common to all nucleic acid molecules (e.g., including nucleic acid molecule 11302) coupled to the same bead 11304. Alternatively or in addition, the barcode sequence 11310 can be partition-specific such that the barcode sequence 11310 is common to all nucleic acid molecules coupled to one or more beads that are partitioned into the same partition. The nucleic acid molecule 11302 may comprise a specific priming sequence 11312, such as an mRNA (e.g., gRNA, TRA, TRB, etc.) specific priming sequence (e.g., poly-T sequence), a targeted priming sequence, and/or a random priming sequence. The nucleic acid molecule 11302 may comprise an anchoring sequence 11314 to ensure that the specific priming sequence 11312 hybridizes at the sequence end (e.g., of the mRNA). For example, the anchoring sequence 11314 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 11302 may comprise a unique molecular identifying sequence 11316 (e.g., unique molecular identifier (UMI)). In some cases, the unique molecular identifying sequence 11316 may comprise from about 5 to about 113 nucleotides. Alternatively, the unique molecular identifying sequence 11316 may compress less than about 5 or more than about 113 nucleotides. The unique molecular identifying sequence 11316 may be a unique sequence that varies across individual nucleic acid molecules (e.g., 11302, 11318, 11320, etc.) coupled to a single bead (e.g., bead 11304). In some cases, the unique molecular identifying sequence 11316 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 113 shows three nucleic acid molecules 11302, 11318, 11320 coupled to the surface of the bead 11304, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 11308, 11310, 11312, etc.) and variable or unique sequence segments (e.g., 11316) between different individual nucleic acid molecules coupled to the same bead.

In operation, a biological particle (e.g., cell, DNA, RNA, etc.) can be co-partitioned along with a barcode bearing bead 11304. The barcoded nucleic acid molecules 11302, 11318, 11320 can be released from the bead 11304 in the partition. By way of example, in the context of analyzing sample RNA, the poly-T segment (e.g., 11312) of one of the released nucleic acid molecules (e.g., 11302) can hybridize to the poly-A tail of a mRNA molecule. Reverse transcription may result in a cDNA transcript of the mRNA, but which transcript includes each of the sequence segments 11308, 11310, 11316 of the nucleic acid molecule 11302. Because the nucleic acid molecule 11302 comprises an anchoring sequence 11314, it will more likely hybridize to and prime reverse transcription at the sequence end of the poly-A tail of the mRNA. Within any given partition, all of the cDNA transcripts of the individual mRNA molecules may include a common barcode sequence segment 11310. However, the transcripts made from the different mRNA molecules within a given partition may vary at the unique molecular identifying sequence 11312 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl) cystamine can be co-polymerized together to generate a gel bead comprising free COOH groups. The COOH groups of the gel bead can be activated (e.g., via 1-Ethyl-3-(3-dimethylaminopropyl) carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes, may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in alkaline conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the dissociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV-sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Although FIG. 106 and FIG. 107 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 500 nanoliters (nL), 100 nL, 50 nL, 900 picoliters (pL), 800 pL, 700 pL, 600 pL, 500 pL, 400 pL, 300 pL, 200 pL, 100 pL, 50 pL, 20 pL, 10 pL, 1 pL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 108:
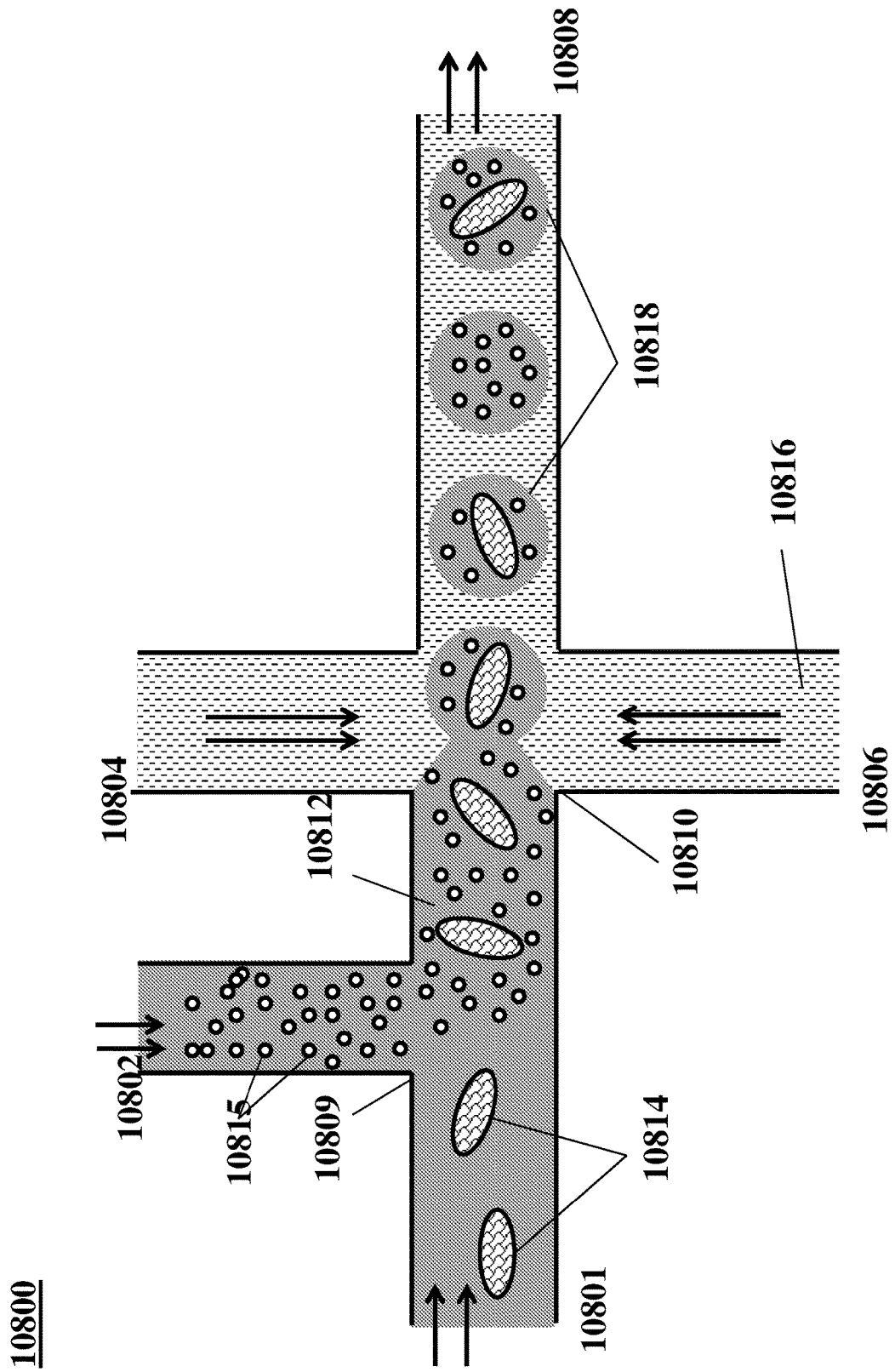
FIG. 108 shows an example of a microfluidic channel structure for co-partitioning biological particles and reagents.

FIG. 108 shows an example of a microfluidic channel structure 10800 for co-partitioning biological particles and reagents. The channel structure 10800 can include channel segments 10801, 10802, 10804, 10806 and 10808. Channel segments 10801 and 10802 communicate at a first channel junction 10809. Channel segments 10802, 10804, 10806, and 10808 communicate at a second channel junction 10810.

In an example operation, the channel segment 10801 may transport an aqueous fluid 10812 that includes a plurality of biological particles 10814 along the channel segment 10801 into the second junction 10810. As an alternative or in addition to, channel segment 10801 may transport beads (e.g., gel beads). The beads may comprise barcode molecules.

For example, the channel segment 10801 may be connected to a reservoir comprising an aqueous suspension of biological particles 10814. Upstream of, and immediately prior to reaching, the second junction 10810, the channel segment 10801 may meet the channel segment 10802 at the first junction 10809. The channel segment 10802 may transport a plurality of reagents 10815 (e.g., lysis agents) suspended in the aqueous fluid 10812 along the channel segment 10802 into the first junction 10809. For example, the channel segment 10802 may be connected to a reservoir comprising the reagents 10815. After the first junction 10809, the aqueous fluid 10812 in the channel segment 10801 can carry both the biological particles 10814 and the reagents 10815 towards the second junction 10810. In some instances, the aqueous fluid 10812 in the channel segment 10801 can include one or more reagents, which can be the same or different reagents as the reagents 10815. A second fluid 10816 that is immiscible with the aqueous fluid 10812 (e.g., oil) can be delivered to the second junction 10810 from each of channel segments 10804 and 10806. Upon meeting of the aqueous fluid 10812 from the channel segment 10801 and the second fluid 10816 from each of channel segments 10804 and 10806 at the second channel junction 10810, the aqueous fluid 10812 can be partitioned as discrete droplets 10818 in the second fluid 10816 and flow away from the second junction 10810 along channel segment 10808. The channel segment 10808 may deliver the discrete droplets 10818 to an outlet reservoir fluidly coupled to the channel segment 10808, where they may be harvested.

The second fluid 10816 can comprise an oil, such as a fluorinated oil, that includes a fluorosurfactant for stabilizing the resulting droplets, for example, inhibiting subsequent coalescence of the resulting droplets 10818.

A discrete droplet generated may include an individual biological particle 10814 and/or one or more reagents 10815. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 10800 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, magnetic force, electrokinetic pumping, vacuum, capillary or gravity flow, or the like.

Examples of lysis agents include bioactive reagents, such as lysis enzymes that are used for lysis of different cell types, e.g., gram-positive or gram-negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion-based systems where the surfactants can interfere with stable emulsions. In some cases, lysis solutions may include non-ionic surfactants such as, for example, TritonX-100, CHAPS, and Tween 20. In some cases, lysis solutions may include ionic surfactants such as, for example, sarcosyl and sodium dodecyl sulfate (SDS). In some cases, lysis may be achieved through osmotic pressure, e.g., using a hypotonic lysis buffer. Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase, inactivating agents or inhibitors, such as proteinase K and/or other protease inhibitors, phosphatase inhibitors, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down and/or collecting barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 109:
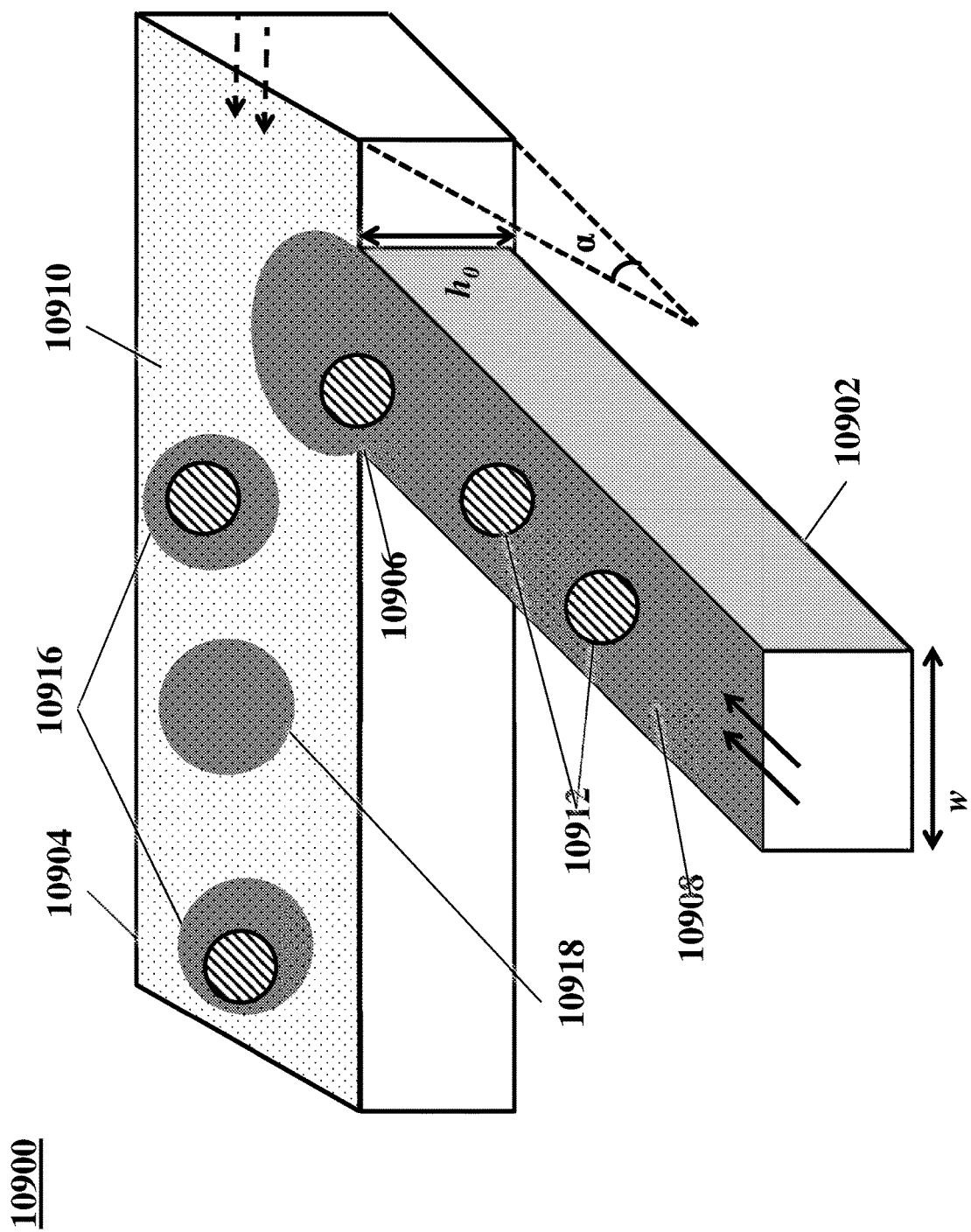
FIG. 109 shows an example of a microfluidic channel structure for the controlled partitioning of beads into discrete droplets.

FIG. 109 shows an example of a microfluidic channel structure for the controlled partitioning of beads into discrete droplets. A channel structure 10900 can include a channel segment 10902 communicating at a channel junction 10906 (or intersection) with a reservoir 10904. The reservoir 10904 can be a chamber. Any reference to "reservoir," as used herein, can also refer to a "chamber." In operation, an aqueous fluid 10908 that includes suspended beads 10912 may be transported along the channel segment 10902 into the junction 10906 to meet a second fluid 10910 that is immiscible with the aqueous fluid 10908 in the reservoir 10904 to create droplets 10916, 10918 of the aqueous fluid 10908 flowing into the reservoir 10904. At the junction 10906 where the aqueous fluid 10908 and the second fluid 10910 meet, droplets can form based on factors such as the hydrodynamic forces at the junction 10906, flow rates of the two fluids 10908, 10910, fluid properties, and certain geometric parameters (e.g., w, $h_0$, $\alpha$, etc.) of the channel structure 10900. A plurality of droplets can be collected in the reservoir 10904 by continuously injecting the aqueous fluid 10908 from the channel segment 10902 through the junction 10906.

A discrete droplet generated may include a bead (e.g., as in occupied droplets 10916). Alternatively, a discrete droplet generated may include more than one bead. Alternatively, a discrete droplet generated may not include any beads (e.g., as in unoccupied droplet 10918). In some instances, a discrete droplet generated may contain one or more biological particles, as described elsewhere herein. In some instances, a discrete droplet generated may comprise one or more reagents, as described elsewhere herein.

In some instances, the aqueous fluid 10908 can have a substantially uniform concentration or frequency of beads 10912. The beads 10912 can be introduced into the channel segment 10902 from a separate channel (not shown in FIG. 109). The frequency of beads 10912 in the channel segment 10902 may be controlled by controlling the frequency in which the beads 10912 are introduced into the channel segment 10902 and/or the relative flow rates of the fluids in the channel segment 10902 and the separate channel. In some instances, the beads can be introduced into the channel segment 10902 from a plurality of different channels, and the frequency controlled accordingly.

In some instances, the aqueous fluid 10908 in the channel segment 10902 can comprise biological particles (e.g., described with reference to FIGS. 106 and 107). In some instances, the aqueous fluid 10908 can have a substantially uniform concentration or frequency of biological particles. As with the beads, the biological particles can be introduced into the channel segment 10902 from a separate channel. The frequency or concentration of the biological particles in the aqueous fluid 10908 in the channel segment 10902 may be controlled by controlling the frequency in which the biological particles are introduced into the channel segment 10902 and/or the relative flow rates of the fluids in the channel segment 10902 and the separate channel. In some instances, the biological particles can be introduced into the channel segment 10902 from a plurality of different channels, and the frequency controlled accordingly. In some instances, a first separate channel can introduce beads and a second separate channel can introduce biological particles into the channel segment 10902. The first separate channel introducing the beads may be upstream or downstream of the second separate channel introducing the biological particles.

The second fluid 10910 can comprise an oil, such as a fluorinated oil, that includes a fluorosurfactant for stabilizing the resulting droplets, for example, inhibiting subsequent coalescence of the resulting droplets.

In some instances, the second fluid 10910 may not be subjected to and/or directed to any flow in or out of the reservoir 10904. For example, the second fluid 10910 may be substantially stationary in the reservoir 10904. In some instances, the second fluid 10910 may be subjected to flow within the reservoir 10904, but not in or out of the reservoir 10904, such as via application of pressure to the reservoir 10904 and/or as affected by the incoming flow of the aqueous fluid 10908 at the junction 10906. Alternatively, the second fluid 10910 may be subjected and/or directed to flow in or out of the reservoir 10904. For example, the reservoir 10904 can be a channel directing the second fluid 10910 from upstream to downstream, transporting the generated droplets.

The channel structure 10900 at or near the junction 10906 may have certain geometric features that at least partly determine the sizes of the droplets formed by the channel structure 10900. The channel segment 10902 can have a height, $h_0$ and width, w, at or near the junction 10906. By way of example, the channel segment 10902 can comprise a rectangular cross-section that leads to a reservoir 10904 having a wider cross-section (such as in width or diameter). Alternatively, the cross-section of the channel segment 10902 can be other shapes, such as a circular shape, trapezoidal shape, polygonal shape, or any other shapes. The top and bottom walls of the reservoir 10904 at or near the junction 10906 can be inclined at an expansion angle, a. The expansion angle, a, allows the tongue (portion of the aqueous fluid 10908 leaving channel segment 10902 at junction 10906 and entering the reservoir 10904 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan \alpha} \, \frac{w}{h_0}\right)\frac{h_0}{\sqrt{\tan \alpha}}$$

By way of example, for a channel structure with w=21 μm, h=21 μm, and α=3°, the predicted droplet diameter is 121 μm. In another example, for a channel structure with w=25 μm, h=25 μm, and α=5°, the predicted droplet diameter is 123 μm. In another example, for a channel structure with w=28 μm, h=28 μm, and α=7°, the predicted droplet diameter is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 10908 entering the junction 10906 can be between about 0.04 microliters (μL)/minute (min) and about 40 μL/min. In some instances, the flow rate of the aqueous fluid 10908 entering the junction 10906 can be between about 0.01 microliters (μL)/minute (min) and about 100 μL/min. Alternatively, the flow rate of the aqueous fluid 10908 entering the junction 10906 can be less than about 0.01 μL/min. Alternatively, the flow rate of the aqueous fluid 10908 entering the junction 10906 can be greater than about 40 μL/min, such as 45 L/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 10908 entering the junction 10906.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 10906) between aqueous fluid 10908 channel segments (e.g., channel segment 10902) and the reservoir 10904. Alternatively or in addition, the throughput of droplet generation can be increased by increasing the flow rate of the aqueous fluid 10908 in the channel segment 10902.

Figure 110:
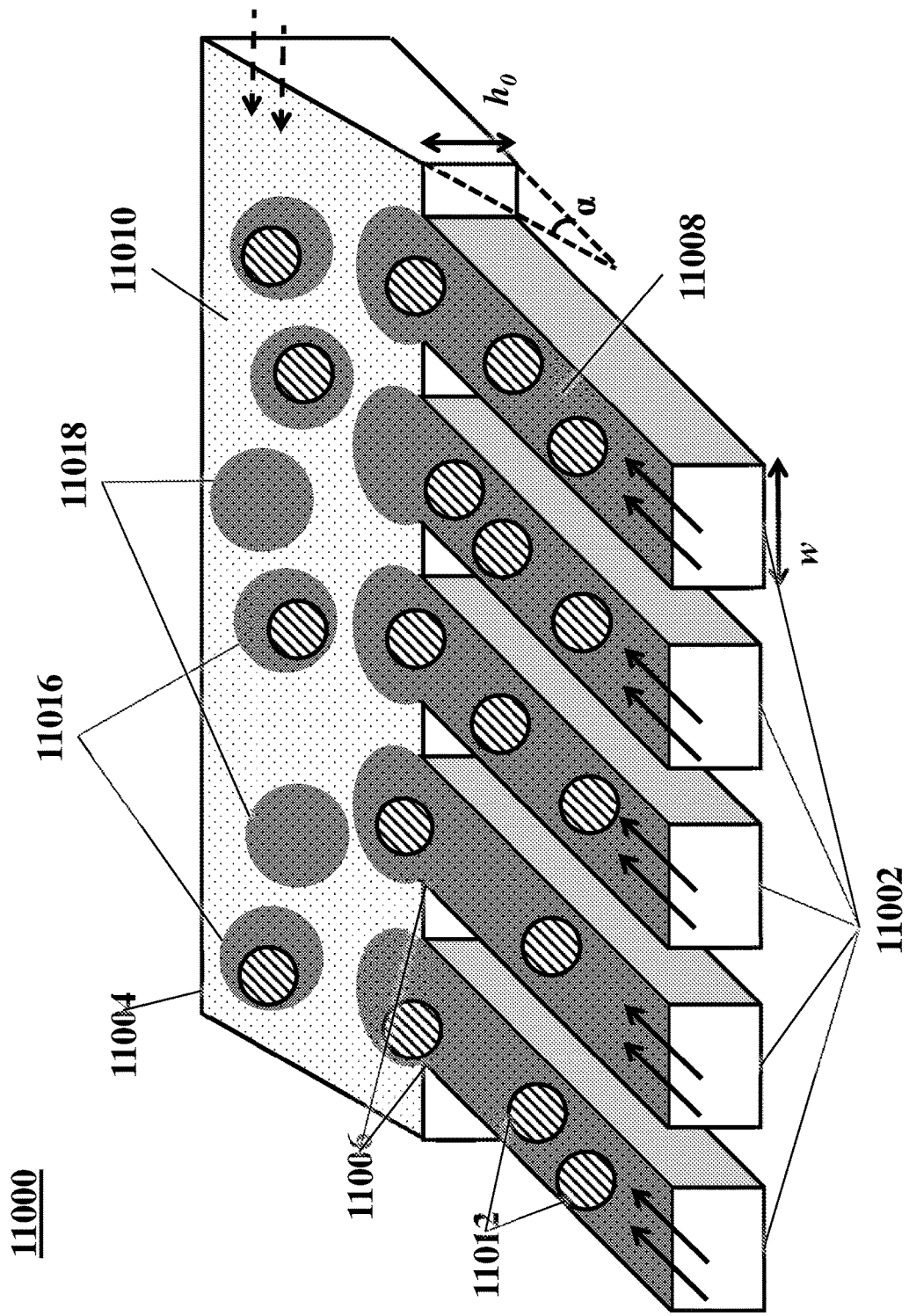
FIG. 110 shows an example of a microfluidic channel structure for increased droplet generation throughput.

FIG. 110 shows an example of a microfluidic channel structure for increased droplet generation throughput. A microfluidic channel structure 11000 can comprise a plurality of channel segments 11002 and a reservoir 11004. Each of the plurality of channel segments 11002 may be in fluid communication with the reservoir 11004. The channel structure 11000 can comprise a plurality of channel junctions 11006 between the plurality of channel segments 11002 and the reservoir 11004. Each channel junction can be a point of droplet generation. The channel segment 402 from the channel structure 400 in FIG. 4 and any description to the components thereof may correspond to a given channel segment of the plurality of channel segments 11002 in channel structure 11000 and any description to the corresponding components thereof. The reservoir 10904 from the channel structure 10900 and any description to the components thereof may correspond to the reservoir 11004 from the channel structure 11000 and any description to the corresponding components thereof.

Each channel segment of the plurality of channel segments 11002 may comprise an aqueous fluid 11008 that includes suspended beads 11012. The reservoir 11004 may comprise a second fluid 11010 that is immiscible with the aqueous fluid 11008. In some instances, the second fluid 11010 may not be subjected to and/or directed to any flow in or out of the reservoir 11004. For example, the second fluid 11010 may be substantially stationary in the reservoir 11004. In some instances, the second fluid 11010 may be subjected to flow within the reservoir 11004, but not in or out of the reservoir 11004, such as via application of pressure to the reservoir 11004 and/or as affected by the incoming flow of the aqueous fluid 11008 at the junctions. Alternatively, the second fluid 11010 may be subjected and/or directed to flow in or out of the reservoir 11004. For example, the reservoir 11004 can be a channel directing the second fluid 11010 from upstream to downstream, transporting the generated droplets.

In operation, the aqueous fluid 11008 that includes suspended beads 11012 may be transported along the plurality of channel segments 11002 into the plurality of junctions 11006 to meet the second fluid 11010 in the reservoir 11004 to create droplets 11016, 11018. A droplet may form from each channel segment at each corresponding junction with the reservoir 11004. At the junction where the aqueous fluid 11008 and the second fluid 11010 meet, droplets can form based on factors such as the hydrodynamic forces at the junction, flow rates of the two fluids 11008, 11010, fluid properties, and certain geometric parameters (e.g., w, $h_0$, α, etc.) of the channel structure 11000, as described elsewhere herein. A plurality of droplets can be collected in the reservoir 11004 by continuously injecting the aqueous fluid 11008 from the plurality of channel segments 11002 through the plurality of junctions 11006. Throughput may significantly increase with the parallel channel configuration of channel structure 11000. For example, a channel structure having five inlet channel segments comprising the aqueous fluid 11008 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 11002. For example, each channel segment may have the same or different widths at or near its respective channel junction with the reservoir 11004. For example, each channel segment may have the same or different height at or near its respective channel junction with the reservoir 11004. In another example, the reservoir 11004 may have the same or different expansion angle at the different channel junctions with the plurality of channel segments 11002. When the geometric parameters are uniform, beneficially, droplet size may also be controlled to be uniform even with the increased throughput. In some instances, when it is desirable to have a different distribution of droplet sizes, the geometric parameters for the plurality of channel segments 11002 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 111:
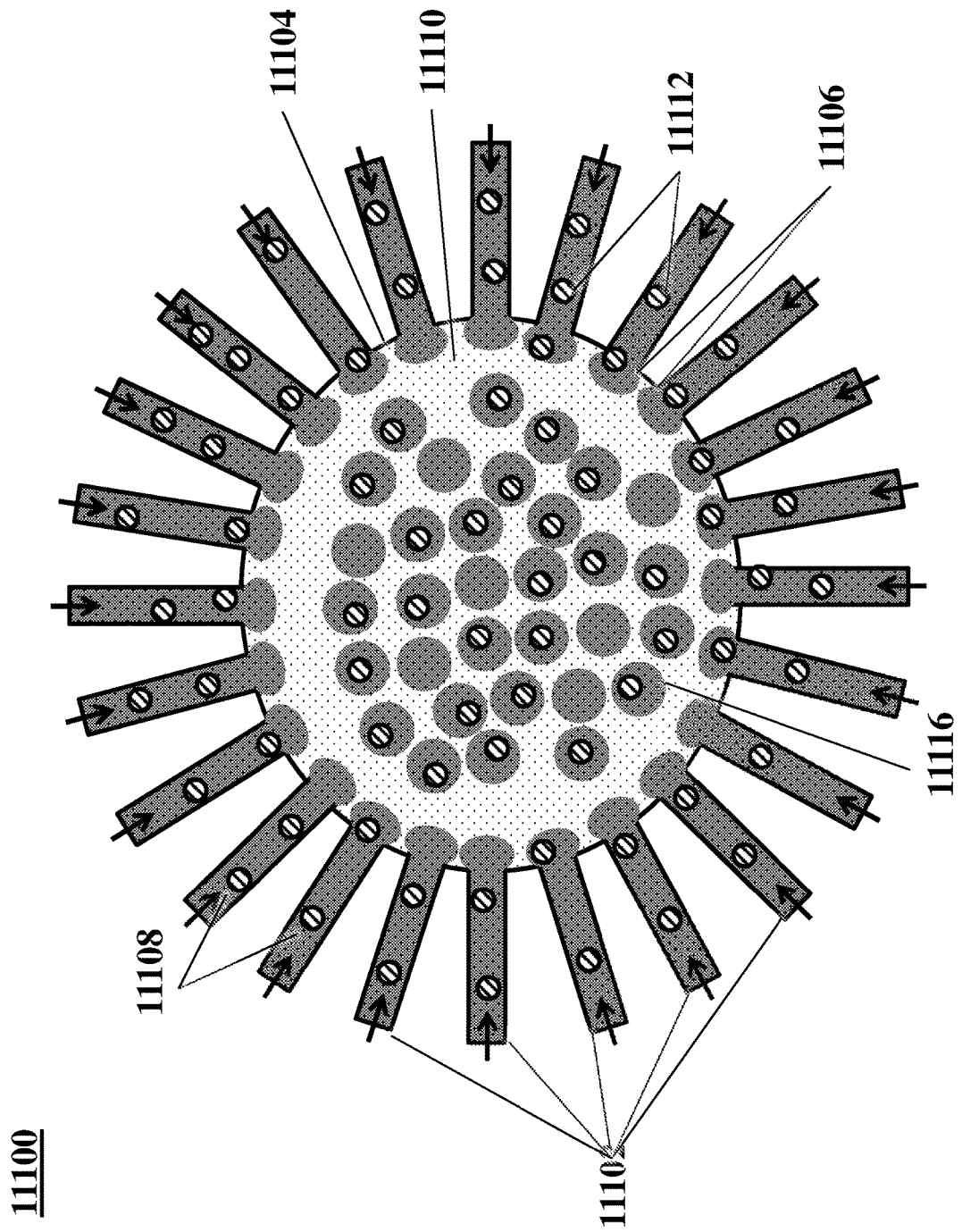
FIG. 111 shows another example of a microfluidic channel structure for increased droplet generation throughput.

FIG. 111 shows another example of a microfluidic channel structure for increased droplet generation throughput. A microfluidic channel structure 11100 can comprise a plurality of channel segments 11102 arranged generally circularly around the perimeter of a reservoir 11104. Each of the plurality of channel segments 11102 may be in fluid communication with the reservoir 11104. The channel structure 11100 can comprise a plurality of channel junctions 11106 between the plurality of channel segments 11102 and the reservoir 11104. Each channel junction can be a point of droplet generation. The channel segment 10902 from the channel structure 10900 in FIG. 109 and any description to the components thereof may correspond to a given channel segment of the plurality of channel segments 11102 in channel structure 11100 in FIG. 111 and any description to the corresponding components thereof. The reservoir 10904 from the channel structure 10900 in FIG. 109 and any description to the components thereof may correspond to the reservoir 11104 from the channel structure 11100 in FIG. 111 and any description to the corresponding components thereof.

Each channel segment of the plurality of channel segments 11102 may comprise an aqueous fluid 11108 that includes suspended beads 11112. The reservoir 11104 may comprise a second fluid 11110 that is immiscible with the aqueous fluid 11108. In some instances, the second fluid 11110 may not be subjected to and/or directed to any flow in or out of the reservoir 11104. For example, the second fluid 11110 may be substantially stationary in the reservoir 11104. In some instances, the second fluid 11110 may be subjected to flow within the reservoir 11104, but not in or out of the reservoir 11104, such as via application of pressure to the reservoir 11104 and/or as affected by the incoming flow of the aqueous fluid 11108 at the junctions. Alternatively, the second fluid 11110 may be subjected and/or directed to flow in or out of the reservoir 11104. For example, the reservoir 11104 can be a channel directing the second fluid 11110 from upstream to downstream, transporting the generated droplets.

In operation, the aqueous fluid 11108 that includes suspended beads 11112 may be transported along the plurality of channel segments 11102 into the plurality of junctions 11106 to meet the second fluid 11110 in the reservoir 11104 to create a plurality of droplets 11116. A droplet may form from each channel segment at each corresponding junction with the reservoir 11104. At the junction where the aqueous fluid 11108 and the second fluid 11110 meet, droplets can form based on factors such as the hydrodynamic forces at the junction, flow rates of the two fluids 11108, 11110, fluid properties, and certain geometric parameters (e.g., widths and heights of the channel segments 11102, expansion angle of the reservoir 11104, etc.) of the channel structure 11100, as described elsewhere herein. A plurality of droplets can be collected in the reservoir 11104 by continuously injecting the aqueous fluid 11108 from the plurality of channel segments 11102 through the plurality of junctions 11106. Throughput may significantly increase with the substantially parallel channel configuration of the channel structure 11100. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 11104 may have an expansion angle, α (not shown in FIG. 111) at or near each channel junction. Each channel segment of the plurality of channel segments 11102 may have a width, w, and a height, $h_0$, at or near the channel junction. The geometric parameters, w, $h_0$, and α, may or may not be uniform for each of the channel segments in the plurality of channel segments 11102. For example, each channel segment may have the same or different widths at or near its respective channel junction with the reservoir 11104. For example, each channel segment may have the same or different height at or near its respective channel junction with the reservoir 11104.

The reservoir 11104 may have the same or different expansion angle at the different channel junctions with the plurality of channel segments 11102. For example, a circular reservoir (as shown in FIG. 111) may have a conical, dome-like, or hemispherical ceiling (e.g., top wall) to provide the same or substantially same expansion angle for each channel segments 11102 at or near the plurality of channel junctions 11106. When the geometric parameters are uniform, beneficially, resulting droplet size may be controlled to be uniform even with the increased throughput. In some instances, when it is desirable to have a different distribution of droplet sizes, the geometric parameters for the plurality of channel segments 11102 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 112A:
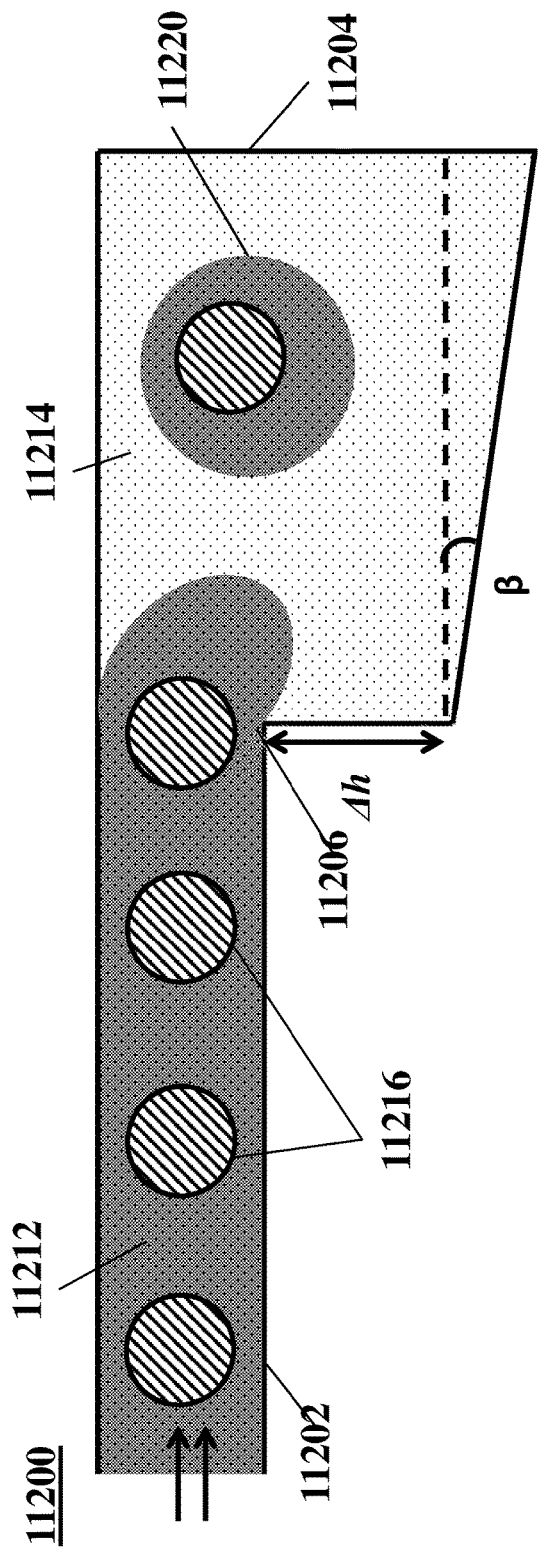
FIG. 112A shows a cross-section view of another example of a microfluidic channel structure with a geometric feature for controlled partitioning.
Figure 112B:
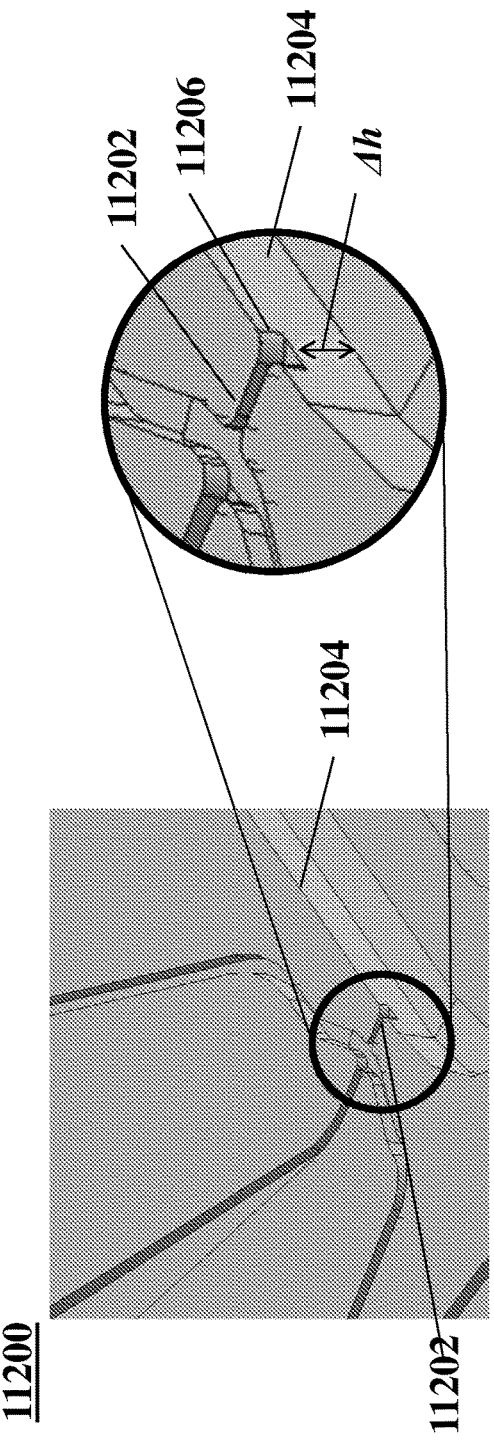
FIG. 112B shows a perspective view of the channel structure of FIG. 112A.

FIG. 112A shows a cross-section view of another example of a microfluidic channel structure with a geometric feature for controlled partitioning. A channel structure 11200 can include a channel segment 11202 communicating at a channel junction 11206 (or intersection) with a reservoir 11204. In some instances, the channel structure 11200 in FIGS. 112A-112B and one or more of its components can correspond to the channel structure 10600 in FIG. 106 and one or more of its components. FIG. 112B shows a perspective view of the channel structure 11200 of FIG. 112A.

An aqueous fluid 11212 comprising a plurality of particles 11216 may be transported along the channel segment 11202 into the junction 11206 to meet a second fluid 11214 (e.g., oil, etc.) that is immiscible with the aqueous fluid 11212 in the reservoir 11204 to create droplets 11220 of the aqueous fluid 11212 flowing into the reservoir 11204. At the junction 11206 where the aqueous fluid 11212 and the second fluid 11214 meet, droplets can form based on factors such as the hydrodynamic forces at the junction 11206, relative flow rates of the two fluids 11212, 11214, fluid properties, and certain geometric parameters (e.g., Δh, etc.) of the channel structure 11200. A plurality of droplets can be collected in the reservoir 11204 by continuously injecting the aqueous fluid 11212 from the channel segment 11202 at the junction 11206.

A discrete droplet generated may comprise one or more particles of the plurality of particles 11216. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 11212 can have a substantially uniform concentration or frequency of particles 11216. As described elsewhere herein (e.g., with reference to FIG. 109), the particles 11216 (e.g., beads) can be introduced into the channel segment 11202 from a separate channel (not shown in FIG. 112). The frequency of particles 11216 in the channel segment 11202 may be controlled by controlling the frequency in which the particles 11216 are introduced into the channel segment 11202 and/or the relative flow rates of the fluids in the channel segment 11202 and the separate channel. In some instances, the particles 11216 can be introduced into the channel segment 11202 from a plurality of different channels, and the frequency controlled accordingly. In some instances, different particles may be introduced via separate channels. For example, a first separate channel can introduce beads and a second separate channel can introduce biological particles into the channel segment 11202. The first separate channel introducing the beads may be upstream or downstream of the second separate channel introducing the biological particles.

In some instances, the second fluid 11214 may not be subjected to and/or directed to any flow in or out of the reservoir 11204. For example, the second fluid 11214 may be substantially stationary in the reservoir 11204. In some instances, the second fluid 11214 may be subjected to flow within the reservoir 11204, but not in or out of the reservoir 11204, such as via application of pressure to the reservoir 11204 and/or as affected by the incoming flow of the aqueous fluid 11212 at the junction 11206. Alternatively, the second fluid 11214 may be subjected and/or directed to flow in or out of the reservoir 11204. For example, the reservoir 11204 can be a channel directing the second fluid 11214 from upstream to downstream, transporting the generated droplets.

The channel structure 11200 at or near the junction 11206 may have certain geometric features that at least partly determine the sizes and/or shapes of the droplets formed by the channel structure 11200. The channel segment 11202 can have a first cross-section height, $h_1$, and the reservoir 11204 can have a second cross-section height, $h_2$. The first cross-section height, $h_1$, and the second cross-section height, $h_2$, may be different, such that at the junction 11206, there is a height difference of Δh. The second cross-section height, $h_2$, may be greater than the first cross-section height, $h_1$. In some instances, the reservoir may thereafter gradually increase in cross-section height, for example, the more distant it is from the junction 11206. In some instances, the cross-section height of the reservoir may increase in accordance with expansion angle, β, at or near the junction 11206. The height difference, Δh, and/or expansion angle, β, can allow the tongue (portion of the aqueous fluid 11212 leaving channel segment 11202 at junction 11206 and entering the reservoir 11204 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, δ, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 11212 entering the junction 11206 can be between about 0.04 microliters (μL)/minute (min) and about 40 μL/min. In some instances, the flow rate of the aqueous fluid 11212 entering the junction 11206 can be between about 0.01 microliters (μL)/minute (min) and about 100 μL/min. Alternatively, the flow rate of the aqueous fluid 11212 entering the junction 11206 can be less than about 0.01 μL/min. Alternatively, the flow rate of the aqueous fluid 11212 entering the junction 11206 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 L/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 11212 entering the junction 11206. The second fluid 11214 may be stationary, or substantially stationary, in the reservoir 11204. Alternatively, the second fluid 11214 may be flowing, such as at the above flow rates described for the aqueous fluid 11212.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 112A and 112B illustrate the height difference, Δh, being abrupt at the junction 11206 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 11206, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 112A and 112B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidically coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 10708 in FIG. 107, reservoir 11104 in FIG. 111, etc.) may be fluidically coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single-cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 114:
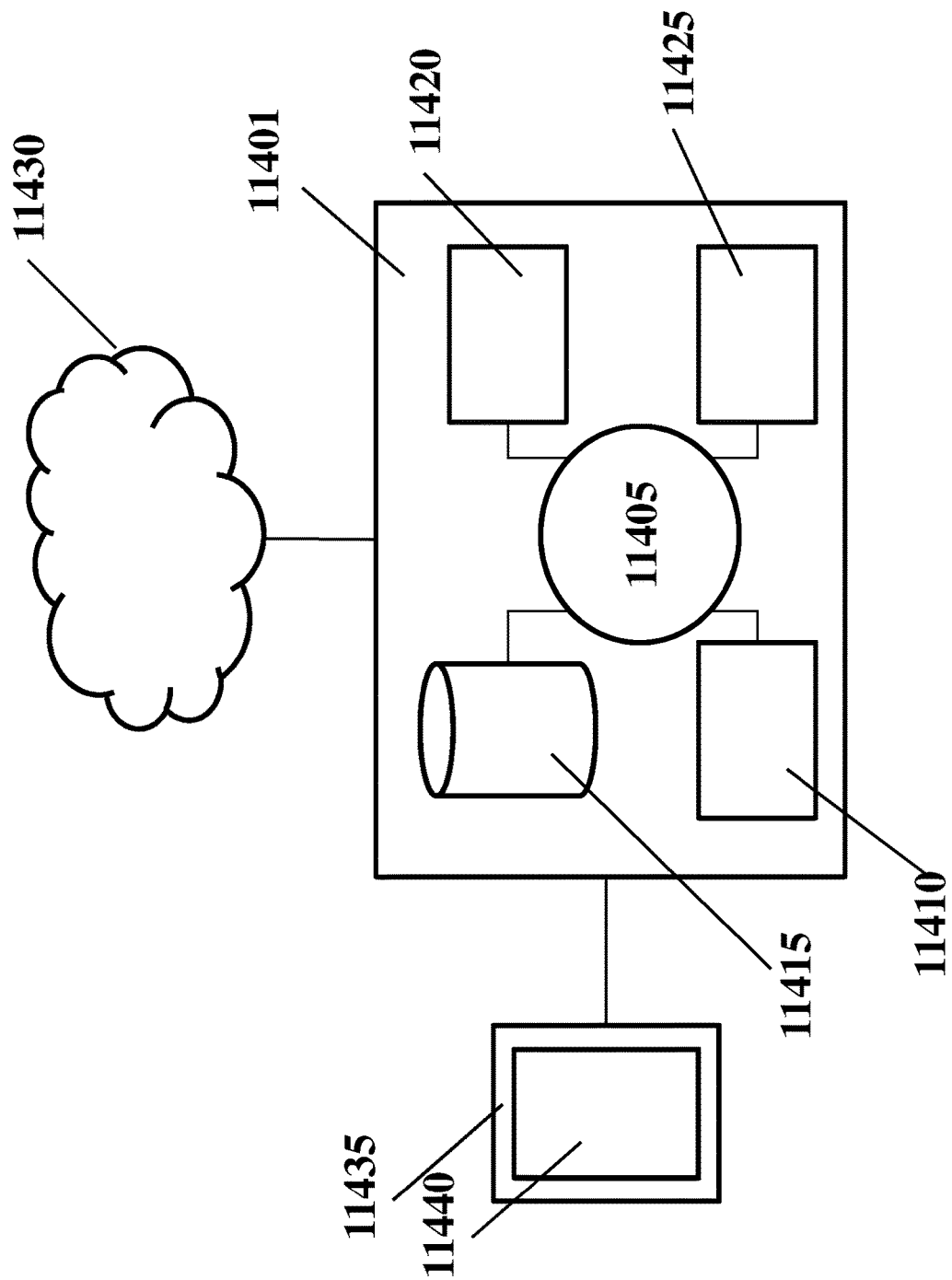
FIG. 114 shows a computer system that is programmed or otherwise configured to implement methods provided herein.

The present disclosure provides computer systems that are programmed to implement methods of the disclosure. FIG. 114 shows a computer system 11401 that is programmed or otherwise configured to control a microfluidics system (e.g., fluid flow) and perform sequencing applications. The computer system 11401 can regulate various aspects of the present disclosure. The computer system 11401 can be an electronic device of a user or a computer system that is remotely located with respect to the electronic device. The electronic device can be a mobile electronic device.

The computer system 11401 includes a central processing unit (CPU, also "processor" and "computer processor" herein) 11405, which can be a single core or multi core processor, or a plurality of processors for parallel processing. The computer system 11401 also includes memory or memory location 11410 (e.g., random-access memory, read-only memory, flash memory), electronic storage unit 11415 (e.g., hard disk), communication interface 11420 (e.g., network adapter) for communicating with one or more other systems, and peripheral devices 11425, such as cache, other memory, data storage and/or electronic display adapters. The memory 11410, storage unit 11415, interface 11420 and peripheral devices 11425 are in communication with the CPU 11405 through a communication bus (solid lines), such as a motherboard. The storage unit 11415 can be a data storage unit (or data repository) for storing data. The computer system 11401 can be operatively coupled to a computer network ("network") 11430 with the aid of the communication interface 11420. The network 11430 can be the Internet, an internet and/or extranet, or an intranet and/or extranet that is in communication with the Internet. The network 11430 in some cases is a telecommunication and/or data network. The network 11430 can include one or more computer servers, which can enable distributed computing, such as cloud computing. The network 11430, in some cases with the aid of the computer system 11401, can implement a peer-to-peer network, which may enable devices coupled to the computer system 11401 to behave as a client or a server.

The CPU 11405 can execute a sequence of machine-readable instructions, which can be embodied in a program or software. The instructions may be stored in a memory location, such as the memory 11410. The instructions can be directed to the CPU 11405, which can subsequently program or otherwise configure the CPU 11405 to implement methods of the present disclosure. Examples of operations performed by the CPU 11405 can include fetch, decode, execute, and writeback.

The CPU 11405 can be part of a circuit, such as an integrated circuit. One or more other components of the system 11401 can be included in the circuit. In some cases, the circuit is an application specific integrated circuit (ASIC).

The storage unit 11415 can store files, such as drivers, libraries and saved programs. The storage unit 11415 can store user data, e.g., user preferences and user programs. The computer system 11401 in some cases can include one or more additional data storage units that are external to the computer system 11401, such as located on a remote server that is in communication with the computer system 11401 through an intranet or the Internet.

The computer system 11401 can communicate with one or more remote computer systems through the network 11430. For instance, the computer system 11401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 11401 via the network 11430.

Methods as described herein can be implemented by way of machine (e.g., computer processor) executable code stored on an electronic storage location of the computer system 11401, such as, for example, on the memory 11410 or electronic storage unit 11415. The machine executable or machine readable code can be provided in the form of software. During use, the code can be executed by the processor 11405. In some cases, the code can be retrieved from the storage unit 11415 and stored on the memory 11410 for ready access by the processor 11405. In some situations, the electronic storage unit 11415 can be precluded, and machine-executable instructions are stored on memory 11410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 11401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 11401 can include or be in communication with an electronic display 11435 that comprises a user interface (UI) 11440 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 11405. The algorithm can, for example, perform sequencing.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EXAMPLES

Examples 1: T-ATAC-Seq in Single Cells

Cell culture and T cell isolation. Jurkat cells were obtained from the ATCC (clone E6-1) and were cultured in RPMI-1640 medium (Thermo Fisher Scientific) with 10% FBS and penicillin-streptomycin. For single-cell experiments with Jurkat cells, the cells were sorted into a single-cell suspension before capture on the C1 IFC microfluidic chips (Fluidigm). Mouse 58 αβ-negative hybridoma cells were retrovirally transduced with a paired TCR-αβ-encoding sequence, and these cells were used in the mouse and human cell mixing experiments. CD4$^+$ T cells from healthy volunteers or patients with Sézary syndrome were enriched from peripheral blood using the RosetteSep Human CD4$^+$T Cell Enrichment Cocktail (StemCell Technology). For single-cell experiments, CD4$^+$ T cells were sorted as naive T cells (CD4$^+$CD25$^-$CD45RA$^+$), memory T cells (CD4$^+$CD25$^-$CD45RA$^-$) or $T_H$17 cells (CD4$^+$CD25$^-$CD45RA$^-$CCR6$^+$CXCR5$^-$). 200,000 cells from two healthy volunteers were sorted into RPMI-1640 medium supplemented with 10% FBS, washed and loaded onto the C1 IFC microfluidic chips, as described below. For ensemble ATAC-seq experiments, CD4$^+$ T cells were sorted as naive T cells (CD4$^+$CD25$^-$CD45RA$^+$), $T_{reg}$ cells (CD4$^+$CD25$^+$IL7R1$^{lo}$), TH1 cells (CD4$^+$CD25$^-$IL7R$^{hi}$CD45RA$^-$CXCR3$^+$CCR6$^-$), $T_H$2 cells (CD4$^+$CD25$^-$IL7R$^{hi}$CD45RA$^-$CXCR3$^-$CCR6$^-$), $T_H$17 cells (CD4$^+$CD25$^-$IL7R$^{hi}$CD45RA$^-$CXCR3$^-$CCR6$^+$) and $T_H$1-17 cells (CD4$^+$CD25$^-$IL7R$^{hi}$CD45RA$^-$CXCR3$^+$CCR6$^+$) (FIGS. 132-137). 55,000 cells from two healthy volunteers (three replicates total) were sorted into RPMI-1640 medium supplemented with 10% FBS, washed with PBS and immediately transposed as described below. Post-sort purities of >95% were confirmed by flow cytometry for all of the samples.

Antibodies. The following antibodies were used in this study: PERCP-Cy5.5-conjugated anti-human-CD45RA (clone HI100, lot no. B213966, cat. no. 304107, BioLegend), anti-human-CD127 conjugated to Brilliant Violet 510 (clone A019D5, lot no. B197159, cat. no. 351331, BioLegend), allophycocyanin (APC)-Cy7-conjugated anti-human-CD4 (clone OKT4, lot no. B207751, cat. no. 317417, BioLegend), phycoerythrin (PE)-conjugated anti-human-CCR6 (clone G034E3, lot no. B203239, cat. no. 353409, BioLegend), fluorescein isothiocyanate (FITC)-conjugated anti-human-CD25 (clone BC96, lot no. B168869, cat. no. 302603, BioLegend), anti-human-CXCR3 conjugated to Brilliant Violet 421 (clone G025H7, lot no. B206003, cat. no. 353715, BioLegend), Alexa-Fluor-647-conjugated anti-human-CXCR5 (clone RF8B2, lot no. 5302868, cat. no. 558113, BD Pharmingen), PE-conjugated anti-human-CD26 (clone 2A6, lot no. 4301881, cat. no. 12-0269-42, Thermo Fisher) and anti-human-CD3E conjugated to Pacific Blue (clone UCHT1, lot no. 4341657, cat. no. 558117, BD Biosciences). All of the antibodies were validated by the manufacturer in human peripheral blood samples, used at a 1:200 dilution and compared to isotype and no-staining control samples.

Ensemble ATAC-seq. Cell isolation and transposase reaction: Cells were isolated and subjected to ATAC-seq as previously described. Briefly, 55,000 cells were pelleted after sorting and washed once with 100 μl PBS. Cell pellets were then resuspended in 50 μl lysis buffer (10 mM Tris-HCl, pH 7.4, 3 mM MgCl$_2$, 10 mM NaCl, 0.1% NP-40 (Igepal CA-630)) and immediately centrifuged at 500 g for 10 min at 4° C. The nuclei-containing pellets were resuspended in 50 μl transposition buffer (25 μl 2×TD buffer, 22.5 μl dH$_2$O, 2.5 μl Illumina Tn5 transposase) and incubated at 37° C. for 30 min. Transposed DNA was purified with MinElute PCR Purification Kit (Qiagen) and eluted in 10 μl EB buffer.

Primary data processing and peak calling: ATAC-seq libraries were prepared as previously described, and barcoded and sequenced on an Illumina Nextseq instrument. Adaptor sequence trimming, mapping to the human hg19 reference genome using Bowtie2 and PCR duplicate removal using Picard Tools were performed. All samples were merged for peak calling using MACS2. The number of aligned reads, Tn5 offset corrected, mapped to the union peak set for each sample was quantified using intersectBed in BedTools. Peak counts were normalized using the 'CQN' package in R. Peak intensity was defined as the variance-stabilized log 2 counts using the 'DESeq2' package in R. After these steps, an N×M data matrix was obtained, where N indicates the number of merged peaks, M indicates the number of samples, and the value $D_{i,j}$ indicates the number of reads that fall within peak i (i=1 to N) in sample j (j=1 to M). Pearson correlation was calculated based on the log 2-normalized counts of all the peaks. Unsupervised correlation of the Pearson correlation matrix was performed using Cluster 3.0 and visualized in Java Treeview.

Transcript-indexed single-cell ATAC-seq (T-ATAC-seq). Step 1. Cell isolation and loading onto the IFC: The C1 Single-Cell Auto Prep System with its Open App program (Fluidigm) was adapted to perform T-ATAC-seq. Single T cells were captured using the C1 IFC microfluidic chips (small; 5-10 µm), and custom-built T-ATAC-seq scripts were generated using the C1 Script Builder Software (scripts available from Fluidigm and upon request). Jurkat cells or peripheral blood T cells were first isolated by FACS Seq sorting and then washed three times in C1 DNA Seq Cell Wash Buffer (Fluidigm). Cells were resuspended in DNA Seq Cell Wash Buffer at a concentration of 300 cells/µl and mixed with C1 Cell Suspension Reagent at a ratio of 3:2. 15 µl of this cell mix was loaded onto the IFC. After cell loading, the captured cells were visualized by imaging on a Leica CTR 6000 microscope.

Step 2. Microfluidic reactions on the IFC: reagents and conditions: On the C1, cells were subjected sequentially to lysis and transposition, transposase release, $MgCl_2$ quenching, reverse transcription and PCR, as described (FIGS. 52-54 and FIG. 116), using the custom T-ATAC-seq script 'T-ATAC-seq: Sample Prep (1,861×, 1,862×, 1,863×)'. For lysis and transposition (in chamber 1), 30 µl of Tn5 transposition mix was prepared (22.5 µl 2× TD buffer, 2.25 µl transposase (Nextera DNA Sample Prep Kit, Illumina), 2.25 µl C1 Loading Reagent without salt (Fluidigm), 0.45 µl 10% NP40, 0.30 µl water, and 2.25 µl Superase In RNase inhibitor (20 U/µl; Thermo Fisher Scientific)).

For transposase release (in chamber 2), 20 µl of Tn5 release buffer mix was prepared (2 µl 500 mM EDTA, 1 µl C1 Loading Reagent without salt and 17 µl 10 mM Tris-HCl buffer, pH 8). For MgCl2 quenching (in chamber 3), 20 µl of MgCl2 quenching buffer mix was prepared (18 µl 50 mM MgCl2, 1 µl C1 Loading Reagent without salt and 1 µl 10 mM Tris-HCl buffer, pH 8). For reverse transcription (in chamber 4), 30 µl of RT mix was prepared (15.55 µl water, 3.7 µl 10 x Sensiscript RT buffer (Qiagen), 3.7 µl 5 mM dNTPs, 1.5 µl C1 Loading Reagent without salt (Fluidigm), 1.85 µl Sensiscript (Qiagen) and 3.7 µl 6 µM TCR primer mix (described below)). Finally, for PCR of TRA, and TRB and ATAC fragments (in chamber 5), 30 µl of PCR mix was prepared (8.62 µl water, 13.4 µl 5× Q5 polymerase buffer (NEB), 1.2 µl 5 mM dNTPs, 1.5 µl C1 Loading Reagent without salt, 0.67 µl Q5 polymerase (2 U/µl; NEB), 0.8 µl 25 µM non-indexed custom Nextera ATAC-seq PCR primer 1, 0.8 µl 25 µM non-indexed custom Nextera ATAC-seq primer 2 and 3 µl 6 µM TCR primer mix).

The primer sequences for the non-indexed custom Nextera ATAC-seq primers are listed in Supplementary Table 1 of a prior study. 7 µl lysis and transposition mix, 7 µl transposase release buffer, 7 µl MgCl2 quenching buffer, 24 µl RT mix and 24 µl PCR mix were added to the IFC inlets. On the IFC, Tn5 lysis and transposition reaction was carried out for 30 min at 37° C. Next, transposase release was carried out for 30 min at 50° C. MgCl2 quenching buffer was immediately added, and chamber contents were immediately incubated with RT mix for 30 min at 50° C. Finally, gap-filling and eight cycles of PCR were performed using the following conditions: 72° C. for 5 min and then thermocycling at 94° C. for 30 s, 62° C. for 60 s and 72° C. for 60 s. The amplified transposed DNA was harvested in a total of 13.5 µl C1 Harvest Reagent. Following completion of the on-chip protocol (~4-5 h), chamber contents were transferred to 96-well PCR plates, mixed and divided for further amplification of ATAC-seq fragments (5 µl) or TCR-seq fragments (6-7 µl).

Step 3. Amplification of TCR-seq libraries. The TRA and TRB sequences (collectively referred to as TCR sequences) from single cells were obtained by a series of three PCR reactions (phases) as previously described, with slight modifications for implementation on the IFC. The design principles and validation of all TCR primers have been previously described. To integrate TCR sequence amplification into the T-ATAC-seq protocol, the RT and first-phase PCR was performed in chambers 4 and 5 of the IFC using the conditions described above. The phase 1 TCR primer mix included multiple Vα- and Vβ-region-specific primers and Cα- and Cβ-region-specific; each V-region-specific primer was at a concentration of 0.06 µM, and each C-region-specific primer was at a concentration of 0.3 µM. RT was performed using the Cα- and Cβ-region-specific primers, and the cDNA was then subjected to eight cycles of PCR using both Vα- and Vβ-region-specific primers and Cα- and Cβ-region-specific primers (simultaneously, as ATAC fragments were also being amplified in the same chamber using distinct primers, as described above). For off-chip phase 1 PCR, following completion of the on-chip protocol, 6-7 µl of the harvested libraries were further amplified using TCR primers. First, an additional eight cycles of PCR was performed using the following cycling conditions: 95° C. for 15 min and thermocycling at 94° C. for 30 s, 62° C. for 1 min and 72° C. for 1 min; 72° C. 10 min; and a hold at 4° C.

For off-chip phase 2 PCR, a 1-µl aliquot of this final phase 1 product was used as a template for a 12-µl phase 2 PCR reaction. The following cycling conditions were used for a 25-cycle phase 2 PCR: 95° C. for 15 min and thermocycling at 94° C. for 30 s, 64° C. for 1 min and 72° C. for 1 min; 72° C. for 5 min; and a hold at 4° C. For the phase 2 reaction, multiple internally nested Vα-, Vβ-, Cα- and Cβ-specific primers were used (V primers 0.6 µM, C primers 0.3 µM). The phase 2 primers targeting the V-region contained a common 23-b sequence at the 5' end to enable further amplification (during the phase 3 reaction) with a common 23-b primer. For off-chip phase 3 PCR, 1 µl of the final phase 2 PCR product was used as a template for a 14-µl phase 3 PCR reaction, which incorporated barcodes and enabled sequencing on the Illumina MiSeq platform. For the phase 3 PCR reaction, amplification was performed using a 5' barcoding primer (0.05 µM) containing the common 23-b sequence and a 3' barcoding primer (0.05 µM) containing sequence of a third internally nested Cα-specific and/or Cβ-specific primer, and Illumina paired-end primers (0.5 µM each). The following cycling conditions were used for a 25-cycle phase 3 PCR: 95° C. for 15 min and thermocycling at 94° C. for 30 s, 66° C. for 30 s and 72° C. for 1 min; 72° C. for 5 min; and a hold at 4° C. The final phase 3 barcoding PCR reactions for the TRA and TRB sequences were done separately.

For the phase 3 reaction, 0.5 µM of the 3' Cα-specific barcoding primer and the 3' Cβ-specific barcoding primer were used. In addition to the common 23-b sequence at the 3' end (which enabled amplification of products from the second reaction) and a common 23-b sequence at the 5' end (which enabled amplification with Illumina paired-end primers), each 5' barcoding primer contained a unique 5-b barcode that specified the plate and a unique 5-b barcode that specified the row within the plate. In addition to the internally nested TCR C-region-specific sequence and a common 23-b sequence at the 3' end (which enabled amplification with Illumina paired-end primers), each 3' barcoding primer contained a unique 5-nt barcode that specified the column within the plate.

For library purification and sequencing, after the phase 3 PCR reaction, each PCR product should have had a unique set of barcodes incorporated that specified the plate, row and column, as well as Illumina paired-end sequences that enabled sequencing on the Illumina MiSeq platform. The PCR products were combined at equal proportions by volume and run on a 1.2% agarose gel; a band ~350-380 bp in size was excised and gel-purified using a Qiaquick gel extraction kit (Qiagen). This purified product was then sequenced.

Step 4. Amplification of ATAC-seq libraries. 5 µl of harvested libraries were amplified in a 50-µl PCR reaction for an additional 17 cycles with 1.25 µM Nextera dual-index PCR primers8 in 1× NEBnext High-Fidelity PCR Master Mix, using the following PCR conditions: 72° C. for 5 min; 98° C. for 30 s; and thermocycling at 98° C. for 10 s, 72° C. for 30 s and 72° C. for 1 min. The PCR products were pooled and purified on a single MinElute PCR purification column (Qiagen). Libraries were quantified using qPCR prior to sequencing.

Data processing of single-cell TCR-seq libraries. TCR sequencing data were analyzed as previously described. Briefly, raw sequencing data were demultiplexed using a custom computational pipeline, and primer dimers were removed. All paired-end reads were assembled by finding a consensus of at least 100 b in the middle of each read. A consensus sequence was obtained for each TCR gene. Because multiple TCR genes might have been present in a given well sequence-identity cutoffs were established according to sequence-identity distributions in each experiment (generally >80% sequence identity within a given well). The sequence-identity cutoff ensured that all of the sequences derived from the same transcript would be properly assigned, even given a PCR error rate of 1/9,000 bases and a sequencing error rate of up to 0.4%. TCR V, D and J segments were assigned by VDJFasta. For downstream analysis, an additional read cut-off of 100 reads was used for each identified TCR sequence. For confirmation of identified TRB sequences, select patient samples were also sequenced by immunoSEQ (Adaptive Biotechnologies), according to the Survey protocol.

Data processing of single-cell ATAC-seq libraries. All single-cell ATAC-seq libraries were sequenced using paired-end, dual-index sequencing. ATAC-seq data were pre-processed as previously described. Briefly, adaptor sequences were trimmed, sequences were mapped to the hg19 reference genome (or mm9 for mixing experiments) using Bowtie2 and the parameter-X2000, and PCR duplicates were removed. Reads that mapped to mitochondria and unmapped contigs were also removed and not considered in further analyses. Filtered single-cell libraries were required to contain >15% of unique fragments in called peaks from ensemble profiles (described below) and a library size of >500 unique nuclear fragments for most of the downstream analysis. For t-SNE projections, a further filtering step was performed to include only high-quality libraries that contained >40% of unique fragments in called peaks and a library size of >500 unique nuclear fragments. For example, conclusions regarding primary T cell subsets were derived from 450 single T cells that passed the 15% fragments in the peaks cut-off. t-SNE projections showed 320 high-quality cells that passed the 40% fragments in peaks cut-off (using the 455,057 peaks described below) to ensure that all conclusions based on clustering results were also true for high-quality single-cell libraries. Validation to ensure ATAC-seq libraries did not contain contaminating fragments from TCR libraries in the T-ATAC-seq protocol was performed. First, the phase 1 TCR primer mix used on the IFC (described above) was designed to exclude ATAC-seq Nextera-primer-binding sites. Therefore, TCR-encoding fragments present in the ATAC-seq library would not amplify in library preparation steps or be sequenced. Second, TCR library fragments in filtered and aligned ATAC-seq reads were not observed. Third, ATAC-seq data derived from T-ATAC-seq in Jurkat cells displayed similar accessibility and TF motif measurements as ATAC-seq data derived from scATAC-seq in Jurkat cells.

Principal component analysis (PCA) and t-SNE clustering. PCA projections of ensemble ATAC-seq and single-cell T-ATAC-seq profiles were performed as previously described. For ensemble ATAC-seq T cell profiles, after removing unmapped contigs, 97,395 peaks were used for further downstream analysis, and PCA analysis was performed on the 2,500 peaks that exhibited the highest variance across T cell subtypes (log 2 variance-stabilized). For single-cell T-ATAC-seq analysis of primary T cells, peaks were called on a reference set of ensemble ATACseq profiles encompassing a wide array of hematopoietic cell types that included previously published hematopoietic progenitors and end-stage cell types, as well as CD4+ T subtypes generated in this study (FIGS. 127-129 and 133). After removing peaks that aligned to annotated promoters, chromosome X, chromosome Y and unmapped contigs, 455,057 peaks were used for the PCA projection analysis.

To normalize ensemble ATAC-seq profiles, 18,858 low-variance promoters were identified across all ensemble samples and normalized each sample by the mean fragment counts within the low-variance promoters. PCA was performed on the normalized values aggregated by similar ensemble cell types, resulting in 24 PCs. To score single cells for each component, the weighted coefficients were used for each peak and PC (determined using PCA-SVD of the ensemble data above) and calculated the product of the weighted PC coefficients by the centered count values for each cell; taking the sum of this value resulted in a matrix of cells by PCs. Each cell was then normalized across the PC-scored values using the sum-of-squares. The matrix of cells by PCs, normalized by the sum-of-squares, was used as an input to a MATLAB implementation of t-SNE. Data were visualized with scHemeR10.

Transcription factor deviation and variability scores using ChromVAR. Single-cell ATAC-seq data processing and calculation of TF deviation were performed using chromVAR11. Human TF motifs were obtained from the JASPAR database and included many T cell-specific motifs derived from highthroughput 'systematic evolution of ligands by exponential enrichment' (SELEX) and chromatin immunoprecipitation with sequencing (ChIP-seq) experiments. All analysis was repeated using a curated list of human TF motifs from the cisBP database, without substantial differences11,60. JASPAR motif results are presented in all of the figures, except for FIGS. 132-137. Briefly, for each TF, 'raw accessibility deviations' were computed by subtracting the expected number of ATAC-seq fragments in peaks for a given motif (from the population average) from the observed number of ATAC-seq fragments in peaks for each single cell. For accessibility deviation calculations in primary T cells, either 455,057 hematopoietic peaks (as defined above) or a subset of 87,360 peaks was used to call from ensemble T cell subsets, monocyte and LMPP cell data, with similar results. For accessibility deviation calculations in Jurkat cells and other cell lines, 114,654 peaks were used called from ensemble DHS-seq profiles from Jurkat, K562, GM12878, and H1 ESC (ENCODE). Next, the accessibility deviation value for each cell was subtracted by the mean deviation calculated for sets of ATAC-seq peaks with similar accessibility and GC content (background peak set) to obtain a bias-corrected deviation value, and additionally divided by the s.d. of the deviation calculated for the background peak sets to obtain a z-score. For TF differences between single cells or aggregate single-cell populations, either bias-corrected deviations or z-scores were used to identify cell-specific motifs, as indicated in the figure legends. Volcano plots were generated by calculating the mean difference in the bias-corrected TF deviation score between two aggregate single-cell populations. Significance was tested by using a two-tailed Student's t-test. The variability of a TF motif across single cells was determined by computing the s.d. of the z-scores across the cells8,11. The expected value of this metric was 1 if the motif was no more variable than the background peak sets for that motif.

Modification of T-ATAC-seq for additional RNA targets. For method development and RT primer troubleshooting, the T-ATAC-seq protocol could be performed on 1,000 cells in microcentrifuge tubes, with each reaction performed in 1,000× volume. Following lysis, transposition and transposase release, RNA could be reverse-transcribed and subjected to PCR amplification to check RNA quality and quantity for a chosen primer set.

Reporting Summary. Further information on experimental design is available in the Nature Research Reporting Summary.

Code availability. All custom code used in this work is available upon request.

Data availability. All ensemble and single-cell sequencing data are available through the Gene Expression Omnibus (GEO) under accession GSE107817. Two replicates of the ensemble ATAC-seq data for naive, TH17 and Treg cells were previously published and are available under GEO accession GSE10149861. In addition, \an open-access interactive web browser is available, which enables single-cell TCR-seq and ATAC-seq TF deviation exploration (FIGS. 146-150). This browser includes all single-cell data presented in the study, links to ensemble ATAC-seq profile browsers, and processed T-ATAC-seq data matrices. A WashU browser session with ensemble T cell subtype ATAC-seq data is publically available. A WashU browser session with ensemble and aggregated single-cell Jurkat ATAC-seq data is also publically available.

Examples 2: Perturb-Seq in Single Cells

CRISPRi targeting in GM12878. To generate the Perturb-ATAC vector with guide barcodes used in the GM12878 experiments, CRISPRi vectors were modified. Briefly, three sgRNAs per target gene were designed, each targeting a different region between the transcriptional start site and 200 nucleotides into the gene body. One sgRNA each was cloned into pMJ114 (bovine U6, Addgene, Cat #85995), pMJ117 (human U6, Addgene, Cat #85997) or pMJ179 (mouse U6, Addgene, Cat #85996), digested with BstXI and BlpI, using NEBuilder Hifi DNA Assembly Master Mix. Then the respective U6 promoter and sgRNA sequences were amplified by PCR and assembled into the lentiviral vector (digested using XbaI and XhoI) using NEBuilder Hifi DNA Assembly Master Mix. Subsequently, individual colonies for each 3× sgRNA plasmid were digested using PciI and EcoRI, and a randomized 22 bp barcode (ordered from IDT as 5'-[overhang] [NNN . . . ] [overhang]-3') was assembled with NEBuilder Hifi DNA Assembly Master Mix. The sgRNA sequences and GBC sequences of all plasmids were confirmed by Sanger sequencing.

To generate CRISPRi virus, HEK 293T cells were maintained in DMEM with 10% FBS, 1% Pen-Strep. Cells were seeded at 4 million per 10 cm dish, and the following day transfected with 4.5 ug pMP.G, 1.5 ug psPAX2, and 6 ug sgRNA vector using OptiMEM and Lipofectamine 3000. Two days later, the supernatant was collected and filtered with a 0.44 µm filter, and virus was concentrated 1:10 using Lenti-X Concentrator (Clontech). GM12878 maintained in RPMI 1640 (Thermo Fisher) with 10% FBS and 1% Penicillin-Streptomycin (Thermo Fisher) were then seeded at 300,000 cells per well of a 6-well plate and 40 µl of concentrated virus was added to the media the following day. Two days later, the media was exchanged for media containing 1ug/ml puromycin to select for the sgRNA vector. Selection media was refreshed on day five, and on day seven cells selection media was exchanged 1441 for regular media (containing no puromycin) and cells were either assayed or frozen in viable conditions with BamBanker cryopreservation media. Cells were sorted by flow cytometry for viability and expression of mCherry before being assayed by Perturb ATAC-seq. Cells were maintained between 200,000 and 1 million per mL. RNA was extracted with Trizol and purified using Qiagen RNeasy columns, and gene expression knockdown was confirmed using the Agilent Brilliant II qRT-PCR 1-Step kit. qRT-PCR was performed in duplicate, and expression values for each sample were normalized against 18S. Gene expression values for CRISPRi are reported as average fold change against both non-targeting control samples.

Culture, differentiation, and CRISPR knockout in primary keratinocytes. Primary human keratinocytes were isolated from fresh, surgically discarded neonatal foreskin. Keratinocytes were grown in 1:1 KCSFM and Medium 154 (Life Technologies). Keratinocytes were induced to differentiate by addition of 1.2 mM calcium for 3 or 6 days in full confluence. Custom Cas9 and sgRNA expression vectors were generated for CRISPR knockout in keratinocytes. For Cas9 expression, the Cas9 gene was amplified from the lentiCRISPRv2 vector (Sanjana et al., 2014) and cloned this fragment into pLex-MCS (Thermo Fisher) along with a fusion P2A-blasticidin resistance cassette in exchange for the IRES-puromycin resistance cassette in pLex-MCS. For sgRNA expression, the sgRNA F+E scaffold was modified in two ways. First, the murine U6 promoter and telomerase-targeting sgRNA was exchanged for the human U6 promoter, stuffer region, and associated BsmBI cloning sites from lentiCRISPRv2. Additionally, a BsmBI restriction site in the puromycin resistance gene was removed by introducing a non-synonymous mutation.

To generate lentivirus, 400,000 HEK 293T cells were seeded into a single well of a 6-well dish, and the following day transfected with either Cas9 vector or sgRNA vector (1.3 ug) along with pMDG (0.3 ug) and p8.91 (1 ug) using Lipofectamine 3000 (Thermo Fisher). Supernatant was collected at 48 hrs and 72 hrs, filtered through a 0.45 µm PES membrane, and concentrated to a pellet with Lenti-X Concentrator. One unit of Cas9 virus corresponded to the concentrated supernatant from one 6-well of HEK 293T. One unit of sgRNA virus corresponded to one eighth of the concentrated supernatant from one 6-well of HEK 293T. Primary keratinocytes were seeded at 300,000 cells per well of a 6-well dish along with one unit of Cas9 virus and polybrene (0.1 ug/ml). After one day, two wells were harvested, mixed, and expanded into a 15 cm dish containing normal culture media with 2 ug/ml blasticidin. After four to six days of selection, cells were again seeded at 300,000 cells per well of a 6-well dish along with one unit of sgRNA virus and polybrene (0.1 ug/ml). After one day, one well was harvested and transferred to a 15 cm dish containing normal culture media, puromycin (1 ug/ml) and blasticidin (2 ug/ml). After six days of selection, cells were seeded at high confluence with 1.2 mM calcium for differentiation. Cells were harvested 1484 after three days of differentiation and viably frozen in culture media with 10% DMSO. Cas9 nuclease activity was assessed by PCR amplifying ~800 bp fragments of cDNA surrounding sgRNA binding sites and analyzing the resulting fragments by Sanger sequencing. cDNA was generated by extracting RNA from cells with the RNeasy Mini Kit (Qiagen) and performing reverse transcription with the iScript cDNA Synthesis Kit (Bio-Rad).

Bulk ATAC-seq. Cells were isolated and subjected to ATAC-seq. 50,000 cells were pelleted after sorting and resuspended in 50 µl of ATAC resuspension buffer (RSB) with 0.1% NP40, 0.1% Tween-20, and 0.01%. After three minutes, 1 ml of ATAC RSB with 0.1% Tween-20 was added, tubes were inverted, and nuclei were centrifuged at 500 rcf for 10 min. Supernatant was carefully removed and nuclei were resuspended in 50 µl transposition mix (25 µl TD buffer, 2.5 µl transposase, 16.5 µl PBS, 0.5 µl 0.1% digitonin, 0.5 µl 10% Tween-20, and 5 µl water). Transposition was performed for 30 minutes at 37 C with shaking in a thermomixer at 1000 RPM. Reactions were purified with a Zymo DNA Clean & Concentrator 5 kit and library generation was performed.

Single-cell ATAC-seq Cells were sorted by flow cytometry for viability and to remove cell aggregates. The C1 Single-Cell Auto Prep System was used with the Open App™ program (Fluidigm, Inc.). The Open App scripts from the "ATAC Seq" collection from Fluidigm were used to prime the C1 IFC microfluidic chip, load cells, and run the ATAC sample prep protocol. Fluidigm scripts are available from Fluidigm Script Hub.

Perturb ATAC-Seq

Cell isolation and microfluidic reactions on the IFC. The C1 Single-Cell Auto Prep System with its Open App™ program (Fluidigm, Inc.) was used to perform Perturb-ATAC-seq. C1 IFC microfluidic chips were first primed by following the Open App script "Biomodal Single-Cell Genomics: Prime". Single cells were then captured using the Fluidigm Open App script "Biomodal Single-Cell Genomics: Cell Load." GM12878 or keratinocyte cells were first isolated by FACS sorting and then washed three times in C1 DNA Seq Cell Wash Buffer (Fluidigm). Cells were resuspended in DNA Seq Cell Wash Buffer at a concentration of 300 cells/µL and mixed with C1 Cell Suspension Reagent at a ratio of 3:2 (cells: reagent). 15 µl of this cell mix was loaded onto the IFC. After cell loading, all wells were visualized by imaging on a Leica CTR 6000 microscope to identify captured cells. Cells were then subjected sequentially to lysis 1528 and transposition, transposase release, quenching with MgCl2, reverse transcription, and PCR, using the custom Open App IFC script "Biomodal Single-Cell Omics: Sample Prep." For lysis and transposition, 30 µL of Tn5 transposition mix was prepared (22.5 µL 2× TD buffer, 2.25 µL transposase (Nextera DNA Sample Prep Kit, Illumina), 2.25 µL C1 Loading Reagent without salt (Fluidigm), 0.45 µL 10% NP40, 2.25 µL SuperaseIN RNase inhibitor, and 0.3 µL water). For transposase release, 20 µL of Tn5 release buffer mix was prepared (2 µL 500 mM EDTA, 1 µL C1 Loading Reagent without salt, and 17 µL 10 mM Tris-HCl Buffer, pH 8). For MgCl2 quenching, 20 µL of MgCl2 quenching buffer mix was prepared (18 µL 50 mM MgCl2, 1 µL C1 Loading Reagent without salt, and 1 µL 10 mM Tris-HCl Buffer, pH 8). For reverse transcription, 30 µL of RT mix was prepared (15.55 µL H20, 3.7 µL 10× Sensiscript RT buffer (Qiagen), 3.7 µL 5 mM dNTPs, 1.5 µL C1 Loading Reagent without salt (Fluidigm), 1.85 µL Sensiscript RT (Qiagen), and 3.7 µL 6 µM RT primer mix (6 µM each of a first set of GBC sequencing oligos or 6 µM each of a first set of sgRNA sequencing oligos, see Supplementary Tables 3 and 6 for oligo sequences). Finally, for ATAC and GBC/sgRNA PCR, 30 µL of PCR mix was prepared (8.62 µL H20, 13.4 µL 5× Q5 polymerase buffer (NEB), 1.2 µL 5 mM dNTPs, 1.5 µL C1 Loading Reagent without salt, 0.67 µL Q5 polymerase (2 U/µL; NEB), 0.8 µL 25 µM non-indexed custom Nextera ATAC-seq PCR primer 1, 0.8 µL 25 µM non-indexed custom Nextera ATAC-seq primer 2, and 3 µL 6 µM GBC or sgRNA primer mix. 7 µL lysis and transposition mix, 7 µL transposase release buffer, 7 µL MgCl2 quenching buffer, 24 µL RT mix, and 24 µL PCR mix were added to the IFC inlets. On the IFC, Tn5 lysis and transposition reaction was carried out for 30 minutes at 37°. Next, transposase release was carried out for 30 min at 50° C. MgCl2 quenching buffer was immediately added and chamber contents were immediately incubated with RT mix for 30 minutes at 50° C. Finally, gap filling and 8 cycles of PCR were performed using the following conditions: 72° C. for 5 min and then thermocycling at 94° C. for 30 s, 62° C. for 60 s, and 72° C. for 60 s. The amplified transposed DNA was harvested in a total of 13.5 µL C1 Harvest Reagent.

Following completion of the on-chip protocol (~4-5 hrs), chamber contents were transferred to 96-well PCR plates, mixed, and divided for further amplification of ATAC-seq fragments (6-7 µl) or GBC/sgRNA fragments (6.5 µl). For method development and RT primer troubleshooting, the Perturb-ATAC-seq protocol can be exactly scaled 1000× and performed on 1000 cells in Eppendorf tubes. Following lysis, transposition, and transposase release, RNA can be reverse-transcribed and subjected to PCR amplification to check the amplification efficiency and specificity of a chosen primer set.

Amplification of ATAC-seq libraries. ~7 µL of harvested libraries were amplified in 50 µL PCR for an additional 15 cycles with 1.25 µM Nextera dual-index PCR primers in 1× NEBnext High-Fidelity PCR Master Mix using the following PCR conditions: 72° C. for 5 min; 98° C. for 30 s; and thermocycling at 98° C. for 10 s, 72° C. for 30 s, and 72° C. for 1 min. The PCR products were pooled and purified on a single MinElute 1572 PCR purification column (Qiagen). Libraries were quantified using qPCR (Kapa Library Quantification Kit for Illumina, Roche) prior to sequencing using 2×76 bp paired1575 end reads on an Illumina NextSeq 550 or 2×75 bp reads on an Illumina MiSeq.

Amplification of guide barcode and guide RNA sequencing libraries. Three rounds of off-C1 PCR were performed to generate GBC and sgRNA sequencing libraries (See "PCR 1"; "PCR 2" and "PCR 3" in FIG. 55). First (first PCR), 6.5 µl of harvested libraries were amplified in a 20 µl PCR (harvested DNA with 10 μl NEBNext Master Mix, 0.1 μl of each of a first set of primers at 200 uM, and remaining volume of water). Reactions amplified for 17 cycles with the following parameters: 98 C for 30 s, then cycling of 98 C for 10 s, 63 C for 30 s, and 72 C for 45 s, followed by 72 C for 5 min. Second, 2 μl of the first set of PCR product (without purification) was transferred to a subsequent 20 μl reaction with 10 μl NEBNext Master Mix, 0.1 μl of each of a second set of primers at 200 uM, and remaining volume of water. Reactions were amplified for 15 cycles using the same parameters used for the first set of reactions. A final 20 ul third cell indexing PCR was performed using 2 ul of the second set of reaction product, 2 ul each of Illumina Indexing primers at 10 uM, 10 ul NEBNext Master Mix, and the remaining volume of water. Reactions were amplified for 15 cycles using the same parameters used for the first set and the second set of reactions. Finally, the third set of reactions were pooled and purified using the Qiagen MinElute kit. Libraries were further purified by size selection on polyacrylamide gel electrophoresis (6% TBE Novex gel, Thermo Fisher). Libraries were mixed with BlueJuice loading dye (Thermo Fisher), run for 35 min at 160 V and visualized using SybrSafe stain (Thermo Fisher), using 5 ul of stain in 30 ml of TBE running buffer for 10 min. Gels were visualized on a blue-light transilluminator and slices in size range for GBC library fragments (289 bp) or sgRNA library fragments (232 bp) were cut using a scalpel. Gel slices were placed in a 0.75 ml tube with a hole punctured in the bottom using a syringe, and this tube was placed in a 1.5 ml DNA LoBind tube (Eppendorf). These tubes were centrifuged for 3 min at 13k RPM to crush the gel slice, then 300 ul Salt Crush Buffer (500 mM NaCl, 1 mM EDTA, 0.05% SDS) was added and this mix was incubated at 55 C overnight in a thermomixer with 1000 RPM shaking. The next day, samples were cooled to RT, centrifuged through a Spin-X column (one minute, 13k RPM), and purified with a Zymo DNA Clean & Concentrator 5 kit. Libraries were quantified by qPCR (Kapa Library Quantification Kit for Illumina, Roche) before sequencing on an Illumina MiSeq at 10-14 pM final concentration with 15-40% PhiX.

Quantification and statistical analysis. Single cell and bulk ATAC primary processing and chromVAR analysis. Single cell and bulk ATAC read alignment, quality filtering, and duplicate
removal were performed. Briefly, adapter sequences were trimmed, sequences were mapped to the hg19 reference genome using Bowtie2 (Langmead and Salzberg, 1616 2012; and the parameter-X2000), and PCR duplicates were removed using Picard Tools. Reads mapping to the mitochondria were discarded for further analysis. A low rate of ATAC reads matching the CRISPR viral construct (median 0.0049%) was observed, and no evidence of the abundance of CRISPR construct matching reads influencing epigenomic profiles was observed. Single cell ATAC-seq calculation of TF deviation was performed using chromVAR (in R, version 1.1.1; Schep et al., 2017). Briefly, for each TF, 'raw accessibility deviations' were computed by subtracting the expected number of ATAC-seq reads in peaks for a given motif from the observed number of ATAC1626 seq reads in peaks for each single cell. Expected reads were calculated from the population average of all cells for the GM12878 experiment and unperturbed cells only for the keratinocyte experiment. This value is subtracted by the mean deviation calculated for sets of ATAC-seq peaks with similar accessibility and GC content to obtain a bias-corrected deviation value, and additionally divided by standard deviation of the deviation calculated for the background sets to obtain a Z-score.

For the GM12878 experiments, a set of peaks derived from DNAse I hypersensitivity data was used from a broad variety of hemopoietic cell lines (all GM lines, HL-60, Th1, Jurkat, K562) plus additional lines (HepG2, HUVEC, NHEK), to account for the possibility of opening peaks outside the blood lineage. These peaks were each filtered against the wgEncodeDacMapabilityConsensusExcludable.bed blacklist, sorted by intensity, and the top 75,000 peaks for each sample were merged. These peaks were then centered and resized to 1 kb uniform peaks (238,349 final peaks). For the keratinocyte experiment, peaks called on bulk ATAC1643 seq from undifferentiated cells and cells differentiated for three or six days were merged. Peaks were called using the MACS2 command macs2 callpeak-no-model-nolambda-call-summits-shift-75-extsize 150 (Zhang et al., 2008). First, peaks with q-value <0.01 from each day were merged. In the case of overlapping peaks, the summit associated with the lowest q-value was selected as the merged peak summit, and the 1 kb window centered on that summit was used as the uniform peak for chromVAR (94,633 final peaks).

For GM1878 analysis, narrowPeak ChIP-seq files (optimal IDR thresholded peaks) were downloaded from ENCODE and imported as supplementary annotations in chromVAR. Prior to use, these files were filtered against the wgEncodeDacMapabilityConsensusExcludable.bed blacklist. H3K27me3 and H3K27ac narrowPeak files for different tissues were downloaded from the Roadmap Epigenomics website.

Guide barcode sequencing analysis for GM12878 experiments. For GM12878 experiments, raw reads for GBC libraries were matched to a list of GBC sequences to generate a table of counts for each cell and each GBC analyzed in the experiment. First, any read not containing the expected 27 nt sequence prior to the GBC was discarded, allowing for a maximum Levenshtein distance of 2 to account for sequencing errors. The subsequent 22 nt sequence was then compared to a list of GBC sequences, allowing for a maximum Levenshtein distance of 3 to be considered a match. Note that the minimum Levenshtein distance between any two of our GBC sequences was 10. This generated a counts-per-cell table for each GBC sequence and cell. This table was normalized for read depth by plate by assessing the maximum density of log-transformed counts using the scipy.stats.gaussian_kde function. This distribution exhibits a bimodal distribution corresponding to wells with productive and unproductive GBC detection. A normalized GBC read cutoff of 1000 reads/cell was set (this was empirically determined based off the separation between wells with and without a cell capture). Cells displaying high background reads, as determined by having greater than 0.005 proportion reads not aligning to the top two GBC sequences, were further filtered (this cutoff was set from empirical observations of "background" in doublet wells, which are expected to contain up to four GBC sequences). Wells expressing a single or double sgRNAs were distinguished based off the percent of reads aligning to the second-most common GBC (single, <1% double, >5%). This workflow resulted in far more double-targeted cells than would be observed solely from the observed doublet rate calculated from the appearance of double GBC-expressing cells in our initial single-targeting experiment (~2.9%). tSNE plots were generated using the manifold.TSNE function in the Python package scikit-learn.

A target minimum cell number required for analysis was determined by down-sampling cells from a larger pool and comparing accessibility profiles. This analysis indicated that the vast majority of samples of five cells were highly correlated (r>0.8) with a bulk ATAC-seq profile. Additionally, previous reports have shown that aggregation of five or more cells is sufficient to accurately reproduce chromatin accessibility profiles (Satpathy et al., 2018; Schep et al., 2017). In line with these findings, Perturb-ATAC experiments were designed to yield the maximal number of genotypes supported by at least five cells; indeed 38/40 genotypes for GM12878 cells and 23/23 genotypes for keratinocytes consist of greater than five cells.

Direct sgRNA sequencing and analysis for keratinocyte experiments. For keratinocyte experiments, raw reads for sgRNA sequencing were matched to a list of sgRNA sequences used in the experiment (e.g., alternatively or in addition to sequencing reads from the GBC; see FIG. 92). Strict matching of the 20 bp variable sequence along with 18 bp of the standard sgRNA backbone was required. Matching was performed with custom scripts (available upon request) and resulted in the counts-per-cell table for each sgRNA. This table was normalized for read depth by assessing the plate-specific distribution of log-transformed total counts per cell. The collection of counts per cell exhibited a bimodal distribution likely corresponding 1704 to productive and failed sgRNA detection. A cutoff in between the two modes as a first Filter was drawn, and further required cells to exhibit low background (reads associated with the third most common sgRNA in each cell). Cells with greater than 1% of reads associated with background were excluded from analysis. Finally, cells expressing one or two sgRNAs based on the distribution of proportions of reads associated with the second most common sgRNA in each cell were distinguished. Cells with fewer than 1% of reads associated with the second most common sgRNA formed a clear mode in this distribution and were considered to express only the most common sgRNA, while cells with greater than 10% of reads associated with the second most common sgRNA were considered to express both the first and second most common sgRNAs.

Identification of differentially accessible genomic features and regions. An empirical null distribution of accessibility values for each feature was generated in order to assess the significance of any observed difference between mean accessibility in a set of perturbed cells compared to cells expressing non targeting control sgRNAs. For each genomic feature (peak or chromVAR motif/annotation), the median deviation z-score (for chrom VAR features) or fragment counts (for peaks) in cells expressing each sgRNA or combination of sgRNAs was calculated. Cells expressing a targeting sgRNA in combination with a non-targeting sgRNA were analyzed with targeting sgRNA-only cells. With the goal of assessing the null hypothesis that targeting and non-targeting cells exhibit the same accessibility, equal numbers of cells from targeting and non targeting cells were pooled. This population was then randomly divided into two sets by permuting the cell-genotype labels, and the permuted median accessibility difference of these two populations were compared to the observed median accessibility difference. This process was repeated 5000 times to generate a null distribution, and the rate of detecting a median accessibility difference as extreme or greater in the null distribution compared to the observed targeting cells was reported as the false discovery rate (FDR).

Differentially accessible regions were found using a similar approach with the exception that the set of total regions under consideration was limited to those exhibiting at least one read per five cells in one of the conditions under consideration for each comparison. Genome browser tracks of differentially accessible regions were generated by pooling cells associated with a particular sgRNA genotype. BedGraph files were generated and scaled to 500,000 reads using the genomeCoverageBed tool (BedTools v2.17.0) then generated big Wig files using the bedGraphToBigWig tool from UCSC. Tracks were finally displayed in the WashU Epigenome Browser.

Statistical analysis of SPI1 motif-containing region accessibility in SPI1-depleted cells. An empirical false 1748 discovery rate for the observed changes in SPI1 motif region accessibility was determined. For bulk-ATAC and Perturb-ATAC samples separately, the z-score of the SPI1 motif accessibility change in perturbed cells was compared to all other features. Then to generate a null distribution, the sample labels between Non-targeting #1, Non targeting #2, and SPI1-targeting were permuted 1000 times and in each trial recorded the z-score of SPI1 motif change in accessibility compared to the non-targeting controls. In this analysis, for both bulk-ATAC and Perturb-ATAC, no trial yielded a result as extreme as the result observed in the unpermuted sample.

Inferred nucleosome and sub-nucleosome profiles and score calculation. The aggregate profiles of nucleosomal signals at differentially accessible regions were derived from total ATAC fragments. Briefly, ATAC fragments sized 180-247 bp were considered nucleosome-spanning and used to infer positions of nucleosomes in aggregate locus profiles (metaplots). Differentially accessible regions were centered based on the signal summit as identified by Macs2 (using the flags-call-summits-shift-75-extsize 150) and filtered for an FDR <0.1 and log 2 fold change >1. The fragment count in 10 bp windows spanning 1000 bp upstream and downstream of the region summit was then calculated. These profiles were normalized to the average signal in the 25 downstream windows to account for sequencing depth and the resulting enrichment values were smoothed in R using the smooth.spline ( ) function with parameter spar=0.5.

To quantify the presence of peak central versus flanking nucleosome in each metaplot, the ratio of flanking nucleosome signal density (−180 to −80 bp relative to peak summit and +80 to +180 bp relative to peak summit) to central nucleosome signal density (−20 to +20 bp relative to peak summit) was calculated. This ratio is reported as the central nucleosome score.

Analysis of inferred regulatory networks. To identify sets of genomic features whose activities were correlated across single cells, suggestive of shared regulatory relationships, the Pearson correlation was computed of each feature with each other feature across all single cells of a given genotype. Only features that were significantly altered in at least one genotype were considered, and redundant annotations were removed, resulting in 390 motif/ChIP feature annotations for analysis. Ward's hierarchical clustering was performed and features displaying low intra-cluster correlation were excluded from further analysis. The modules shown in subsequent analysis were defined based off Ward's hierarchical clustering of the remaining features in non-targeting cells. Clustering was performed using the Seaborn clustermap function using Ward's method for clustering.

For each Perturb-ATAC genotype, the feature-feature correlation across single cells was computed. The difference in correlation between a given genotype and non-targeting cells was computed by subtracting the Pearson correlation in the respective genotype from non-targeting cells. A permutation 1792 test was used to assess the significance of the observed change in correlation for any pair of features. For each genotype, the same number of cells was randomly sampled from all perturbed cells 10,000 times, and the changes in correlation in the randomly sampled cells relative to non-targeting cells were used to create a null distribution for each feature-feature pair (in each genotype). A 5% cutoff was used to call significantly altered correlations. To quantify module-level changes in regulatory relationships, the percent of all feature-feature pairs in a given module whose correlations were significantly altered was calculated.

Analysis of epistasis for accessibility of genomic features. The degree of epistasis in double perturbation conditions was evaluated by comparing observed phenotypes in double perturbation conditions to phenotypes expected based on a model of non-interaction. For this analysis, the accessibility of genomic features based on the sum of raw reads accumulating in peaks associated with that feature in each cell was scored. Feature counts were normalized by the total number of reads for features in each cell and log 2-transformed with the addition of a pseudocount. For each collection of cells sharing a genotype, the mean value of log 2 counts was compared to the mean value of log 2 counts for a mix of cells expressing non-targeting sgRNAs, resulting in a log 2 (fold change of perturbation vs. non-targeting). The additive expectation was based on a multiplicative model of non-interaction, (i.e., CRISPR AB=CRISPR A×CRISPR B), which was calculated by adding the single perturbation fold changes in log 2-space. For each genomic feature, the degree of interaction (difference between observed accessibility change and that expected under the non-interaction model) was calculated.

To identify generally additive vs. non-additive features the interaction degree was averaged across perturbations. To compute the permuted background, the single-double pairings was permuted by randomly choosing a double sgRNA genotype and two random single sgRNA genotypes. The difference between the "expected" change (based on the two random sgRNA genotypes) and the "observed" changed (based on the random double sgRNA genotype) was then computed. This process was repeated once for each double sgRNA genotype observed in our dataset.

Features were further categorized as additive, synergizing, and buffering for a particular interaction by comparing the observed degree of interaction to a null distribution generated by permuting cell identities. This procedure was performed separately for each feature to account for differences in scale and variability across features. The null distribution was generated by randomly sampling three pools of cells from all perturbed cells: a null double perturbation set, and two null single perturbation sets. The difference between observed double perturbation phenotype and the expected value from the non-interaction model was calculated, and this procedure was repeated 1000 times. Genotypes exhibiting interaction degrees beyond 95% of the null values were considered interacting. Interactions in which the double phenotype had a more extreme magnitude than expected were labeled synergistic, while others were labeled buffering.

Analysis of tissue H3K27me3 and autoimmune-associated SNPs. 128 consolidated narrowPeak files for H3K27me3 peaks (corresponding to different tissues/cell-types) were downloaded from the Roadmap Epigenomics Consortium website. Peaks that were found across at least 30 samples were considered common H3K27me3 peaks. Individual narrowPeak files were then filtered against this set of common H3K27me3 peaks, as well as the wgEncodeDacMapabilityConsensusExcludable blacklist. The resulting files were subsequently centered and resized to create uniform 1 kb peaks, and imported into chromVAR as an annotation set. To identify peaks repressed in the GM12878 lineage but active in other tissues, H3K27ac narrowPeaks from blood tissues present in the Roadmap Epigenomics Consortium dataset were downloaded and intersected with the GM12878 H3K27me3 narrowPeak set using the bedtools intersect command. These were similarly filtered aginst the same blacklist, centered, and resized to create uniform 1 kb peaks, and imported as a chromVAR annotation set.

SNPs associated with autoimmune diseases were aggregated by each autoimmune disease, and intersected with FitHiC calls (processed using 10 kb genomic windows) from GM12878 H3K27ac HiChIP data (Mumbach et al., 2017). For each disease, the SNP (ultimately resized to a 10 kb genomic window), as well as any windows in contact with that SNP, were aggregated to create a disease-specific chromVAR annotation set. As it is difficult to determine a priori whether a disease state would result from increased or decreased accessibility at a given site, absolute value change chromVAR deviation z-score was reported for each genotype.

Pseudotime calculation and identification of feature modules. For the keratinocyte experiment, the normal differentiation pseudotime trajectory was calculated using Monocle 2 (Qiu et al., 2017b). The feature deviation matrix including unperturbed and CRISPR knockout cells was first processed using Seruat 2.0.1 (Butler et al., 2018) to regress out plate and experiment batch effects. The Seurat function ScaleData was used (with parameters do.scale=F and do.center=F) to perform batch regression. To identify modules of dynamic features across differentiation, the features that exhibited standard deviation greater than 1.3 were filtered in any comparison of normal differentiation conditions (Day 0, 3, or 6). Similar features associated with the AP1 motif were merged into a single feature. The matrix of these features vs. cells (arranged by increasing pseudotime) was hierarchically clustered using the heatmap.2 function in the gplots R package, resulting in three major clusters (referred to as modules). Individual peaks approximately matching the kinetics of modules were identified in order to find associated genes. Peaks exhibiting a log 2 fold change less than 0.5 between conditions were considered stable and a fold change greater than 2 was considered dynamic. Peaks exhibiting decreased accessibility on both Day 3 and Day 6 (relative to Day 0) were considered Module 1 peaks. Peaks exhibiting increased accessibility on Day 3 versus Day 0 but stable accessibility between Day 6 and Day 0 were considered Module 2 peaks. Peaks exhibiting stable accessibility between Day 3 and Day 0 but gained accessibility on Day 6 versus Day 0 were considered Module 3 peaks. Genes were considered potential regulatory targets of a peak if the gene transcription start site fell within 50 kb of the peak.

Altered differentiation trajectory and module activity analyses. For each single perturbation in the keratinocyte experiment, a custom pseudotime was calculated in order assess the enrichment or depletion of cell occupancy along the differentiation trajectory. ChromVAR deviations regressed for experimental batch effects and merged AP1 features were used for this analysis. Cells from each perturbation were pooled with non-targeting cells and a custom principal component analysis (PCA) space was generated. Features altered in each perturbation (FDR<0.1, change in z-score >0.25) were selected in order to achieve maximum separation of control and perturbed cells, and a PCA was generated with the R prcomp function (center=T, scale=T). Next, non-perturbed cells from all stages of differentiation were analyzed and a trajectory was calculated progressing from undifferentiated cells (Day 0) to mid-differentiation (Day 3) and finally late-differentiation (Day 6). The trajectory was determined by plotting a linear path between centroids of the three cell populations representing each stage of differentiation. Finally, the distribution of non-targeting cells and targeted cells was calculated along eight equally sized bins in this trajectory, and the log 2 fold change of the proportion of cells in each been was reported as an enrichment.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of processing immune cells, comprising:
   (a) isolating a single immune cell comprising genomic deoxyribonucleic acid (gDNA) and a plurality of messenger ribonucleic acid (mRNA) molecules;
   (b) tagmenting one or more regions of accessible chromatin in the gDNA of the single immune cell to produce a plurality of tagged gDNA fragments in a tagmentation reaction, wherein the tagmentation reaction comprises cleaving and tagging the gDNA in the same reaction;
   (c) adding a primer, reverse transcriptase, and dNTPs to the single immune cell to reverse transcribe the plurality of mRNA molecules of the single immune cell to produce a plurality of complementary DNA (cDNA) molecules, wherein said cDNA molecules comprise sequences that correspond to a V(D)J region of a genome of the single immune cell;
   (d) sequencing the plurality of cDNA molecules and the plurality of tagged gDNA fragments that were both produced from the single immune cell to generate a plurality of sequencing reads; and
   (e) generating an epigenetic map of the one or more regions of accessible chromatin of the gDNA and the sequences that correspond to the V(D)J region of the single immune cell by correlating:
      one or more sequencing reads of the plurality of tagged gDNA fragments or amplicons thereof; and
      one or more sequencing reads of the plurality of cDNA molecules or amplicons thereof.

2. The method of claim 1, wherein said plurality of immune cells comprises T cells or B cells.

3. The method of claim 1, wherein (a) isolating the single immune cell comprises capturing the single immune cell in a partition.

4. The method of claim 3, wherein said partition comprises a chamber, a well, or a droplet.

5. The method of claim 1, wherein (a) isolating the single cell comprises flow cytometry sorting or magnetic cell sorting.

6. The method of claim 1, further comprising lysing said single immune cell.

7. The method of claim 1, wherein each of said tagged gDNA fragments comprises one or more adapters.

8. The method of claim 7, wherein said one or more adapters comprise an adapter sequence.

9. The method of claim 1, wherein said primer comprises a sequence specific to or targeted for a sequence of said plurality of mRNA molecules.

10. The method of claim 1, wherein said plurality of mRNA molecules comprise T cell receptor alpha (TRA) or T cell receptor beta (TRB) mRNA molecules.

11. The method of claim 10, wherein (c) comprises contacting the plurality of mRNA molecules with a plurality of primers, wherein said plurality of primers comprises a sequence specific to or targeted for a sequence encoding a constant region of said TRA or TRB mRNA molecules.

12. The method of claim 1, wherein said plurality of mRNA molecules comprise T cell receptor alpha (TRA) and T cell receptor beta (TRB) mRNA molecules.

13. The method of claim 1, further comprising contacting said plurality of tagged gDNA fragments and said plurality of cDNA molecules with a plurality of primers and a polymerase to generate tagged gDNA fragment amplicons or cDNA molecule amplicons.

14. The method of claim 13, wherein each of at least a subset of said plurality of primers comprises a sequence specific to or targeted for a sequence encoding a constant region or variable region of a T cell receptor (TCR).

15. The method of claim 13, wherein each of at least a subset of said plurality of primers comprises a sequence specific to or targeted for a sequence encoding a constant region and variable region of a T cell receptor (TCR).

16. The method of claim 1, further comprising contacting said plurality of tagged gDNA fragments and said plurality of cDNA molecules with a plurality of primers and a polymerase to generate tagged gDNA fragment amplicons and cDNA molecule amplicons.

17. The method of claim 1, further comprising generating amplicons from said plurality of tagged gDNA fragments and said plurality of cDNA molecules, wherein said amplicons each comprise a barcode sequence that identifies said single immune cell.

18. The method of claim 17, wherein said amplicons each comprising said barcode sequence that identifies said single immune cell are generated from other amplicons of said plurality of tagged gDNA fragments or said plurality of cDNA molecules.

19. The method of claim 17, further comprising sequencing said amplicons.

20. The method of claim 1, further comprising, subsequent to (b), terminating said tagmentation reaction.

21. The method of claim 20, wherein said terminating comprises contacting said single immune cell with a chelating agent.

22. The method of claim 21, wherein said chelating agent is selected from the group consisting of: ethylenediamine tetraacetatic acid (EDTA), nitriloacetic acid (NTA), and diethylenetriamine pentaacetic acid (DTPA).

23. The method of claim 1, wherein said tagmentation reaction comprises using a detergent.

24. The method of claim 23, wherein said detergent comprises a non-ionic surfactant.

25. The method of claim 24, wherein said detergent is an ethoxylated nonylphenol.

26. The method of claim 1, wherein the tagmentation reaction comprises cleaving and tagging the gDNA using an insertional enzyme complex comprising a transposase and one or more one or more adapters.

27. The method of claim 1, wherein each mRNA molecule comprises an immune cell receptor comprising the V(D)J region.

28. The method of claim 27, wherein the immune cell receptor is a TCR or a B cell Receptor (BCR).

* * * * *